United States Patent
Beaudegnies et al.

(10) Patent No.: US 7,776,888 B2
(45) Date of Patent: Aug. 17, 2010

(54) HERBICIDES

(75) Inventors: Renaud Beaudegnies, Basel (CH); Andrew Edmunds, Basel (CH); Christoph Lüthy, Basel (CH); Roger Graham Hall, Basel (CH); Sebastian Volker Wendeborn, Basel (CH); Jürgen Schaetzer, Basel (CH)

(73) Assignee: Syngenta Crop Protection, Inc., Greensboro, NC (US)

( * ) Notice: Subject to any disclaimer, the term of this patent is extended or adjusted under 35 U.S.C. 154(b) by 1286 days.

(21) Appl. No.: 10/540,769

(22) PCT Filed: Dec. 29, 2003

(86) PCT No.: PCT/EP03/14949

§ 371 (c)(1),
(2), (4) Date: Jun. 24, 2005

(87) PCT Pub. No.: WO2004/058712

PCT Pub. Date: Jul. 15, 2004

(65) Prior Publication Data

US 2006/0052247 A1 Mar. 9, 2006

(30) Foreign Application Priority Data

Dec. 30, 2002 (CH) .................................. 2217/02

(51) Int. Cl.
*A61K 31/44* (2006.01)
*A61K 31/4427* (2006.01)
*C07D 421/06* (2006.01)
*C07D 213/02* (2006.01)

(52) U.S. Cl. .................... 514/337; 514/354; 546/268.1; 546/314

(58) Field of Classification Search ............... 546/268.1, 546/314
See application file for complete search history.

(56) References Cited

FOREIGN PATENT DOCUMENTS

| WO | 0015615 A1 | 3/2000 |
| WO | 0166522 A1 | 9/2001 |
| WO | 0194339 A1 | 12/2001 |

OTHER PUBLICATIONS

Isomers [online], [retrieved on Mar. 11, 2007]. Retrieved from internet, URL; http://chemed.chem.purdue.edu/genchem/topicreview/bp/1organic/isomers.html>.*
Database Caplus 'Online! Chemical Abstracts Service, Columbus, Ohio, US; Chen, Ling Ching et al: 1,3-Dipolar cycloaddition of 5-substituted-1-methyl-3-oxidopyridiniums; & Journal of The Chinese Chemical Society (Taipei, Taiwan), 31(3) 227-80 Coden: JCCTAC; ISSN: 0009-4536, 1984.
Garst, Michael E., et al.: "Even regioselectivity in [6+4] Cycloadditions of unsymmetrical tropones with dienes" Journal of The American Chemical Society 106(13), 3882-84 Coden: JACSAT; ISSN: 0002-7863, 1984, compounds 9e, 9f.
Law, David C.F. et al: "Diels-Alder reactions of tetrahalocyclopropenes" Journal of The American Chemical Society, 90(9), 2376-86 Coden: FACSSAT; ISSN: 0002-7863, 1968, XP002284552 compounds 17a, 17b, 17c, 18a, 18b, 18c.
Tamura, Yasumitsu et al: "Synthesis of stipitatic acid and hinokitiol" Tetrahedron Letters, (47), 4075-8 Coden: TELEAY; ISSN: 0040-4039, 1977, XP002284553, compound 8.

* cited by examiner

*Primary Examiner*—Kamal A Saeed
*Assistant Examiner*—Shawquia Young
(74) *Attorney, Agent, or Firm*—William A. Teoli, Jr.

(57) ABSTRACT

Compounds of formula (I), wherein the substituents are as defined in claim 1, and the agrochemically acceptable salts and all stereoisomers and tautomeric forms of the compounds of formula I are suitable for use as herbicides.

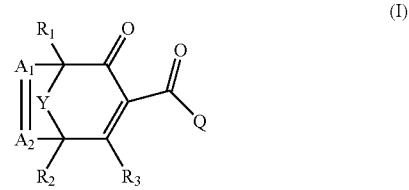

4 Claims, No Drawings

HERBICIDES

The present invention relates to novel, herbicidally active nicotinoyl derivatives, to processes for their preparation, to compositions comprising those compounds, and to their use in controlling weeds, especially in crops of useful plants, or in inhibiting plant growth.

Nicotinoyl derivatives having herbicidal action are described, for example, in WO 00/15615 and WO 01/94339.

There have now been found novel nicotinoyl derivatives having herbicidal and growth-inhibiting properties, the structures of which are distinguished by a double bond in the 6,7-position of the bicyclo[3.2.1]oct-3-en-2-one, bicyclo [3.2.1]nona-3-en-2-one, 8-oxa-bicyclo-[3.2.1]octa-3-en-2-one, 8-aza-bicyclo[3.2.1]octa-3-en-2-one, 8-thia-bicyclo [3.2.1]octa-3-en-2-one and bicyclo[3.2.1]octa-3-ene-2,8-dione group. Some of the compounds of that kind are covered by WO 00/15615 but none of those compounds is specifically disclosed. WO 01/66522 includes pyridine ketones having bicyclo[3.2.1]oct-3-en-2-one groups as intermediates in the preparation of aroyl ketones. There is no mention therein of those compounds having a herbicidal action.

The present invention accordingly relates to compounds of formula I

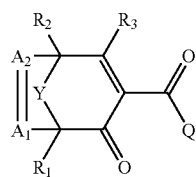

wherein

Y is oxygen, $NR_{4a}$, sulfur, sulfonyl, sulfinyl, $C(O)$, $C(=NR_{4b})$, $C(=CR_{6a}R_{6b})$ or a $C_1$-$C_4$alkylene or $C_2$-$C_4$alkenylene chain, which may be interrupted by oxygen, $NR_{5a}$, sulfur, sulfonyl, sulfinyl, $C(O)$ or $C(=NR_{5b})$ and/or mono- or poly-substituted by $R_6$;

$A_1$ is nitrogen or $CR_7$;

$A_2$ is nitrogen or $CR_8$;

$R_1$, $R_2$, $R_6$, $R_7$ and $R_8$ are each independently of the others hydrogen, hydroxy, mercapto, $NO_2$, cyano, halogen, formyl, oxyiminomethylene, $C_1$-$C_6$alkoxyiminomethylene, $C_1$-$C_6$alkyl, $C_1$-$C_6$haloalkyl, $C_2$-$C_6$alkenyl, $C_2$-$C_6$haloalkenyl, $C_2$-$C_6$alkynyl, $C_2$-$C_6$haloalkynyl, $C_1$-$C_6$alkoxy, $C_1$-$C_6$haloalkoxy, $C_3$-$C_6$alkenyloxy, $C_3$-$C_6$alkynyloxy, $C_3$-$C_6$oxacycloalkyl, $C_3$-$C_6$thiacycloalkyl, $C_3$-$C_6$dioxacycloalkyl, $C_3$-$C_6$dithiacycloalkyl, $C_3$-$C_6$oxathiacycloalkyl, $C_1$-$C_6$alkoxycarbonyl, $C_1$-$C_6$alkylcarbonyl, $C_1$-$C_6$alkoxycarbonyloxy, $C_1$-$C_6$alkylcarbonyloxy, $C_1$-$C_6$alkylthio, $C_1$-$C_6$alkylsulfonyl, $C_1$-$C_6$alkylsulfinyl, $NR_9R_{10}$, $C_3$-$C_6$cycloalkyl, tri($C_1$-$C_6$alkyl)silyl, di($C_1$-$C_6$alkyl)phenylsilyl, tri($C_1$-$C_6$alkyl)silyloxy, di($C_1$-$C_6$alkyl)phenylsilyloxy or $Ar_1$;

or $R_1$, $R_2$, $R_6$, $R_7$, $R_8$ are each independently of the others a $C_1$-$C_6$alkyl, $C_2$-$C_6$alkenyl, $C_2$-$C_6$alkynyl or $C_3$-$C_6$cycloalkyl group, which may be interrupted by oxygen, sulfur, sulfonyl, sulfinyl, $-NR_{11}-$ or $-C(O)-$ and/or mono-, di- or tri-substituted by hydroxy, mercapto, $NO_2$, cyano, halogen, formyl, $C_1$-$C_6$alkoxy, $C_3$-$C_6$alkenyloxy, $C_3$-$C_6$alkynyloxy, $C_1$-$C_6$haloalkoxy, $C_1$-$C_2$alkoxy-$C_1$-$C_2$alkoxy, $C_1$-$C_4$alkylcarbonyloxy, $C_1$-$C_4$alkoxycarbonyloxy, $C_1$-$C_4$alkoxy-carbonyl, $C_1$-$C_4$alkylcarbonyl, $C_1$-$C_6$alkylthio, $C_1$-$C_6$alkylsulfinyl, $C_1$-$C_6$alkylsulfonyl, $NR_{12}R_{13}$, $C_1$-$C_6$alkyl, $C_2$-$C_6$alkenyl, $C_2$-$C_6$alkynyl, $C_3$-$C_6$cycloalkyl, tri($C_1$-$C_6$alkyl)silyl, tri($C_1$-$C_6$alkyl)-silyloxy or $Ar_2$;

or two substituents $R_6$ at the same carbon atom together form a $-CH_2O-$ or a $C_2$-$C_5$alkylene chain, which may be interrupted once or twice by oxygen, sulfur, sulfinyl or sulfonyl and/or mono- or poly-substituted by $R_{6c}$, with the proviso that two hetero atoms may not be located next to one another;

or two substituents $R_6$ at different carbon atoms together form an oxygen bridge or a $C_1$-$C_4$alkylene chain, which may in turn be substituted by $R_{6c}$;

or $R_7$ and $R_8$ together form a $-CH_2CH=CH-$, $-OCH=CH-$ or $-CH=CH-CH=CH-$ bridge or a $C_3$-$C_4$alkylene chain, which may be interrupted by oxygen or $-S(O)_{n1}-$ and/or mono- or poly-substituted by $R_{6d}$;

$R_3$ is hydroxy, halogen, mercapto, $C_1$-$C_8$alkylthio, $C_1$-$C_8$alkylsulfinyl, $C_1$-$C_8$alkylsulfonyl, $C_1$-$C_8$haloalkylthio, $C_1$-$C_8$haloalkylsulfinyl, $C_1$-$C_8$haloalkylsulfonyl, $C_1$-$C_4$alkoxy-$C_1$-$C_4$alkylthio, $C_1$-$C_4$alkoxy-$C_1$-$C_4$alkylsulfinyl, $C_1$-$C_4$alkoxy-$C_1$-$C_4$alkylsulfonyl, $C_3$-$C_8$alkenylthio, $C_3$-$C_8$-alkynylthio, $C_1$-$C_4$alkylthio-$C_1$-$C_4$alkylthio, $C_3$-$C_4$alkenylthio-$C_1$-$C_4$alkylthio, $C_1$-$C_4$alkoxycarbonyl-$C_1$-$C_4$alkylthio, $C_1$-$C_4$alkoxycarbonyl-$C_1$-$C_4$alkylsulfinyl, $C_1$-$C_4$alkoxycarbonyl-$C_1$-$C_4$alkylsulfonyl, $C_3$-$C_8$cycloalkylthio, $C_3$-$C_8$cycloalkylsulfinyl, $C_3$-$C_8$cycloalkylsulfonyl, phenyl-$C_1$-$C_4$alkylthio, phenyl-$C_1$-$C_4$alkylsulfinyl, phenyl-$C_1$-$C_4$alkylsulfonyl, $S(O)n_1-$$Ar_3$, phenylthio, phenylsulfinyl, phenylsulfonyl, it being possible for the phenyl-containing groups to be substituted by one or more $C_1$-$C_3$alkyl, $C_1$-$C_3$haloalkyl, $C_1$-$C_3$alkoxy, $C_1$-$C_3$haloalkoxy, $C_1$-$C_4$alkoxycarbonyl, halogen, cyano, hydroxy or nitro groups;

or $R_3$ is $O^-M^+$, wherein $M^+$ is an alkali metal cation or an ammonium cation;

Q is a radical

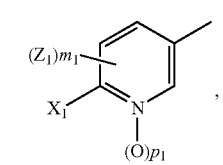

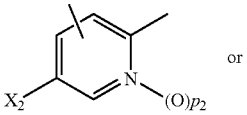

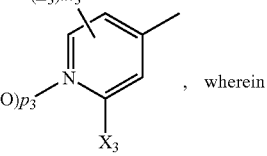

, wherein $p_1$, $p_2$ and $p_3$ are 0 or 1;

$m_1$, $m_2$ and $m_3$ are 1, 2 or 3;

$X_1$, $X_2$ and $X_3$ are hydroxy, halogen, $C_1$-$C_6$alkyl, $C_1$-$C_6$haloalkyl, $C_2$-$C_6$alkenyl, $C_2$-$C_6$haloalkenyl, C$_2$-C$_6$alkynyl, C$_2$-C$_6$haloalkynyl, C$_1$-C$_6$alkoxy, C$_1$-C$_6$haloalkoxy, C$_1$-C$_6$alkylthio, C$_1$-C$_6$alkylsulfinyl, C$_1$-C$_6$alkylsulfonyl, C$_1$-C$_6$haloalkylthio, C$_1$-C$_6$haloalkylsulfinyl or C$_1$-C$_6$haloalkylsulfonyl;

Z$_1$, Z$_2$ and Z$_3$ are C$_1$-C$_6$alkyl which is substituted by the following substituents: C$_3$-C$_4$cycloalkyl or C$_3$-C$_4$cycloalkyl substituted by halogen, C$_1$-C$_6$alkyl, C$_1$-C$_3$alkoxy or C$_1$-C$_3$alkoxy-C$_1$-C$_3$alkyl; oxiranyl or oxiranyl substituted by C$_1$-C$_6$alkyl or C$_1$-C$_3$alkoxy-C$_1$-C$_3$alkyl; 3-oxetanyl or 3-oxetanyl substituted by C$_1$-C$_6$alkyl, C$_1$-C$_3$alkoxy or C$_1$-C$_3$alkoxy-C$_1$-C$_3$alkyl; 3-oxetanyloxy or 3-oxetanyloxy substituted by C$_1$-C$_6$alkyl, C$_1$-C$_3$alkoxy or C$_1$-C$_3$alkoxy-C$_1$-C$_3$alkyl; C$_3$-C$_6$cycloalkyloxy or C$_3$-C$_4$cycloalkyloxy substituted by halogen, C$_1$-C$_6$alkyl, C$_1$-C$_3$alkoxy or C$_1$-C$_3$alkoxy-C$_1$-C$_3$alkyl; C$_1$-C$_6$haloalkoxy; C$_1$-C$_6$alkylsulfonyloxy; C$_1$-C$_6$haloalkylsulfonyloxy; phenylsulfonyloxy; benzylsulfonyloxy; benzoyloxy; phenoxy; phenylthio; phenylsulfinyl; phenylsulfonyl; Ar$_{10}$; OAr$_{12}$; tri(C$_1$-C$_6$alkyl)silyl or tri(C$_1$-C$_6$alkyl)silyloxy, it being possible for the phenyl-containing groups to be mono- or poly-substituted by C$_1$-C$_3$alkyl, C$_1$-C$_3$haloalkyl, C$_1$-C$_3$alkoxy, C$_1$-C$_3$haloalkoxy, halogen, cyano, hydroxy or nitro;

or Z$_1$, Z$_2$ and Z$_3$ are 3-oxetanyl; 3-oxetanyl substituted by C$_1$-C$_3$alkoxy, C$_1$-C$_3$alkoxy-C$_1$-C$_3$-alkyl or C$_1$-C$_6$alkyl; C$_3$-C$_6$cycloalkyl substituted by halogen, C$_1$-C$_3$alkyl or C$_1$-C$_3$alkoxy-C$_1$-C$_3$-alkyl; tri(C$_1$-C$_6$alkyl)silyl; tri(C$_1$-C$_6$alkyl)silyloxy or CH=P(phenyl)$_3$;

or Z$_1$, Z$_2$ and Z$_3$ are a C$_1$-C$_6$alkyl, C$_2$-C$_6$alkenyl or C$_2$-C$_6$alkynyl group, which is interrupted by oxygen, —O(CO)—, —(CO)O—, —O(CO)O—, —N(R$_{14}$)O—, —ONR$_{15}$—, sulfur, sulfinyl, sulfonyl, —SO$_2$NR$_{16}$—, —NR$_{17}$SO$_2$— or —NR$_{18}$— and is mono- or poly-substituted by L$_1$; it also being possible for L$_1$ to be bonded at the terminal carbon atom of the C$_1$-C$_6$alkyl, C$_2$-C$_6$alkenyl or C$_2$-C$_6$alkynyl group;

or Z$_1$, Z$_2$ and Z$_3$ are hydrogen, hydroxy, mercapto, NO$_2$, cyano, halogen, formyl, C$_1$-C$_6$alkyl, C$_1$-C$_6$haloalkyl, C$_2$-C$_6$alkenyl, C$_2$-C$_6$haloalkenyl, C$_2$-C$_6$alkynyl, C$_2$-C$_6$haloalkynyl, C$_1$-C$_6$alkoxy, C$_1$-C$_6$haloalkoxy, C$_1$-C$_6$alkoxycarbonyl, C$_1$-C$_6$alkylcarbonyl, C$_1$-C$_6$alkylthio, C$_1$-C$_6$alkylsulfonyl, C$_1$-C$_6$alkylsulfinyl, NR$_{22}$R$_{23}$, phenyl which may be mono- or poly-substituted by C$_1$-C$_3$alkyl, C$_1$-C$_3$haloalkyl, C$_1$-C$_3$alkoxy, C$_1$-C$_3$haloalkoxy, halogen, cyano, hydroxy or nitro, C$_3$-C$_6$cycloalkyl, C$_5$-C$_6$cycloalkyl substituted by C$_1$-C$_3$alkoxy, C$_1$-C$_3$alkoxy-C$_1$-C$_3$alkyl or C$_1$-C$_6$alkyl, or Ar$_5$, O—Ar$_6$, N(R$_{24}$)Ar$_7$ or S(O)n$_6$Ar$_8$;

L$_1$ is hydrogen, halogen, hydroxy, amino, formyl, nitro, cyano, mercapto, carbamoyl, P(O)(OC$_1$-C$_6$alkyl)$_2$, C$_1$-C$_6$alkoxy, C$_1$-C$_6$haloalkoxy, C$_1$-C$_6$alkoxycarbonyl, C$_2$-C$_6$alkenyl, C$_2$-C$_6$haloalkenyl, C$_2$-C$_6$alkynyl, C$_2$-C$_6$haloalkynyl, C$_3$-C$_6$cycloalkyl, halo-substituted C$_3$-C$_6$cycloalkyl, C$_3$-C$_6$alkenyloxy, C$_3$-C$_6$alkynyloxy, C$_3$-C$_6$haloalkenyloxy, cyano-C$_1$-C$_6$alkoxy, C$_1$-C$_6$alkoxy-C$_1$-C$_6$alkoxy, C$_1$-C$_6$alkylthio-C$_1$-C$_6$alkoxy, C$_1$-C$_6$alkylsulfinyl-C$_1$-C$_6$alkoxy, C$_1$-C$_6$alkylsulfonyl-C$_1$-C$_6$alkoxy, C$_1$-C$_6$alkoxycarbonyl-C$_1$-C$_6$alkoxy, C$_1$-C$_6$alkylcarbonyloxy-C$_1$-C$_6$alkylcarbonyl, C$_1$-C$_6$alkylthio, C$_1$-C$_6$alkylsulfinyl, C$_1$-C$_6$alkylsulfonyl, C$_1$-C$_6$haloalkylthio, C$_1$-C$_6$haloalkylsulfinyl, C$_1$-C$_6$haloalkylsulfonyl or oxiranyl, which may in turn be substituted by C$_1$-C$_6$alkyl, C$_1$-C$_3$alkoxy or C$_1$-C$_3$alkoxy-C$_1$-C$_3$alkyl, or (3-oxetanyl)-oxy, which may in turn be substituted by C$_1$-C$_6$alkyl, C$_1$-C$_3$alkoxy or C$_1$-C$_3$alkoxy-C$_1$-C$_3$alkyl, or benzoyloxy, benzyloxy, benzylthio, benzylsulfinyl, benzylsulfonyl, C$_1$-C$_6$alkylamino, di(C$_1$-C$_6$alkyl) amino, R$_{19}$S(O)$_2$O—, R$_{20}$N(R$_{21}$)SO$_2$—, rhodano, phenyl, phenoxy, phenylthio, phenylsulfinyl, phenylsulfonyl, Ar$_4$ or OAr$_{11}$, it being possible for the phenyl-containing groups in turn to be substituted by one or more C$_1$-C$_3$alkyl, C$_1$-C$_3$haloalkyl, C$_1$-C$_3$alkoxy, C$_1$-C$_3$haloalkoxy, halogen, cyano, hydroxy or nitro groups;

R$_{4a}$ and R$_{5a}$ are each independently of the other hydrogen, C$_1$-C$_6$alkyl, C$_1$-C$_6$haloalkyl, cyano, formyl, C$_1$-C$_6$alkylcarbonyl, C$_1$-C$_6$alkoxycarbonyl, carbamoyl, C$_1$-C$_6$alkylaminocarbonyl, di(C$_1$-C$_6$alkylamino)carbonyl, di(C$_1$-C$_6$alkylamino)sulfonyl, C$_3$-C$_6$cycloalkylcarbonyl, C$_1$-C$_6$-alkylsulfonyl, phenylcarbonyl, phenylaminocarbonyl or phenylsulfonyl, it being possible for the phenyl groups to be mono- or poly-substituted by C$_1$-C$_6$alkyl, C$_1$-C$_6$haloalkyl, C$_1$-C$_6$-alkoxy, C$_1$-C$_6$haloalkoxy, halogen, cyano, hydroxy or nitro;

R$_{4b}$ and R$_{5b}$ are each independently of the other hydroxy, C$_1$-C$_6$alkoxy, C$_3$-C$_6$alkenyloxy, C$_3$-C$_6$alkynyloxy or benzyloxy, it being possible for the benzyl group to be mono- or poly-substituted by C$_1$-C$_6$alkyl, C$_1$-C$_6$haloalkyl, C$_1$-C$_6$alkoxy, C$_1$-C$_6$haloalkoxy, halogen, cyano, hydroxy or nitro;

R$_9$, R$_{11}$, R$_{13}$, R$_{16}$, R$_{17}$, R$_{18}$, R$_{20}$, R$_{23}$ and R$_{24}$ are each independently of the others hydrogen, C$_1$-C$_6$alkyl, Ar$_9$, C$_1$-C$_6$haloalkyl, C$_1$-C$_6$alkylcarbonyl, C$_1$-C$_6$alkoxycarbonyl, C$_1$-C$_6$alkylsulfonyl, phenyl, it being possible for the phenyl group in turn to be mono- or poly-substituted by C$_1$-C$_6$alkyl, C$_1$-C$_6$haloalkyl, C$_1$-C$_6$alkoxy, C$_1$-C$_6$haloalkoxy, halogen, cyano, hydroxy or nitro;

R$_{6a}$ is hydrogen, C$_1$-C$_6$alkyl or C$_1$-C$_6$alkylcarbonyl; or together with R$_{6b}$ is a C$_2$-C$_5$alkylene chain;

R$_{6b}$, R$_{6d}$, R$_{10}$, R$_{12}$ and R$_{22}$ are each independently of the others hydrogen or C$_1$-C$_6$alkyl;

R$_{6c}$, R$_{14}$, R$_{15}$, R$_{19}$ and R$_{21}$ are each independently of the others C$_1$-C$_6$alkyl or C$_1$-C$_6$haloalkyl;

Ar$_1$, Ar$_2$, Ar$_3$, Ar$_4$, Ar$_5$, Ar$_6$, Ar$_7$, Ar$_8$, Ar$_9$, Ar$_{10}$, Ar$_{11}$ and Ar$_{12}$ are each independently of the others a five- to ten-membered, monocyclic or fused bicyclic ring system, which may be aromatic, partially saturated or fully saturated and may contain from 1 to 4 hetero atoms selected from nitrogen, oxygen, sulfur, C(O) and C(=NR$_{25}$), and each ring system may contain not more than two oxygen atoms, not more than two sulfur atoms, not more than two C(O) groups and not more than one C(=NR$_{25}$) group, and each ring system may itself be mono- or poly-substituted by C$_1$-C$_6$alkyl, C$_1$-C$_6$haloalkyl, C$_2$-C$_6$alkenyl, C$_2$-C$_6$haloalkenyl, C$_2$-C$_6$alkynyl, C$_2$-C$_6$haloalkynyl, C$_1$-C$_6$alkoxy, C$_1$-C$_6$haloalkoxy, C$_3$-C$_6$alkenyloxy, C$_3$-C$_6$alkynyloxy, mercapto, amino, hydroxy, C$_1$-C$_6$alkylthio, C$_1$-C$_6$haloalkylthio, C$_3$-C$_6$alkenylthio, C$_3$-C$_6$-haloalkenylthio, C$_3$-C$_6$alkynylthio, C$_1$-C$_3$alkoxy-C$_1$-C$_3$alkylthio, C$_1$-C$_4$alkylcarbonyl-C$_1$-C$_3$alkylthio, C$_1$-C$_4$alkoxycarbonyl-C$_1$-C$_3$alkylthio, cyano-C$_1$-C$_3$alkylthio, C$_1$-C$_6$alkylsulfinyl, C$_1$-C$_6$haloalkylsulfinyl, C$_1$-C$_6$alkylsulfonyl, C$_1$-C$_6$haloalkylsulfonyl, aminosulfonyl, C$_1$-C$_2$alkylaminosulfonyl, N,N-di(C$_1$-C$_2$alkyl)aminosulfonyl, di(C$_1$-C$_4$alkyl)amino, halogen, cyano, nitro or phenyl, it being possible for the phenyl group in turn to be substituted by hydroxy, C$_1$-C$_6$-alkylthio, C$_1$-C$_6$haloalkylthio, C$_3$-C$_6$alkenylthio, C$_3$-C$_6$haloalkenylthio, C$_3$-C$_6$alkynylthio, C$_1$-C$_3$alkoxy-C$_1$-C$_3$alkylthio, C$_1$-C$_4$alkylcarbonyl-C$_1$-C$_3$alkylthio, C$_1$-C$_4$alkoxycarbonyl-C$_1$-C$_3$-alkylthio, cyano-C$_1$-C$_3$alkylthio, C$_1$-C$_6$alkylsulfinyl, C$_1$-C$_6$haloalkylsulfinyl, C$_1$-C$_6$alkylsulfonyl, C$_1$-C$_6$haloalkylsulfonyl, aminosulfonyl, C$_1$-C$_2$alkylaminosulfonyl, N,N-di(C$_1$-C$_2$alkyl)aminosulfonyl, di($C_1$-$C_4$alkyl)amino, halogen, cyano or nitro, and the substituents at the nitrogen atom in the heterocyclic ring being other than halogen, and two oxygen atoms not being located next to one another;

$R_{25}$ is hydrogen, hydroxy, $C_1$-$C_6$alkyl, $C_1$-$C_6$haloalkyl, $C_1$-$C_6$alkoxy, $C_1$-$C_6$alkylcarbonyl, $C_1$-$C_6$alkoxycarbonyl or $C_1$-$C_6$alkylsulfonyl; and $n_1$ is 0, 1 or 2; and $n_6$ is 0, 1 or 2;

and agronomically acceptable salts/isomers/enantiomers/tautomers of those compounds.

The alkyl groups appearing in the substituent definitions may be straight-chain or branched and are, for example, methyl, ethyl, n-propyl, isopropyl, n-butyl, sec-butyl, isobutyl, tert-butyl, pentyl, hexyl, heptyl and octyl and the branched isomers thereof. Alkoxy, alkenyl and alkynyl radicals are derived from the mentioned alkyl radicals. The alkenyl and alkynyl groups may be mono- or poly-unsaturated. $C_1$-$C_4$alkylene and $C_2$-$C_4$alkenylene chains may likewise be straight-chain or branched.

Halogen is generally fluorine, chlorine, bromine or iodine, preferably fluorine or chlorine. The same is true of halogen in conjunction with other meanings, such as haloalkyl or halophenyl.

Haloalkyl groups preferably have a chain length of from 1 to 6 carbon atoms. Haloalkyl is, for example, fluoromethyl, difluoromethyl, trifluoromethyl, chloromethyl, dichloromethyl, trichloromethyl, 2,2,2-trifluoroethyl, 2-fluoroethyl, 2-chloroethyl, pentafluoroethyl, 1,1-difluoro-2,2,2-trichloroethyl, 2,2,3,3-tetrafluoroethyl or 2,2,2-trichloroethyl; preferably trichloromethyl, difluorochloromethyl, difluoromethyl, trifluoromethyl or dichlorofluoromethyl.

In the context of the present invention, the term "mono- or poly-substituted" is generally to be understood as meaning mono- to penta-substituted, especially mono- to tri-substituted.

As haloalkenyl there come into consideration alkenyl groups mono- or poly-substituted by halogen, halogen being fluorine, chlorine, bromine or iodine, and especially fluorine or chlorine, for example 2,2-difluoro-1-methylvinyl, 3-fluoropropenyl, 3-chloropropenyl, 3-bromopropenyl, 2,3,3-trifluoropropenyl, 2,3,3-trichloropropenyl and 4,4,4-trifluorobut-2-en-1-yl. Of the $C_3$-$C_8$alkenyl groups mono-, di- or tri-substituted by halogen preference is given to those having a chain length of from 3 to 5 carbon atoms.

As haloalkynyl there come into consideration, for example, alkynyl groups mono- or poly-substituted by halogen, halogen being bromine, iodine and especially fluorine or chlorine, for example 3-fluoropropynyl, 3-chloropropynyl, 3-bromopropynyl, 3,3,3-trifluoropropynyl and 4,4,4-trifluoro-but-2-yn-1-yl. Of the alkynyl groups mono- or poly-substituted by halogen preference is given to those having a chain length of from 3 to 5 carbon atoms.

$Ar_1, Ar_2, Ar_3, Ar_4, Ar_5, Ar_6, Ar_7, Ar_8, Ar_9, Ar_{10}, Ar_{11}$ and $Ar_{12}$ are, for example, phenyl, naphthyl or the following heterocyclic groups: (1-methyl-1H-pyrazol-3-yl)-; (1-ethyl-1H-pyrazol-3-yl)-; (1-propyl-1H-pyrazol-3-yl)-; (1H-pyrazol-3-yl)-; (1,5-dimethyl-1H-pyrazol-3-yl)-; (4-chloro-1-methyl-1H-pyrazol-3-yl)-; (1H-pyrazol-1-yl)-; (3-methyl-1H-pyrazol-1-yl)-; (3,5-dimethyl-1H-pyrazol-1-yl)-; (3-isoxazolyl)-; (5-methyl-3-isoxazolyl)-; (3-methyl-5-isoxazolyl)-; (5-isoxazolyl)-; (1H-pyrrol-2-yl)-; (1-methyl-1H-pyrrol-2-yl)-; (1H-pyrrol-1-yl)-; (1-methyl-1H-pyrrol-3-yl)-; (2-furanyl)-; (5-methyl-2-furanyl)-; (3-furanyl)-; (5-methyl-2-thienyl)-; (2-thienyl)-; (3-thienyl)-; (1-methyl-1H-imidazol-2-yl)-; (1H-imidazol-2-yl)-; (1-methyl-1H-imidazol-4-yl)-; (1-methyl-1H-imidazol-5-yl)-; (4-methyl-2-oxazolyl)-; (5-methyl-2oxazolyl)-; (2-oxazolyl)-; (2-methyl-5-oxazolyl)-; (2-methyl-4-oxazolyl)-; (4-methyl-2-thiazolyl)-; (5-methyl-2-thiazolyl)-; (2-thiazolyl)-; (2-methyl-5-thiazolyl)-; (2-methyl-4-thiazolyl)-; (3-methyl-4-isothiazolyl)-; (3-methyl-5-isothiazolyl)-; (5-methyl-3-isothiazolyl)-; (1-methyl-1H-1,2,3-triazol-4-yl)-; (2-methyl-2H-1,2,3-triazol-4-yl)-; (4-methyl-2H-1,2,3-triazol-2-yl)-; (1-methyl-1H-1,2,4-triazol-3-yl)-; (1,5-dimethyl-1H-1,2,4-triazol-3-yl)-; (3-methyl-1H-1,2,4-triazol-1-yl)-; (5-methyl-1H-1,2,4-triazol-1-yl)-; (4,5-dimethyl-4H-1,2,4-triazol-3-yl)-; (4-methyl-4H-1,2,4-triazol-3-yl)-; (4H-1,2,4-triazol-4-yl)-; (5-methyl-1,2,3-oxadiazol-4-yl)-; (1,2,3-oxadiazol-4-yl)-; (3-methyl-1,2,4-oxadiazol-5-yl)-; (5-methyl-1,2,4-oxadiazol-3-yl)-; (4-methyl-3-furazanyl)-; (3-furazanyl)-; (5-methyl-1,2,4-oxadiazol-2-yl)-; (5-methyl-1,2,3-thiadiazol-4-yl)-; (1,2,3-thiadiazol-4-yl)-; (3-methyl-1,2,4-thiadiazol-5-yl)-; (5-methyl-1,2,4-thiadiazol-3-yl)-; (4-methyl-1,2,5-thiadiazol-3-yl)-; (5-methyl-1,3,4-thiadiazol-2-yl)-; (1-methyl-1H-tetrazol-5-yl)-; (1H-tetrazol-5-yl)-; (5-methyl-1H-tetrazol-1-yl)-; (2-methyl-2H-tetrazol-5-yl)-; (2-ethyl-2H-tetrazol-5-yl)-; (5-methyl-2H-tetrazol-2-yl)-; (2H-tetrazol-2-yl)-; (2-pyridyl)-; (6-methyl-2-pyridyl)-; (4-pyridyl)-; (3-pyridyl)-; (6-methyl-3-pyridazinyl)-; (5-methyl-3-pyridazinyl)-; (3-pyridazinyl)-; (4,6-dimethyl-2-pyrimidinyl)-; (4-methyl-2-pyrimidinyl)-; (2-pyrimidinyl)-; (2-methyl-4-pyrimidinyl)-; (2-chloro-4-pyrimidinyl)-; (2,6-dimethyl-4-pyrimidinyl)-; (4-pyrimidinyl)-; (2-methyl-5-pyrimidinyl)-; (6-methyl-2-pyrazinyl)-; (2-pyrazinyl)-; (4,6-dimethyl-1,3,5-triazin-2-yl)-; (4,6-dichloro-1,3,5-triazin-2-yl)-; (1,3,5-triazin-2-yl)-; (4-methyl-1,3,5-triazin-2-yl)-; (3-methyl-1,2,4-triazin-5-yl)-; (3-methyl-1,2,4-triazin-6-yl)-;

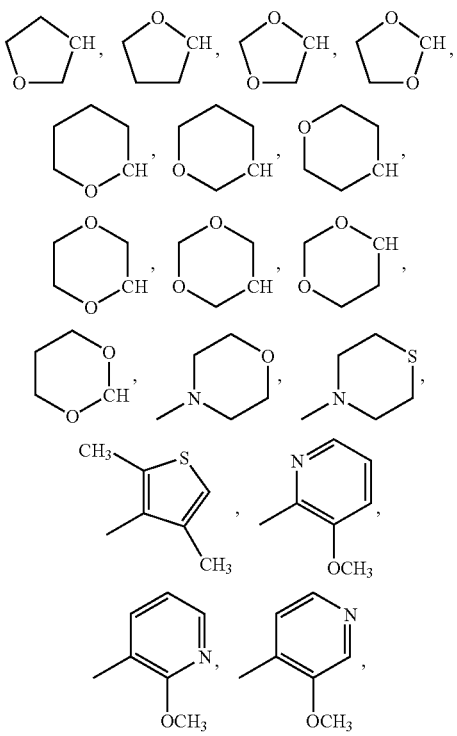

and $Ar_{10}$ may also be, for example, a carbonyl-containing heterocyclic group

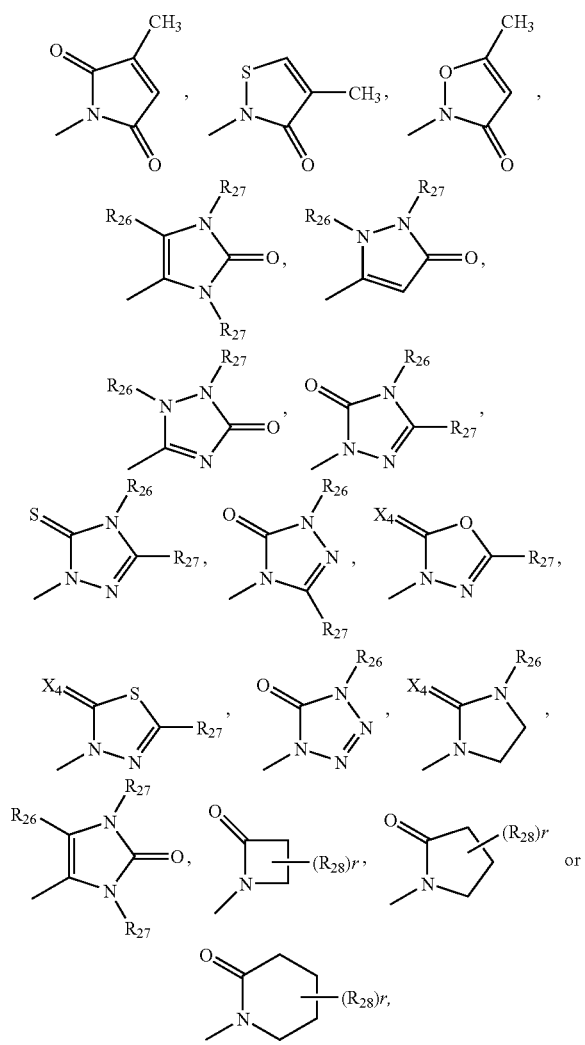

wherein each $R_{26}$ is methyl, each $R_{27}$ and each $R_{28}$ are independently hydrogen, $C_1$-$C_3$alkyl, $C_1$-$C_3$alkoxy, $C_1$-$C_3$alkylthio or trifluoromethyl, $X_4$ is oxygen or sulfur and r=1, 2, 3 or 4.

Where no free valency is indicated in those definitions of $Ar_1$, $Ar_2$, $Ar_3$, $Ar_4$, $Ar_5$, $Ar_6$, $Ar_7$, $Ar_8$, $A_9$, $Ar_{10}$, $Ar_{11}$ and $Ar_{12}$, for example as in

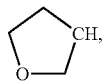

the linkage site is located at the carbon atom labelled "CH" or in a case such as, for example,

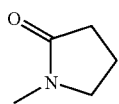

at the bonding site indicated at the bottom left.

The alkali metal cation $M^+$ (for example in the meaning of $O^-M^+$ in $R_3$) denotes in the context of the present invention preferably the sodium cation or the potassium cation.

Alkoxy groups preferably have a chain length of from 1 to 6 carbon atoms. Alkoxy is, for example, methoxy, ethoxy, propoxy, isopropoxy, n-butoxy, isobutoxy, sec-butoxy and tert-butoxy and the isomers of pentyloxy and hexyloxy; preferably methoxy and ethoxy. Alkylcarbonyl is preferably acetyl, propionyl or pivaloyl. Alkoxycarbonyl is, for example, methoxycarbonyl, ethoxycarbonyl, propoxycarbonyl, isopropoxycarbonyl, n-butoxycarbonyl, isobutoxycarbonyl, sec-butoxycarbonyl or tert-butoxycarbonyl; preferably methoxycarbonyl or ethoxycarbonyl. Haloalkoxy groups preferably have a chain length of from 1 to 6 carbon atoms. Haloalkoxy is e.g. fluoromethoxy, difluoromethoxy, trifluoromethoxy, 2,2,2-trifluoroethoxy, 1,1,2,2-tetrafluoroethoxy, 2-fluoroethoxy, 2-chloroethoxy, 2,2-difluoroethoxy and 2,2,2-trichloroethoxy; preferably difluoromethoxy, 2-chloroethoxy and trifluoromethoxy.

Alkylthio groups preferably have a chain length of from 1 to 8 carbon atoms. Alkylthio is, for example, methylthio, ethylthio, propylthio, isopropylthio, n-butylthio, isobutylthio, sec-butylthio or tert-butylthio, preferably methylthio and ethylthio. Alkylsulfinyl is, for example, methylsulfinyl, ethylsulfinyl, propylsulfinyl, isopropylsulfinyl, n-butylsulfinyl, isobutylsulfinyl, sec-butylsulfinyl, tert-butylsulfinyl; preferably methylsulfinyl and ethylsulfinyl. Alkylsulfonyl is, for example, methylsulfonyl, ethylsulfonyl, propylsulfonyl, isopropylsulfonyl, n-butylsulfonyl, isobutylsulfonyl, sec-butylsulfonyl or tert-butylsulfonyl; preferably methylsulfonyl or ethylsulfonyl.

Alkylamino is, for example, methylamino, ethylamino, n-propylamino, isopropylamino or the isomers of butylamine. Dialkylamino is, for example, dimethylamino, methylethylamino, diethylamino, n-propylmethylamino, di-butylamino and di-isopropylamino. Preference is given to alkylamino and dialkylamino groups—including as a component of (N-alkyl)sulfonylamino and N-(alkylamino)sulfonyl groups, such as (N,N-dimethyl)sulfonylamino and N,N-(dimethylamino)sulfonyl—each having a chain length of from 1 to 4 carbon atoms.

Alkoxyalkoxy groups preferably have a chain length of from 1 to 8 carbon atoms. Examples of alkoxyalkoxy are: methoxymethoxy, methoxyethoxy, methoxypropoxy, ethoxymethoxy, ethoxyethoxy, propoxymethoxy and butoxybutoxy. Alkoxyalkyl groups have a chain length of preferably from 1 to 6 carbon atoms. Alkoxyalkyl is, for example, methoxymethyl, methoxyethyl, ethoxymethyl, ethoxyethyl, n-propoxymethyl, n-propoxyethyl, isopropoxymethyl or isopropoxyethyl.

Alkylthioalkyl groups preferably have from 1 to 8 carbon atoms. Alkylthioalkyl is, for example, methylthiomethyl, methylthioethyl, ethylthiomethyl, ethylthioethyl, n-propylthiomethyl, n-propylthioethyl, isopropylthiomethyl, isopropylthioethyl, butylthiomethyl, butylthioethyl or butylthiobutyl.

The cycloalkyl groups having up to 8 carbon atoms preferably have from 3 to 6 ring carbon atoms, for example cyclopropyl, cyclobutyl, cyclopentyl, cyclohexyl. A cycloalkyl group having up to 8 carbon atoms also includes a $C_3$-$C_6$alkyl group bonded by way of a methylene or ethylene bridge, for example cyclopropylmethyl, cyclobutylmethyl and cyclopentylmethyl. Cycloalkyl groups, as well as, for example, the oxygen-containing oxiranyl, oxiranylmethyl, 3-oxetanyl, 2- and 3-tetrahydrofuranyl, 2-(2- and 3-tetrahydrofuranyl)methyl, 2-, 3- and 4-tetrahydropyranyl, 2-(2-tetrahydropyranyl)methyl, 1,3-dioxolanyl, 2-(1,3-dioxolanyl)methyl, 4-(1,3-dioxolanyl)methyl, 1,3-dioxanyl, 1,4-dioxanyl and similar saturated groups—especially as a component of $Ar_5$ in $L_1$—can also be mono- or poly-substituted by $C_1$-$C_3$alkyl, preferably mono- to tetra-substituted by methyl.

Phenyl, including as a component of a substituent such as phenoxy, benzyl, benzyloxy, benzoyl, phenylthio, phenylalkyl, phenoxyalkyl, may be in substituted form. The substituents may in that case be in the ortho-, meta- and/or para-position(s). Preferred substituent positions are the ortho- and para-positions relative to the ring linkage site. The phenyl groups are preferably unsubstituted or mono- or di-substituted, especially unsubstituted or mono-substituted.

$Z_1$, $Z_2$ and $Z_3$ as a $C_1$-$C_6$alkyl group which is interrupted by oxygen, —O(CO)—, —(CO)O—, —O(CO)O—, —N($R_{14}$)O—, —ONR$_{15}$—, sulfur, sulfinyl, sulfonyl, —SO$_2$NR$_{16}$—, —NR$_{17}$SO$_2$— or —NR$_{18}$— and may be mono- or poly-substituted by a group $L_1$ when that $C_1$-$C_6$alkyl group is interrupted by oxygen, —O(CO)O—, sulfur, sulfinyl or sulfonyl, is to be understood as meaning, for example, a bidentate bridging member —CH$_2$OCH$_2$—, —CH$_2$CH$_2$OCH$_2$—, —CH$_2$OCH$_2$CH$_2$—, —CH$_2$OCH$_2$CH$_2$CH$_2$—, —CH$_2$OC(O)CH$_2$—, —CH$_2$(CO)OCH$_2$—, —CH$_2$O(CO)OCH$_2$—, —CH$_2$SCH$_2$—, —CH$_2$S(O)CH$_2$—, —CH$_2$SO$_2$CH$_2$—, —CH$_2$SCH$_2$CH$_2$—, —CH$_2$S(O)CH$_2$CH$_2$—, —CH$_2$SO$_2$CH$_2$CH$_2$—, —CH$_2$N(CH$_3$)SO$_2$CH$_2$—, —CH$_2$N(SO$_2$CH$_3$)CH$_2$—, —CH$_2$N(C(O)CH$_3$)CH$_2$—, —CH$_2$N(COOCH$_2$CH$_3$)CH$_2$— or —CH$_2$N(COOCH$_3$)CH$_2$—, the left-hand bonding site being bonded to the pyridine moiety and the right-hand side to the substituent $L_1$. And $Z_1$, $Z_2$ and $Z_3$ as a $C_2$-$C_6$alkenyl or $C_2$-$C_6$alkynyl group which is interrupted by oxygen, —O(CO)—, —(CO)O—, —O(CO)O—, —N($R_{14}$)O—, —ONR$_{15}$—, sulfur, sulfinyl, sulfonyl, —SO$_2$NR$_{16}$—, —NR$_{17}$SO$_2$— or —NR$_{18}$— and may be mono- or poly-substituted by a group $L_1$ is to be understood as meaning, for example, a bidentate bridging member —CH=CHCH$_2$OCH$_2$— or —C≡CCH$_2$OCH$_2$—. Such an unsubstituted or $L_1$-substituted $C_1$-$C_6$alkyl, $C_2$-$C_6$alkenyl or $C_2$-$C_6$alkynyl group $Z_1$, $Z_2$ or $Z_3$ which is interrupted by oxygen, —O(CO)—, —(CO)O—, —O(CO)O—, —N($R_{14}$)O—, —ONR$_{15}$—, sulfur, sulfinyl, sulfonyl, —SO$_2$NR$_{16}$—, —NR$_{17}$OS$_2$— or —NR$_{18}$— can be either straight-chain or branched, for example as in the case of the bidentate bridging members —CH(CH$_3$)OCH$_2$— and —CH$_2$OCH(CH$_3$)CH$_2$—.

The compounds of formula I may occur in various tautomeric forms such as, for example, when $R_3$ is hydroxy and Q is $Q_1$, in formulae I', I", I'" and I"", preference being given to formulae I' and I".

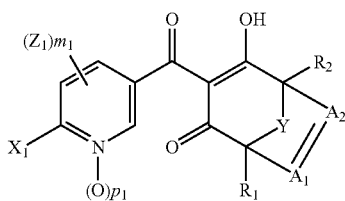

I'

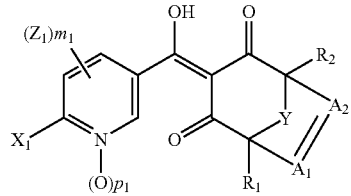

I"

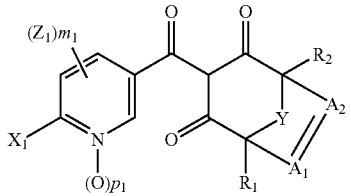

I'"

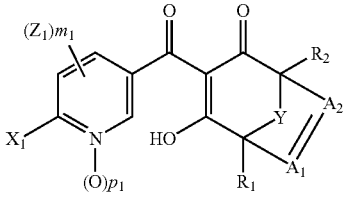

I""

Since compounds of formula I may also contain asymmetric carbon atoms, for example in the case of $R_1$, $R_2$, $A_1$, $A_2$ and Y, their substituents $R_6$, $R_7$ and $R_8$, and also in the case of carbon atoms carrying $X_1$, $X_2$, $X_3$, $Z_1$, $Z_2$ and $Z_3$, and accordingly in any sulfoxides, all the stereoisomers and all chiral <R> and <S> forms are also included. Also included are all constitutional isomeric <E> and <Z> forms in respect of any —C=C— and —C=N— double bonds.

Since $R_1$ and $R_2$, like $R_7$ and $R_8$ in $A_1$ and $A_2$, may each independently of the other have the same or different meanings, the compound of formula I may also occur in various constitutional isomeric forms. The invention therefore relates also to all those constitutional isomeric forms in respect of the spatial arrangement of $A_1$ and $A_2$ and the substituents $R_1$ and $R_2$ in respect of the substituent $R_3$ as shown in formulae $D_1$ to $D_4$.

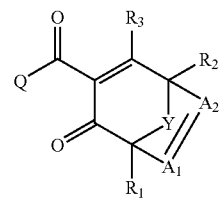

$D_1$

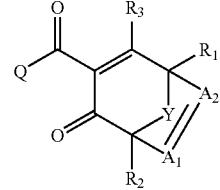

$D_2$

-continued

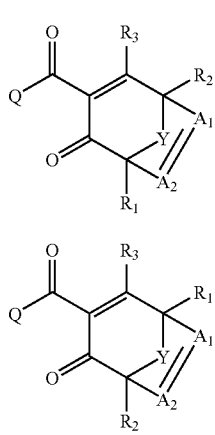

The same applies also to the spatial arrangement of the bridging member Y in respect of the carbon atoms carrying $R_1$ and $R_2$ when Y is a $C_1$-$C_4$alkylene or $C_2$-$C_4$alkenylene chain which may be interrupted by oxygen, $NR_{5a}$, sulfur, sulfonyl, sulfinyl, C(O) or C(=$NR_{5b}$) and/or mono- or poly-substituted by $R_6$.

The substituent $R_3$ may also be located on the bridging member, as has already been shown above in formula I" wherein $R_3$ is hydroxy. The present invention relates also to those constitutional isomeric forms $D_5$

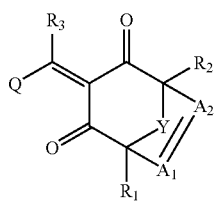

of the compounds of formula I.

That arrangement of $A_1$, $A_2$, Y and the substituents $R_1$, $R_2$, $R_4$, $R_5$, $R_6$, $R_7$ and $R_8$ relates accordingly also to all possible tautomeric and stereoisomeric forms of the compounds used as intermediates.

The present invention relates also to the salts which the compounds of formula I are able to form with amines, alkali metal and alkaline earth metal bases or quaternary ammonium bases. Among the alkali metal and alkaline earth metal bases as salt formers, special mention should be made of the hydroxides of lithium, sodium, potassium, magnesium, barium and calcium, but especially the hydroxides of sodium, barium and potassium.

Examples of amines suitable for ammonium salt formation include ammonia as well as primary, secondary and tertiary $C_1$-$C_{18}$alkylamines, $C_1$-$C_4$hydroxyalkylamines and $C_2$-$C_4$-alkoxyalkylamines, for example methylamine, ethylamine, n-propylamine, isopropylamine, the four butylamine isomers, n-amylamine, isoamylamine, hexylamine, heptylamine, octylamine, nonylamine, decylamine, pentadecylamine, hexadecylamine, heptadecylamine, octadecylamine, methylethylamine, methylisopropylamine, methylhexylamine, methylnonylamine, methylpentadecylamine, methyloctadecylamine, ethylbutylamine, ethylheptylamine, ethyloctylamine, hexylheptylamine, hexyloctylamine, dimethylamine, diethylamine, di-n-propylamine, diisopropylamine, di-n-butylamine, di-n-amylamine, diisoamylamine, dihexylamine, diheptylamine, dioctylamine, ethanolamine, n-propanolamine, isopropanolamine, N,N-diethanolamine, N-ethylpropanolamine, N-butylethanolamine, allylamine, n-butenyl-2-amine, n-pentenyl-2-amine, 2,3-dimethylbutenyl-2-amine, dibutenyl-2-amine, n-hexenyl-2-amine, propylenediamine, trimethylamine, triethylamine, tri-n-propylamine, triisopropylamine, tri-n-butylamine, triisobutylamine, tri-sec-butylamine, tri-n-amylamine, methoxyethylamine and ethoxyethylamine; heterocyclic amines, for example pyridine, quinoline, isoquinoline, morpholine, piperidine, pyrrolidine, indoline, quinuclidine and azepine; primary arylamines, for example anilines, methoxyanilines, ethoxyanilines, o-, m- and p-toluidines, phenylenediamines, benzidines, naphthylamines and o-, m- and p-chloroanilines; but especially triethylamine, isopropylamine and diisopropylamine.

Preferred quaternary ammonium bases suitable for salt formation correspond, for example, to the formula $[N(R_aR_bR_cR_d)]OH$ wherein $R_a$, $R_b$, $R_c$ and $R_d$ are each independently of the others $C_1$-$C_4$alkyl. Further suitable tetraalkylammonium bases with other anions can be obtained, for example, by anion exchange reactions.

Preference is given to compounds of formula I wherein $R_1$, $R_2$, $R_6$, $R_7$ and $R_8$ are each independently of the others hydrogen, hydroxy, mercapto, $NO_2$, cyano, halogen, formyl, $C_1$-$C_6$alkyl, $C_1$-$C_6$haloalkyl, $C_2$-$C_6$alkenyl, $C_2$-$C_6$haloalkenyl, $C_2$-$C_6$alkynyl, $C_2$-$C_6$haloalkynyl, $C_1$-$C_6$alkoxy, $C_1$-$C_6$haloalkoxy, $C_3$-$C_6$alkenyloxy, $C_3$-$C_6$alkynyloxy, $C_3$-$C_6$oxacycloalkyl, $C_3$-$C_6$thiacycloalkyl, $C_3$-$C_6$dioxacycloalkyl, $C_3$-$C_6$dithiacycloalkyl, $C_3$-$C_6$oxathiacycloalkyl, $C_1$-$C_6$alkoxycarbonyl, $C_1$-$C_6$alkylcarbonyl, $C_1$-$C_6$alkoxycarbonyloxy, $C_1$-$C_6$alkylcarbonyloxy, $C_1$-$C_6$alkylthio, $C_1$-$C_6$alkylsulfonyl, $C_1$-$C_6$alkylsulfinyl, $NR_9R_{10}$, $C_3$-$C_6$cycloalkyl, tri($C_1$-$C_6$alkyl)silyl, tri($C_1$-$C_6$alkyl)silyloxy or $Ar_1$;

or $R_1$, $R_2$, $R_6$, $R_7$, $R_8$ are each independently of the others a $C_1$-$C_6$alkyl, $C_2$-$C_6$alkenyl, $C_2$-$C_6$alkynyl or $C_3$-$C_6$cycloalkyl group, which may be interrupted by oxygen, sulfur, sulfonyl, sulfinyl, —$NR_{11}$— or —C(O)— and/or mono-, di- or tri-substituted by hydroxy, mercapto, $NO_2$, cyano, halogen, formyl, $C_1$-$C_6$alkoxy, $C_3$-$C_6$alkenyloxy, $C_3$-$C_6$alkynyloxy, $C_1$-$C_6$haloalkoxy, $C_1$-$C_2$alkoxy-$C_1$-$C_2$alkoxy, $C_1$-$C_4$alkoxycarbonyloxy, $C_1$-$C_4$alkylcarbonyloxy, $C_1$-$C_4$alkoxycarbonyl, $C_1$-$C_4$alkylcarbonyl, $C_1$-$C_6$alkylthio, $C_1$-$C_6$alkylsulfinyl, $C_1$-$C_6$alkylsulfonyl, $NR_{12}R_{13}$, $C_1$-$C_6$alkyl, $C_2$-$C_6$alkenyl, $C_2$-$C_6$alkynyl, $C_3$-$C_6$cycloalkyl, tri($C_1$-$C_6$alkyl)silyl, tri($C_1$-$C_6$alkyl)silyloxy or $Ar_2$;

or two substituents $R_6$ at the same carbon atom together form a —$CH_2O$— or a $C_2$-$C_5$alkylene chain, which may be interrupted once or twice by oxygen, sulfur, sulfonyl or sulfinyl and/or mono- or poly-substituted by $R_{6c}$, with the proviso that two hetero atoms may not be located next to one another;

or two substituents $R_6$ at different carbon atoms together form an oxygen bridge or a $C_1$-$C_4$alkylene chain, which may in turn be substituted by $R_{6c}$;

or $R_7$ and $R_8$ together form an oxygen bridge, a —CH=CH—CH=CH— bridge or a $C_3$-$C_4$alkylene chain, which may be interrupted by oxygen or —S(O)$_{n1}$— and/or mono- or poly-substituted by $R_{6d}$;

$Z_1$, $Z_2$ and $Z_3$ are each independently of the others $C_1$-$C_3$alkoxy-$C_1$-$C_3$alkyl-substituted $C_3$-$C_6$cycloalkyl, tri($C_1$-$C_6$alkyl)silyl, tri($C_1$-$C_6$alkyl)silyloxy or CH=P(phenyl)$_3$;

or $Z_1$, $Z_2$ and $Z_3$ are a $C_1$-$C_6$alkyl, $C_2$-$C_6$alkenyl or $C_2$-$C_6$alkynyl group, which is interrupted by oxygen, —O(CO)—, —(CO)O—, —O(CO)O—, —N($R_{14}$)—O—, —O—$NR_{15}$—, sulfur, sulfinyl, sulfonyl, —SO$_2$$NR_{16}$—, —$NR_{17}$SO$_2$— or —$NR_{18}$— and is mono- or poly-substituted by $L_1$;

$L_1$ is halogen, hydroxy, amino, formyl, nitro, cyano, mercapto, carbamoyl, P(O)(O$C_1$-$C_6$alkyl)$_2$, $C_1$-$C_6$alkoxy, $C_1$-$C_6$haloalkoxy, $C_1$-$C_6$alkoxycarbonyl, $C_2$-$C_6$alkenyl, $C_2$-$C_6$haloalkenyl, $C_2$-$C_6$alkynyl, $C_2$-$C_6$haloalkynyl, $C_3$-$C_6$cycloalkyl, halo-substituted $C_3$-$C_6$-cycloalkyl, $C_3$-$C_6$alkenyloxy, $C_3$-$C_6$alkynyloxy, $C_3$-$C_6$haloalkenyloxy, cyano-$C_1$-$C_6$alkoxy, $C_1$-$C_6$alkoxy-$C_1$-$C_6$alkoxy, $C_1$-$C_6$alkylthio-$C_1$-$C_6$alkoxy, $C_1$-$C_6$alkylsulfinyl-$C_1$-$C_6$alkoxy, $C_1$-$C_6$alkylsulfonyl-$C_1$-$C_6$alkoxy, $C_1$-$C_6$alkoxycarbonyl-$C_1$-$C_6$alkoxy, $C_1$-$C_6$alkylcarbonyloxy-$C_1$-$C_6$alkylcarbonyl, $C_1$-$C_6$alkylthio, $C_1$-$C_6$alkylsulfinyl, $C_1$-$C_6$alkylsulfonyl, $C_1$-$C_6$haloalkylthio, $C_1$-$C_6$haloalkylsulfinyl, $C_1$-$C_6$haloalkylsulfonyl or oxiranyl, which may in turn be substituted by $C_1$-$C_6$alkyl, $C_1$-$C_3$alkoxy or $C_1$-$C_3$alkoxy-$C_1$-$C_3$alkyl, or (3-oxetanyl)-oxy, which may in turn be substituted by $C_1$-$C_6$alkyl, $C_1$-$C_3$alkoxy or $C_1$-$C_3$alkoxy-$C_1$-$C_3$alkyl, or benzoyloxy, benzyloxy, benzylthio, benzylsulfinyl, benzylsulfonyl, $C_1$-$C_6$alkylamino, di($C_1$-$C_6$alkyl)amino, $R_{19}$S(O)$_2$O, $R_{20}$N($R_{21}$)SO$_2$—, rhodano, phenyl, phenoxy, phenylthio, phenylsulfinyl, phenylsulfonyl or $Ar_4$, it being possible for the phenyl-containing groups in turn to be substituted by one or more $C_1$-$C_3$alkyl, $C_1$-$C_3$haloalkyl, $C_1$-$C_3$alkoxy, $C_1$-$C_3$haloalkoxy, halogen, cyano, hydroxy or nitro groups;

or, when $R_1$ and $R_2$ are hydrogen, methyl, halogen or $C_1$-$C_3$alkoxycarbonyl and at the same time Y is other than $C_1$-$C_2$alkylene which may be substituted by hydrogen, halogen or methyl, or is other than oxygen, sulfur, sulfonyl, sulfinyl, C(O) or $NR_{4a}$ wherein $R_{4a}$ is hydrogen, $C_1$-$C_4$alkyl, formyl or $C_1$-$C_4$alkylcarbonyl, $L_1$ may additionally be hydrogen and $Z_1$, $Z_2$ and $Z_3$ may additionally be hydrogen, hydroxy, mercapto, NO$_2$, cyano, halogen, formyl, $C_1$-$C_6$alkyl, $C_1$-$C_6$haloalkyl, $C_2$-$C_6$alkenyl, $C_2$-$C_6$haloalkenyl, $C_2$-$C_6$alkynyl, $C_2$-$C_6$haloalkynyl, $C_1$-$C_6$haloalkoxy, $C_1$-$C_6$alkoxycarbonyl, $C_1$-$C_6$alkylcarbonyl, $C_1$-$C_6$alkylthio, $C_1$-$C_6$alkylsulfinyl, $C_1$-$C_6$alkylsulfinyl, $NR_{22}R_{23}$, phenyl which may be mono- or poly-substituted by $C_1$-$C_3$alkyl, $C_1$-$C_3$haloalkyl, $C_1$-$C_3$alkoxy, $C_1$-$C_3$haloalkoxy, halogen, cyano, hydroxy or nitro, or $C_3$-$C_6$cycloalkyl, $C_3$-$C_6$cycloalkyl substituted by $C_1$-$C_3$alkoxy, $C_1$-$C_3$alkoxy-$C_1$-$C_3$alkyl or $C_1$-$C_6$alkyl, 3-oxetanyl, 3-oxetanyl substituted by $C_1$-$C_3$alkoxy, $C_1$-$C_3$alkoxy-$C_1$-$C_3$alkyl or $C_1$-$C_6$alkyl; or $Ar_5$, O—$Ar_6$, N($R_{24}$)$Ar_7$ or S(O)$n_6$$Ar_8$;

$R_9$, $R_{11}$, $R_{13}$, $R_{23}$, $R_{16}$, $R_{17}$, $R_{18}$, $R_{20}$ and $R_{24}$ are each independently of the others hydrogen, $C_1$-$C_6$alkyl, $C_1$-$C_6$haloalkyl, $C_1$-$C_6$alkylcarbonyl, $C_1$-$C_6$alkoxycarbonyl, $C_1$-$C_6$alkylsulfonyl, phenyl, it being possible for the phenyl group in turn to be mono- or poly-substituted by $C_1$-$C_6$alkyl, $C_1$-$C_6$haloalkyl, $C_1$-$C_6$alkoxy, $C_1$-$C_6$haloalkoxy, halogen, cyano, hydroxy or nitro, or $Ar_9$;

$R_{6a}$ and $R_{6b}$ are each independently of the other hydrogen or $C_1$-$C_6$alkyl; or $R_{6a}$ and $R_{6b}$ together are a $C_2$-$C_5$alkylene chain;

$R_{6c}$, $R_{14}$, $R_{15}$, $R_{19}$ and $R_{21}$ are each independently of the others $C_1$-$C_6$alkyl or $C_1$-$C_6$haloalkyl;

$R_{6d}$, $R_{10}$, $R_{12}$ and $R_{22}$ are each independently of the others hydrogen or $C_1$-$C_6$alkyl;

$Ar_1$, $Ar_2$, $Ar_3$, $Ar_4$, $Ar_5$, $Ar_6$, $Ar_7$, $A_8$ and $A_9$ are each independently of the others a five- to ten-membered, monocyclic or fused bicyclic ring system, which may be aromatic, partially saturated or fully saturated and may contain from 1 to 4 hetero atoms selected from nitrogen, oxygen, sulfur, C(O) and C(=$NR_{25}$), and each ring system contains not more than two oxygen atoms and not more than two sulfur atoms, and each ring system may itself be mono- or poly-substituted by $C_1$-$C_6$alkyl, $C_1$-$C_6$haloalkyl, $C_2$-$C_6$alkenyl, $C_2$-$C_6$haloalkenyl, $C_2$-$C_6$alkynyl, $C_2$-$C_6$haloalkynyl, $C_1$-$C_6$alkoxy, $C_1$-$C_6$haloalkoxy, $C_3$-$C_6$alkenyloxy, $C_3$-$C_6$alkynyloxy, mercapto, amino, hydroxy, $C_1$-$C_6$alkylthio, $C_1$-$C_6$haloalkylthio, $C_3$-$C_6$alkenylthio, $C_3$-$C_6$-haloalkenylthio, $C_3$-$C_6$alkynylthio, $C_1$-$C_3$alkoxy-$C_1$-$C_3$alkylthio, $C_1$-$C_4$alkylcarbonyl-$C_1$-$C_3$alkylthio, $C_1$-$C_4$alkoxycarbonyl-$C_1$-$C_3$alkylthio, cyano-$C_1$-$C_3$alkylthio, $C_1$-$C_6$alkylsulfinyl, $C_1$-$C_6$haloalkylsulfinyl, $C_1$-$C_6$alkylsulfonyl, $C_1$-$C_6$haloalkylsulfonyl, aminosulfonyl, $C_1$-$C_2$alkylaminosulfonyl, N,N-di($C_1$-$C_2$alkyl)aminosulfonyl, di($C_1$-$C_4$alkyl)amino, halogen, cyano, nitro or phenyl, it being possible for the phenyl group in turn to be substituted by hydroxy, $C_1$-$C_6$-alkylthio, $C_1$-$C_6$haloalkylthio, $C_3$-$C_6$alkenylthio, $C_3$-$C_6$haloalkenylthio, $C_3$-$C_6$alkynylthio, $C_1$-$C_3$-alkoxy-$C_1$-$C_3$alkylthio, $C_1$-$C_4$alkylcarbonyl-$C_1$-$C_3$alkylthio, $C_1$-$C_4$alkoxycarbonyl-$C_1$-$C_3$alkylthio, cyano-$C_1$-$C_3$alkylthio, $C_1$-$C_6$alkylsulfinyl, $C_1$-$C_6$haloalkylsulfinyl, $C_1$-$C_6$alkylsulfonyl, $C_1$-$C_6$haloalkylsulfonyl, aminosulfonyl, $C_1$-$C_2$alkylaminosulfonyl, N,N-di($C_1$-$C_2$alkyl)aminosulfonyl, di($C_1$-$C_4$alkyl)amino, halogen, cyano or nitro, and the substituents at the nitrogen atom in the heterocyclic ring being other than halogen.

Special mention should be made of compounds of formula I wherein $L_1$ is hydrogen only when $Z_1$, $Z_2$ and $Z_3$ are a $C_1$-$C_6$alkyl group which is interrupted by —O(CO)—, —(CO)O—, —N($R_{14}$)O—, —O$NR_{15}$—, —SO$_2$$NR_{16}$—, —$NR_{17}$SO$_2$— or —$NR_{18}$—, or is a $C_2$-$C_6$alkenyl or $C_2$-$C_6$alkynyl group which is interrupted by oxygen, —O(CO)—, —(CO)O—, —O(CO)O—, —N($R_{14}$)O—, —ONR$_{15}$—, sulfur, sulfinyl, sulfonyl, —SO$_2$$NR_{16}$—, —$NR_{17}$SO$_2$— or —$NR_{18}$—; and when, further, either $R_1$ and $R_2$ are hydrogen or methyl, or $R_1$ is halogen or $R_2$ is $C_1$-$C_3$alkoxycarbonyl, and at the same time Y is other than $C_1$-$C_2$alkylene which may be substituted by halogen or methyl, or Y is other than oxygen, sulfur, sulfonyl, sulfinyl, C(O) or $NR_{4a}$ wherein $R_{4a}$ is hydrogen, $C_1$-$C_4$alkyl, formyl or $C_1$-$C_4$alkylcarbonyl.

An outstanding group of compounds of formula I comprises those compounds wherein $Z_1$, $Z_2$, $Z_3$ are $C_1$-$C_3$alkylene which is substituted by the following substituents: halogen, hydroxy, amino, formyl, nitro, cyano, mercapto, carbamoyl, P(O)(O$C_1$-$C_6$alkyl)$_2$, $C_1$-$C_6$alkoxy, $C_1$-$C_6$haloalkoxy, $C_1$-$C_6$alkoxycarbonyl, $C_2$-$C_6$alkenyl, $C_2$-$C_6$haloalkenyl, $C_2$-$C_6$alkynyl, $C_2$-$C_6$-haloalkynyl, $C_3$-$C_6$cycloalkyl, halo-substituted $C_3$-$C_6$cycloalkyl, $C_3$-$C_6$alkenyloxy, $C_3$-$C_6$alkynyloxy, $C_3$-$C_6$haloalkenyloxy, cyano-$C_1$-$C_6$alkoxy, $C_1$-$C_6$alkoxy-$C_1$-$C_6$alkoxy, $C_1$-$C_6$alkylthio-$C_1$-$C_6$alkoxy, $C_1$-$C_6$alkylsulfinyl-$C_1$-$C_6$alkoxy, $C_1$-$C_6$alkylsulfonyl-$C_1$-$C_6$alkoxy, $C_1$-$C_6$alkoxy-carbonyl-$C_1$-$C_6$alkoxy, $C_1$-$C_6$alkylcarbonyloxy, $C_1$-$C_6$alkylcarbonyl, $C_1$-$C_6$alkylthio, $C_1$-$C_6$alkylsulfinyl, $C_1$-$C_6$alkylsulfonyl, $C_1$-$C_6$haloalkylthio, $C_1$-$C_6$haloalkylsulfinyl, $C_1$-$C_6$haloalkylsulfonyl or oxiranyl, which may in turn be substituted by $C_1$-$C_3$alkyl, $C_1$-$C_3$alkoxy or $C_1$-$C_3$alkoxy-$C_1$-$C_3$alkyl, or (3-oxetanyl)-oxy, which may in turn be substituted by $C_1$-$C_6$alkyl, $C_1$-$C_3$alkoxy or $C_1$-$C_3$alkoxy-$C_1$-$C_3$alkyl, or benzoyloxy, benzyloxy, benzylthio, benzylsulfinyl, benzylsulfonyl, $C_1$-$C_6$alkylamino, di($C_1$-$C_6$alkyl)amino, $R_{19}S(O)_2O$, $R_{20}N(R_{21})SO_2$—, rhodano, phenyl, phenoxy, phenylthio, phenylsulfinyl, phenylsulfonyl or $Ar_4$, it being possible for the phenyl-containing groups in turn to be substituted by one or more $C_1$-$C_3$alkyl, $C_1$-$C_3$haloalkyl, $C_1$-$C_3$-alkoxy, $C_1$-$C_3$haloalkoxy, halogen, cyano, hydroxy or nitro groups;

or, when $R_1$ and $R_2$ are hydrogen, methyl, halogen or $C_1$-$C_3$alkoxycarbonyl and at the same time Y is other than $C_1$-$C_2$alkylene which may be substituted by halogen or methyl, or is other than oxygen, sulfur, sulfonyl, sulfinyl, $C(O)$ or $NR_{4a}$ wherein $R_{4a}$ is hydrogen, $C_1$-$C_4$-alkyl, formyl or $C_1$-$C_4$alkylcarbonyl, $L_1$ may additionally be hydrogen and $Z_1$, $Z_2$ and $Z_3$ may additionally be hydrogen, hydroxy, mercapto, $NO_2$, cyano, halogen, formyl, $C_1$-$C_6$alkyl, $C_1$-$C_6$haloalkyl, $C_2$-$C_6$alkenyl, $C_2$-$C_6$haloalkenyl, $C_2$-$C_6$alkynyl, $C_2$-$C_6$haloalkynyl, $C_1$-$C_6$alkoxy, $C_1$-$C_6$haloalkoxy, $C_1$-$C_6$alkoxycarbonyl, $C_1$-$C_6$alkylcarbonyl, $C_1$-$C_6$alkylthio, $C_1$-$C_6$alkylsulfonyl, $C_1$-$C_6$alkylsulfinyl, $NR_{22}R_{23}$, phenyl which may be mono- or poly-substituted by $C_1$-$C_3$alkyl, $C_1$-$C_3$haloalkyl, $C_1$-$C_3$alkoxy, $C_1$-$C_3$-haloalkoxy, halogen, cyano, hydroxy or nitro, or $C_3$-$C_6$cycloalkyl, $C_3$-$C_6$cycloalkyl substituted by $C_1$-$C_3$alkoxy, $C_1$-$C_3$alkoxy-$C_1$-$C_3$alkyl or $C_1$-$C_3$alkyl, 3-oxetanyl, 3-oxetanyl substituted by $C_1$-$C_3$alkoxy, $C_1$-$C_3$alkoxy-$C_1$-$C_3$alkyl or $C_1$-$C_6$alkyl, or $Ar_5$, $O$—$Ar_6$, $N(R_{24})Ar_7$ or $S(O)n_6Ar_8$.

Preferred compounds of formula I are those wherein p is 0. Preferably at least one group $Z_1$, $Z_2$ or $Z_3$ is in the ortho-position relative to the carbonyl group; in preferred compounds, in addition, $m_1$, $m_2$ and $m_3$ are the number 1. Also preferred are compounds of formula I wherein Q is a group $Q_1$ or $Q_2$, especially the group $Q_1$.

Also preferred are those compounds of formula I wherein Y is oxygen, $NCO_2$methyl, $NSO_2CH_3$, $NC(O)CH_3$, sulfur, sulfinyl, sulfonyl, $C(O)$ or a $C_1$-$C_2$alkylene chain. Outstanding compounds are those wherein Y is a $C_1$-$C_2$alkylene chain or oxygen, and wherein $A_1$ is $CR_7$, $A_2$ is $CR_8$ and $R_1$, $R_2$, $R_6$, $R_7$, $R_8$ are each independently of the others hydrogen or methyl, especially Y is methylene or ethylene and $R_1$, $R_2$, $R_6$, $R_7$, $R_8$ are each hydrogen.

Especially interesting compounds of formula I are those wherein $Z_1$ is $C_1$-$C_3$alkylene which may be interrupted by oxygen, especially a bidentate group of form —$CH_2$—, —$CH_2CH_2$—, —$OCH_2$—, —$OCH_2CH_2$—, —$CH_2O$—, —$CH_2CH_2O$—, —$CH_2OCH_2$— or —$CH_2CH_2CH_2O$—, and $L_1$ is preferably hydrogen, halogen, cyano, $C_1$-$C_6$alkyl, $C_2$-$C_6$alkenyl, $C_2$-$C_6$haloalkenyl, $C_2$-$C_6$alkynyl, $C_2$-$C_6$haloalkynyl, $C_1$-$C_6$alkoxy, $C_1$-$C_6$haloalkoxy, $C_1$-$C_6$alkoxy-$C_1$-$C_6$alkoxy. Especially preferred are compounds of formula I wherein $Z_1$ or $Z_1$-$L_1$ is $CH_3$, $CH_2CH_3$, $CH_2CH_2CH_3$, $CHC(CH_3)_2$, $CH_2OCH_2CH_2OCH_3$, $CH_2OCH_2CH_2OCH_2CH_3$, $CH_2OCH_3$, $CH_2OCH_2CH_3$, $CH_2OCH(CH_3)_2$, $CH_2OCH_2CF_3$, $CH_2OCH_2CH=CH_2$, $CH_2OCH_2CCH$, $CH_2OCH_2CCCH_3$, $CH_2OCH_2CH_2CCH$, $CH_2OCH_2CN$, $CH_2OCH_2C_2CN$, $CH_2OCH_2CH_2CH_2OCH_3$, $CH_2OCH_2CH_2OCH_2CH_2OCH_3$, $CH_2OCH_2CH_2CH_2OCF_3$, $CH_2CH_2OCH_3$, $CH_2CH_2OCH_2CH_3$, $CH_2CH_2CH_2OCH_3$, $CH_2CH_2CH_2OCH_2CH_3$ or $CH_2CH_2OCH_2CH_2OCH_3$, more especially $CH_3$, $CH_2CH_2CH_2OCH_3$ or $CH_2OCH_2CH_2OCH_3$, especially prominent compounds being those wherein Y is methylene, ethylene or oxygen, $A_1$ is $CR_7$, $A_2$ is $CR_8$ and $R_1$, $R_2$, $R_6$, $R_7$, $R_8$ are each independently of the others hydrogen or methyl. Of that group, preference is given to those compounds wherein Q is $Q_1$, $p_1$ is 0 and $m_1$ is 1, the group $(Z_1)m_1$ is in the ortho-position relative to the carbonyl group, and $R_3$ is hydroxy.

Special emphasis should also be given to compounds of formula I wherein Q is $Q_1$, $Z_1$ is $C_1$-$C_3$alkylene which may be interrupted by oxygen, $Z_1$ being especially a bidentate group of form —$CH_2$—, —$CH_2CH_2$—, —$OCH_2$—, —$OCH_2CH_2$—, —$CH_2O$—, —$CH_2CH_2O$—, —$CH_2OCH_2$— or —$CH_2CH_2CH_2O$—, and $L_1$ is preferably a monocyclic group

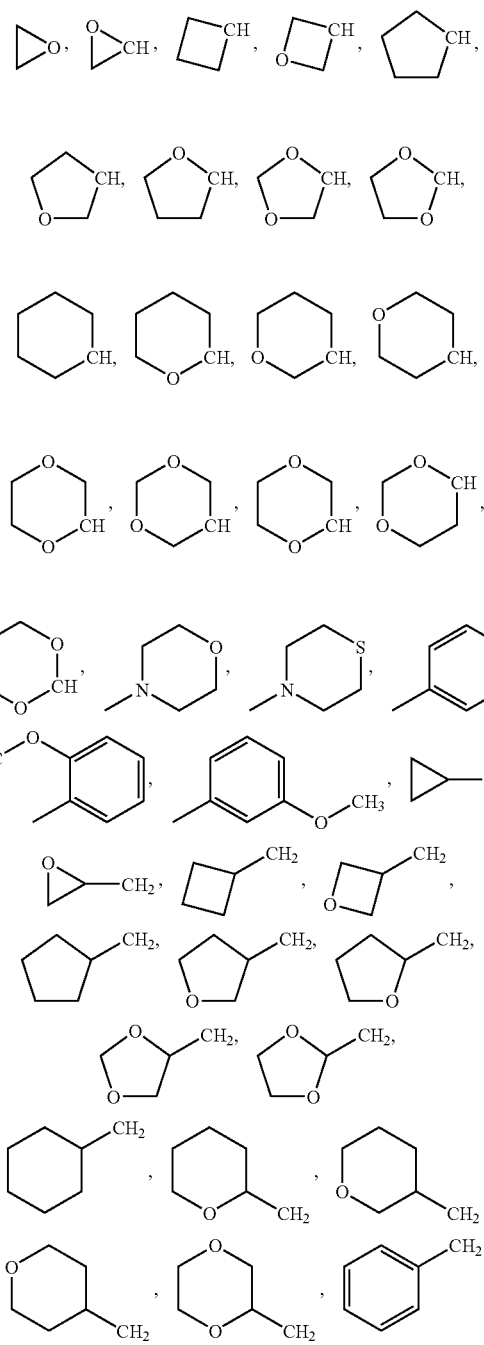

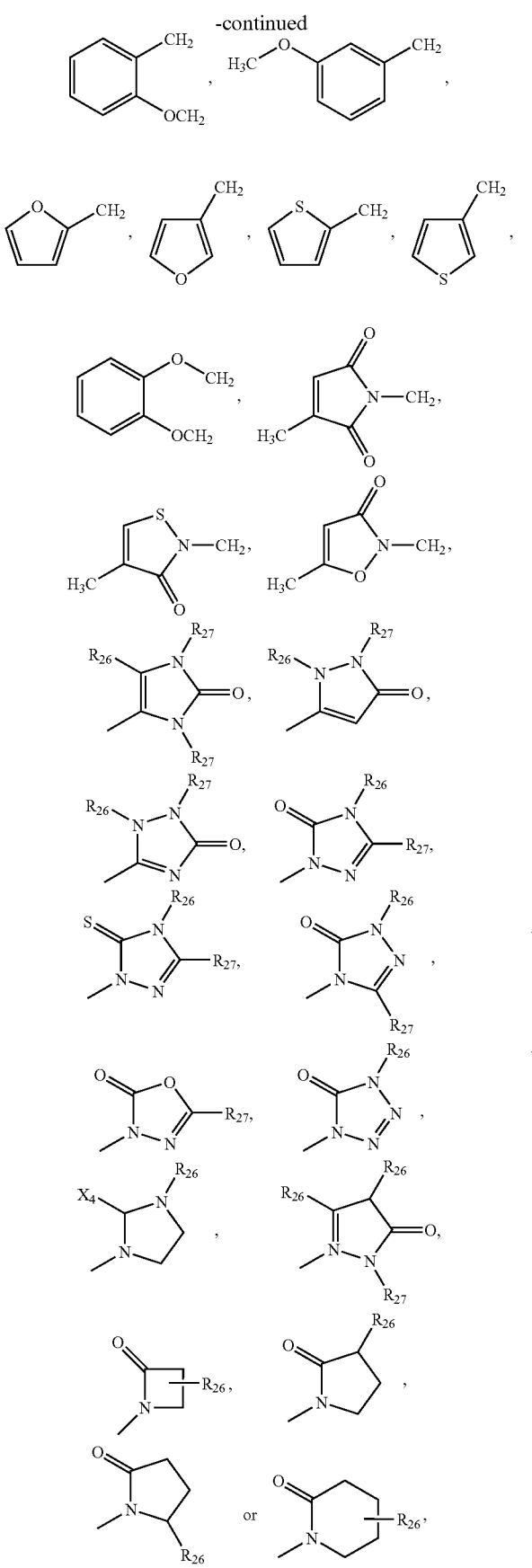

wherein $R_{26}$ is hydrogen or methyl, $R_{27}$ is hydrogen, $C_1$-$C_3$alkyl, $C_1$-$C_3$alkoxy, $C_1$-$C_3$alkylthio or trifluoromethyl and $X_4$ is oxygen or sulfur.

Where no free valency is indicated in those preferred definitions of $L_1$, for example as in

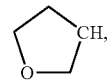

the linkage site is located at the carbon atom labelled "CH" or in the case of

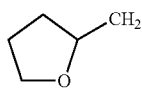

at the carbon atom labelled "$CH_2$" or in a case such as, for example,

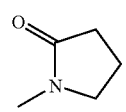

at the bonding site indicated at the bottom left.

In a further preferred group of compounds of formula I, $X_1$, $X_2$ and $X_3$ are $C_1$-$C_3$haloalkyl, especially $CF_3$, $CF_2CF_3$, $CF_2Cl$ or $CF_2H$, more especially $CF_3$ or $CF_2H$.

An especially preferred group of compounds of formula I comprises those compounds wherein Y is oxygen, $C(=CR_{6a}R_{6b})$ or a $C_1$-$C_4$alkylene chain which may be mono- or poly-substituted by $R_6$;

$A_1$ is $CR_7$;

$A_2$ is $CR_8$;

$R_1$, $R_2$, $R_6$, $R_{6a}$, $R_{6b}$, $R_7$ and $R_8$ are each independently of the others hydrogen, $C_1$-$C_6$alkyl or $C_1$-$C_6$alkoxycarbonyl;

or two substituents $R_6$ at the same carbon atom together form a $C_2$-$C_5$alkylene chain;

$R_3$ is hydroxy;

Q is the radical $Q_1$;

$p_1$ is 0;

$m_1$ is 1;

$X_1$ is $C_1$-$C_6$haloalkyl;

$Z_1$ is a $C_1$-$C_6$alkyl group which is interrupted by oxygen and is mono- or poly-substituted by $L_1$; it also being possible for $L_1$ to be bonded at the terminal carbon atom of the $C_1$-$C_6$alkyl group;

or $Z_1$ is $C_1$-$C_6$alkyl;

and $L_1$ is $C_1$-$C_6$alkoxy;

and agronomically acceptable salts/isomers/enantiomers/tautomers of those compounds.

The compounds of formula I can be prepared by means of processes known per se, e.g. as described in WO/0039094, as indicated below with reference to the examples of compounds of formula Ia

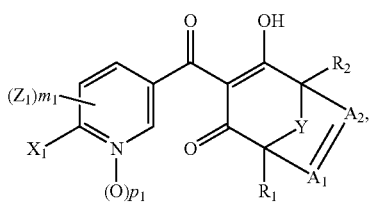

(Ia)

wherein $R_1$, $R_2$, $A_1$, $A_2$, Y, $X_1$, $Z_1$, $m_1$ and $p_1$ are as defined above.

In a preferred process, for example in the case of compounds of formula Ia

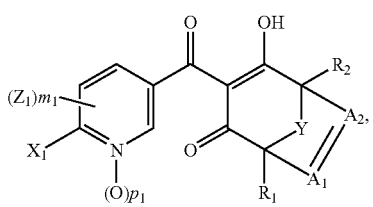

(Ia)

wherein $R_1$, $R_2$, $A_1$, $A_2$ and Y are as defined above and Q is a group $Q_1$, a) a compound of formula $Q_1a$

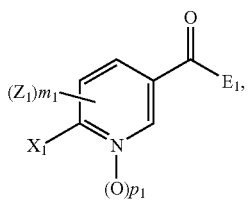

(Q₁a)

wherein $Z_1$, $m_1$, $X_1$ and $p_1$ are as defined above and $E_1$ is a leaving group, for example halogen or cyano, is reacted in an inert organic solvent, in the presence of a base, with a compound of formula Da

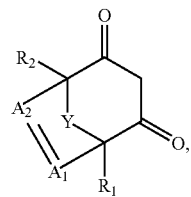

(Da)

wherein Y, $R_1$, $R_2$, $A_2$ and $A_1$ are as defined for formula I, to form compound(s) of formula IIa and/or IIb

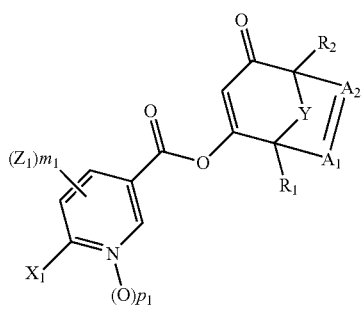

IIa

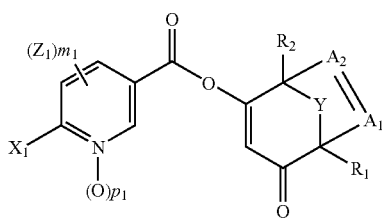

IIb and the latter is(are) then isomerised, for example in the presence of a base and a catalytic amount of an acylating agent, for example dimethylaminopyridine (DMAP), or a cyanide source, e.g. acetone cyanohydrin, potassium cyanide or trimethylsilyl cyanide; or b) a compound of formula $Q_1b$

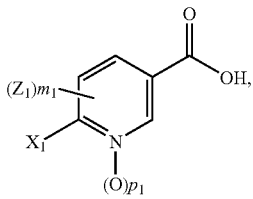

(Q₁b)

wherein $Z_1$, $m_1$, $p_1$ and $X_1$ are as defined for formula I, is reacted with a compound of formula Da

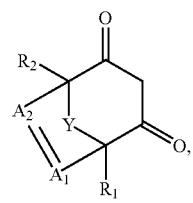

(Da)

wherein Y, $R_1$, $R_2$, $A_1$ and $A_2$ are as defined for formula I, in an inert organic solvent, in the presence of a base and a coupling reagent, to form compound(s) of formula IIa and/or IIb

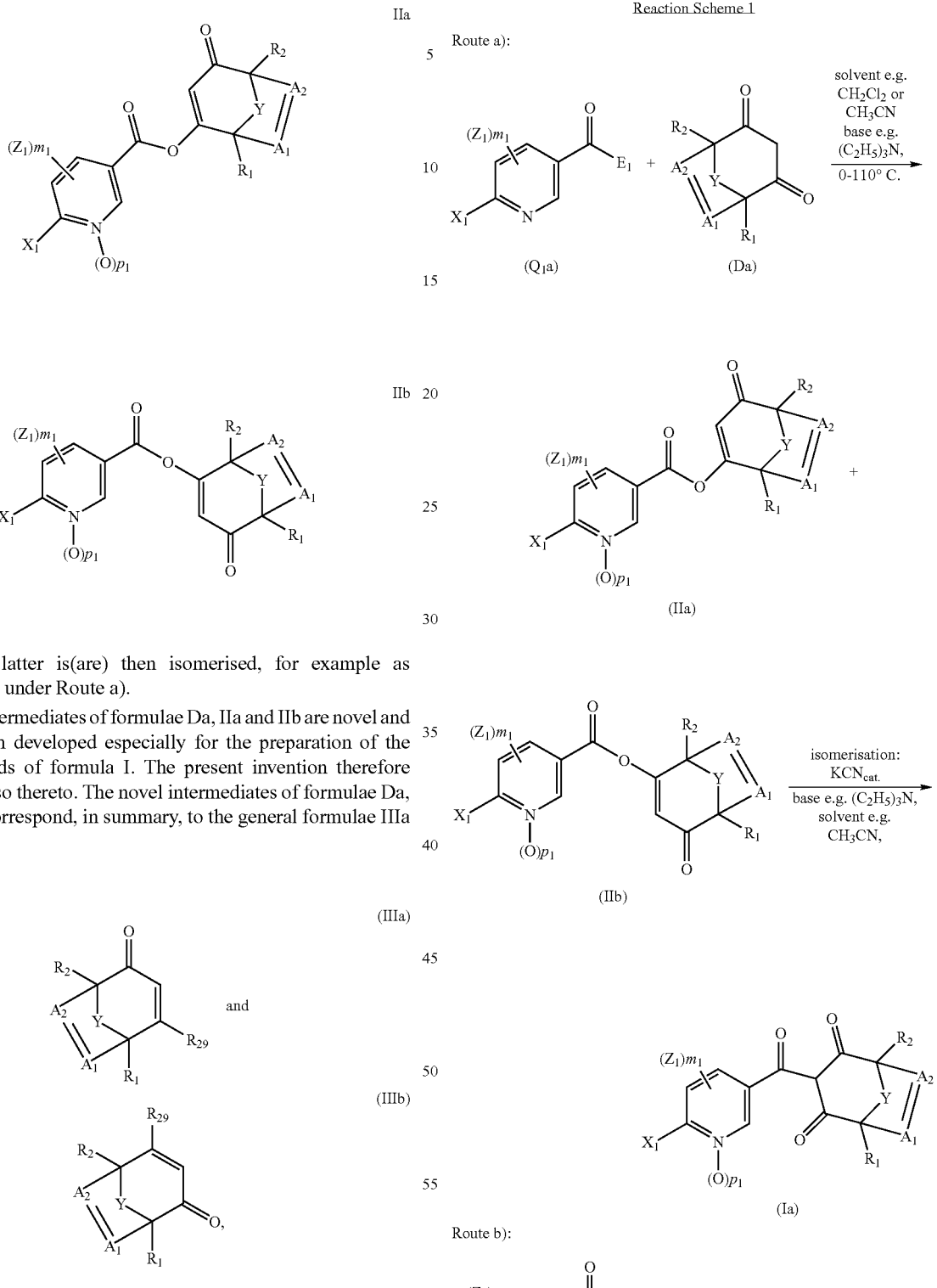

and the latter is(are) then isomerised, for example as described under Route a).

The intermediates of formulae Da, IIa and IIb are novel and have been developed especially for the preparation of the compounds of formula I. The present invention therefore relates also thereto. The novel intermediates of formulae Da, IIa, IIb correspond, in summary, to the general formulae IIIa and IIIb wherein $R_1$, $R_2$, Y, $A_1$ and $A_2$ are as defined above and $R_{29}$ is OH or OC(O)Q wherein Q is as defined for formula I.

The preparation of the compounds of formula I is illustrated in greater detail in the following Reaction Schemes.

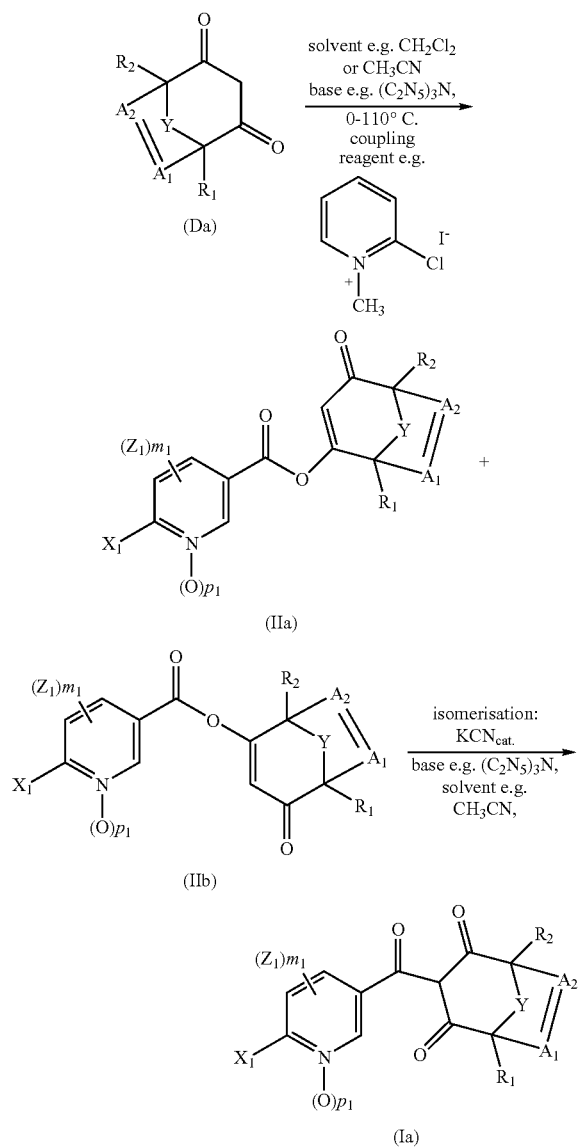

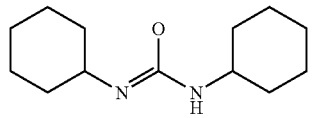

(formed from dicyclohexylcarbodiimide (DCC) and the corresponding carboxylic acid) or

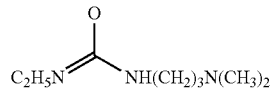

(formed from N-ethyl-N'-(3-dimethylaminopropyl)-carbodiimide (EDC) and the corresponding carboxylic acid) are used as starting materials. They are reacted in an inert, organic solvent, e.g. a halogenated hydrocarbon, for example dichloromethane, a nitrile, for example acetonitrile, or an aromatic hydrocarbon, for example toluene, and in the presence of a base, e.g. an alkylamine, for example triethylamine, an aromatic amine, for example pyridine or 4-dimethylaminopyridine (DMAP), with the dione derivatives of formula Da to form the isomeric enol esters of formula IIa or IIb. That esterification can be carried out at temperatures of from 0° C. to 110° C.

The isomerisation of the enol ester derivatives of formulae IIa and IIb to form the derivatives of formula I wherein $R_3$ is hydroxy can be carried out, for example, analogously to EP-A-0 353 187, EP-A-0 316 491 or WO 97/46530 in the presence of a base. e.g. an alkylamine, for example triethylamine, a carbonate, for example potassium carbonate, and a catalytic amount of DMAP or a catalytic amount of a cyanide source, for example acetone cyano-hydrin, potassium cyanide or trimethylsilyl cyanide. The two reaction steps can be carried out in situ, especially when a cyanide compound of formula $Q_1a$ ($E_1$=cyano) is used, or in the presence of a catalytic amount of acetone cyanohydrin or potassium cyanide, without isolation of the intermediates IIa and IIb.

According to Reaction Scheme 1, Route b), the desired derivatives of formula I wherein $R_3$ is hydroxy can be obtained e.g. analogously to E. Haslem, *Tetrahedron*, 2409-2433, 36, 1980 by first preparing enol esters of formula IIa and/or IIb by means of esterification of the carboxylic acids of formula $Q_1b$ with the dione derivatives of formula Da in an inert solvent, for example a halogenated hydrocarbon, for example dichloromethane, a nitrile, for example acetonitrile, or an aromatic hydrocarbon, for example toluene, in the presence of a base, e.g. an alkylamine, for example triethylamine, and a coupling agent, for example 2-chloro-1-methyl-pyridinium iodide, which enol esters are then converted in situ or in a second step into the compounds of formula I. That reaction takes place, depending upon the solvent used, at temperatures of from 0° C. to 110° C. and yields first, as described under Route a), the isomeric esters of formulae IIa and IIb, which can be isomerised to the desired derivatives of formula I ($R_3$=hydroxy) as described under Route a), for example in the presence of a base and a catalytic amount of DMAP, or a cyanide source, e.g. acetone cyanohydrin.

The activated carboxylic acid derivatives of formula $Q_1a$ in Reaction Scheme 1 (Route a) wherein $E_1$ is a leaving group, e.g. halogen, for example bromine, iodine or especially chlorine, can be prepared according to known standard methods, According to Reaction Scheme 1 it is preferable to prepare the compounds of formula I having the group $Q_1$, $Q_2$ and $Q_3$ wherein $R_3$ is hydroxy and $p_1$, $p_2$ and $p_3$ are 0.

Compounds of formula I wherein $p_1$, $p_2$ and $p_3$ are 1, that is to say the corresponding N-oxides of formula I, can be prepared by reacting a compound of formula I wherein $p_1$, $p_2$ and $p_3$ are 0 with a suitable oxidising agent, for example with the $H_2O_2$-urea adduct in the presence of an acid anhydride, e.g. trifluoroacetic anhydride. Such oxidations are known in the literature, for example from *J. Med. Chem.*, 32 (12), 2561-73, 1989 or WO 00/15615.

For the preparation of the compounds of formula I wherein Q is the groups $Q_1$, $Q_2$ and $Q_3$ and $R_3$ is hydroxy, for example in accordance with Reaction Scheme 1, Route a), the carboxylic acid derivatives of formula $Q_1a$ wherein $E_1$ is a leaving group, e.g. halogen, for example iodine, bromine and especially chlorine, N-oxyphthalimide or N,O-dimethylhydroxylamino, or part of an activated ester, e.g.

as described e.g. in C. Ferri "Reaktionen der organischen Synthese", Georg Thieme Verlag, Stuttgart, 1978, page 460 ff. Such reactions are generally known and various variations in respect of the leaving group $E_1$ are described in the literature.

Compounds of formula I wherein $R_3$ is other than hydroxy or halogen can be prepared in accordance with conversion reactions generally known from the literature by nucleophilic substitution reactions on chlorides of formula I wherein $R_3$ is chlorine, which are readily obtainable from compounds of formula I wherein $R_3$ is hydroxy, likewise in accordance with known processes, by reaction with a chlorinating agent, such as phosgene, thionyl chloride or oxalyl chloride. In such a reaction there are used, for example, mercaptans, thiophenols or heterocyclic thiols in the presence of a base, for example 5-ethyl-2-methylpyridine, diisopropyl-ethylamine, triethylamine, sodium hydrogen carbonate, sodium acetate or potassium carbonate.

Compounds of formula I wherein the substituent $R_3$ contains thio groups can be oxidised to the corresponding sulfones and sulfoxides of formula I analogously to known standard methods, e.g. with peracids, for example meta-chloroperbenzoic acid (m-CPBA) or peracetic acid. In that reaction the degree of oxidation at the sulfur atom (SO— or $SO_2$—) can be controlled by the amount of oxidising agent. Other sulfur-containing groups, for example those in the meanings of $R_1, R_2, R_6, R_7, R_8, L_1, X_1, X_2, X_3$ or Y, or in alkyl groups and chains interrupted by sulfur, as may occur, for example, in $Z_1, Z_2$ and $Z_3$, can be oxidised with a suitable oxidising agent, such as m-CPBA or sodium periodate, to the corresponding sulfone and sulfine (sulfoxido) groups directly in compounds of formula I, as well as in intermediates of formulae IIa, IIb, Da and Db (hereinbelow).

The derivatives of formula I so obtained wherein $R_3$ is other than hydroxy can also be in various isomeric forms, which can optionally be isolated in pure form. The invention therefore includes all those stereoisomeric forms. Examples of those isomeric forms are the following formulae I', I" and I"', as shown with reference to compounds of formula I wherein Q is group $Q_1$.

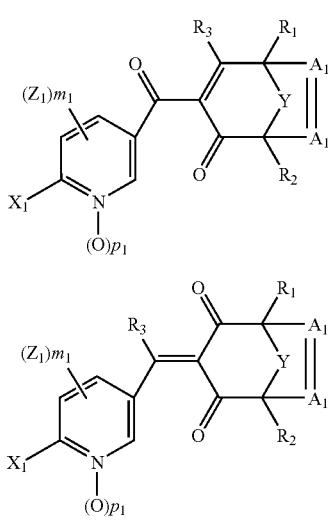

The compounds of formula Da used as starting materials can be prepared, for example, by treating a compound of formula Db

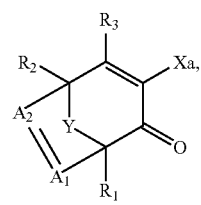

wherein $A_1, A_2, R_1, R_2$ and Y are as defined for formula I, Xa is chlorine or bromine and $R_3$ is hydroxy or $C_1$-$C_6$alkoxy, in the presence of a suitable reducing agent, e.g. tributyltin hydride, or zinc in acetic acid, optionally followed, when $R_3$ is $C_1$-$C_6$alkoxy, by aftertreatment in the presence of a hydrolysing agent, e.g. dilute hydrochloric acid or aqueous p-toluenesulfonic acid.

Specifically the compounds of formula Db above wherein $R_1$ and $R_2$ are each hydrogen or methyl, $A_1$ and $A_2$ are each methylene, Y is oxygen, methylene or ethylene, $R_3$ is chlorine, bromine or hydroxy and Xa is chlorine or bromine are known from Organic Letters 2002, 4, 1997; Archiv der Pharmazie 1987, 320, 1138; J. Amer. Chem. Soc. 1968, 90 2376 and from U.S. Pat. No. 3,538,117 and can be prepared in accordance with the methods described therein.

The compounds of formula Da used as starting materials can accordingly also be prepared very generally in accordance with those known methods, by reacting a dienophilic compound of formula IV

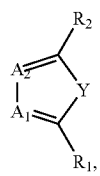

wherein $A_1, A_2, R_1, R_2$ and Y are as defined above, in an inert solvent, such as dichloromethane, 1,2-dichloroethane, toluene or chlorobenzene, optionally at elevated temperature or under elevated pressure, in a reaction similar to a Diels-Alder reaction, with a tetrahalocyclopropene of formula V

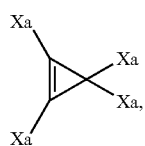

(V)

wherein Xa is chlorine or bromine, and then hydrolysing the resulting bicyclic compound of formula VI

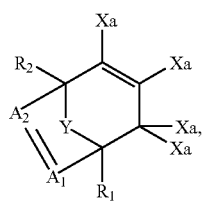

(VI)

wherein $A_1$, $A_2$, $R_1$, $R_2$, Xa and Y are as defined above, optionally in the presence of a suitable catalyst, for example silver nitrate or the silver tetrafluoroborate salt, or an acid, such as 90-98% sulfuric acid, 90% trifluoroacetic acid or p-toluenesulfonic acid, or reacting it with an alcoholate, for example sodium methanolate, potassium ethanolate or lithium isopropanolate, in order thus to obtain a compound of formula Db

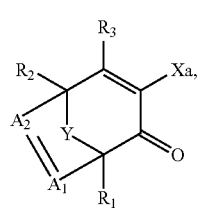

(Db)

wherein $A_1$, $A_2$, $R_1$, $R_2$, Xa and Y are as defined above, and $R_3$ depending upon the reaction conditions is either hydroxy, $C_1$-$C_6$alkoxy, chlorine or bromine, which is then further reduced and/or hydrolysed to form a novel compound of formula Da

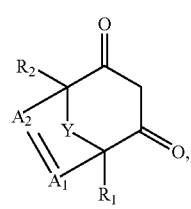

(Da)

wherein $A_1$, $A_2$, $R_1$, $R_2$ and Y are as defined above.

Compounds of formula VI can thus be reacted further, for example in the presence of 90-98% sulfuric acid at elevated temperature of about 80-100° C., to form compounds of formula Db wherein $R_3$ is hydroxy and Xa is chlorine or bromine, as described in greater detail in J. Amer. Chem. Soc. 1968, 90, 2376.

It is also possible for compounds of formula VI to be converted into compounds of formula Db wherein $R_3$ and Xa are both chlorine or bromine, for example in the presence of 90% trifluoroacetic acid at boiling temperature or in the presence of aqueous silver nitrate at ambient temperature, as described in Archiv der Pharmazie 1987, 320, 1138 and in Organic Letters 2002, 4, 1997.

On the other hand, compounds of formula VI can be converted into compounds of formula Db wherein $R_3$ is $C_1$-$C_6$alkoxy and Xa is chlorine or bromine in good yields at ambient temperature in the presence of alcoholates of formula $R_{3a}O^-M^+$ wherein $R_{3a}$ is accordingly $C_1$-$C_6$alkyl and $M^+$ is an alkali metal salt, in a solvent, such as an alcohol $R_{3a}OH$, toluene or ether, e.g. tetrahydrofuran, dimethoxyethane.

It is also possible for compounds of formula Db wherein Xa is chlorine or bromine and $R_3$ is hydroxy or $C_1$-$C_6$alkoxy to be reduced in the presence of reducing agents, e.g. tributyltin hydride, in an organic solvent, such as toluene or tetrahydrofuran, to form compounds of formula Db wherein Xa is hydrogen, as is well known according to general methods from the literature for the reduction of a halogen in a position adjacent to a carbonyl group (see e.g. *Comprehensive Org. Funct. Group, Transformations*, Vol. 1. ed. S. M. Roberts, Pergamon Press Oxford, 1995, pages 1-11).

Finally, compounds of formula Db wherein $R_3$ is $C_1$-$C_6$alkoxy, chlorine or bromine and Xa is hydrogen can be hydrolysed to compounds of formula Da in the presence of acids, e.g. dilute hydrochloric acid, dilute sulfuric acid or p-toluenesulfonic acid.

The general reaction sequences for the preparation of compounds of formulae Da and Db from compounds of formulae IV and V via intermediates of formula VI are shown in the following Scheme.

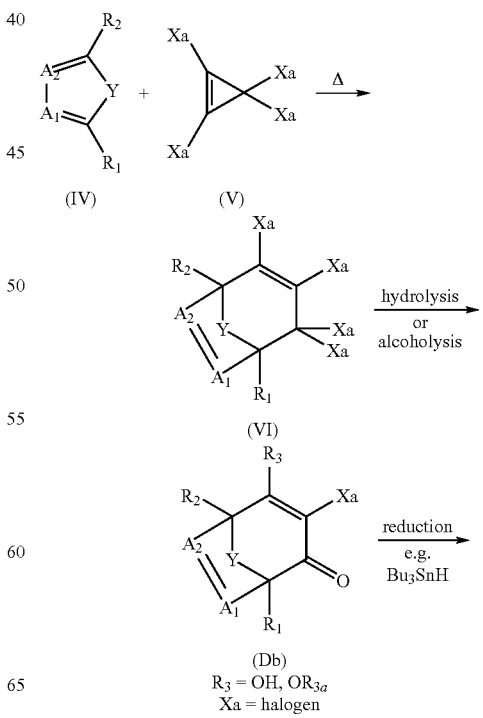

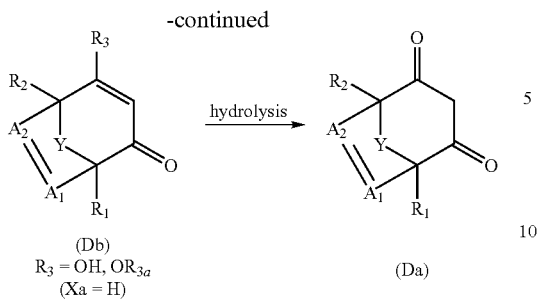

(Db)
R₃ = OH, OR₃ₐ
(Xa = H)

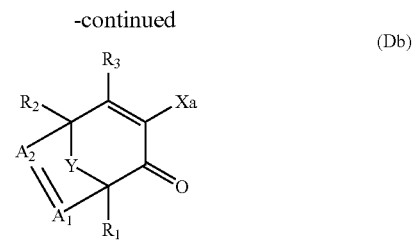
(Da)

wherein $A_1$, $A_2$, $R_1$, $R_2$ and Y are as defined above and $R_3$ is hydroxy and Xa is hydrogen, as is shown generally in the following Scheme.

In the reaction of compounds of formula VI and/or Db wherein $A_1$, $A_2$, $R_1$, $R_2$, Xa and Y are as defined above and $R_3$ is $C_1$-$C_6$alkoxy with alcoholates of formula $R_{3a}O^-M^+$, it is also possible for compounds of formula VII to be formed

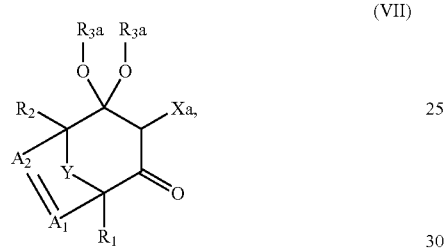
(VII)

wherein $A_1$, $A_2$, $R_1$, $R_2$, Xa and Y are as defined above and $R_{3a}$ is $C_1$-$C_6$alkyl or, when glycol is used, two $R_{3a}$ together are —CH₂CH₂—. Those compounds too can be reacted under the reduction conditions mentioned above, for example with tributyltin hydride or with zinc in the presence of acetic acid, by way of a compound of formula VIIa

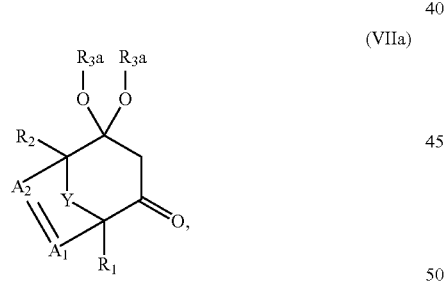
(VIIa)

wherein $A_1$, $A_2$, $R_1$, $R_2$, $R_{3a}$ and Y are as defined above, and subsequent hydrolysis, for example with dilute hydrochloric acid or a catalytic amount of p-toluenesulfonic acid in water, to form the compounds of formulae Da and Db

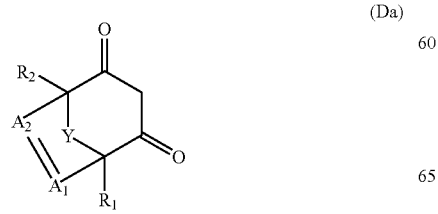
(Da)

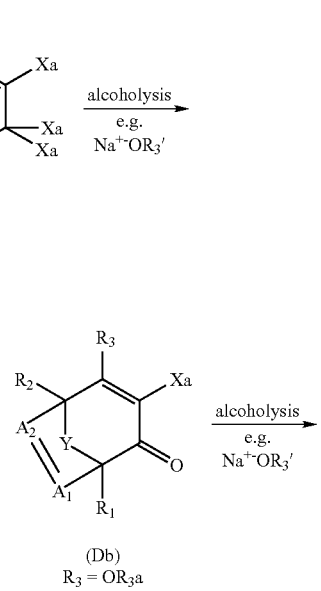

(Db)
R₃ = OR₃ₐ

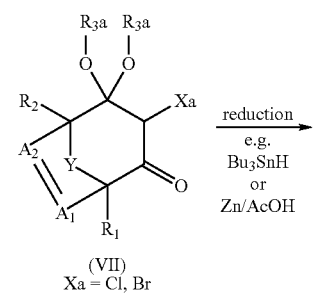
(VII)
Xa = Cl, Br

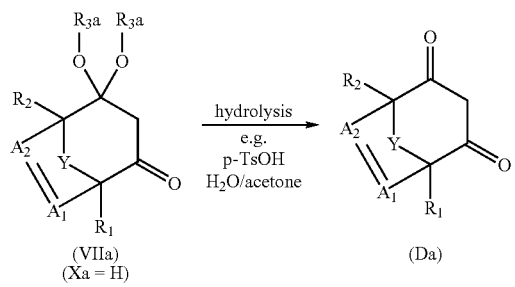
(VIIa)
(Xa = H)
(Da)

In a further process, compounds of formula Da can also be prepared either by conversion of a compound of formula VIII

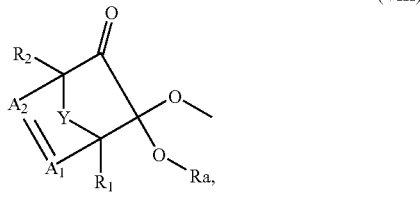

(VIII)

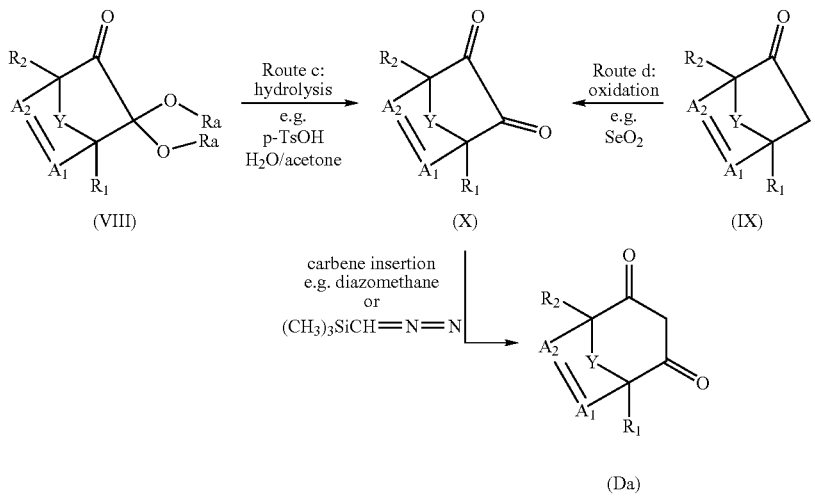

wherein $R_1$, $R_2$, $A_1$, $A_2$, Y are as defined above and Ra is $C_1$-$C_6$alkyl or, when glycol is used, two $R_{3a}$ together are —$CH_2CH_2$—, by hydrolysis, e.g. by treatment with an aqueous acid, Route c), or by conversion of a compound of formula IX

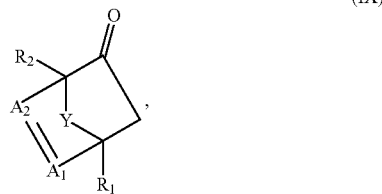

(IX)

wherein $R_1$, $R_2$, $A_1$, $A_2$, Y are as defined above, by means of oxidation, e.g. with selenium dioxide, Route d), first into a diketo compound of formula X

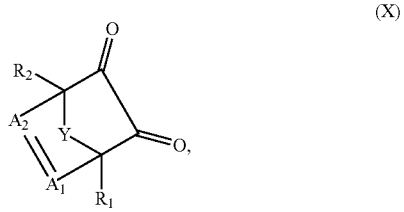

(X)

wherein $R_1$, $R_2$, $A_1$, $A_2$, Y are as defined above, and subsequent conversion of that compound by carbene insertion, e.g. with diazomethane or with trimethylsilyl-diazomethane, into the 1,3-dione compound Da.

Those processes are also known per se to the person skilled in the art; the compounds can be prepared, depending upon the functionality of the groups $R_1$, $R_2$, $A_1$, $A_2$ and Y, by general reaction routes shown in the following Scheme:

Using such routes it is readily possible to obtain, in particular, those compounds of formula VIII wherein Y is a $C_2$alkylene chain substituted by $R_6$, wherein $R_6$ is for example alkoxy, benzyloxy, alkylcarbonyl, alkoxycarbonyl, alkylthio or alkylsulfonyl.

Methods of obtaining the starting compounds of formula VII used in the above-mentioned process are known, for example, from Acc. Chem. Res. 2002, 856; J.O.C. 2002, 67, 6493; Organic Letters 2002, 2477; Synlett, 2002,1520; Chem. Commun. 2001, 1624; Synlett, 2000, 421; Tetrahedron Letters, 1999, 8431; J.O.C. 1999, 64, 4102; J.A.C.S. 1998, 129, 13254; Tetrahedron Letters, 1998, 659; Synlett, 1997, 1351. Methods of obtaining the starting compounds of formula IX are described, for example, in Org. Lettr. 2002, 2063; Synthetic Commun. 2001, 707; J.A.C.S. 2001, 123, 1569; Synlett, 1999, 225; Synlett, 1997, 786; Tetrahedron Letters, 1996, 7295; Synthesis, 1995, 845. Compounds of formula X are known, for example, from Synthesis, 2000, 850.

The transformations according to Route d) are likewise known, for example from Tetr. 1986, 42, 3491. Oxidation is preferably carried out with selenium dioxide in a solvent, such as acetic acid, at temperatures of from about 20° C. to about 120° C. and the carbene insertion with diazomethane is preferably effected at from about −40° C. to about 50° C. in a solvent, such as dichloromethane or diethyl ether. The carbene insertion can also be carried out with trimethylsilyldiazomethane, it having proved advantageous to work in the presence of a Lewis acid catalyst, such as boron trifluoride etherate, for example at temperatures of from about −15° C. to about +25° C.

In principle, however, the compounds of formulae Da, Db, VII, VIIa, VIII, IX and X used as starting materials and as intermediates can be prepared, in dependence upon the substituent pattern $A_1$, $A_2$, $R_1$, $R_2$ and Y and also in dependence upon the availability of the starting materials, according to any desired methods and reaction routes, there being no limitation in respect of the process variants indicated above.

The compounds of formula Da wherein $R_1$, $R_2$, $A_1$, $A_2$ and Y are as defined above, and also compounds of formula Db wherein $R_1$, $R_2$, $A_1$, $A_2$ and Y are as defined above and $R_3$ is chlorine, bromine, hydroxy or $C_1$-$C_6$alkoxy and Xa is hydrogen, chlorine or bromine, with the exception of the compounds 3-chloro-8-oxa-bicyclo[3.2.1]oct-6-ene-2,4-dione; 3-chloro-bicyclo[3.2.1]oct-6-ene-2,4-dione; 3-chloro-4-hydroxy-bicyclo[3.2.1]octa-3,6-dien-2-one; 3,4-dibromo-8-oxa-bicyclo[3.2.1]octa-3,6-dien-2-one; 3,4-dibromo-1,5-dimethyl-8-oxa-bicyclo-[3.2.1]octa-3,6-dien-2-one; 3,4-dibromo-bicyclo[3.2.1]octa-3,6-dien-2-one; 3,4-dichloro-8-oxa-bicyclo[3.2.1]octa-3,6-dien-2-one; 3,4-dichloro-bicyclo[3.2.1]octa-3,6-dien-2-one and 7,8-dibromo-5,9-dihydro-5,9-methano-benzocyclohepten-6-one, and also the compounds of formula VII are novel and constitute valuable intermediates for the preparation of compounds of formula I. The present invention accordingly relates likewise thereto.

The compounds of formulae $Q_{1a}$, $Q_{2a}$ and $Q_{3a}$ used as starting materials and their corresponding acids $Q_{1b}$, $Q_{2b}$ and $Q_{3b}$ are known from the publications WO 00/15615 and WO 01/94339 or can be prepared in accordance with the methods described therein.

The compounds of formula V used as starting material are likewise known, for example from Synthesis 1987, 260 and from J. Amer. Chem. Soc. 1968, 90 2376.

A large number of known standard methods are available for the preparation of all further compounds of formula I functionalised in accordance with the definition of $A_1$, $A_2$, $R_1$, $R_2$, Y and Q, for example alkylation, halogenation, acylation, amidation, oximation, oxidation and reduction, the choice of a suitable preparation process being governed by the properties (reactivities) of the substituents in question in the respective intermediates of formulae I, Da, Db, VI, VII and VIIa, and especially the starting materials of formulae IV and V and $Q_{1b}$, $Q_{2b}$ and $Q_{3b}$.

The reactions to form compounds of formula I are advantageously carried out in aprotic, inert organic solvents. Such solvents are hydrocarbons, such as benzene, toluene, xylene or cyclohexane, chlorinated hydrocarbons, such as dichloromethane, trichloromethane, tetrachloromethane or chlorobenzene, ethers, such as diethyl ether, ethylene glycol dimethyl ether, diethylene glycol dimethyl ether, tetrahydrofuran or dioxane, nitriles, such as acetonitrile or propionitrile, amides, such as N,N-dimethylformamide, diethylformamide or N-methylpyrrolidinone. The reaction temperatures are preferably from −20° C. to +120° C. The reactions generally proceed slightly exothermically and can generally be carried out at room temperature. In order to shorten the reaction time or to initiate the reaction, brief heating, up to the boiling point of the reaction mixture, can be carried out. The reaction times can likewise be shortened by the addition of a few drops of base as reaction catalyst. Suitable bases are especially tertiary amines, such as trimethylamine, triethylamine, quinuclidine, 1,4-diazabicyclo[2.2.2]octane, 1,5-diazabicyclo[4.3.0]non-5-ene or 1,5-diazabicyclo[5.4.0]undec-7-ene. It is also possible, however, to use as bases inorganic bases, such as hydrides, e.g. sodium or calcium hydride, hydroxides, e.g. sodium or potassium hydroxide, carbonates, e.g. sodium or potassium carbonate, or hydrogen carbonates, e.g. potassium or sodium hydrogen carbonate. The bases can be used as such or alternatively with catalytic amounts of a phase transfer catalyst, e.g. crown ethers, especially 18-crown-6, or tetraalkylammonium salts.

The end products of formula I can be isolated in conventional manner by concentration or evaporation of the solvent and purified by recrystallisation or trituration of the solid residue in solvents in which they are not readily soluble, such as ethers, aromatic hydrocarbons or chlorinated hydrocarbons, by distillation or by means of column chromatography or by means of the HPLC technique using a suitable eluant.

The sequence in which the reactions should be carried out in order as far as possible to avoid secondary reactions will be familiar to the person skilled in the art. Unless the synthesis is specifically aimed at the isolation of pure isomers, the product may be obtained in the form of a mixture of two or more isomers, for example chiral centres in the case of alkyl groups or cis/trans isomerism in the case of alkenyl groups or <E> or <Z> forms. All such isomers can be separated by methods known per se, for example chromatography, crystallisation, or produced in the desired form by means of a specific reaction procedure.

For the use according to the invention of the compounds of formula I, or of compositions comprising them, there come into consideration all methods of application customary in agriculture, for example pre-emergence application, post-emergence application and seed dressing, and also various methods and techniques such as, for example, the controlled release of active ingredient. For that purpose a solution of the active ingredient is applied to mineral granule carriers or polymerised granules (urea/formaldehyde) and dried. If required, it is additionally possible to apply a coating (coated granules), which allows the active ingredient to be released in metered amounts over a specific period of time.

The invention therefore relates also to a herbicidal and plant-growth-inhibiting composition comprising a herbicidally effective amount of a compound of formula I according to claim 1 on an inert carrier.

The compounds of formula I can be used as herbicides in unmodified form, that is to say as obtained in the synthesis, but they are preferably formulated in customary manner together with the adjuvants conventionally employed in formulation technology e.g. into emulsifiable concentrates, directly sprayable or dilutable solutions, dilute emulsions, suspensions, mixtures of a suspension and an emulsion (suspoemulsions), wettable powders, soluble powders, dusts, granules or microcapsules. Such formulations are described, for example, on pages 9 to 13 of WO 97/34485. As with the nature of the compositions, the methods of application, such as spraying, atomising, dusting, wetting, scattering or pouring, are selected in accordance with the intended objectives and the prevailing circumstances.

The formulations, that is to say the compositions, preparations or mixtures comprising the compound (active ingredient) of formula I or at least one compound of formula I and, usually, one or more solid or liquid formulation adjuvants, are prepared in known manner, e.g. by homogeneously mixing and/or grinding the active ingredients with the formulation adjuvants, for example solvents or solid carriers. Surface-active compounds (surfactants) may also be used in addition in the preparation of the formulations. Examples of solvents and solid carriers are given, for example, on page 6 of WO 97/34485.

Depending upon the nature of the compound of formula I to be formulated, suitable surface-active compounds are non-ionic, cationic and/or anionic surfactants and surfactant mixtures having good emulsifying, dispersing and wetting properties.

Examples of suitable anionic, non-ionic and cationic surfactants are listed, for example, on pages 7 and 8 of WO 97/34485.

In addition, the surfactants conventionally employed in formulation technology, which are described, inter alia, in "McCutcheon's Detergents and Emulsifiers Annual" MC Publishing Corp., Ridgewood N.J., 1981, Stache, H., "Tensid-Taschenbuch", Carl Hanser Verlag, Munich/Vienna 1981, and M. and J. Ash, "Encyclopedia of Surfactants", Vol. I-III, Chemical Publishing Co., New York, 1980-81, are also suitable for the preparation of the herbicidal compositions according to the invention.

The compositions according to the invention can additionally include an additive comprising an oil of vegetable or animal origin, a mineral oil, alkyl esters thereof or mixtures of such oils and oil derivatives.

The amount of oil additive in the composition according to the invention is generally from 0.01 to 2%, based on the spray mixture. For example, the oil additive can be added to the spray tank in the desired concentration after the spray mixture has been prepared.

Preferred oil additives comprise mineral oils or an oil of vegetable origin, for example rapeseed oil, olive oil or sunflower oil, emulsified vegetable oil, such as AMIGO® obtainable from Rhône-Poulenc Canada Inc., alkyl esters of oils of vegetable origin, for example the methyl derivatives, or an oil of animal origin, such as fish oil or beef tallow. A preferred additive contains as active components essentially 80% by weight alkyl esters of fish oils and 15% by weight methylated rapeseed oil, and also 5% by weight of customary emulsifiers and pH modifiers.

Especially preferred oil additives comprise alkyl esters of higher fatty acids ($C_8$-$C_{22}$), especially the methyl derivatives of $C_{12}$-$C_{18}$ fatty acids, for example the methyl esters of lauric acid, palmitic acid and oleic acid. Those esters are known as methyl laurate (CAS-111-82-0), methyl palmitate (CAS-112-39-0) and methyl oleate (CAS-112-62-9). A preferred fatty acid methyl ester derivative is Emery® 2230 and 2231 (Henkel subsidiary Cognis GMBH, DE).

The application and action of the oil additives can be improved by combining them with surface-active substances, such as non-ionic, anionic or cationic surfactants. Examples of suitable anionic, non-ionic and cationic surfactants are listed on pages 7 and 8 of WO 97/34485.

Preferred surface-active substances are anionic surfactants of the dodecylbenzylsulfonate type, especially the calcium salts thereof, and also non-ionic surfactants of the fatty alcohol ethoxylate type. Special preference is given to ethoxylated $C_{12}$-$C_{22}$ fatty alcohols having a degree of ethoxylation of from 5 to 40. Examples of commercially available, preferred surfactants are the Genapol types (Clariant AG, Muttenz, Switzerland). Also preferred for use as surface-active substances are silicone surfactants, especially polyalkyl-oxide-modified heptamethyltrisiloxanes, such as are commercially available as e.g. Silwet L-77®, and also perfluorinated surfactants. The concentration of surface-active substances in relation to the total additive is generally from 1 to 30% by weight.

Examples of oil additives that consist of mixtures of oils or mineral oils or derivatives thereof with surfactants are Edenor ME SU®, Turbocharge® (Zeneca Agro, Stoney Creek, Ontario, Calif.) and Actipron® (BP Oil UK Limited, GB).

The addition of an organic solvent to the oil additive/surfactant mixture can also bring about a further enhancement of action. Suitable solvents are, for example, Solvesso® (ESSO) and Aromatic Solvent® (Exxon Corporation) types.

The concentration of such solvents can be from 10 to 80% by weight of the total weight.

Such oil additives, which are also described, for example, in U.S. Pat. No. 4,834,908, are suitable for the composition according to the invention. A commercially available oil additive is known by the name MERGE®, is obtainable from the BASF Corporation and is essentially described, for example, in U.S. Pat. No. 4,834,908 in col. 5, as Example COC-1. A further oil additive that is preferred according to the invention is SCORE® (Novartis Crop Protection Canada.)

In addition to the oil additives listed above, in order to enhance the action of the compositions according to the invention it is also possible for formulations of alkyl pyrrolidones, such as are commercially available e.g. as Agrimax®, to be added to the spray mixture. Formulations of synthetic latices, such as, for example, polyacrylamide, polyvinyl compounds or poly-1-p-menthene, such as are commercially available as e.g. Bond®, Courier® or Emerald®, can also be used to enhance action. Solutions that contain propionic acid, for example Eurogkem Pen-e-trate®, can also be added as action-enhancing agent to the spray mixture.

The herbicidal formulations generally contain from 0.1 to 99% by weight, especially from 0.1 to 95% by weight, of herbicide, from 1 to 99.9% by weight, especially from 5 to 99.8% by weight, of a solid or liquid formulation adjuvant, and from 0 to 25% by weight, especially from 0.1 to 25% by weight, of a surfactant. Whereas commercial products will preferably be formulated as concentrates, the end user will normally employ dilute formulations. The compositions may also comprise further ingredients, such as stabilisers, for example vegetable oils or epoxidised vegetable oils (epoxidised coconut oil, rapeseed oil or soybean oil), anti-foams, for example silicone oil, preservatives, viscosity regulators, binders, tackifiers, and also fertilisers or other active ingredients.

The compounds of formula I are generally applied to the plant or to the locus thereof at rates of application of from 0.001 to 4 kg/ha, especially from 0.005 to 2 kg/ha. The concentration required to achieve the desired effect can be determined by experiment. It is dependent upon the nature of the action, the stage of development of the cultivated plant and of the weed and on the application (place, time, method) and may vary within wide limits as a function of those parameters.

The compounds of formula I are distinguished by herbicidal and growth-inhibiting properties, allowing them to be used in crops of useful plants, especially cereals, cotton, soybeans, sugar beet, sugar cane, plantation crops, rape, maize and rice, and also for non-selective weed control. The term "crops" is to be understood as including also crops that have been rendered tolerant to herbicides or classes of herbicides (such as, for example, HPPD inhibitors, ALS inhibitors, EPSPS (5-enol-pyrovyl-shikimate-3-phosphate-synthase) inhibitors, GS (glutamine synthetase) inhibitors) as a result of conventional methods of breeding or genetic engineering. An example of a crop that has been rendered tolerant to imidazolinones, e.g. imazamox, by conventional methods of breeding (mutagenesis) is Clearfield® summer rape (Canola). Examples of crops that have been rendered tolerant to herbicides or classes of herbicides by genetic engineering methods include glyphosate- and glufosinate-resistant maize varieties commercially available under the trade names RoundupReady® and LibertyLink®.

Crops are also to be understood as being those which have been rendered resistant to harmful insects by genetic engineering methods, for example Bt maize (resistant to European corn borer), Bt cotton (resistant to cotton boll weevil) and also Bt potatoes (resistant to the Colorado beetle). Examples of Bt maize are the Bt 176 maize hybrids of NK® (Syngenta Seeds). The Bt toxin is a protein that is formed naturally by *Bacillus thuringiensis* soil bacteria. Examples of toxins, or transgenic plants able to synthesise such toxins, are described in EP-A-0 451 878, EP-A-0 374 753, WO 93/07278, WO 95/34656 and EP-A-0 427 529.

Plant crops or seed material thereof can be both herbicide-tolerant and at the same time resistant to insect feeding ("stacked" transgenic events).

The weeds to be controlled may be both monocotyledonous and dicotyledonous weeds, such as, for example, *Stellaria, Nasturtium, Agrostis, Digitaria, Avena, Setaria, Sinapis, Lolium, Solanum, Echinochloa, Scirpus, Monochoria, Sagittaria, Bromus, Alopecurus, Sorghum halepense, Rottboellia, Cyperus, Abutilon, Sida, Xanthium, Amaranthus, Chenopodium, Ipomoea, Chrysanthemum, Galium, Viola* and *Veronica*.

The compositions according to the invention may additionally comprise growth regulators, for example trinexapac (744), chlormequat chloride (129), clofencet (148), cyclanilide (170), ethephon (281), flurprimidol (355), gibberellic acid (379), inabenfide (421), maleic hydrazide (449), mefluidide (463), mepiquat chloride (465), paclobutrazol (548), prohexadione-calcium (595), uniconazole (746) or thidiazuron (703). It is also possible for a composition according to the invention to comprise fungicides, for example azoxystrobin (43), epoxiconazole (48), benomyl (60), bromuconazole (89), bitertanol (77), carbendazim (107), cyproconazole (189), cyprodinil (190), diclomezine (220), difenoconazole (228), diniconazole (247), epoxiconazole (48), ethirimol (284), etridiazole (294), fenarimol (300), fenbuconazole (302), fenpiclonil (311), fenpropidin (313), fenpropimorph (314), ferimzone (321), fludioxonil (334), fluquinconazole (349), flutolanil (360), flutriafol (361), imazalil (410), ipconazole (426), iprodione (428), isoprothiolane (432), kasugamycin (438), kresoxim-methyl (439), spiroxamine (441), mepronil (466), myclobutanil (505), nuarimol (528), pefurazoate (554), pencycuron (556), phthalide (576), probenazole (590), prochloraz (591), propiconazole (607), pyrazophos (619), pyroquilone (633), quinoxyfen (638), quintozene (639), tebuconazole (678), tetraconazole (695), thiabendazole (701), thifluzamide (705), triadimefon (720), triadimenol (721), tricyclazole (734), tridemorph (736), triflumizole (738), triforine (742), triticonazole (745) or vinclozolin (751). The number in brackets after each active ingredient refers to the entry number of that active ingredient in the Pesticide Manual, eleventh ed., British Crop Protection Council, 1997.

The following Examples further illustrate the invention but do not limit the invention.

PREPARATION EXAMPLE 1

Preparation of 2,3,4,4-tetrachloro-1,5-dimethyl-8-oxa-bicyclo-[3.2.1]octa-2,6-diene

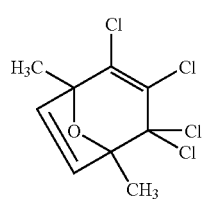

6.49 g (67.48 mmol) of 2,5-dimethylfuran and 10 g (56.23 mmol) of tetrachlorocyclopropene are heated at boiling temperature in 70 ml of toluene for 16 hours. The toluene and excess 2,5-dimethylfuran are then removed under reduced pressure. The product, 14.77 g (95.9% of theory) of 2,3,4,4-tetrachloro-1,5-dimethyl-8-oxa-bicyclo[3.2.1]octa-2,6-diene, which remains behind in the form of an oil, can be transferred to the next reaction step without further purification ($^1$H NMR).

$^1$H NMR (300 MHz; CDCl$_3$) δ 6.50 (d, 1H); 6.15 (d, 1H); 1.82 (s, 3H); 1.63 (s, 3H).

PREPARATION EXAMPLE P2

Preparation of 3,4-dichloro-1,5-dimethyl-8-oxa-bicyclo[3.2.1]octa-3,6-dien-2-one

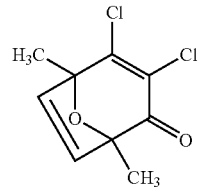

14 g (51.1 mmol) of unpurified 2,3,4,4-tetrachloro-1,5-dimethyl-8-oxa-bicyclo[3.2.1]octa-2,6-diene and 17.36 g (102.2 mmol) of silver nitrate are dissolved in 500 ml of acetone/water 1:1 mixture and heated for 15 hours at a temperature of 65-70° C. until the reaction of the reactants is complete (thin-layer chromatography (TLC) monitoring (mobile phase hexane/ethyl acetate 4:1)). After the reaction mixture has cooled to ambient temperature, solid sodium hydrogen carbonate is then stirred into the mixture in portions in order to neutralise the nitric acid. The precipitated silver bromide is filtered off and most of the acetone is distilled off under reduced pressure. The aqueous phase that remains behind is extracted three times with ethyl acetate. The organic extract is washed with water, dried over sodium sulfate and concentrated by evaporation. The oily residue is purified by means of silica gel chromatography (eluant gradient: 3-50% ethyl acetate in hexane). 6.1 g (54%) of pure 3,4-dichloro-1,5-dimethyl-8-oxa-bicyclo[3.2.1]octa-3,6-dien-2-one are obtained in the form of a pale yellow solid.

$^1$H NMR (300 MHz; CDCl$_3$) δ 6.65 (d, 1H); 6.23 (d, 1H); 1.72 (s, 3H); 1.61 (s, 3H).

PREPARATION EXAMPLE P3

Preparation of 3-chloro-1,5-dimethyl-4-methoxy-8-oxa-bicyclo-[3.2.1]octa-3,6-dien-2-one and 3-chloro-4,4-dimethoxy-1,5-dimethyl-8-oxa-bicyclo[3.2.1]oct-6-en-2-one

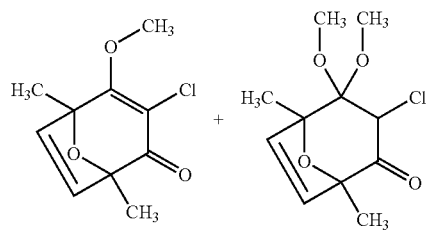

6.0 g (27.39 mmol) of 3,4-dichloro-1,5-dimethyl-8-oxa-bicyclo[3.2.1]octa-3,6-dien-2-one is introduced into 39 ml of anhydrous methanol. At a temperature of 0° C., the reaction mixture is further diluted dropwise with a solution of 15.2 ml of 5.4M sodium methanolate (82.17 mmol) and treated with 10 ml of absolute methanol. The reaction mixture is then heated to ambient temperature with 35 minutes' stirring. Using thin-layer chromatography (hexane/ethyl acetate 8:2) it can be established that reaction of the starting material is complete. The reaction solution is then concentrated under reduced pressure. The residue is then extracted by means of carbon tetrachloride against water. The aqueous phase is extracted a further three times using fresh carbon tetrachloride. The combined organic extracts are dried over sodium sulfate and concentrated by evaporation under reduced pressure; with ice-cooling, the oily product that remains behind crystallises out in the form of a ~1:1 mixture. The mixture is separated by means of column chromatography on silica gel (eluant: gradient from 1-5% ethyl acetate/hexane). 3.1 g (52.9%) of pure 3-chloro-1,5-dimethyl-4-methoxy-8-oxa-bicyclo[3.2.1]octa-3,6-dien-2-one are isolated.

$^1$H NMR (300 MHz; CDCl$_3$) δ 6.48 (d, 1H); 6.24 (d, 1H); 4.24 (s, 3H); 1.60 (s, 3H); 1.56 (s, 3H).

A second fraction yields 3.17 g (46.9%) of pure 3-chloro-4,4-dimethoxy-1,5-dimethyl-8-oxa-bicyclo[3.2.1]oct-6-en-2-one.

$^1$H NMR (300 MHz; CDCl$_3$) δ 6.25 (d, 1H); 6.05 (d, 1H); 5.15 (s, 1H); 3.48 (s, 3H); 3.46 (s, 3H); 1.53 (s, 3H); 1.51 (s, 3H).

PREPARATION EXAMPLE P4

Preparation of 4,4-dimethoxy-1,5-dimethyl-8-oxa-bicyclo[3.2.1]oct-6-en-2-one

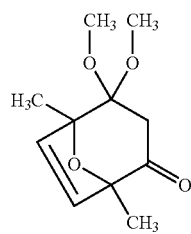

2.2 g (8.92 mmol) of 3-chloro-4,4-dimethoxy-1,5-dimethyl-8-oxa-bicyclo[3.2.1]oct-6-en-2-one in 240 ml of toluene are degassed, with heating at reflux temperature, and a catalytic amount of 66 mg of azaisobutyronitrile (AIBN) and a solution of 5.9 ml (22.3 mmol) of tributyltin hydride are added in succession. The reaction mixture is maintained at reflux temperature for a further 20 minutes to complete the reaction (TLC monitoring: hexane/ethyl acetate 4:1). The reaction mixture is then concentrated by evaporation under reduced pressure. The residue is then taken up in acetonitrile and the tin-containing residues are extracted by means of hexane. The acetonitrile phase is concentrated by evaporation in vacuo, 1.56 g (82.4% of theory) of 4,4-dimethoxy-1,5-dimethyl-8-oxa-bicyclo[3.2.1]oct-6-en-2-one remaining behind in the form of a yellow oil, which can be used for the next reaction step without further purification.

$^1$H NMR (300 MHz; CDCl$_3$) δ 6.22 (d, 1H); 5.90 (d, 1H); 3.41 (s, 3H); 3.25 (s, 3H); 2.92 and 2.84 (AB syst., 2H, J=16.5 Hz); 1.55 (s, 3H); 1.45 (s, 3H).

PREPARATION EXAMPLE P5

Preparation of 1,5-dimethyl-8-oxa-bicyclo[3.2.1]oct-6-ene-2,4-dione

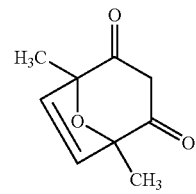

1.61 g (7.59 mmol) of 4,4-dimethoxy-1,5-dimethyl-8-oxa-bicyclo[3.2.1]oct-6-en-2-one and 0.432 g (2.28 mmol) of p-toluenesulfonic acid are dissolved in a 2:1 mixture of acetone and water and heated for 50 minutes at a temperature of 70° C. (TLC monitoring: hexane/ethyl acetate 9:1). The acetone is then removed under reduced pressure. The aqueous phase is then adjusted to pH 9 with saturated sodium hydrogen carbonate solution and extracted three times with ethyl acetate to remove neutral components. The aqueous phase is then adjusted to pH 5 with dilute hydrochloric acid and extracted three times with fresh ethyl acetate. The organic phase is dried over sodium sulfate and concentrated by evaporation under reduced pressure, there being obtained 1.04 g (82.5%) of technically pure 1,5-dimethyl-8-oxa-bicyclo[3.2.1]oct-6-ene-2,4-dione in the form of a yellowish product, which can be used without further purification in the next reaction step to form compounds of formula I.

$^1$H NMR (300 MHz; CDCl$_3$) δ 6.46 (d, 1H); 6.23 (d, 1H); 5.54 (hept., 1H); 1.58 (d, 6H); 1.40 (d, 3H); 1.25 (d, 3H).

PREPARATION EXAMPLE P6

Preparation of 3-bromo-1,5-dimethyl-4-isopropoxy-8-oxa-bicyclo-[3.2.1]octa-3,6-dien-2-one

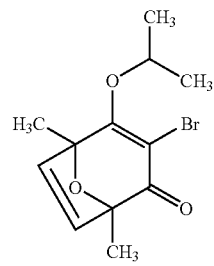

A solution of 2.74 g (8.9 mmol) of 3,4-dibromo-1,5-dimethyl-8-oxa-bicyclo[3.2.1]octa-3,6-dien-2-one (prepared according to Organic Lett. 4(12), 1997 (2002)) dissolved in 10 ml of tetrahydrofuran is added dropwise at ambient temperature to a solution of 5.4 ml (10.7 mmol) of 2M lithium isopropanolate diluted with 10 ml of tetrahydrofuran. The mixture is stirred for 3 hours at ambient temperature until the starting material has reacted completely (TLC monitoring: hexane/ethyl acetate/hexane 4:1). The reaction solution is then treated at a temperature of 0° C. with a 10% sodium dihydrogen phosphate solution (20 ml) and water (30 ml) and extracted three times with ethyl acetate. Drying over sodium sulfate and concentration by evaporation are carried out. For further purification, the dark oil so obtained is purified by chromatography over silica gel with 5% ethyl acetate in hexane. 1.73 g (68% of theory) of pure 3-bromo-1,5-dimethyl-4-isopropoxy-8-oxa-bicyclo[3.2.1]octa-3,6-dien-2-one are isolated.

$^1$H NMR (300 MHz; CDCl$_3$) δ 6.46 (d, 1H); 6.23 (d, 1H); 5.54 (hept., 1H); 1.58 (d, 6H); 1.40 (d, 3H); 1.25 (d, 3H).

PREPARATION EXAMPLE P7

Preparation of 3-bromo-4,4-(1',2'-ethylenedioxy)-bicyclo[3.2.1]oct-6-en-2-one

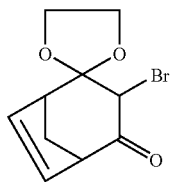

A sodium glycolate solution is prepared by stirring 124 mg (5.4 mmol) of metallic sodium into 2.7 ml (42.42 mmol) of anhydrous ethylene glycol at ambient temperature and, when the sodium has completely dissolved, 1.5 ml of tetrahydrofuran are added. To the resulting monosodium glycolate solution there is then added dropwise a solution of 1 g (3.6 mmol) of 3,4-dibromo-bicyclo[3.2.1]octa-3,6-dien-2-one (prepared according to *Organic Lett.* 4(12), 1997 (2002)) dissolved in 5 ml of tetrahydrofuran. The reaction mixture is then stirred at ambient temperature for 90 minutes with TLC monitoring (mobile phase hexane/ethyl acetate 4:1). The reaction mixture is then treated with 8 ml of 10% sodium dihydrogen phosphate solution and extracted with ethyl acetate (3×). The organic phase is washed with water to remove ethylene glycol, then dried and concentrated by evaporation. 930 mg (~100%) of 3-bromo-4,4-ethylenedioxy-bicyclo[3.2.1]oct-6-en-2-one are obtained in the form of a white solid.

$^1$H NMR (300 MHz; CDCl$_3$) δ 6.38 (m, 1H); 6.25 (m, 1H); 5.46 (s, 1H); 4.25 (m, 2H); 4.04 (m, 2H); 3.38 (m, 1H); 2.98 (m, 1H); 2.40 (m, 1H); 2.25 (m, 1H).

PREPARATION EXAMPLE P8

Preparation of 4,4-(1',2'-ethylenedioxy)-bicyclo[3.2.1]oct-6-en-2-one

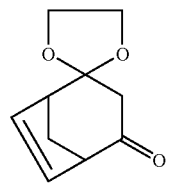

A degassed solution of 920 mg (3.55 mmol) of 3-bromo-4,4-(1',2'-ethylenedioxy)-bicyclo-[3.2.1]oct-6-en-2-one in 90 ml of toluene is treated at boiling temperature in succession with a catalytic amount (30 mg) of AIBN and with 2.35 ml (8.88 mmol) of tributyltin hydride. To complete the reaction, the reaction mixture is maintained at reflux for a further 20 minutes, with TLC monitoring (mobile phase hexane/ethyl acetate 1:1). The reaction mixture is then concentrated by evaporation under reduced pressure. The residue is taken up in a small amount of acetonitrile and extracted five times with a small amount of hexane in order to remove tin-containing secondary products. The acetonitrile phase is then again concentrated by evaporation. 800 mg of 4,4-(1',2'-ethylenedioxy)-bicyclo[3.2.1]oct-6-en-2-one are obtained in the form of a yellow oil, which can be transferred directly to the next reaction step without further purification.

$^1$H NMR (300 MHz; CDCl$_3$) δ 6.30 (m, 1H); 6.12 (m, 1H); 4.02-3.90 (m, 2×2H); 3.10 (m, 1H); 3.06 (d, 1H); 2.83 (m, 1H); 2.45 (d, 1H); 2.40-2.25 (m, 2×1H).

PREPARATION EXAMPLE P9

Bicyclo[3.2.1]oct-6-ene-2,4-dione

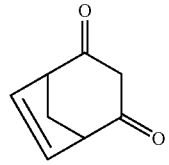

a) 640 mg (3.55 mmol) of 4,4-(1',2'-ethylenedioxy)-bicyclo[3.2.1]oct-6-en-2-one are heated for 16 hours at a temperature of 70° C. in the presence of 200 mg of p-toluenesulfonic acid in a 2:1 mixture of acetone and water. After hydrolysis is complete (TLC monitoring: ethyl acetate/hexane 1:1), the acetone is distilled off under reduced pressure and the aqueous phase is adjusted to pH 9 with saturated sodium hydrogen carbonate solution. After extraction of the aqueous phase three times with ethyl acetate, it is acidified to pH 5 with dilute hydrochloric acid. Extraction is carried out three times with fresh ethyl acetate, followed by drying over sodium sulfate and concentration by evaporation in vacuo. 364 mg (75%) of pure bicyclo[3.2.1]oct-6-ene-2,4-dione are obtained in the form of a yellow oil for further reaction to form compounds of formula I.

$^1$H NMR (300 MHz; CDCl$_3$) δ 6.22 (m, 2H); 3.50 (d, 1H); 3.45 (m, 2H); 3.22 (d, 1H); 2.60-2.45 (m, 2×1H).

b) One-pot process: 100 mg (0.39 mmol) of 3-bromo-4,4-(1',2'-ethylenedioxy)-bicyclo[3.2.1]-oct-6-en-2-one are taken up in concentrated acetic acid and treated at ambient temperature with 80 mg (1.16 mmol) of zinc powder. The progress of the reaction is monitored by means of thin-layer chromatography (mobile phase: hexane/ethyl acetate 1:1). When after 2 hours brominated starting material can no longer be detected, the reaction mixture is heated continuously at a temperature of 95° C. After a further 2 hours, according to thin-layer chromatography all the reference material 4,4-(1',2'-ethylenedioxy)-bicyclo[3.2.1]oct-6-en-2-one has reacted. The reaction mixture is filtered and concentrated in vacuo. The residue is treated with saturated sodium-hydrogen carbonate solution and extracted three times with ethyl acetate. The alkaline aqueous phase is adjusted to pH 3-4 with dilute hydrochloric acid and extracted three times with fresh ethyl acetate. After drying of the organic phase over sodium sulfate and subsequent concentration by evaporation, 45 mg (85% of theory) of technically pure bicyclo[3.2.1]oct-6-ene-2,4-dione are obtained.

PREPARATION EXAMPLE P10

Preparation of 3-[2-(2-methoxy-ethoxymethyl)-6-trifluoromethyl-pyridine-3-carbonyl]-1,5-dimethyl-8-oxa-bicyclo[3.2.1]oct-6-ene-2,4-dione

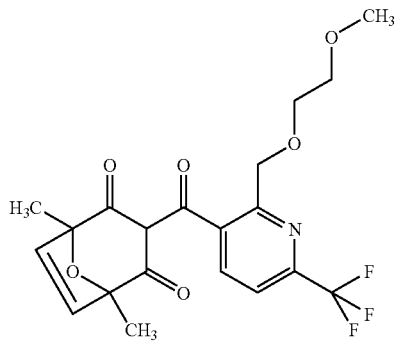

146 mg (0.879 mmol) of 1,5-dimethyl-8-oxa-bicyclo[3.2.1]oct-6-ene-2,4-dione and 245 mg (0.879 mmol) of 2-(2-methoxy-ethoxymethyl)-6-trifluoromethyl-nicotinic acid (preparation as described in WO 01/94339) are dissolved in 29 ml of acetonitrile and treated at ambient temperature with 199 mg (0.966 mmol) of dicyclohexylcarbodiimide. The reaction mixture is stirred for 2 hours and then 0.184 ml (1.318 mmol) of triethylamine and 0.08 ml (0.879 mmol) of acetone cyanohydrin are added. Stirring is carried out for a further 16 hours at ambient temperature, followed by concentration under reduced pressure. The residue that remains behind is chromatographed over silica gel (eluant: toluene/ethanol/dioxane/triethylamine/water 20:8:4:4:1). The product-containing fraction is concentrated. The oily residue is again dissolved in fresh ethyl acetate and washed with 10 ml of dilute hydrochloric acid (pH 1), and then with water (2×) and sodium chloride solution (2×). After the solution has been dried over sodium sulfate and concentrated by evaporation under reduced pressure, 128 mg (34%) of 3-[2-(2-methoxy-ethoxymethyl)-6-trifluoromethyl-pyridine-3-carbonyl]-1,5-dimethyl-8-oxa-bicyclo[3.2.1]oct-6-ene-2,4-dione are obtained in the form of a yellow oil.

$^1$H NMR (300 MHz; CDCl$_3$) δ 16.1 (br. s, 1H); 7.68 (m, 2×1H); 6.29 (d, 1H); 6.22 (d, 1H); 4.72 (m, 2H); 3.48 (m, 2H); 3.37 (m, 2H); 3.32 (s, 3H); 1.68 (s, 3H); 1.48 (s, 3H).

PREPARATION EXAMPLE P11
3-Chloro-bicyclo[3.2.2]non-6-ene-2,4-dione

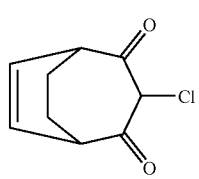

0.7 g (2.7 mmol) of 2,3,4,4-tetrachloro-bicyclo[3.2.2]nona-2,6-diene (known from U.S. Pat. No. 3,538,117) is heated in a mixture of 1 ml of trifluoroacetic acid, 4 ml of acetic acid and 1 ml of water for 18 hours at a temperature of 70° C. The cooled reaction solution is then taken up in diethyl ether and extracted first with water and then with saturated sodium chloride solution. After chromatographic purification (ethyl acetate/hexane 1:4), 0.33 g of 3-chloro-bicyclo-[3.2.2]non-6-ene-2,4-dione is obtained as a tautomeric mixture of the forms Da and Db.

$^1$H-NMR (300 MHz; CDCl$_3$) δ 8.58 (b, 1H); 6.38 (m, 2H); 3.78 (m, 2H); 2.05 to 1.80 (m, 4H); tautomeric form Db.

PREPARATION EXAMPLE P12

Bicyclo[3.2.2]non-6ene-2,4-dione

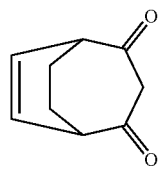

0.19 g (1 mmol) of 3-chloro-bicyclo[3.2.2]non-6-ene-2,4-dione is treated in the presence of 4 ml of acetic acid with 0.27 g (4 mmol) of zinc and the mixture is heated for 3 hours at a temperature of 95° C. The cooled reaction mixture is then extracted with ethyl acetate against water and then washed again with saturated sodium chloride solution. 0.14 g of amorphous bicyclo[3.2.2]non-6-ene-2,4-dione is obtained as tautomeric form Da.

$^1$H-NMR (300 MHz; CDCl$_3$) δ 6.22 (m, 2H); 3.58 to 3.51 (m, 2H); 2.12 (m, 2H); 1.92 (m, 2H).

PREPARATION EXAMPLE P13

5-Bromo-7,8-dioxo-bicyclo[2.2.2]oct-5-ene-2-carboxylic acid methyl ester

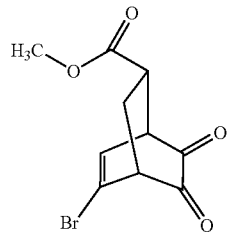

3 g (9.4 mmol) of 5-bromo-8,8-dimethoxy-7-oxo-bicyclo[2.2.2]oct-5-ene-2-carboxylic acid methyl ester (J.O.C. (202), 67, 6493) are stirred in a mixture of 15 ml of trifluoroacetic acid and 1 ml of water for 12 hours at room temperature. Extraction is then carried out with dichloromethane against water. The organic phase is dried over sodium sulfate and yields, after removal of the solvent, the 5-bromo-7,8-dioxo-bicyclo[2.2.2]oct-5-ene-2-carboxylic acid methyl ester in the form of an orange-coloured oil and as a pure isomer.

$^1$H-NMR (300 MHz; CDCl$_3$) δ 6.62 (d, 1H); 3.97 (d, 1H); 3.80 (s, 3H); 3.70 (m, 1H); 3.20 (d, 1H); 2.63 (m, 1H); 2.40 (m, 1H).

PREPARATION EXAMPLE P14

8-Bromo-2,4-dioxo-bicyclo[3.2.2]non-8-ene-6-carboxylic acid methyl ester

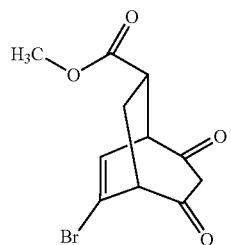

4.2 ml of trimethylsilyl-diazomethane are added dropwise at a temperature of −10° C. to a solution of 1.91 g (7 mmol) of 5-bromo-7,8-dioxo-bicyclo[2.2.2]oct-5-ene-2-carboxylic acid methyl ester in 20 ml of dichloromethane and 0.089 ml (0.7 mmol) of boron trifluoride etherate. The cooling is removed and the reaction mixture is stirred for 4 hours at a temperature of 20° C. The reaction solution is then extracted with water, the organic phase is dried over sodium sulfate and concentrated by evaporation using a rotary evaporator, and the residue is purified by silica gel chromatography. An isomer of 8-bromo-2,4-dioxo-bicyclo[3.2.2]non-8-ene-6-carboxylic acid methyl ester is obtained.

$^1$H-NMR (300 MHz; CDCl$_3$) δ 6.42 (d, 1H); 3.86 (d, 1H); 3.75 (d, 1H); 3.68 (s, 3H); 3.65 (m, 1H); 3.43 (d, 1H); 3.10 (m, 1H); 2.52 (m, 1H); 2.34 (m, 1H); tautomeric form Da.

PREPARATION EXAMPLE P15

3-(2-Methyl-6-difluoromethyl-pyridine-3-carbonyl)-2,4-dioxo-bicyclo[3.2.2]non-8-ene-6-carboxylic acid methyl ester

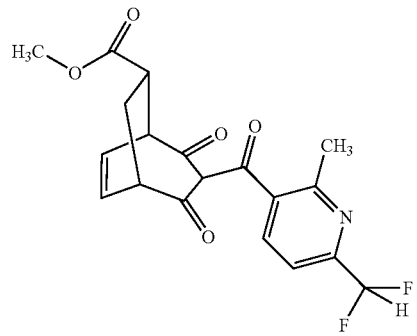

Catalytic amounts (10 mg) of azaisobutyronitrile are added to a solution of 0.10 g (0.24 mmol) of 8-bromo-3-(2-methyl-6-difluoromethyl-pyridine-3-carbonyl)-2,4-dioxo-bicyclo-[3.2.2]non-8-ene-6-carboxylic acid methyl ester (Example 1.1155) and 0.149 ml (0.48 mmol) of tris(trimethylsilyl)silane in 3.5 ml of toluene and the reaction mixture is stirred at a temperature of 80° C. 5 mg portions of fresh azaisobutyronitrile dissolved in a small amount of toluene are then added four times until, after 6 days, the reaction has come to a complete standstill (LC-MS monitoring). The solvent is then removed under reduced pressure and the residue is purified by silica gel chromatography (eluant: gradient mixture of ethyl acetate/tetrahydrofuran/hexane and 3% triethylamine). After removal of the solvents the triethyl-ammonium salt of 3-(2-methyl-6-difluoromethyl-pyridine-3-carbonyl)-2,4-dioxo-bicyclo-[3.2.2]non-8-ene-6-carboxylic acid methyl ester is obtained.

$^1$H-NMR (300 MHz; CDCl$_3$) δ 7.30 (m, 2H); 6.51 (t, 1H); 6.35 (m, 1H); 6.18 (m, 1H); 3.68 (m, 1H); 3.52 (s, 3H); 3.35 (m, 1H); 3.24 (m, 1H); 3.00 (q, 6H); 2.40 (s, 3H); 2.38 (m, 1H); 2.14 (m, 1H); 1.18 (t, 9H).

The following Tables 1 to 3 list preferred compounds of formula I. The linkage site of the substituent $Z_1$ to the pyridine ring is the unsaturated valency; the free bonds represent methyl groups. For example, in the group

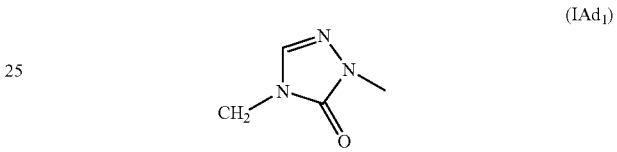

(IAd$_1$)

the —CH$_2$ group at the nitrogen atom adjacent to the keto group is the linkage site; the free bond at the nitrogen atom represents methyl. That group can also be depicted as follows:

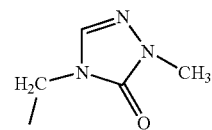

TABLE 1

Compounds of formula Ib:

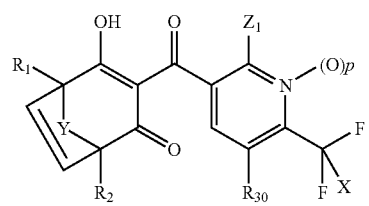

(Ib)

| No. | R$_1$ | R$_2$ | Z$_1$ | R$_{30}$ | X | Y | p | Physical data |
|---|---|---|---|---|---|---|---|---|
| 1.0000 | H | H | CH$_3$ | H | F | NSO$_2$CH$_3$ | 0 | |
| 1.0001 | H | H | CH$_3$ | H | Cl | NSO$_2$CH$_3$ | 0 | |
| 1.0002 | H | H | CH$_3$ | H | H | NSO$_2$CH$_3$ | 0 | |
| 1.0003 | H | H | CH$_3$ | CH$_3$ | F | NSO$_2$CH$_3$ | 0 | |
| 1.0004 | H | H | CH$_3$ | CH$_3$ | Cl | NSO$_2$CH$_3$ | 0 | |
| 1.0005 | H | H | CH$_3$ | CH$_3$ | H | NSO$_2$CH$_3$ | 0 | |
| 1.0006 | H | H | CH$_2$CH$_3$ | H | F | NSO$_2$CH$_3$ | 0 | |
| 1.0007 | H | H | CH$_2$CH$_3$ | H | Cl | NSO$_2$CH$_3$ | 0 | |
| 1.0008 | H | H | CH$_2$CH$_3$ | H | H | NSO$_2$CH$_3$ | 0 | |
| 1.0009 | H | H | CH$_2$CH$_2$CH$_3$ | H | F | NSO$_2$CH$_3$ | 0 | |
| 1.0010 | H | H | CH$_2$CH$_2$CH$_3$ | H | Cl | NSO$_2$CH$_3$ | 0 | |

TABLE 1-continued

Compounds of formula Ib:

(Ib)

| No. | $R_1$ | $R_2$ | $Z_1$ | $R_{30}$ | X | Y | p | Physical data |
|---|---|---|---|---|---|---|---|---|
| 1.0011 | H | H | $CH_2CH_2CH_3$ | H | H | $NSO_2CH_3$ | 0 | |
| 1.0012 | H | H | $CH_2OCH_3$ | H | F | $NSO_2CH_3$ | 0 | |
| 1.0013 | H | H | $CH_2OCH_3$ | H | Cl | $NSO_2CH_3$ | 0 | |
| 1.0014 | H | H | $CH_2OCH_3$ | H | H | $NSO_2CH_3$ | 0 | |
| 1.0015 | H | H | $CH_2OCH_2CH_3$ | H | F | $NSO_2CH_3$ | 0 | |
| 1.0016 | H | H | $CH_2OCH_2CH_3$ | H | Cl | $NSO_2CH_3$ | 0 | |
| 1.0017 | H | H | $CH_2OCH_2CH_3$ | H | H | $NSO_2CH_3$ | 0 | |
| 1.0018 | H | H | $CH_2OCH_2CH_2OCH_3$ | H | F | $NSO_2CH_3$ | 0 | |
| 1.0019 | H | H | $CH_2OCH_2CH_2OCH_3$ | H | Cl | $NSO_2CH_3$ | 0 | |
| 1.0020 | H | H | $CH_2OCH_2CH_2OCH_3$ | H | H | $NSO_2CH_3$ | 0 | |
| 1.0021 | H | H | $CH_2OCH_2CH_2OCH_2CH_3$ | H | F | $NSO_2CH_3$ | 0 | |
| 1.0022 | H | H | $CH_2OCH_2CH_2OCH_2CH_3$ | H | Cl | $NSO_2CH_3$ | 0 | |
| 1.0023 | H | H | $CH_2OCH_2CH_2OCH_2CH_3$ | H | H | $NSO_2CH_3$ | 0 | |
| 1.0024 | H | H | $CH_2CH_2OCH_3$ | H | F | $NSO_2CH_3$ | 0 | |
| 1.0025 | H | H | $CH_2CH_2OCH_3$ | H | Cl | $NSO_2CH_3$ | 0 | |
| 1.0026 | H | H | $CH_2CH_2OCH_3$ | H | H | $NSO_2CH_3$ | 0 | |
| 1.0027 | H | H | $CH_2OCH_2C\equiv CH$ | H | F | $NSO_2CH_3$ | 0 | |
| 1.0028 | H | H | $CH_2OCH_2C\equiv CH$ | H | Cl | $NSO_2CH_3$ | 0 | |
| 1.0029 | H | H | $CH_2OCH_2C\equiv CH$ | H | H | $NSO_2CH_3$ | 0 | |
| 1.0030 | H | H | $CH_2OCH_2C\equiv CCH_3$ | H | F | $NSO_2CH_3$ | 0 | |
| 1.0031 | H | H | $CH_2OCH_2C\equiv CCH_3$ | H | Cl | $NSO_2CH_3$ | 0 | |
| 1.0032 | H | H | $CH_2OCH_2C\equiv CCH_3$ | H | H | $NSO_2CH_3$ | 0 | |
| 1.0033 | H | H | $CH_2CH_2CH_2OCH_3$ | H | F | $NSO_2CH_3$ | 0 | |
| 1.0034 | H | H | $CH_2CH_2CH_2OCH_3$ | H | Cl | $NSO_2CH_3$ | 0 | |
| 1.0035 | H | H | $CH_2CH_2CH_2OCH_3$ | H | H | $NSO_2CH_3$ | 0 | |
| 1.0036 | H | H | $CH_2OCH_2OCH_3$ | H | F | $NSO_2CH_3$ | 0 | |
| 1.0037 | H | H | $CH_2OCH_2OCH_3$ | H | Cl | $NSO_2CH_3$ | 0 | |
| 1.0038 | H | H | $CH_2OCH_2OCH_3$ | H | H | $NSO_2CH_3$ | 0 | |
| 1.0039 | H | H | $CH_2N(CH_3)SO_2CH_3$ | H | F | $NSO_2CH_3$ | 0 | |
| 1.0040 | H | H | $CH_2N(CH_3)SO_2CH_3$ | H | Cl | $NSO_2CH_3$ | 0 | |
| 1.0041 | H | H | $CH_2N(CH_3)SO_2CH_3$ | H | H | $NSO_2CH_3$ | 0 | |
| 1.0042 | H | H | $CF_3$ | H | F | $NSO_2CH_3$ | 0 | |
| 1.0043 | H | H | $CF_3$ | H | Cl | $NSO_2CH_3$ | 0 | |
| 1.0044 | H | H | $CF_3$ | H | H | $NSO_2CH_3$ | 0 | |
| 1.0045 | H | H | $CH_2OCH_2CF_3$ | H | F | $NSO_2CH_3$ | 0 | |
| 1.0046 | H | H | $CH_2OCH_2CF_3$ | H | Cl | $NSO_2CH_3$ | 0 | |
| 1.0047 | H | H | $CH_2OCH_2CF_3$ | H | H | $NSO_2CH_3$ | 0 | |
| 1.0048 | H | H | $CH_2OCH_2Ph$ | H | F | $NSO_2CH_3$ | 0 | |
| 1.0049 | H | H | $CH_2OCH_2Ph$ | H | Cl | $NSO_2CH_3$ | 0 | |
| 1.0050 | H | H | $CH_2OCH_2Ph$ | H | H | $NSO_2CH_3$ | 0 | |
| 1.0051 | H | H | $CH_2OCH_2CH=CH_2$ | H | F | $NSO_2CH_3$ | 0 | |
| 1.0052 | H | H | $CH_2OCH_2CH=CH_2$ | H | Cl | $NSO_2CH_3$ | 0 | |
| 1.0053 | H | H | $CH_2OCH_2CH=CH_2$ | H | H | $NSO_2CH_3$ | 0 | |
| 1.0054 | H | H | (N-methyl-triazolone-CH2) | H | F | $NSO_2CH_3$ | 0 | |
| 1.0055 | H | H | (N-methyl-triazolone-CH2) | H | Cl | $NSO_2CH_3$ | 0 | |

TABLE 1-continued

Compounds of formula Ib:

(Ib)

[Structure: A cyclohexenone ring with OH, R1, R2, Y substituents connected via C(=O) to a pyridine ring bearing Z1, N→(O)p, CF2X, and R30]

| No. | R1 | R2 | Z1 | R30 | X | Y | p | Physical data |
|---|---|---|---|---|---|---|---|---|
| 1.0056 | H | H | 4-(2-methyl-3-oxo-2,3-dihydro-1,2,4-triazol-4-yl)methyl | H | H | NSO$_2$CH$_3$ | 0 | |
| 1.0057 | H | H | (3-methyl-5-oxo-1,3,4-oxadiazol-2-yl)methyl... | H | F | NSO$_2$CH$_3$ | 0 | |
| 1.0058 | H | H | (3-methyl-5-oxo-1,3,4-oxadiazol-2-yl)methyl | H | Cl | NSO$_2$CH$_3$ | 0 | |
| 1.0059 | H | H | (3-methyl-5-oxo-1,3,4-oxadiazol-2-yl)methyl | H | H | NSO$_2$CH$_3$ | 0 | |
| 1.0060 | H | H | CH$_2$-oxiranyl | H | F | NSO$_2$CH$_3$ | 0 | |
| 1.0061 | H | H | CH$_2$-oxiranyl | H | Cl | NSO$_2$CH$_3$ | 0 | |
| 1.0062 | H | H | CH$_2$-oxiranyl | H | H | NSO$_2$CH$_3$ | 0 | |
| 1.0063 | H | H | CH$_2$OCH$_2$-oxiranyl | H | F | NSO$_2$CH$_3$ | 0 | |
| 1.0064 | H | H | CH$_2$OCH$_2$-oxiranyl | H | Cl | NSO$_2$CH$_3$ | 0 | |
| 1.0065 | H | H | CH$_2$OCH$_2$-oxiranyl | H | H | NSO$_2$CH$_3$ | 0 | |
| 1.0066 | H | H | CH$_2$O-oxetanyl | H | F | NSO$_2$CH$_3$ | 0 | |
| 1.0067 | H | H | CH$_2$O-oxetanyl | H | Cl | NSO$_2$CH$_3$ | 0 | |

TABLE 1-continued

Compounds of formula Ib:

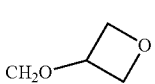

(Ib)

| No. | $R_1$ | $R_2$ | $Z_1$ | $R_{30}$ | X | Y | p | Physical data |
|---|---|---|---|---|---|---|---|---|
| 1.0068 | H | H | 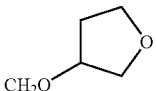 | H | H | $NSO_2CH_3$ | 0 | |
| 1.0069 | H | H | 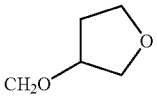 | H | F | $NSO_2CH_3$ | 0 | |
| 1.0070 | H | H | 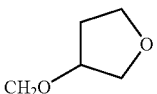 | H | Cl | $NSO_2CH_3$ | 0 | |
| 1.0071 | H | H | 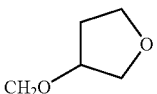 | H | H | $NSO_2CH_3$ | 0 | |
| 1.0072 | H | H | $CH_3$ | H | F | $NSO_2CH_3$ | 1 | |
| 1.0073 | H | H | $CH_2OCH_3$ | H | F | $NSO_2CH_3$ | 1 | |
| 1.0074 | H | H | $CH_2OCH_2CH_2OCH_3$ | H | F | $NSO_2CH_3$ | 1 | |
| 1.0075 | H | H | $CH_2CH_2CH_2OCH_3$ | H | F | $NSO_2CH_3$ | 1 | |
| 1.0076 | H | H | $CH_2CH_3$ | H | F | $NSO_2CH_3$ | 1 | |
| 1.0077 | H | H | $CH_3$ | H | H | $NSO_2CH_3$ | 1 | |
| 1.0078 | H | H | $CH_2OCH_3$ | H | H | $NSO_2CH_3$ | 1 | |
| 1.0079 | H | H | $CH_2OCH_2CH_2OCH_3$ | H | H | $NSO_2CH_3$ | 1 | |
| 1.0080 | H | H | $CH_2CH_2CH_2OCH_3$ | H | H | $NSO_2CH_3$ | 1 | |
| 1.0081 | H | H | $CH_2CH_3$ | H | H | $NSO_2CH_3$ | 1 | |
| 1.0082 | $CH_3$ | $CH_3$ | $CH_3$ | H | F | $NSO_2CH_3$ | 0 | |
| 1.0083 | $CH_3$ | $CH_3$ | $CH_3$ | H | Cl | $NSO_2CH_3$ | 0 | |
| 1.0084 | $CH_3$ | $CH_3$ | $CH_3$ | H | H | $NSO_2CH_3$ | 0 | |
| 1.0085 | $CH_3$ | $CH_3$ | $CH_3$ | $CH_3$ | F | $NSO_2CH_3$ | 0 | |
| 1.0086 | $CH_3$ | $CH_3$ | $CH_3$ | $CH_3$ | Cl | $NSO_2CH_3$ | 0 | |
| 1.0087 | $CH_3$ | $CH_3$ | $CH_3$ | $CH_3$ | H | $NSO_2CH_3$ | 0 | |
| 1.0088 | $CH_3$ | $CH_3$ | $CH_2CH_3$ | H | F | $NSO_2CH_3$ | 0 | |
| 1.0089 | $CH_3$ | $CH_3$ | $CH_2CH_3$ | H | Cl | $NSO_2CH_3$ | 0 | |
| 1.0090 | $CH_3$ | $CH_3$ | $CH_2CH_3$ | H | H | $NSO_2CH_3$ | 0 | |
| 1.0091 | $CH_3$ | $CH_3$ | $CH_2CH_2CH_3$ | H | F | $NSO_2CH_3$ | 0 | |
| 1.0092 | $CH_3$ | $CH_3$ | $CH_2CH_2CH_3$ | H | Cl | $NSO_2CH_3$ | 0 | |
| 1.0093 | $CH_3$ | $CH_3$ | $CH_2CH_2CH_3$ | H | H | $NSO_2CH_3$ | 0 | |
| 1.0094 | $CH_3$ | $CH_3$ | $CH_2OCH_3$ | H | F | $NSO_2CH_3$ | 0 | |
| 1.0095 | $CH_3$ | $CH_3$ | $CH_2OCH_3$ | H | Cl | $NSO_2CH_3$ | 0 | |
| 1.0096 | $CH_3$ | $CH_3$ | $CH_2OCH_3$ | H | H | $NSO_2CH_3$ | 0 | |
| 1.0097 | $CH_3$ | $CH_3$ | $CH_2OCH_2CH_3$ | H | F | $NSO_2CH_3$ | 0 | |
| 1.0098 | $CH_3$ | $CH_3$ | $CH_2OCH_2CH_3$ | H | Cl | $NSO_2CH_3$ | 0 | |
| 1.0099 | $CH_3$ | $CH_3$ | $CH_2OCH_2CH_3$ | H | H | $NSO_2CH_3$ | 0 | |
| 1.0100 | $CH_3$ | $CH_3$ | $CH_2OCH_2CH_2OCH_3$ | H | F | $NSO_2CH_3$ | 0 | |
| 1.0101 | $CH_3$ | $CH_3$ | $CH_2OCH_2CH_2OCH_3$ | H | Cl | $NSO_2CH_3$ | 0 | |
| 1.0102 | $CH_3$ | $CH_3$ | $CH_2OCH_2CH_2OCH_3$ | H | H | $NSO_2CH_3$ | 0 | |
| 1.0103 | $CH_3$ | $CH_3$ | $CH_2OCH_2CH_2OCH_2CH_3$ | H | F | $NSO_2CH_3$ | 0 | |
| 1.0104 | $CH_3$ | $CH_3$ | $CH_2OCH_2CH_2OCH_2CH_3$ | H | Cl | $NSO_2CH_3$ | 0 | |
| 1.0105 | $CH_3$ | $CH_3$ | $CH_2OCH_2CH_2OCH_2CH_3$ | H | H | $NSO_2CH_3$ | 0 | |
| 1.0106 | $CH_3$ | $CH_3$ | $CH_2CH_2OCH_3$ | H | F | $NSO_2CH_3$ | 0 | |
| 1.0107 | $CH_3$ | $CH_3$ | $CH_2CH_2OCH_3$ | H | Cl | $NSO_2CH_3$ | 0 | |
| 1.0108 | $CH_3$ | $CH_3$ | $CH_2CH_2OCH_3$ | H | H | $NSO_2CH_3$ | 0 | |
| 1.0109 | $CH_3$ | $CH_3$ | $CH_2OCH_2C{\equiv}CH$ | H | F | $NSO_2CH_3$ | 0 | |
| 1.0110 | $CH_3$ | $CH_3$ | $CH_2OCH_2C{\equiv}CH$ | H | Cl | $NSO_2CH_3$ | 0 | |
| 1.0111 | $CH_3$ | $CH_3$ | $CH_2OCH_2C{\equiv}CH$ | H | H | $NSO_2CH_3$ | 0 | |
| 1.0112 | $CH_3$ | $CH_3$ | $CH_2OCH_2C{\equiv}CCH_3$ | H | F | $NSO_2CH_3$ | 0 | |
| 1.0113 | $CH_3$ | $CH_3$ | $CH_2OCH_2C{\equiv}CCH_3$ | H | Cl | $NSO_2CH_3$ | 0 | |

TABLE 1-continued

Compounds of formula Ib:

(Ib)

| No. | $R_1$ | $R_2$ | $Z_1$ | $R_{30}$ | X | Y | p | Physical data |
|---|---|---|---|---|---|---|---|---|
| 1.0114 | $CH_3$ | $CH_3$ | $CH_2OCH_2C\equiv CCH_3$ | H | H | $NSO_2CH_3$ | 0 | |
| 1.0115 | $CH_3$ | $CH_3$ | $CH_2CH_2CH_2OCH_3$ | H | F | $NSO_2CH_3$ | 0 | |
| 1.0116 | $CH_3$ | $CH_3$ | $CH_2CH_2CH_2OCH_3$ | H | Cl | $NSO_2CH_3$ | 0 | |
| 1.0117 | $CH_3$ | $CH_3$ | $CH_2CH_2CH_2OCH_3$ | H | H | $NSO_2CH_3$ | 0 | |
| 1.0118 | $CH_3$ | $CH_3$ | $CH_2OCH_2OCH_3$ | H | F | $NSO_2CH_3$ | 0 | |
| 1.0119 | $CH_3$ | $CH_3$ | $CH_2OCH_2OCH_3$ | H | Cl | $NSO_2CH_3$ | 0 | |
| 1.0120 | $CH_3$ | $CH_3$ | $CH_2OCH_2OCH_3$ | H | H | $NSO_2CH_3$ | 0 | |
| 1.0121 | $CH_3$ | $CH_3$ | $CH_2N(CH_3)SO_2CH_3$ | H | F | $NSO_2CH_3$ | 0 | |
| 1.0122 | $CH_3$ | $CH_3$ | $CH_2N(CH_3)SO_2CH_3$ | H | Cl | $NSO_2CH_3$ | 0 | |
| 1.0123 | $CH_3$ | $CH_3$ | $CH_2N(CH_3)SO_2CH_3$ | H | H | $NSO_2CH_3$ | 0 | |
| 1.0124 | $CH_3$ | $CH_3$ | $CF_3$ | H | F | $NSO_2CH_3$ | 0 | |
| 1.0125 | $CH_3$ | $CH_3$ | $CF_3$ | H | Cl | $NSO_2CH_3$ | 0 | |
| 1.0126 | $CH_3$ | $CH_3$ | $CF_3$ | H | H | $NSO_2CH_3$ | 0 | |
| 1.0127 | $CH_3$ | $CH_3$ | $CH_2OCH_2CF_3$ | H | F | $NSO_2CH_3$ | 0 | |
| 1.0128 | $CH_3$ | $CH_3$ | $CH_2OCH_2CF_3$ | H | Cl | $NSO_2CH_3$ | 0 | |
| 1.0129 | $CH_3$ | $CH_3$ | $CH_2OCH_2CF_3$ | H | H | $NSO_2CH_3$ | 0 | |
| 1.0130 | $CH_3$ | $CH_3$ | $CH_2OCH_2Ph$ | H | F | $NSO_2CH_3$ | 0 | |
| 1.0131 | $CH_3$ | $CH_3$ | $CH_2OCH_2Ph$ | H | Cl | $NSO_2CH_3$ | 0 | |
| 1.0132 | $CH_3$ | $CH_3$ | $CH_2OCH_2Ph$ | H | H | $NSO_2CH_3$ | 0 | |
| 1.0133 | $CH_3$ | $CH_3$ | $CH_2OCH_2CH=CH_2$ | H | F | $NSO_2CH_3$ | 0 | |
| 1.0134 | $CH_3$ | $CH_3$ | $CH_2OCH_2CH=CH_2$ | H | Cl | $NSO_2CH_3$ | 0 | |
| 1.0135 | $CH_3$ | $CH_3$ | $CH_2OCH_2CH=CH_2$ | H | H | $NSO_2CH_3$ | 0 | |
| 1.0136 | $CH_3$ | $CH_3$ | 4-(CH2)-2-methyl-1,2,4-triazol-3(2H)-one | H | F | $NSO_2CH_3$ | 0 | |
| 1.0137 | $CH_3$ | $CH_3$ | 4-(CH2)-2-methyl-1,2,4-triazol-3(2H)-one | H | Cl | $NSO_2CH_3$ | 0 | |
| 1.0138 | $CH_3$ | $CH_3$ | 4-(CH2)-2-methyl-1,2,4-triazol-3(2H)-one | H | H | $NSO_2CH_3$ | 0 | |
| 1.0139 | $CH_3$ | $CH_3$ | 3-methyl-1,3,4-oxadiazol-2(3H)-one-CH2- | H | F | $NSO_2CH_3$ | 0 | |
| 1.0140 | $CH_3$ | $CH_3$ | 3-methyl-1,3,4-oxadiazol-2(3H)-one-CH2- | H | Cl | $NSO_2CH_3$ | 0 | |

TABLE 1-continued

Compounds of formula Ib:

(Ib)

| No. | $R_1$ | $R_2$ | $Z_1$ | $R_{30}$ | X | Y | p | Physical data |
|---|---|---|---|---|---|---|---|---|
| 1.0141 | $CH_3$ | $CH_3$ | 3-methyl-5-(CH_2-)-1,3,4-oxadiazol-2(3H)-one | H | H | $NSO_2CH_3$ | 0 | |
| 1.0142 | $CH_3$ | $CH_3$ | $CH_2$-oxiranyl | H | F | $NSO_2CH_3$ | 0 | |
| 1.0143 | $CH_3$ | $CH_3$ | $CH_2$-oxiranyl | H | Cl | $NSO_2CH_3$ | 0 | |
| 1.0144 | $CH_3$ | $CH_3$ | $CH_2$-oxiranyl | H | H | $NSO_2CH_3$ | 0 | |
| 1.0145 | $CH_3$ | $CH_3$ | $CH_2OCH_2$-oxiranyl | H | F | $NSO_2CH_3$ | 0 | |
| 1.0146 | $CH_3$ | $CH_3$ | $CH_2OCH_2$-oxiranyl | H | Cl | $NSO_2CH_3$ | 0 | |
| 1.0147 | $CH_3$ | $CH_3$ | $CH_2OCH_2$-oxiranyl | H | H | $NSO_2CH_3$ | 0 | |
| 1.0148 | $CH_3$ | $CH_3$ | $CH_2O$-oxetan-3-yl | H | F | $NSO_2CH_3$ | 0 | |
| 1.0149 | $CH_3$ | $CH_3$ | $CH_2O$-oxetan-3-yl | H | Cl | $NSO_2CH_3$ | 0 | |
| 1.0150 | $CH_3$ | $CH_3$ | $CH_2O$-oxetan-3-yl | H | H | $NSO_2CH_3$ | 0 | |
| 1.0151 | $CH_3$ | $CH_3$ | $CH_2O$-tetrahydrofuran-3-yl | H | F | $NSO_2CH_3$ | 0 | |
| 1.0152 | $CH_3$ | $CH_3$ | $CH_2O$-tetrahydrofuran-3-yl | H | Cl | $NSO_2CH_3$ | 0 | |
| 1.0153 | $CH_3$ | $CH_3$ | $CH_2O$-tetrahydrofuran-3-yl | H | H | $NSO_2CH_3$ | 0 | |
| 1.0154 | $CH_3$ | $CH_3$ | $CH_3$ | H | F | $NSO_2CH_3$ | 1 | |
| 1.0155 | $CH_3$ | $CH_3$ | $CH_2OCH_3$ | H | F | $NSO_2CH_3$ | 1 | |

TABLE 1-continued

Compounds of formula Ib:

$$(Ib)$$

| No. | $R_1$ | $R_2$ | $Z_1$ | $R_{30}$ | X | Y | p | Physical data |
|---|---|---|---|---|---|---|---|---|
| 1.0156 | $CH_3$ | $CH_3$ | $CH_2OCH_2CH_2OCH_3$ | H | F | $NSO_2CH_3$ | 1 | |
| 1.0157 | $CH_3$ | $CH_3$ | $CH_2CH_2CH_2OCH_3$ | H | F | $NSO_2CH_3$ | 1 | |
| 1.0158 | $CH_3$ | $CH_3$ | $CH_2CH_3$ | H | F | $NSO_2CH_3$ | 1 | |
| 1.0159 | $CH_3$ | $CH_3$ | $CH_3$ | H | H | $NSO_2CH_3$ | 1 | |
| 1.0160 | $CH_3$ | $CH_3$ | $CH_2OCH_3$ | H | H | $NSO_2CH_3$ | 1 | |
| 1.0161 | $CH_3$ | $CH_3$ | $CH_2OCH_2CH_2OCH_3$ | H | H | $NSO_2CH_3$ | 1 | |
| 1.0162 | $CH_3$ | $CH_3$ | $CH_2CH_2CH_2OCH_3$ | H | H | $NSO_2CH_3$ | 1 | |
| 1.0163 | $CH_3$ | $CH_3$ | $CH_2CH_3$ | H | H | $NSO_2CH_3$ | 1 | |
| 1.0164 | H | $CH_3$ | $CH_3$ | H | F | $NSO_2CH_3$ | 0 | |
| 1.0165 | H | $CH_3$ | $CH_3$ | H | Cl | $NSO_2CH_3$ | 0 | |
| 1.0166 | H | $CH_3$ | $CH_3$ | H | H | $NSO_2CH_3$ | 0 | |
| 1.0167 | H | $CH_3$ | $CH_3$ | $CH_3$ | F | $NSO_2CH_3$ | 0 | |
| 1.0168 | H | $CH_3$ | $CH_3$ | $CH_3$ | Cl | $NSO_2CH_3$ | 0 | |
| 1.0169 | H | $CH_3$ | $CH_3$ | $CH_3$ | H | $NSO_2CH_3$ | 0 | |
| 1.0170 | H | $CH_3$ | $CH_2CH_3$ | H | F | $NSO_2CH_3$ | 0 | |
| 1.0171 | H | $CH_3$ | $CH_2CH_3$ | H | Cl | $NSO_2CH_3$ | 0 | |
| 1.0172 | H | $CH_3$ | $CH_2CH_3$ | H | H | $NSO_2CH_3$ | 0 | |
| 1.0173 | H | $CH_3$ | $CH_2CH_2CH_3$ | H | F | $NSO_2CH_3$ | 0 | |
| 1.0174 | H | $CH_3$ | $CH_2CH_2CH_3$ | H | Cl | $NSO_2CH_3$ | 0 | |
| 1.0175 | H | $CH_3$ | $CH_2CH_2CH_3$ | H | H | $NSO_2CH_3$ | 0 | |
| 1.0176 | H | $CH_3$ | $CH_2OCH_3$ | H | F | $NSO_2CH_3$ | 0 | |
| 1.0177 | H | $CH_3$ | $CH_2OCH_3$ | H | Cl | $NSO_2CH_3$ | 0 | |
| 1.0178 | H | $CH_3$ | $CH_2OCH_3$ | H | H | $NSO_2CH_3$ | 0 | |
| 1.0179 | H | $CH_3$ | $CH_2OCH_2CH_3$ | H | F | $NSO_2CH_3$ | 0 | |
| 1.0180 | H | $CH_3$ | $CH_2OCH_2CH_3$ | H | Cl | $NSO_2CH_3$ | 0 | |
| 1.0181 | H | $CH_3$ | $CH_2OCH_2CH_3$ | H | H | $NSO_2CH_3$ | 0 | |
| 1.0182 | H | $CH_3$ | $CH_2OCH_2CH_2OCH_3$ | H | F | $NSO_2CH_3$ | 0 | |
| 1.0183 | H | $CH_3$ | $CH_2OCH_2CH_2OCH_3$ | H | Cl | $NSO_2CH_3$ | 0 | |
| 1.0184 | H | $CH_3$ | $CH_2OCH_2CH_2OCH_3$ | H | H | $NSO_2CH_3$ | 0 | |
| 1.0185 | H | $CH_3$ | $CH_2OCH_2CH_2OCH_2CH_3$ | H | F | $NSO_2CH_3$ | 0 | |
| 1.0186 | H | $CH_3$ | $CH_2OCH_2CH_2OCH_2CH_3$ | H | Cl | $NSO_2CH_3$ | 0 | |
| 1.0187 | H | $CH_3$ | $CH_2OCH_2CH_2OCH_2CH_3$ | H | H | $NSO_2CH_3$ | 0 | |
| 1.0188 | H | $CH_3$ | $CH_2CH_2OCH_3$ | H | F | $NSO_2CH_3$ | 0 | |
| 1.0189 | H | $CH_3$ | $CH_2CH_2OCH_3$ | H | Cl | $NSO_2CH_3$ | 0 | |
| 1.0190 | H | $CH_3$ | $CH_2CH_2OCH_3$ | H | H | $NSO_2CH_3$ | 0 | |
| 1.0191 | H | $CH_3$ | $CH_2OCH_2C\equiv CH$ | H | F | $NSO_2CH_3$ | 0 | |
| 1.0192 | H | $CH_3$ | $CH_2OCH_2C\equiv CH$ | H | Cl | $NSO_2CH_3$ | 0 | |
| 1.0193 | H | $CH_3$ | $CH_2OCH_2C\equiv CH$ | H | H | $NSO_2CH_3$ | 0 | |
| 1.0194 | H | $CH_3$ | $CH_2OCH_2C\equiv CCH_3$ | H | F | $NSO_2CH_3$ | 0 | |
| 1.0195 | H | $CH_3$ | $CH_2OCH_2C\equiv CCH_3$ | H | Cl | $NSO_2CH_3$ | 0 | |
| 1.0196 | H | $CH_3$ | $CH_2OCH_2C\equiv CCH_3$ | H | H | $NSO_2CH_3$ | 0 | |
| 1.0197 | H | $CH_3$ | $CH_2CH_2CH_2OCH_3$ | H | F | $NSO_2CH_3$ | 0 | |
| 1.0198 | H | $CH_3$ | $CH_2CH_2CH_2OCH_3$ | H | Cl | $NSO_2CH_3$ | 0 | |
| 1.0199 | H | $CH_3$ | $CH_2CH_2CH_2OCH_3$ | H | H | $NSO_2CH_3$ | 0 | |
| 1.0200 | H | $CH_3$ | $CH_2OCH_2OCH_3$ | H | F | $NSO_2CH_3$ | 0 | |
| 1.0201 | H | $CH_3$ | $CH_2OCH_2OCH_3$ | H | Cl | $NSO_2CH_3$ | 0 | |
| 1.0202 | H | $CH_3$ | $CH_2OCH_2OCH_3$ | H | H | $NSO_2CH_3$ | 0 | |
| 1.0203 | H | $CH_3$ | $CH_2N(CH_3)SO_2CH_3$ | H | F | $NSO_2CH_3$ | 0 | |
| 1.0204 | H | $CH_3$ | $CH_2N(CH_3)SO_2CH_3$ | H | Cl | $NSO_2CH_3$ | 0 | |
| 1.0205 | H | $CH_3$ | $CH_2N(CH_3)SO_2CH_3$ | H | H | $NSO_2CH_3$ | 0 | |
| 1.0206 | H | $CH_3$ | $CF_3$ | H | F | $NSO_2CH_3$ | 0 | |
| 1.0207 | H | $CH_3$ | $CF_3$ | H | Cl | $NSO_2CH_3$ | 0 | |
| 1.0208 | H | $CH_3$ | $CF_3$ | H | H | $NSO_2CH_3$ | 0 | |
| 1.0209 | H | $CH_3$ | $CH_2OCH_2CF_3$ | H | F | $NSO_2CH_3$ | 0 | |
| 1.0210 | H | $CH_3$ | $CH_2OCH_2CF_3$ | H | Cl | $NSO_2CH_3$ | 0 | |
| 1.0211 | H | $CH_3$ | $CH_2OCH_2CF_3$ | H | H | $NSO_2CH_3$ | 0 | |
| 1.0212 | H | $CH_3$ | $CH_2OCH_2Ph$ | H | F | $NSO_2CH_3$ | 0 | |
| 1.0213 | H | $CH_3$ | $CH_2OCH_2Ph$ | H | Cl | $NSO_2CH_3$ | 0 | |
| 1.0214 | H | $CH_3$ | $CH_2OCH_2Ph$ | H | H | $NSO_2CH_3$ | 0 | |
| 1.0215 | H | $CH_3$ | $CH_2OCH_2CH=CH_2$ | H | F | $NSO_2CH_3$ | 0 | |
| 1.0216 | H | $CH_3$ | $CH_2OCH_2CH=CH_2$ | H | Cl | $NSO_2CH_3$ | 0 | |
| 1.0217 | H | $CH_3$ | $CH_2OCH_2CH=CH_2$ | H | H | $NSO_2CH_3$ | 0 | |

TABLE 1-continued

Compounds of formula Ib:

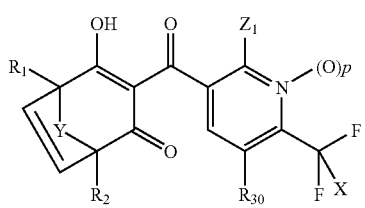

(Ib)

| No. | R₁ | R₂ | Z₁ | R₃₀ | X | Y | p | Physical data |
|---|---|---|---|---|---|---|---|---|
| 1.0218 | H | CH₃ | 4-(2-methyl-3-oxo-2,3-dihydro-1,2,4-triazol-4-yl)methyl | H | F | NSO₂CH₃ | 0 | |
| 1.0219 | H | CH₃ | 4-(2-methyl-3-oxo-2,3-dihydro-1,2,4-triazol-4-yl)methyl | H | Cl | NSO₂CH₃ | 0 | |
| 1.0220 | H | CH₃ | 4-(2-methyl-3-oxo-2,3-dihydro-1,2,4-triazol-4-yl)methyl | H | H | NSO₂CH₃ | 0 | |
| 1.0221 | H | CH₃ | (3-methyl-2-oxo-2,3-dihydro-1,3,4-oxadiazol-5-yl)methyl | H | F | NSO₂CH₃ | 0 | |
| 1.0222 | H | CH₃ | (3-methyl-2-oxo-2,3-dihydro-1,3,4-oxadiazol-5-yl)methyl | H | Cl | NSO₂CH₃ | 0 | |
| 1.0223 | H | CH₃ | (3-methyl-2-oxo-2,3-dihydro-1,3,4-oxadiazol-5-yl)methyl | H | H | NSO₂CH₃ | 0 | |
| 1.0224 | H | CH₃ | CH₂-oxiranyl | H | F | NSO₂CH₃ | 0 | |
| 1.0225 | H | CH₃ | CH₂-oxiranyl | H | Cl | NSO₂CH₃ | 0 | |
| 1.0226 | H | CH₃ | CH₂-oxiranyl | H | H | NSO₂CH₃ | 0 | |
| 1.0227 | H | CH₃ | CH₂OCH₂-oxiranyl | H | F | NSO₂CH₃ | 0 | |
| 1.0228 | H | CH₃ | CH₂OCH₂-oxiranyl | H | Cl | NSO₂CH₃ | 0 | |

TABLE 1-continued

Compounds of formula Ib:

(Ib)

| No. | R₁ | R₂ | Z₁ | R₃₀ | X | Y | p | Physical data |
|---|---|---|---|---|---|---|---|---|
| 1.0229 | H | CH$_3$ | CH$_2$OCH$_2$-(oxiranyl) | H | H | NSO$_2$CH$_3$ | 0 | |
| 1.0230 | H | CH$_3$ | CH$_2$O-(oxetan-3-yl) | H | F | NSO$_2$CH$_3$ | 0 | |
| 1.0231 | H | CH$_3$ | CH$_2$O-(oxetan-3-yl) | H | Cl | NSO$_2$CH$_3$ | 0 | |
| 1.0232 | H | CH$_3$ | CH$_2$O-(oxetan-3-yl) | H | H | NSO$_2$CH$_3$ | 0 | |
| 1.0233 | H | CH$_3$ | CH$_2$O-(tetrahydrofuran-3-yl) | H | F | NSO$_2$CH$_3$ | 0 | |
| 1.0234 | H | CH$_3$ | CH$_2$O-(tetrahydrofuran-3-yl) | H | Cl | NSO$_2$CH$_3$ | 0 | |
| 1.0235 | H | CH$_3$ | CH$_2$O-(tetrahydrofuran-3-yl) | H | H | NSO$_2$CH$_3$ | 0 | |
| 1.0236 | H | CH$_3$ | CH$_3$ | H | F | NSO$_2$CH$_3$ | 1 | |
| 1.0237 | H | CH$_3$ | CH$_2$OCH$_3$ | H | F | NSO$_2$CH$_3$ | 1 | |
| 1.0238 | H | CH$_3$ | CH$_2$OCH$_2$CH$_2$OCH$_3$ | H | F | NSO$_2$CH$_3$ | 1 | |
| 1.0239 | H | CH$_3$ | CH$_2$CH$_2$CH$_2$OCH$_3$ | H | F | NSO$_2$CH$_3$ | 1 | |
| 1.0240 | H | CH$_3$ | CH$_2$CH$_3$ | H | F | NSO$_2$CH$_3$ | 1 | |
| 1.0241 | H | CH$_3$ | CH$_3$ | H | H | NSO$_2$CH$_3$ | 1 | |
| 1.0242 | H | CH$_3$ | CH$_2$OCH$_3$ | H | H | NSO$_2$CH$_3$ | 1 | |
| 1.0243 | H | CH$_3$ | CH$_2$OCH$_2$CH$_2$OCH$_3$ | H | H | NSO$_2$CH$_3$ | 1 | |
| 1.0244 | H | CH$_3$ | CH$_2$CH$_2$CH$_2$OCH$_3$ | H | H | NSO$_2$CH$_3$ | 1 | |
| 1.0245 | H | CH$_3$ | CH$_2$CH$_3$ | H | H | NSO$_2$CH$_3$ | 1 | |
| 1.0246 | H | H | CH$_2$OCH$_2$CH$_2$OCH$_3$ | H | F | O | 0 | |
| 1.0247 | H | H | CH$_2$OCH$_2$CH$_2$OCH$_3$ | H | Cl | O | 0 | |
| 1.0248 | H | H | CH$_2$OCH$_2$CH$_2$OCH$_3$ | H | H | O | 0 | |
| 1.0249 | H | H | CH$_2$OCH$_2$CH$_2$OCH$_2$CH$_3$ | H | F | O | 0 | |
| 1.0250 | H | H | CH$_2$OCH$_2$CH$_2$OCH$_2$CH$_3$ | H | Cl | O | 0 | |
| 1.0251 | H | H | CH$_2$OCH$_2$CH$_2$OCH$_2$CH$_3$ | H | H | O | 0 | |
| 1.0252 | H | H | CH$_2$N(CH$_3$)SO$_2$CH$_3$ | H | F | O | 0 | |
| 1.0253 | H | H | CH$_2$N(CH$_3$)SO$_2$CH$_3$ | H | Cl | O | 0 | |
| 1.0254 | H | H | CH$_2$N(CH$_3$)SO$_2$CH$_3$ | H | H | O | 0 | |
| 1.0255 | H | H | CH$_2$OCH$_2$Ph | H | F | O | 0 | |
| 1.0256 | H | H | CH$_2$OCH$_2$Ph | H | Cl | O | 0 | |
| 1.0257 | H | H | CH$_2$OCH$_2$Ph | H | H | O | 0 | |
| 1.0258 | H | H | CH$_2$OCH$_2$CH$_2$OH | H | F | O | 0 | |
| 1.0259 | H | H | CH$_2$OCH$_2$CH$_2$OH | H | Cl | O | 0 | |
| 1.0260 | H | H | CH$_2$OCH$_2$CH$_2$OH | H | H | O | 0 | |
| 1.0261 | H | H | CH$_2$OCH$_2$CH$_2$Cl | H | F | O | 0 | |
| 1.0262 | H | H | CH$_2$OCH$_2$CH$_2$Cl | H | Cl | O | 0 | |
| 1.0263 | H | H | CH$_2$OCH$_2$CH$_2$Cl | H | H | O | 0 | |
| 1.0264 | H | H | CH$_2$OCH$_2$CF$_3$ | H | F | O | 0 | |

TABLE 1-continued

Compounds of formula Ib:

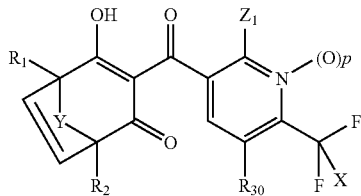
(Ib)

| No. | R$_1$ | R$_2$ | Z$_1$ | R$_{30}$ | X | Y | p | Physical data |
|---|---|---|---|---|---|---|---|---|
| 1.0265 | H | H | CH$_2$OCH$_2$CF$_3$ | H | Cl | O | 0 | |
| 1.0266 | H | H | CH$_2$OCH$_2$CF$_3$ | H | H | O | 0 | |
| 1.0267 | H | H | CH$_2$OCH$_2$CH=CH$_2$ | H | F | O | 0 | |
| 1.0268 | H | H | CH$_2$OCH$_2$CH=CH$_2$ | H | Cl | O | 0 | |
| 1.0269 | H | H | CH$_2$OCH$_2$CH=CH$_2$ | H | H | O | 0 | |
| 1.0270 | H | H | CH$_2$O(CO)CH$_3$ | H | F | O | 0 | |
| 1.0271 | H | H | CH$_2$O(CO)CH$_3$ | H | Cl | O | 0 | |
| 1.0272 | H | H | CH$_2$O(CO)CH$_3$ | H | H | O | 0 | |
| 1.0273 | H | H | CH$_2$OCH$_2$C≡CH | H | F | O | 0 | |
| 1.0274 | H | H | CH$_2$OCH$_2$C≡CH | H | Cl | O | 0 | |
| 1.0275 | H | H | CH$_2$OCH$_2$C≡CH | H | H | O | 0 | |
| 1.0276 | H | H | CH$_2$OCH$_2$C≡CCH$_3$ | H | F | O | 0 | |
| 1.0277 | H | H | CH$_2$OCH$_2$C≡CCH$_3$ | H | Cl | O | 0 | |
| 1.0278 | H | H | CH$_2$OCH$_2$C≡CCH$_3$ | H | H | O | 0 | |
| 1.0279 | H | H | triazolinone-CH$_2$ | H | F | O | 0 | |
| 1.0280 | H | H | triazolinone-CH$_2$ | H | Cl | O | 0 | |
| 1.0281 | H | H | triazolinone-CH$_2$ | H | H | O | 0 | |
| 1.0282 | H | H | oxadiazolone-CH$_2$ | H | F | O | 0 | |
| 1.0283 | H | H | oxadiazolone-CH$_2$ | H | Cl | O | 0 | |
| 1.0284 | H | H | oxadiazolone-CH$_2$ | H | H | O | 0 | |
| 1.0285 | H | H | CH$_2$-oxiranyl | H | F | O | 0 | |

TABLE 1-continued

Compounds of formula Ib:

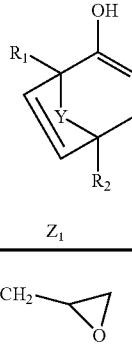

(Ib)

| No. | $R_1$ | $R_2$ | $Z_1$ | $R_{30}$ | X | Y | p | Physical data |
|---|---|---|---|---|---|---|---|---|
| 1.0286 | H | H | 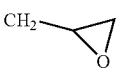 | H | Cl | O | 0 | |
| 1.0287 | H | H | 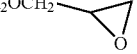 | H | H | O | 0 | |
| 1.0288 | H | H | 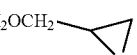 | H | F | O | 0 | |
| 1.0289 | H | H |  | H | Cl | O | 0 | |
| 1.0290 | H | H |  | H | H | O | 0 | |
| 1.0291 | H | H |  | H | F | O | 0 | |
| 1.0292 | H | H | 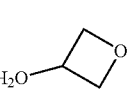 | H | Cl | O | 0 | |
| 1.0293 | H | H | 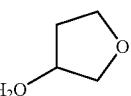 | H | H | O | 0 | |
| 1.0294 | H | H | 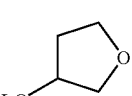 | H | F | O | 0 | |
| 1.0295 | H | H | 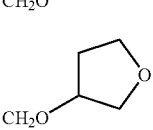 | H | Cl | O | 0 | |
| 1.0296 | H | H | 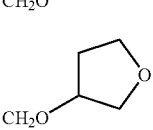 | H | H | O | 0 | |
| 1.0297 | H | H | $CH_2OCH_2CH_2OCH_3$ | H | F | O | 1 | |
| 1.0298 | H | H | $CH_2OCH_2CH_2OCH_3$ | H | H | O | 1 | |
| 1.0299 | H | H | $CH_2OCH_2CH_2OCH_2CH_3$ | H | F | O | 1 | |
| 1.0300 | H | H | $CH_2OCH_2CH_2OCH_2CH_3$ | H | H | O | 1 | |
| 1.0301 | $CH_3$ | $CH_3$ | $CH_2OCH_2CH_2OCH_3$ | H | F | O | 0 | see Example P10 |
| 1.0302 | $CH_3$ | $CH_3$ | $CH_2OCH_2CH_2OCH_3$ | H | Cl | O | 0 | |
| 1.0303 | $CH_3$ | $CH_3$ | $CH_2OCH_2CH_2OCH_3$ | H | H | O | 0 | |
| 1.0304 | $CH_3$ | $CH_3$ | $CH_2OCH_2CH_2OCH_2CH_3$ | H | F | O | 0 | |
| 1.0305 | $CH_3$ | $CH_3$ | $CH_2OCH_2CH_2OCH_2CH_3$ | H | Cl | O | 0 | |
| 1.0306 | $CH_3$ | $CH_3$ | $CH_2OCH_2CH_2OCH_2CH_3$ | H | H | O | 0 | |
| 1.0307 | $CH_3$ | $CH_3$ | $CH_2N(CH_3)SO_2CH_3$ | H | F | O | 0 | |
| 1.0308 | $CH_3$ | $CH_3$ | $CH_2N(CH_3)SO_2CH_3$ | H | Cl | O | 0 | |

TABLE 1-continued

Compounds of formula Ib:

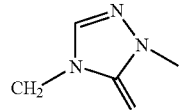
(Ib)

| No. | $R_1$ | $R_2$ | $Z_1$ | $R_{30}$ | X | Y | p | Physical data |
|---|---|---|---|---|---|---|---|---|
| 1.0309 | $CH_3$ | $CH_3$ | $CH_2N(CH_3)SO_2CH_3$ | H | H | O | 0 | |
| 1.0310 | $CH_3$ | $CH_3$ | $CH_2OCH_2Ph$ | H | F | O | 0 | |
| 1.0311 | $CH_3$ | $CH_3$ | $CH_2OCH_2Ph$ | H | Cl | O | 0 | |
| 1.0312 | $CH_3$ | $CH_3$ | $CH_2OCH_2Ph$ | H | H | O | 0 | |
| 1.0313 | $CH_3$ | $CH_3$ | $CH_2OCH_2CH_2OH$ | H | F | O | 0 | |
| 1.0314 | $CH_3$ | $CH_3$ | $CH_2OCH_2CH_2OH$ | H | Cl | O | 0 | |
| 1.0315 | $CH_3$ | $CH_3$ | $CH_2OCH_2CH_2OH$ | H | H | O | 0 | |
| 1.0316 | $CH_3$ | $CH_3$ | $CH_2OCH_2CH_2Cl$ | H | F | O | 0 | |
| 1.0317 | $CH_3$ | $CH_3$ | $CH_2OCH_2CH_2Cl$ | H | Cl | O | 0 | |
| 1.0318 | $CH_3$ | $CH_3$ | $CH_2OCH_2CH_2Cl$ | H | H | O | 0 | |
| 1.0319 | $CH_3$ | $CH_3$ | $CH_2OCH_2CF_3$ | H | F | O | 0 | |
| 1.0320 | $CH_3$ | $CH_3$ | $CH_2OCH_2CF_3$ | H | Cl | O | 0 | |
| 1.0321 | $CH_3$ | $CH_3$ | $CH_2OCH_2CF_3$ | H | H | O | 0 | |
| 1.0322 | $CH_3$ | $CH_3$ | $CH_2OCH_2CH{=}CH_2$ | H | F | O | 0 | |
| 1.0323 | $CH_3$ | $CH_3$ | $CH_2OCH_2CH{=}CH_2$ | H | Cl | O | 0 | |
| 1.0324 | $CH_3$ | $CH_3$ | $CH_2OCH_2CH{=}CH_2$ | H | H | O | 0 | |
| 1.0325 | $CH_3$ | $CH_3$ | $CH_2O(CO)CH_3$ | H | F | O | 0 | |
| 1.0326 | $CH_3$ | $CH_3$ | $CH_2O(CO)CH_3$ | H | Cl | O | 0 | |
| 1.0327 | $CH_3$ | $CH_3$ | $CH_2O(CO)CH_3$ | H | H | O | 0 | |
| 1.0328 | $CH_3$ | $CH_3$ | $CH_2OCH_2C{\equiv}CH$ | H | F | O | 0 | |
| 1.0329 | $CH_3$ | $CH_3$ | $CH_2OCH_2C{\equiv}CH$ | H | Cl | O | 0 | |
| 1.0330 | $CH_3$ | $CH_3$ | $CH_2OCH_2C{\equiv}CH$ | H | H | O | 0 | |
| 1.0331 | $CH_3$ | $CH_3$ | $CH_2OCH_2C{\equiv}CCH_3$ | H | F | O | 0 | |
| 1.0332 | $CH_3$ | $CH_3$ | $CH_2OCH_2C{\equiv}CCH_3$ | H | Cl | O | 0 | |
| 1.0333 | $CH_3$ | $CH_3$ | $CH_2OCH_2C{\equiv}CCH_3$ | H | H | O | 0 | |
| 1.0334 | $CH_3$ | $CH_3$ | 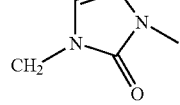 | H | F | O | 0 | |
| 1.0335 | $CH_3$ | $CH_3$ | 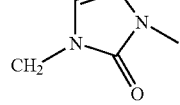 | H | Cl | O | 0 | |
| 1.0336 | $CH_3$ | $CH_3$ | 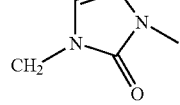 | H | H | O | 0 | |
| 1.0337 | $CH_3$ | $CH_3$ | 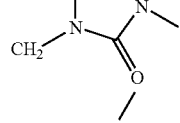 | H | F | O | 0 | |
| 1.0338 | $CH_3$ | $CH_3$ | 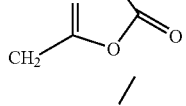 | H | Cl | O | 0 | |
| 1.0339 | $CH_3$ | $CH_3$ | 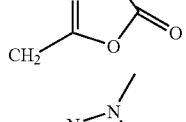 | H | H | O | 0 | |

TABLE 1-continued

Compounds of formula Ib:

(Ib)

| No. | R₁ | R₂ | Z₁ | R₃₀ | X | Y | p | Physical data |
|---|---|---|---|---|---|---|---|---|
| 1.0340 | CH₃ | CH₃ | CH₂-(oxiranyl) | H | F | O | 0 | |
| 1.0341 | CH₃ | CH₃ | CH₂-(oxiranyl) | H | Cl | O | 0 | |
| 1.0342 | CH₃ | CH₃ | CH₂-(oxiranyl) | H | H | O | 0 | |
| 1.0343 | CH₃ | CH₃ | CH₂OCH₂-(oxiranyl) | H | F | O | 0 | |
| 1.0344 | CH₃ | CH₃ | CH₂OCH₂-(oxiranyl) | H | Cl | O | 0 | |
| 1.0345 | CH₃ | CH₃ | CH₂OCH₂-(oxiranyl) | H | H | O | 0 | |
| 1.0346 | CH₃ | CH₃ | CH₂O-(oxetanyl) | H | F | O | 0 | |
| 1.0347 | CH₃ | CH₃ | CH₂O-(oxetanyl) | H | Cl | O | 0 | |
| 1.0348 | CH₃ | CH₃ | CH₂O-(oxetanyl) | H | H | O | 0 | |
| 1.0349 | CH₃ | CH₃ | CH₂O-(tetrahydrofuranyl) | H | F | O | 0 | |
| 1.0350 | CH₃ | CH₃ | CH₂O-(tetrahydrofuranyl) | H | Cl | O | 0 | |
| 1.0351 | CH₃ | CH₃ | CH₂O-(tetrahydrofuranyl) | H | H | O | 0 | |
| 1.0352 | CH₃ | CH₃ | CH₂OCH₂CH₂OCH₃ | H | F | O | 1 | |
| 1.0353 | CH₃ | CH₃ | CH₂OCH₂CH₂OCH₃ | H | H | O | 1 | |
| 1.0354 | CH₃ | CH₃ | CH₂OCH₂CH₂OCH₂CH₃ | H | F | O | 1 | |
| 1.0355 | CH₃ | CH₃ | CH₂OCH₂CH₂OCH₂CH₃ | H | H | O | 1 | |
| 1.0356 | H | CH₃ | CH₂OCH₂CH₂OCH₃ | H | F | O | 0 | |
| 1.0357 | H | CH₃ | CH₂OCH₂CH₂OCH₃ | H | Cl | O | 0 | |
| 1.0358 | H | CH₃ | CH₂OCH₂CH₂OCH₃ | H | H | O | 0 | |
| 1.0359 | H | CH₃ | CH₂OCH₂CH₂OCH₂CH₃ | H | F | O | 0 | |
| 1.0360 | H | CH₃ | CH₂OCH₂CH₂OCH₂CH₃ | H | Cl | O | 0 | |
| 1.0361 | H | CH₃ | CH₂OCH₂CH₂OCH₂CH₃ | H | H | O | 0 | |
| 1.0362 | H | CH₃ | CH₂N(CH₃)SO₂CH₃ | H | F | O | 0 | |
| 1.0363 | H | CH₃ | CH₂N(CH₃)SO₂CH₃ | H | Cl | O | 0 | |
| 1.0364 | H | CH₃ | CH₂N(CH₃)SO₂CH₃ | H | H | O | 0 | |
| 1.0365 | H | CH₃ | CH₂OCH₂Ph | H | F | O | 0 | |
| 1.0366 | H | CH₃ | CH₂OCH₂Ph | H | Cl | O | 0 | |
| 1.0367 | H | CH₃ | CH₂OCH₂Ph | H | H | O | 0 | |
| 1.0368 | H | CH₃ | CH₂OCH₂CH₂OH | H | F | O | 0 | |
| 1.0369 | H | CH₃ | CH₂OCH₂CH₂OH | H | Cl | O | 0 | |
| 1.0370 | H | CH₃ | CH₂OCH₂CH₂OH | H | H | O | 0 | |
| 1.0371 | H | CH₃ | CH₂OCH₂CH₂Cl | H | F | O | 0 | |
| 1.0372 | H | CH₃ | CH₂OCH₂CH₂Cl | H | Cl | O | 0 | |
| 1.0373 | H | CH₃ | CH₂OCH₂CH₂Cl | H | H | O | 0 | |

TABLE 1-continued

Compounds of formula Ib:

(Ib)

| No. | $R_1$ | $R_2$ | $Z_1$ | $R_{30}$ | X | Y | p | Physical data |
|---|---|---|---|---|---|---|---|---|
| 1.0374 | H | $CH_3$ | $CH_2OCH_2CF_3$ | H | F | O | 0 | |
| 1.0375 | H | $CH_3$ | $CH_2OCH_2CF_3$ | H | Cl | O | 0 | |
| 1.0376 | H | $CH_3$ | $CH_2OCH_2CF_3$ | H | H | O | 0 | |
| 1.0377 | H | $CH_3$ | $CH_2OCH_2CH=CH_2$ | H | F | O | 0 | |
| 1.0378 | H | $CH_3$ | $CH_2OCH_2CH=CH_2$ | H | Cl | O | 0 | |
| 1.0379 | H | $CH_3$ | $CH_2OCH_2CH=CH_2$ | H | H | O | 0 | |
| 1.0380 | H | $CH_3$ | $CH_2O(CO)CH_3$ | H | F | O | 0 | |
| 1.0381 | H | $CH_3$ | $CH_2O(CO)CH_3$ | H | Cl | O | 0 | |
| 1.0382 | H | $CH_3$ | $CH_2O(CO)CH_3$ | H | H | O | 0 | |
| 1.0383 | H | $CH_3$ | $CH_2OCH_2C\equiv CH$ | H | F | O | 0 | |
| 1.0384 | H | $CH_3$ | $CH_2OCH_2C\equiv CH$ | H | Cl | O | 0 | |
| 1.0385 | H | $CH_3$ | $CH_2OCH_2C\equiv CH$ | H | H | O | 0 | |
| 1.0386 | H | $CH_3$ | $CH_2OCH_2C\equiv CCH_3$ | H | F | O | 0 | |
| 1.0387 | H | $CH_3$ | $CH_2OCH_2C\equiv CCH_3$ | H | Cl | O | 0 | |
| 1.0388 | H | $CH_3$ | $CH_2OCH_2C\equiv CCH_3$ | H | H | O | 0 | |
| 1.0389 | H | $CH_3$ | (4-methyl-5-oxo-4,5-dihydro-1,2,4-triazol-1-yl)methyl | H | F | O | 0 | |
| 1.0390 | H | $CH_3$ | (4-methyl-5-oxo-4,5-dihydro-1,2,4-triazol-1-yl)methyl | H | Cl | O | 0 | |
| 1.0391 | H | $CH_3$ | (4-methyl-5-oxo-4,5-dihydro-1,2,4-triazol-1-yl)methyl | H | H | O | 0 | |
| 1.0392 | H | $CH_3$ | (4-methyl-5-oxo-4,5-dihydro-1,3,4-oxadiazol-3-yl)methyl | H | F | O | 0 | |
| 1.0393 | H | $CH_3$ | (4-methyl-5-oxo-4,5-dihydro-1,3,4-oxadiazol-3-yl)methyl | H | Cl | O | 0 | |
| 1.0394 | H | $CH_3$ | (4-methyl-5-oxo-4,5-dihydro-1,3,4-oxadiazol-3-yl)methyl | H | H | O | 0 | |
| 1.0395 | H | $CH_3$ | (oxiran-2-yl)methyl | H | F | O | 0 | |

TABLE 1-continued

Compounds of formula Ib:

(Ib)

| No. | $R_1$ | $R_2$ | $Z_1$ | $R_{30}$ | X | Y | p | Physical data |
|---|---|---|---|---|---|---|---|---|
| 1.0396 | H | $CH_3$ |  | H | Cl | O | 0 | |
| 1.0397 | H | $CH_3$ |  | H | H | O | 0 | |
| 1.0398 | H | $CH_3$ |  | H | F | O | 0 | |
| 1.0399 | H | $CH_3$ |  | H | Cl | O | 0 | |
| 1.0400 | H | $CH_3$ |  | H | H | O | 0 | |
| 1.0401 | H | $CH_3$ |  | H | F | O | 0 | |
| 1.0402 | H | $CH_3$ |  | H | Cl | O | 0 | |
| 1.0403 | H | $CH_3$ |  | H | H | O | 0 | |
| 1.0404 | H | $CH_3$ |  | H | F | O | 0 | |
| 1.0405 | H | $CH_3$ | | H | Cl | O | 0 | |
| 1.0406 | H | $CH_3$ |  | H | H | O | 0 | |
| 1.0407 | H | $CH_3$ | $CH_2OCH_2CH_2OCH_3$ | H | F | O | 1 | |
| 1.0408 | H | $CH_3$ | $CH_2OCH_2CH_2OCH_3$ | H | H | O | 1 | |
| 1.0409 | H | $CH_3$ | $CH_2OCH_2CH_2OCH_2CH_3$ | H | F | O | 1 | |
| 1.0410 | H | $CH_3$ | $CH_2OCH_2CH_2OCH_2CH_3$ | H | H | O | 1 | |
| 1.0411 | H | H | $CH_2OCH_2CH_2OCH_3$ | H | F | $CH_2$ | 0 | $^1$H NMR (300 MHz; $CDCl_3$) δ 17.0 (broad s, 1H); 7.62 (s, 2H); 6.47 (m, 1H); 6.35 (m, 1H); 4.73 (m, 2H); 3.50 (m, 3H); 3.39 (m, 2H); 3.31 (s, 3H); 3.30 (m, 1H); 2.72-2.50 (m, 2H). |

TABLE 1-continued

Compounds of formula Ib:

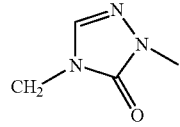

(Ib)

| No. | $R_1$ | $R_2$ | $Z_1$ | $R_{30}$ | X | Y | p | Physical data |
|---|---|---|---|---|---|---|---|---|
| 1.0412 | H | H | $CH_2OCH_2CH_2OCH_3$ | H | Cl | $CH_2$ | 0 | |
| 1.0413 | H | H | $CH_2OCH_2CH_2OCH_3$ | H | H | $CH_2$ | 0 | |
| 1.0414 | H | H | $CH_2OCH_2CH_2OCH_2CH_3$ | H | F | $CH_2$ | 0 | |
| 1.0415 | H | H | $CH_2OCH_2CH_2OCH_2CH_3$ | H | Cl | $CH_2$ | 0 | |
| 1.0416 | H | H | $CH_2OCH_2CH_2OCH_2CH_3$ | H | H | $CH_2$ | 0 | |
| 1.0417 | H | H | $CH_2N(CH_3)SO_2CH_3$ | H | F | $CH_2$ | 0 | |
| 1.0418 | H | H | $CH_2N(CH_3)SO_2CH_3$ | H | Cl | $CH_2$ | 0 | |
| 1.0419 | H | H | $CH_2N(CH_3)SO_2CH_3$ | H | H | $CH_2$ | 0 | |
| 1.0420 | H | H | $CH_2OCH_2Ph$ | H | F | $CH_2$ | 0 | |
| 1.0421 | H | H | $CH_2OCH_2Ph$ | H | Cl | $CH_2$ | 0 | |
| 1.0422 | H | H | $CH_2OCH_2Ph$ | H | H | $CH_2$ | 0 | |
| 1.0423 | H | H | $CH_2OCH_2CH_2OH$ | H | F | $CH_2$ | 0 | |
| 1.0424 | H | H | $CH_2OCH_2CH_2OH$ | H | Cl | $CH_2$ | 0 | |
| 1.0425 | H | H | $CH_2OCH_2CH_2OH$ | H | H | $CH_2$ | 0 | |
| 1.0426 | H | H | $CH_2OCH_2CH_2Cl$ | H | F | $CH_2$ | 0 | |
| 1.0427 | H | H | $CH_2OCH_2CH_2Cl$ | H | Cl | $CH_2$ | 0 | |
| 1.0428 | H | H | $CH_2OCH_2CH_2Cl$ | H | H | $CH_2$ | 0 | |
| 1.0429 | H | H | $CH_2OCH_2CF_3$ | H | F | $CH_2$ | 0 | |
| 1.0430 | H | H | $CH_2OCH_2CF_3$ | H | Cl | $CH_2$ | 0 | |
| 1.0431 | H | H | $CH_2OCH_2CF_3$ | H | H | $CH_2$ | 0 | |
| 1.0432 | H | H | $CH_2OCH_2CH=CH_2$ | H | F | $CH_2$ | 0 | |
| 1.0433 | H | H | $CH_2OCH_2CH=CH_2$ | H | Cl | $CH_2$ | 0 | |
| 1.0434 | H | H | $CH_2OCH_2CH=CH_2$ | H | H | $CH_2$ | 0 | |
| 1.0435 | H | H | $CH_2O(CO)CH_3$ | H | F | $CH_2$ | 0 | |
| 1.0436 | H | H | $CH_2O(CO)CH_3$ | H | Cl | $CH_2$ | 0 | |
| 1.0437 | H | H | $CH_2O(CO)CH_3$ | H | H | $CH_2$ | 0 | |
| 1.0438 | H | H | $CH_2OCH_2C\equiv CH$ | H | F | $CH_2$ | 0 | |
| 1.0439 | H | H | $CH_2OCH_2C\equiv CH$ | H | Cl | $CH_2$ | 0 | |
| 1.0440 | H | H | $CH_2OCH_2C\equiv CH$ | H | H | $CH_2$ | 0 | |
| 1.0441 | H | H | $CH_2OCH_2C\equiv CCH_3$ | H | F | $CH_2$ | 0 | |
| 1.0442 | H | H | $CH_2OCH_2C\equiv CCH_3$ | H | Cl | $CH_2$ | 0 | |
| 1.0443 | H | H | $CH_2OCH_2C\equiv CCH_3$ | H | H | $CH_2$ | 0 | |
| 1.0444 | H | H | 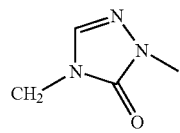 | H | F | $CH_2$ | 0 | |
| 1.0445 | H | H | 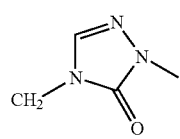 | H | Cl | $CH_2$ | 0 | |
| 1.0446 | H | H | 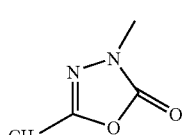 | H | H | $CH_2$ | 0 | |
| 1.0447 | H | H |  | H | F | $CH_2$ | 0 | |

TABLE 1-continued
Compounds of formula Ib:
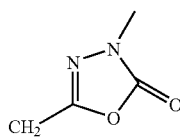
(Ib)
| No. | R₁ | R₂ | Z₁ | R₃₀ | X | Y | p | Physical data |
|---|---|---|---|---|---|---|---|---|
| 1.0448 | H | H | 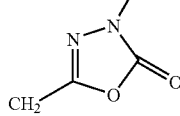 | H | Cl | CH₂ | 0 | |
| 1.0449 | H | H | 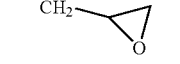 | H | H | CH₂ | 0 | |
| 1.0450 | H | H | 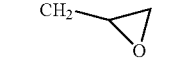 | H | F | CH₂ | 0 | |
| 1.0451 | H | H | 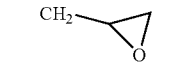 | H | Cl | CH₂ | 0 | |
| 1.0452 | H | H | 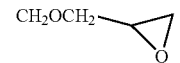 | H | H | CH₂ | 0 | |
| 1.0453 | H | H | 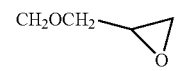 | H | F | CH₂ | 0 | |
| 1.0454 | H | H | 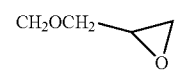 | H | Cl | CH₂ | 0 | |
| 1.0455 | H | H | 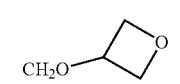 | H | H | CH₂ | 0 | |
| 1.0456 | H | H |  | H | F | CH₂ | 0 | |
| 1.0457 | H | H |  | H | Cl | CH₂ | 0 | |
| 1.0458 | H | H | 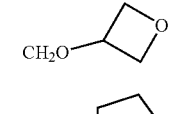 | H | H | CH₂ | 0 | |
| 1.0459 | H | H | 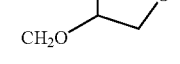 | H | F | CH₂ | 0 | |
| 1.0460 | H | H | 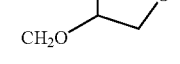 | H | Cl | CH₂ | 0 | |

TABLE 1-continued

Compounds of formula Ib:

(Ib)

| No. | $R_1$ | $R_2$ | $Z_1$ | $R_{30}$ | X | Y | p | Physical data |
|---|---|---|---|---|---|---|---|---|
| 1.0461 | H | H | (tetrahydrofuran-3-yl)OCH$_2$ | H | H | CH$_2$ | 0 | |
| 1.0462 | H | H | CH$_2$OCH$_2$CH$_2$OCH$_3$ | H | F | CH$_2$ | 1 | |
| 1.0463 | H | H | CH$_2$OCH$_2$CH$_2$OCH$_3$ | H | H | CH$_2$ | 1 | |
| 1.0464 | H | H | CH$_2$OCH$_2$CH$_2$OCH$_2$CH$_3$ | H | F | CH$_2$ | 1 | |
| 1.0465 | H | H | CH$_2$OCH$_2$CH$_2$OCH$_2$CH$_3$ | H | H | CH$_2$ | 1 | |
| 1.0466 | CH$_3$ | CH$_3$ | CH$_2$OCH$_2$CH$_2$OCH$_3$ | H | F | CH$_2$ | 0 | |
| 1.0467 | CH$_3$ | CH$_3$ | CH$_2$OCH$_2$CH$_2$OCH$_3$ | H | Cl | CH$_2$ | 0 | |
| 1.0468 | CH$_3$ | CH$_3$ | CH$_2$OCH$_2$CH$_2$OCH$_3$ | H | H | CH$_2$ | 0 | |
| 1.0469 | CH$_3$ | CH$_3$ | CH$_2$OCH$_2$CH$_2$OCH$_2$CH$_3$ | H | F | CH$_2$ | 0 | |
| 1.0470 | CH$_3$ | CH$_3$ | CH$_2$OCH$_2$CH$_2$OCH$_2$CH$_3$ | H | Cl | CH$_2$ | 0 | |
| 1.0471 | CH$_3$ | CH$_3$ | CH$_2$OCH$_2$CH$_2$OCH$_2$CH$_3$ | H | H | CH$_2$ | 0 | |
| 1.0472 | CH$_3$ | CH$_3$ | CH$_2$N(CH$_3$)SO$_2$CH$_3$ | H | F | CH$_2$ | 0 | |
| 1.0473 | CH$_3$ | CH$_3$ | CH$_2$N(CH$_3$)SO$_2$CH$_3$ | H | Cl | CH$_2$ | 0 | |
| 1.0474 | CH$_3$ | CH$_3$ | CH$_2$N(CH$_3$)SO$_2$CH$_3$ | H | H | CH$_2$ | 0 | |
| 1.0475 | CH$_3$ | CH$_3$ | CH$_2$OCH$_2$Ph | H | F | CH$_2$ | 0 | |
| 1.0476 | CH$_3$ | CH$_3$ | CH$_2$OCH$_2$Ph | H | Cl | CH$_2$ | 0 | |
| 1.0477 | CH$_3$ | CH$_3$ | CH$_2$OCH$_2$Ph | H | H | CH$_2$ | 0 | |
| 1.0478 | CH$_3$ | CH$_3$ | CH$_2$OCH$_2$CH$_2$OH | H | F | CH$_2$ | 0 | |
| 1.0479 | CH$_3$ | CH$_3$ | CH$_2$OCH$_2$CH$_2$OH | H | Cl | CH$_2$ | 0 | |
| 1.0480 | CH$_3$ | CH$_3$ | CH$_2$OCH$_2$CH$_2$OH | H | H | CH$_2$ | 0 | |
| 1.0481 | CH$_3$ | CH$_3$ | CH$_2$OCH$_2$CH$_2$Cl | H | F | CH$_2$ | 0 | |
| 1.0482 | CH$_3$ | CH$_3$ | CH$_2$OCH$_2$CH$_2$Cl | H | Cl | CH$_2$ | 0 | |
| 1.0483 | CH$_3$ | CH$_3$ | CH$_2$OCH$_2$CH$_2$Cl | H | H | CH$_2$ | 0 | |
| 1.0484 | CH$_3$ | CH$_3$ | CH$_2$OCH$_2$CF$_3$ | H | F | CH$_2$ | 0 | |
| 1.0485 | CH$_3$ | CH$_3$ | CH$_2$OCH$_2$CF$_3$ | H | Cl | CH$_2$ | 0 | |
| 1.0486 | CH$_3$ | CH$_3$ | CH$_2$OCH$_2$CF$_3$ | H | H | CH$_2$ | 0 | |
| 1.0487 | CH$_3$ | CH$_3$ | CH$_2$OCH$_2$CH=CH$_2$ | H | F | CH$_2$ | 0 | |
| 1.0488 | CH$_3$ | CH$_3$ | CH$_2$OCH$_2$CH=CH$_2$ | H | Cl | CH$_2$ | 0 | |
| 1.0489 | CH$_3$ | CH$_3$ | CH$_2$OCH$_2$CH=CH$_2$ | H | H | CH$_2$ | 0 | |
| 1.0490 | CH$_3$ | CH$_3$ | CH$_2$O(CO)CH$_3$ | H | F | CH$_2$ | 0 | |
| 1.0491 | CH$_3$ | CH$_3$ | CH$_2$O(CO)CH$_3$ | H | Cl | CH$_2$ | 0 | |
| 1.0492 | CH$_3$ | CH$_3$ | CH$_2$O(CO)CH$_3$ | H | H | CH$_2$ | 0 | |
| 1.0493 | CH$_3$ | CH$_3$ | CH$_2$OCH$_2$C≡CH | H | F | CH$_2$ | 0 | |
| 1.0494 | CH$_3$ | CH$_3$ | CH$_2$OCH$_2$C≡CH | H | Cl | CH$_2$ | 0 | |
| 1.0495 | CH$_3$ | CH$_3$ | CH$_2$OCH$_2$C≡CH | H | H | CH$_2$ | 0 | |
| 1.0496 | CH$_3$ | CH$_3$ | CH$_2$OCH$_2$C≡CCH$_3$ | H | F | CH$_2$ | 0 | |
| 1.0497 | CH$_3$ | CH$_3$ | CH$_2$OCH$_2$C≡CCH$_3$ | H | Cl | CH$_2$ | 0 | |
| 1.0498 | CH$_3$ | CH$_3$ | CH$_2$OCH$_2$C≡CCH$_3$ | H | H | CH$_2$ | 0 | |
| 1.0499 | CH$_3$ | CH$_3$ | (4-methyl-5-oxo-4,5-dihydro-1,2,4-triazol-1-yl)CH$_2$ | H | F | CH$_2$ | 0 | |
| 1.0500 | CH$_3$ | CH$_3$ | (4-methyl-5-oxo-4,5-dihydro-1,2,4-triazol-1-yl)CH$_2$ | H | Cl | CH$_2$ | 0 | |

TABLE 1-continued
Compounds of formula Ib:
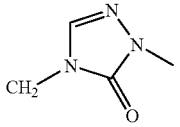
(Ib)
| No. | R$_1$ | R$_2$ | Z$_1$ | R$_{30}$ | X | Y | p | Physical data |
|---|---|---|---|---|---|---|---|---|
| 1.0501 | CH$_3$ | CH$_3$ | 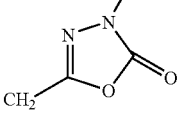 | H | H | CH$_2$ | 0 | |
| 1.0502 | CH$_3$ | CH$_3$ | 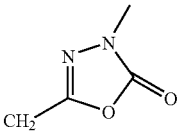 | H | F | CH$_2$ | 0 | |
| 1.0503 | CH$_3$ | CH$_3$ | 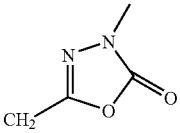 | H | Cl | CH$_2$ | 0 | |
| 1.0504 | CH$_3$ | CH$_3$ | 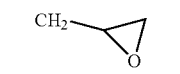 | H | H | CH$_2$ | 0 | |
| 1.0505 | CH$_3$ | CH$_3$ | 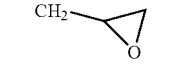 | H | F | CH$_2$ | 0 | |
| 1.0506 | CH$_3$ | CH$_3$ | 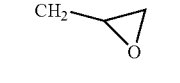 | H | Cl | CH$_2$ | 0 | |
| 1.0507 | CH$_3$ | CH$_3$ |  | H | H | CH$_2$ | 0 | |
| 1.0508 | CH$_3$ | CH$_3$ |  | H | F | CH$_2$ | 0 | |
| 1.0509 | CH$_3$ | CH$_3$ |  | H | Cl | CH$_2$ | 0 | |
| 1.0510 | CH$_3$ | CH$_3$ | CH$_2$OCH$_2$— | H | H | CH$_2$ | 0 | |
| 1.0511 | CH$_3$ | CH$_3$ | 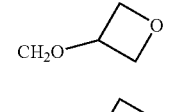 | H | F | CH$_2$ | 0 | |
| 1.0512 | CH$_3$ | CH$_3$ | 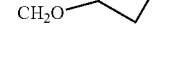 | H | Cl | CH$_2$ | 0 | |

TABLE 1-continued

Compounds of formula Ib:

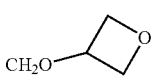

(Ib)

| No. | R₁ | R₂ | Z₁ | R₃₀ | X | Y | p | Physical data |
|---|---|---|---|---|---|---|---|---|
| 1.0513 | CH₃ | CH₃ | 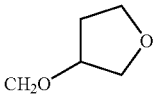 | H | H | CH₂ | 0 | |
| 1.0514 | CH₃ | CH₃ | 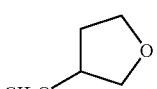 | H | F | CH₂ | 0 | |
| 1.0515 | CH₃ | CH₃ | 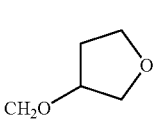 | H | Cl | CH₂ | 0 | |
| 1.0516 | CH₃ | CH₃ | (tetrahydrofuran-3-yl)CH₂O | H | H | CH₂ | 0 | |
| 1.0517 | CH₃ | CH₃ | CH₂OCH₂CH₂OCH₃ | H | F | CH₂ | 1 | |
| 1.0518 | CH₃ | CH₃ | CH₂OCH₂CH₂OCH₃ | H | H | CH₂ | 1 | |
| 1.0519 | CH₃ | CH₃ | CH₂OCH₂CH₂OCH₂CH₃ | H | F | CH₂ | 1 | |
| 1.0520 | CH₃ | CH₃ | CH₂OCH₂CH₂OCH₂CH₃ | H | H | CH₂ | 1 | |
| 1.0521 | H | CH₃ | CH₂OCH₂CH₂OCH₃ | H | F | CH₂ | 0 | |
| 1.0522 | H | CH₃ | CH₂OCH₂CH₂OCH₃ | H | Cl | CH₂ | 0 | |
| 1.0523 | H | CH₃ | CH₂OCH₂CH₂OCH₃ | H | H | CH₂ | 0 | |
| 1.0524 | H | CH₃ | CH₂OCH₂CH₂OCH₂CH₃ | H | F | CH₂ | 0 | |
| 1.0525 | H | CH₃ | CH₂OCH₂CH₂OCH₂CH₃ | H | Cl | CH₂ | 0 | |
| 1.0526 | H | CH₃ | CH₂OCH₂CH₂OCH₂CH₃ | H | H | CH₂ | 0 | |
| 1.0527 | H | CH₃ | CH₂N(CH₃)SO₂CH₃ | H | F | CH₂ | 0 | |
| 1.0528 | H | CH₃ | CH₂N(CH₃)SO₂CH₃ | H | Cl | CH₂ | 0 | |
| 1.0529 | H | CH₃ | CH₂N(CH₃)SO₂CH₃ | H | H | CH₂ | 0 | |
| 1.0530 | H | CH₃ | CH₂OCH₂Ph | H | F | CH₂ | 0 | |
| 1.0531 | H | CH₃ | CH₂OCH₂Ph | H | Cl | CH₂ | 0 | |
| 1.0532 | H | CH₃ | CH₂OCH₂Ph | H | H | CH₂ | 0 | |
| 1.0533 | H | CH₃ | CH₂OCH₂CH₂OH | H | F | CH₂ | 0 | |
| 1.0534 | H | CH₃ | CH₂OCH₂CH₂OH | H | Cl | CH₂ | 0 | |
| 1.0535 | H | CH₃ | CH₂OCH₂CH₂OH | H | H | CH₂ | 0 | |
| 1.0536 | H | CH₃ | CH₂OCH₂CH₂Cl | H | F | CH₂ | 0 | |
| 1.0537 | H | CH₃ | CH₂OCH₂CH₂Cl | H | Cl | CH₂ | 0 | |
| 1.0538 | H | CH₃ | CH₂OCH₂CH₂Cl | H | H | CH₂ | 0 | |
| 1.0539 | H | CH₃ | CH₂OCH₂CF₃ | H | F | CH₂ | 0 | |
| 1.0540 | H | CH₃ | CH₂OCH₂CF₃ | H | Cl | CH₂ | 0 | |
| 1.0541 | H | CH₃ | CH₂OCH₂CF₃ | H | H | CH₂ | 0 | |
| 1.0542 | H | CH₃ | CH₂OCH₂CH=CH₂ | H | F | CH₂ | 0 | |
| 1.0543 | H | CH₃ | CH₂OCH₂CH=CH₂ | H | Cl | CH₂ | 0 | |
| 1.0544 | H | CH₃ | CH₂OCH₂CH=CH₂ | H | H | CH₂ | 0 | |
| 1.0545 | H | CH₃ | CH₂O(CO)CH₃ | H | F | CH₂ | 0 | |
| 1.0546 | H | CH₃ | CH₂O(CO)CH₃ | H | Cl | CH₂ | 0 | |
| 1.0547 | H | CH₃ | CH₂O(CO)CH₃ | H | H | CH₂ | 0 | |
| 1.0548 | H | CH₃ | CH₂OCH₂C≡CH | H | F | CH₂ | 0 | |
| 1.0549 | H | CH₃ | CH₂OCH₂C≡CH | H | Cl | CH₂ | 0 | |
| 1.0550 | H | CH₃ | CH₂OCH₂C≡CH | H | H | CH₂ | 0 | |
| 1.0551 | H | CH₃ | CH₂OCH₂C≡CCH₃ | H | F | CH₂ | 0 | |
| 1.0552 | H | CH₃ | CH₂OCH₂C≡CCH₃ | H | Cl | CH₂ | 0 | |
| 1.0553 | H | CH₃ | CH₂OCH₂C≡CCH₃ | H | H | CH₂ | 0 | |

TABLE 1-continued
Compounds of formula Ib:
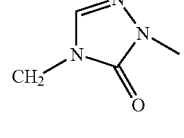
(Ib)
| No. | $R_1$ | $R_2$ | $Z_1$ | $R_{30}$ | X | Y | p | Physical data |
|---|---|---|---|---|---|---|---|---|
| 1.0554 | H | $CH_3$ | 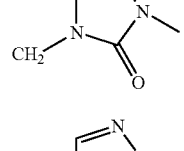 | H | F | $CH_2$ | 0 | |
| 1.0555 | H | $CH_3$ | 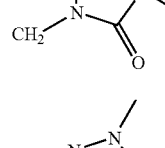 | H | Cl | $CH_2$ | 0 | |
| 1.0556 | H | $CH_3$ | 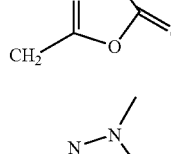 | H | H | $CH_2$ | 0 | |
| 1.0557 | H | $CH_3$ | 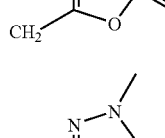 | H | F | $CH_2$ | 0 | |
| 1.0558 | H | $CH_3$ | 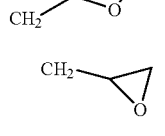 | H | Cl | $CH_2$ | 0 | |
| 1.0559 | H | $CH_3$ | 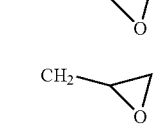 | H | H | $CH_2$ | 0 | |
| 1.0560 | H | $CH_3$ | 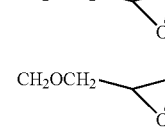 | H | F | $CH_2$ | 0 | |
| 1.0561 | H | $CH_3$ |  | H | Cl | $CH_2$ | 0 | |
| 1.0562 | H | $CH_3$ | $CH_2$—⟨epoxide⟩ | H | H | $CH_2$ | 0 | |
| 1.0563 | H | $CH_3$ | $CH_2OCH_2$—⟨epoxide⟩ | H | F | $CH_2$ | 0 | |
| 1.0564 | H | $CH_3$ | $CH_2OCH_2$—⟨epoxide⟩ | H | Cl | $CH_2$ | 0 | |

TABLE 1-continued

Compounds of formula Ib:

(Ib)

| No. | $R_1$ | $R_2$ | $Z_1$ | $R_{30}$ | X | Y | p | Physical data |
|---|---|---|---|---|---|---|---|---|
| 1.0565 | H | $CH_3$ | $CH_2OCH_2$-(oxiranyl) | H | H | $CH_2$ | 0 | |
| 1.0566 | H | $CH_3$ | $CH_2O$-(oxetan-3-yl) | H | F | $CH_2$ | 0 | |
| 1.0567 | H | $CH_3$ | $CH_2O$-(oxetan-3-yl) | H | Cl | $CH_2$ | 0 | |
| 1.0568 | H | $CH_3$ | $CH_2O$-(oxetan-3-yl) | H | H | $CH_2$ | 0 | |
| 1.0569 | H | $CH_3$ | $CH_2O$-(tetrahydrofuran-3-yl) | H | F | $CH_2$ | 0 | |
| 1.0570 | H | $CH_3$ | $CH_2O$-(tetrahydrofuran-3-yl) | H | Cl | $CH_2$ | 0 | |
| 1.0571 | H | $CH_3$ | $CH_2O$-(tetrahydrofuran-3-yl) | H | H | $CH_2$ | 0 | |
| 1.0572 | H | $CH_3$ | $CH_2OCH_2CH_2OCH_3$ | H | F | $CH_2$ | 1 | |
| 1.0573 | H | $CH_3$ | $CH_2OCH_2CH_2OCH_3$ | H | H | $CH_2$ | 1 | |
| 1.0574 | H | $CH_3$ | $CH_2OCH_2CH_2OCH_2CH_3$ | H | F | $CH_2$ | 1 | |
| 1.0575 | H | $CH_3$ | $CH_2OCH_2CH_2OCH_2CH_3$ | H | H | $CH_2$ | 1 | |
| 1.0576 | H | H | $CH_2OCH_2CH_2OCH_3$ | H | F | $CH_2CH_2$ | 0 | resin |
| 1.0577 | H | H | $CH_2OCH_2CH_2OCH_3$ | H | Cl | $CH_2CH_2$ | 0 | |
| 1.0578 | H | H | $CH_2OCH_2CH_2OCH_3$ | H | H | $CH_2CH_2$ | 0 | |
| 1.0579 | H | H | $CH_2OCH_2CH_2OCH_2CH_3$ | H | F | $CH_2CH_2$ | 0 | |
| 1.0580 | H | H | $CH_2OCH_2CH_2OCH_2CH_3$ | H | Cl | $CH_2CH_2$ | 0 | |
| 1.0581 | H | H | $CH_2OCH_2CH_2OCH_2CH_3$ | H | H | $CH_2CH_2$ | 0 | |
| 1.0582 | H | H | $CH_2N(CH_3)SO_2CH_3$ | H | F | $CH_2CH_2$ | 0 | |
| 1.0583 | H | H | $CH_2N(CH_3)SO_2CH_3$ | H | Cl | $CH_2CH_2$ | 0 | |
| 1.0584 | H | H | $CH_2N(CH_3)SO_2CH_3$ | H | H | $CH_2CH_2$ | 0 | |
| 1.0585 | H | H | $CH_2OCH_2Ph$ | H | F | $CH_2CH_2$ | 0 | |
| 1.0586 | H | H | $CH_2OCH_2Ph$ | H | Cl | $CH_2CH_2$ | 0 | |
| 1.0587 | H | H | $CH_2OCH_2Ph$ | H | H | $CH_2CH_2$ | 0 | |
| 1.0588 | H | H | $CH_2OCH_2CH_2OH$ | H | F | $CH_2CH_2$ | 0 | |
| 1.0589 | H | H | $CH_2OCH_2CH_2OH$ | H | Cl | $CH_2CH_2$ | 0 | |
| 1.0590 | H | H | $CH_2OCH_2CH_2OH$ | H | H | $CH_2CH_2$ | 0 | |
| 1.0591 | H | H | $CH_2OCH_2CH_2Cl$ | H | F | $CH_2CH_2$ | 0 | |
| 1.0592 | H | H | $CH_2OCH_2CH_2Cl$ | H | Cl | $CH_2CH_2$ | 0 | |
| 1.0593 | H | H | $CH_2OCH_2CH_2Cl$ | H | H | $CH_2CH_2$ | 0 | |
| 1.0594 | H | H | $CH_2OCH_2CF_3$ | H | F | $CH_2CH_2$ | 0 | |
| 1.0595 | H | H | $CH_2OCH_2CF_3$ | H | Cl | $CH_2CH_2$ | 0 | |
| 1.0596 | H | H | $CH_2OCH_2CF_3$ | H | H | $CH_2CH_2$ | 0 | |
| 1.0597 | H | H | $CH_2OCH_2CH=CH_2$ | H | F | $CH_2CH_2$ | 0 | |
| 1.0598 | H | H | $CH_2OCH_2CH=CH_2$ | H | Cl | $CH_2CH_2$ | 0 | |
| 1.0599 | H | H | $CH_2OCH_2CH=CH_2$ | H | H | $CH_2CH_2$ | 0 | |
| 1.0600 | H | H | $CH_2O(CO)CH_3$ | H | F | $CH_2CH_2$ | 0 | |

TABLE 1-continued

Compounds of formula Ib:

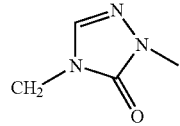

(Ib)

| No. | R$_1$ | R$_2$ | Z$_1$ | R$_{30}$ | X | Y | p | Physical data |
|---|---|---|---|---|---|---|---|---|
| 1.0601 | H | H | CH$_2$O(CO)CH$_3$ | H | Cl | CH$_2$CH$_2$ | 0 | |
| 1.0602 | H | H | CH$_2$O(CO)CH$_3$ | H | H | CH$_2$CH$_2$ | 0 | |
| 1.0603 | H | H | CH$_2$OCH$_2$C≡CH | H | F | CH$_2$CH$_2$ | 0 | |
| 1.0604 | H | H | CH$_2$OCH$_2$C≡CH | H | Cl | CH$_2$CH$_2$ | 0 | |
| 1.0605 | H | H | CH$_2$OCH$_2$C≡CH | H | H | CH$_2$CH$_2$ | 0 | |
| 1.0606 | H | H | CH$_2$OCH$_2$C≡CCH$_3$ | H | F | CH$_2$CH$_2$ | 0 | |
| 1.0607 | H | H | CH$_2$OCH$_2$C≡CCH$_3$ | H | Cl | CH$_2$CH$_2$ | 0 | |
| 1.0608 | H | H | CH$_2$OCH$_2$C≡CCH$_3$ | H | H | CH$_2$CH$_2$ | 0 | |
| 1.0609 | H | H | 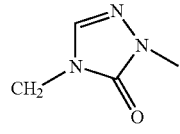 | H | F | CH$_2$CH$_2$ | 0 | |
| 1.0610 | H | H | 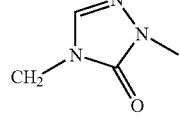 | H | Cl | CH$_2$CH$_2$ | 0 | |
| 1.0611 | H | H | 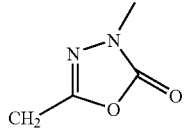 | H | H | CH$_2$CH$_2$ | 0 | |
| 1.0612 | H | H | 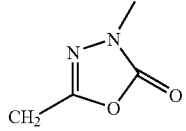 | H | F | CH$_2$CH$_2$ | 0 | |
| 1.0613 | H | H | 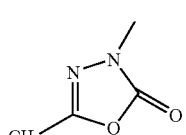 | H | Cl | CH$_2$CH$_2$ | 0 | |
| 1.0614 | H | H | 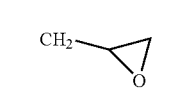 | H | H | CH$_2$CH$_2$ | 0 | |
| 1.0615 | H | H | 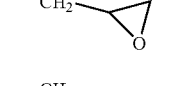 | H | F | CH$_2$CH$_2$ | 0 | |
| 1.0616 | H | H | 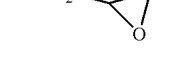 | H | Cl | CH$_2$CH$_2$ | 0 | |
| 1.0617 | H | H | 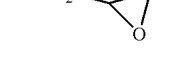 | H | H | CH$_2$CH$_2$ | 0 | |

TABLE 1-continued

Compounds of formula Ib:

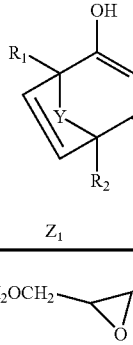

(Ib)

| No. | R₁ | R₂ | Z₁ | R₃₀ | X | Y | p | Physical data |
|---|---|---|---|---|---|---|---|---|
| 1.0618 | H | H | CH₂OCH₂-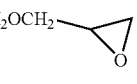 | H | F | CH₂CH₂ | 0 | |
| 1.0619 | H | H | CH₂OCH₂-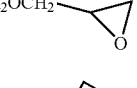 | H | Cl | CH₂CH₂ | 0 | |
| 1.0620 | H | H | CH₂OCH₂-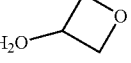 | H | H | CH₂CH₂ | 0 | |
| 1.0621 | H | H | 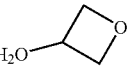 | H | F | CH₂CH₂ | 0 | |
| 1.0622 | H | H | 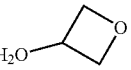 | H | Cl | CH₂CH₂ | 0 | |
| 1.0623 | H | H |  | H | H | CH₂CH₂ | 0 | |
| 1.0624 | H | H | 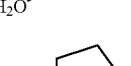 | H | F | CH₂CH₂ | 0 | |
| 1.0625 | H | H | 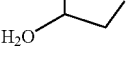 | H | Cl | CH₂CH₂ | 0 | |
| 1.0626 | H | H |  | H | H | CH₂CH₂ | 0 | |
| 1.0627 | H | H | CH₂OCH₂CH₂OCH₃ | H | F | CH₂CH₂ | 1 | |
| 1.0628 | H | H | CH₂OCH₂CH₂OCH₃ | H | H | CH₂CH₂ | 1 | |
| 1.0629 | H | H | CH₂OCH₂CH₂OCH₂CH₃ | H | F | CH₂CH₂ | 1 | |
| 1.0630 | H | H | CH₂OCH₂CH₂OCH₂CH₃ | H | H | CH₂CH₂ | 1 | |
| 1.0631 | CH₃ | CH₃ | CH₂OCH₂CH₂OCH₃ | H | F | CH₂CH₂ | 0 | |
| 1.0632 | CH₃ | CH₃ | CH₂OCH₂CH₂OCH₃ | H | Cl | CH₂CH₂ | 0 | |
| 1.0633 | CH₃ | CH₃ | CH₂OCH₂CH₂OCH₃ | H | H | CH₂CH₂ | 0 | |
| 1.0634 | CH₃ | CH₃ | CH₂OCH₂CH₂OCH₂CH₃ | H | F | CH₂CH₂ | 0 | |
| 1.0635 | CH₃ | CH₃ | CH₂OCH₂CH₂OCH₂CH₃ | H | Cl | CH₂CH₂ | 0 | |
| 1.0636 | CH₃ | CH₃ | CH₂OCH₂CH₂OCH₂CH₃ | H | H | CH₂CH₂ | 0 | |
| 1.0637 | CH₃ | CH₃ | CH₂N(CH₃)SO₂CH₃ | H | F | CH₂CH₂ | 0 | |
| 1.0638 | CH₃ | CH₃ | CH₂N(CH₃)SO₂CH₃ | H | Cl | CH₂CH₂ | 0 | |
| 1.0639 | CH₃ | CH₃ | CH₂N(CH₃)SO₂CH₃ | H | H | CH₂CH₂ | 0 | |
| 1.0640 | CH₃ | CH₃ | CH₂OCH₂Ph | H | F | CH₂CH₂ | 0 | |
| 1.0641 | CH₃ | CH₃ | CH₂OCH₂Ph | H | Cl | CH₂CH₂ | 0 | |
| 1.0642 | CH₃ | CH₃ | CH₂OCH₂Ph | H | H | CH₂CH₂ | 0 | |
| 1.0643 | CH₃ | CH₃ | CH₂OCH₂CH₂OH | H | F | CH₂CH₂ | 0 | |
| 1.0644 | CH₃ | CH₃ | CH₂OCH₂CH₂OH | H | Cl | CH₂CH₂ | 0 | |
| 1.0645 | CH₃ | CH₃ | CH₂OCH₂CH₂OH | H | H | CH₂CH₂ | 0 | |
| 1.0646 | CH₃ | CH₃ | CH₂OCH₂CH₂Cl | H | F | CH₂CH₂ | 0 | |
| 1.0647 | CH₃ | CH₃ | CH₂OCH₂CH₂Cl | H | Cl | CH₂CH₂ | 0 | |

TABLE 1-continued

Compounds of formula Ib:

(Ib)

| No. | R₁ | R₂ | Z₁ | R₃₀ | X | Y | p | Physical data |
|---|---|---|---|---|---|---|---|---|
| 1.0648 | CH₃ | CH₃ | CH₂OCH₂CH₂Cl | H | H | CH₂CH₂ | 0 | |
| 1.0649 | CH₃ | CH₃ | CH₂OCH₂CF₃ | H | F | CH₂CH₂ | 0 | |
| 1.0650 | CH₃ | CH₃ | CH₂OCH₂CF₃ | H | Cl | CH₂CH₂ | 0 | |
| 1.0651 | CH₃ | CH₃ | CH₂OCH₂CF₃ | H | H | CH₂CH₂ | 0 | |
| 1.0652 | CH₃ | CH₃ | CH₂OCH₂CH=CH₂ | H | F | CH₂CH₂ | 0 | |
| 1.0653 | CH₃ | CH₃ | CH₂OCH₂CH=CH₂ | H | Cl | CH₂CH₂ | 0 | |
| 1.0654 | CH₃ | CH₃ | CH₂OCH₂CH=CH₂ | H | H | CH₂CH₂ | 0 | |
| 1.0655 | CH₃ | CH₃ | CH₂O(CO)CH₃ | H | F | CH₂CH₂ | 0 | |
| 1.0656 | CH₃ | CH₃ | CH₂O(CO)CH₃ | H | Cl | CH₂CH₂ | 0 | |
| 1.0657 | CH₃ | CH₃ | CH₂O(CO)CH₃ | H | H | CH₂CH₂ | 0 | |
| 1.0658 | CH₃ | CH₃ | CH₂OCH₂C≡CH | H | F | CH₂CH₂ | 0 | |
| 1.0659 | CH₃ | CH₃ | CH₂OCH₂C≡CH | H | Cl | CH₂CH₂ | 0 | |
| 1.0660 | CH₃ | CH₃ | CH₂OCH₂C≡CH | H | H | CH₂CH₂ | 0 | |
| 1.0661 | CH₃ | CH₃ | CH₂OCH₂C≡CCH₃ | H | F | CH₂CH₂ | 0 | |
| 1.0662 | CH₃ | CH₃ | CH₂OCH₂C≡CCH₃ | H | Cl | CH₂CH₂ | 0 | |
| 1.0663 | CH₃ | CH₃ | CH₂OCH₂C≡CCH₃ | H | H | CH₂CH₂ | 0 | |
| 1.0664 | CH₃ | CH₃ | (4-methyl-5-oxo-4,5-dihydro-1,2,4-triazol-1-yl)methyl | H | F | CH₂CH₂ | 0 | |
| 1.0665 | CH₃ | CH₃ | (4-methyl-5-oxo-4,5-dihydro-1,2,4-triazol-1-yl)methyl | H | Cl | CH₂CH₂ | 0 | |
| 1.0666 | CH₃ | CH₃ | (4-methyl-5-oxo-4,5-dihydro-1,2,4-triazol-1-yl)methyl | H | H | CH₂CH₂ | 0 | |
| 1.0667 | CH₃ | CH₃ | (3-methyl-5-oxo-4,5-dihydro-1,3,4-oxadiazol-4-yl)methyl | H | F | CH₂CH₂ | 0 | |
| 1.0668 | CH₃ | CH₃ | (3-methyl-5-oxo-4,5-dihydro-1,3,4-oxadiazol-4-yl)methyl | H | Cl | CH₂CH₂ | 0 | |
| 1.0669 | CH₃ | CH₃ | (3-methyl-5-oxo-4,5-dihydro-1,3,4-oxadiazol-4-yl)methyl | H | H | CH₂CH₂ | 0 | |
| 1.0670 | CH₃ | CH₃ | CH₂-(oxiran-2-yl) | H | F | CH₂CH₂ | 0 | |

TABLE 1-continued

Compounds of formula Ib:

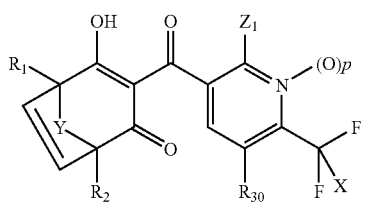

(Ib)

| No. | R$_1$ | R$_2$ | Z$_1$ | R$_{30}$ | X | Y | p | Physical data |
|---|---|---|---|---|---|---|---|---|
| 1.0671 | CH$_3$ | CH$_3$ | CH$_2$-oxirane | H | Cl | CH$_2$CH$_2$ | 0 | |
| 1.0672 | CH$_3$ | CH$_3$ | CH$_2$-oxirane | H | H | CH$_2$CH$_2$ | 0 | |
| 1.0673 | CH$_3$ | CH$_3$ | CH$_2$OCH$_2$-oxirane | H | F | CH$_2$CH$_2$ | 0 | |
| 1.0674 | CH$_3$ | CH$_3$ | CH$_2$OCH$_2$-oxirane | H | Cl | CH$_2$CH$_2$ | 0 | |
| 1.0675 | CH$_3$ | CH$_3$ | CH$_2$OCH$_2$-oxirane | H | H | CH$_2$CH$_2$ | 0 | |
| 1.0676 | CH$_3$ | CH$_3$ | CH$_2$O-oxetane | H | F | CH$_2$CH$_2$ | 0 | |
| 1.0677 | CH$_3$ | CH$_3$ | CH$_2$O-oxetane | H | Cl | CH$_2$CH$_2$ | 0 | |
| 1.0678 | CH$_3$ | CH$_3$ | CH$_2$O-oxetane | H | H | CH$_2$CH$_2$ | 0 | |
| 1.0679 | CH$_3$ | CH$_3$ | CH$_2$O-tetrahydrofuran | H | F | CH$_2$CH$_2$ | 0 | |
| 1.0680 | CH$_3$ | CH$_3$ | CH$_2$O-tetrahydrofuran | H | Cl | CH$_2$CH$_2$ | 0 | |
| 1.0681 | CH$_3$ | CH$_3$ | CH$_2$O-tetrahydrofuran | H | H | CH$_2$CH$_2$ | 0 | |
| 1.0682 | CH$_3$ | CH$_3$ | CH$_2$OCH$_2$CH$_2$OCH$_3$ | H | F | CH$_2$CH$_2$ | 1 | |
| 1.0683 | CH$_3$ | CH$_3$ | CH$_2$OCH$_2$CH$_2$OCH$_3$ | H | H | CH$_2$CH$_2$ | 1 | |
| 1.0684 | CH$_3$ | CH$_3$ | CH$_2$OCH$_2$CH$_2$OCH$_2$CH$_3$ | H | F | CH$_2$CH$_2$ | 1 | |
| 1.0685 | CH$_3$ | CH$_3$ | CH$_2$OCH$_2$CH$_2$OCH$_2$CH$_3$ | H | H | CH$_2$CH$_2$ | 1 | |
| 1.0686 | H | CH$_3$ | CH$_2$OCH$_2$CH$_2$OCH$_3$ | H | F | CH$_2$CH$_2$ | 0 | |
| 1.0687 | H | CH$_3$ | CH$_2$OCH$_2$CH$_2$OCH$_3$ | H | Cl | CH$_2$CH$_2$ | 0 | |
| 1.0688 | H | CH$_3$ | CH$_2$OCH$_2$CH$_2$OCH$_3$ | H | H | CH$_2$CH$_2$ | 0 | |
| 1.0689 | H | CH$_3$ | CH$_2$OCH$_2$CH$_2$OCH$_2$CH$_3$ | H | F | CH$_2$CH$_2$ | 0 | |
| 1.0690 | H | CH$_3$ | CH$_2$OCH$_2$CH$_2$OCH$_2$CH$_3$ | H | Cl | CH$_2$CH$_2$ | 0 | |
| 1.0691 | H | CH$_3$ | CH$_2$OCH$_2$CH$_2$OCH$_2$CH$_3$ | H | H | CH$_2$CH$_2$ | 0 | |
| 1.0692 | H | CH$_3$ | CH$_2$N(CH$_3$)SO$_2$CH$_3$ | H | F | CH$_2$CH$_2$ | 0 | |
| 1.0693 | H | CH$_3$ | CH$_2$N(CH$_3$)SO$_2$CH$_3$ | H | Cl | CH$_2$CH$_2$ | 0 | |
| 1.0694 | H | CH$_3$ | CH$_2$N(CH$_3$)SO$_2$CH$_3$ | H | H | CH$_2$CH$_2$ | 0 | |

TABLE 1-continued

Compounds of formula Ib:

(Ib)

| No. | $R_1$ | $R_2$ | $Z_1$ | $R_{30}$ | X | Y | p | Physical data |
|---|---|---|---|---|---|---|---|---|
| 1.0695 | H | $CH_3$ | $CH_2OCH_2Ph$ | H | F | $CH_2CH_2$ | 0 | |
| 1.0696 | H | $CH_3$ | $CH_2OCH_2Ph$ | H | Cl | $CH_2CH_2$ | 0 | |
| 1.0697 | H | $CH_3$ | $CH_2OCH_2Ph$ | H | H | $CH_2CH_2$ | 0 | |
| 1.0698 | H | $CH_3$ | $CH_2OCH_2CH_2OH$ | H | F | $CH_2CH_2$ | 0 | |
| 1.0699 | H | $CH_3$ | $CH_2OCH_2CH_2OH$ | H | Cl | $CH_2CH_2$ | 0 | |
| 1.0700 | H | $CH_3$ | $CH_2OCH_2CH_2OH$ | H | H | $CH_2CH_2$ | 0 | |
| 1.0701 | H | $CH_3$ | $CH_2OCH_2CH_2Cl$ | H | F | $CH_2CH_2$ | 0 | |
| 1.0702 | H | $CH_3$ | $CH_2OCH_2CH_2Cl$ | H | Cl | $CH_2CH_2$ | 0 | |
| 1.0703 | H | $CH_3$ | $CH_2OCH_2CH_2Cl$ | H | H | $CH_2CH_2$ | 0 | |
| 1.0704 | H | $CH_3$ | $CH_2OCH_2CF_3$ | H | F | $CH_2CH_2$ | 0 | |
| 1.0705 | H | $CH_3$ | $CH_2OCH_2CF_3$ | H | Cl | $CH_2CH_2$ | 0 | |
| 1.0706 | H | $CH_3$ | $CH_2OCH_2CF_3$ | H | H | $CH_2CH_2$ | 0 | |
| 1.0707 | H | $CH_3$ | $CH_2OCH_2CH=CH_2$ | H | F | $CH_2CH_2$ | 0 | |
| 1.0708 | H | $CH_3$ | $CH_2OCH_2CH=CH_2$ | H | Cl | $CH_2CH_2$ | 0 | |
| 1.0709 | H | $CH_3$ | $CH_2OCH_2CH=CH_2$ | H | H | $CH_2CH_2$ | 0 | |
| 1.0710 | H | $CH_3$ | $CH_2O(CO)CH_3$ | H | F | $CH_2CH_2$ | 0 | |
| 1.0711 | H | $CH_3$ | $CH_2O(CO)CH_3$ | H | Cl | $CH_2CH_2$ | 0 | |
| 1.0712 | H | $CH_3$ | $CH_2O(CO)CH_3$ | H | H | $CH_2CH_2$ | 0 | |
| 1.0713 | H | $CH_3$ | $CH_2OCH_2C\equiv CH$ | H | F | $CH_2CH_2$ | 0 | |
| 1.0714 | H | $CH_3$ | $CH_2OCH_2C\equiv CH$ | H | Cl | $CH_2CH_2$ | 0 | |
| 1.0715 | H | $CH_3$ | $CH_2OCH_2C\equiv CH$ | H | H | $CH_2CH_2$ | 0 | |
| 1.0716 | H | $CH_3$ | $CH_2OCH_2C\equiv CCH_3$ | H | F | $CH_2CH_2$ | 0 | |
| 1.0717 | H | $CH_3$ | $CH_2OCH_2C\equiv CCH_3$ | H | Cl | $CH_2CH_2$ | 0 | |
| 1.0718 | H | $CH_3$ | $CH_2OCH_2C\equiv CCH_3$ | H | H | $CH_2CH_2$ | 0 | |
| 1.0719 | H | $CH_3$ | (triazolinone-CH$_2$) | H | F | $CH_2CH_2$ | 0 | |
| 1.0720 | H | $CH_3$ | (triazolinone-CH$_2$) | H | Cl | $CH_2CH_2$ | 0 | |
| 1.0721 | H | $CH_3$ | (triazolinone-CH$_2$) | H | H | $CH_2CH_2$ | 0 | |
| 1.0722 | H | $CH_3$ | (oxadiazolinone-CH$_2$) | H | F | $CH_2CH_2$ | 0 | |
| 1.0723 | H | $CH_3$ | (oxadiazolinone-CH$_2$) | H | Cl | $CH_2CH_2$ | 0 | |

TABLE 1-continued

Compounds of formula Ib:

(Ib)

| No. | $R_1$ | $R_2$ | $Z_1$ | $R_{30}$ | X | Y | p | Physical data |
|---|---|---|---|---|---|---|---|---|
| 1.0724 | H | $CH_3$ | 3-methyl-5-(CH$_2$-)-1,3,4-oxadiazol-2(3H)-one | H | H | $CH_2CH_2$ | 0 | |
| 1.0725 | H | $CH_3$ | $CH_2$-oxiranyl | H | F | $CH_2CH_2$ | 0 | |
| 1.0726 | H | $CH_3$ | $CH_2$-oxiranyl | H | Cl | $CH_2CH_2$ | 0 | |
| 1.0727 | H | $CH_3$ | $CH_2$-oxiranyl | H | H | $CH_2CH_2$ | 0 | |
| 1.0728 | H | $CH_3$ | $CH_2OCH_2$-oxiranyl | H | F | $CH_2CH_2$ | 0 | |
| 1.0729 | H | $CH_3$ | $CH_2OCH_2$-oxiranyl | H | Cl | $CH_2CH_2$ | 0 | |
| 1.0730 | H | $CH_3$ | $CH_2OCH_2$-oxiranyl | H | H | $CH_2CH_2$ | Q | |
| 1.0731 | H | $CH_3$ | $CH_2O$-oxetanyl | H | F | $CH_2CH_2$ | 0 | |
| 1.0732 | H | $CH_3$ | $CH_2O$-oxetanyl | H | Cl | $CH_2CH_2$ | 0 | |
| 1.0733 | H | $CH_3$ | $CH_2O$-oxetanyl | H | H | $CH_2CH_2$ | 0 | |
| 1.0734 | H | $CH_3$ | $CH_2O$-tetrahydrofuranyl | H | F | $CH_2CH_2$ | 0 | |
| 1.0735 | H | $CH_3$ | $CH_2O$-tetrahydrofuranyl | H | Cl | $CH_2CH_2$ | 0 | |
| 1.0736 | H | $CH_3$ | $CH_2O$-tetrahydrofuranyl | H | H | $CH_2CH_2$ | 0 | |
| 1.0737 | H | $CH_3$ | $CH_2OCH_2CH_2OCH_3$ | H | F | $CH_2CH_2$ | 1 | |
| 1.0738 | H | $CH_3$ | $CH_2OCH_2CH_2OCH_3$ | H | H | $CH_2CH_2$ | 1 | |

TABLE 1-continued

Compounds of formula Ib:

(Ib)

| No. | $R_1$ | $R_2$ | $Z_1$ | $R_{30}$ | X | Y | p | Physical data |
|---|---|---|---|---|---|---|---|---|
| 1.0739 | H | $CH_3$ | $CH_2OCH_2CH_2OCH_2CH_3$ | H | F | $CH_2CH_2$ | 1 | |
| 1.0740 | H | $CH_3$ | $CH_2OCH_2CH_2OCH_2CH_3$ | H | H | $CH_2CH_2$ | 1 | |
| 1.0741 | H | $CH_3$ | $CH_2OCH_2CH_2OCH_3$ | H | Cl | $CH_2CH_2$ | 1 | |
| 1.0742 | H | H | $CH_2OCH_2CH_2OCH_3$ | H | F | $NC(O)C(CH_3)_3$ | 0 | |
| 1.0743 | H | H | $CH_2OCH_2CH_2OCH_3$ | H | Cl | $NC(O)C(CH_3)_3$ | 0 | |
| 1.0744 | H | H | $CH_2OCH_2CH_2OCH_3$ | H | H | $NC(O)C(CH_3)_3$ | 0 | |
| 1.0745 | H | H | $CH_2OCH_2CH_2OCH_2CH_3$ | H | F | $NC(O)C(CH_3)_3$ | 0 | |
| 1.0746 | H | H | $CH_2OCH_2CH_2OCH_2CH_3$ | H | Cl | $NC(O)C(CH_3)_3$ | 0 | |
| 1.0747 | H | H | $CH_2OCH_2CH_2OCH_2CH_3$ | H | H | $NC(O)C(CH_3)_3$ | 0 | |
| 1.0748 | H | H | $CH_2N(CH_3)SO_2CH_3$ | H | F | $NC(O)C(CH_3)_3$ | 0 | |
| 1.0749 | H | H | $CH_2N(CH_3)SO_2CH_3$ | H | Cl | $NC(O)C(CH_3)_3$ | 0 | |
| 1.0750 | H | H | $CH_2N(CH_3)SO_2CH_3$ | H | H | $NC(O)C(CH_3)_3$ | 0 | |
| 1.0751 | H | H | $CH_2OCH_2Ph$ | H | F | $NC(O)C(CH_3)_3$ | 0 | |
| 1.0752 | H | H | $CH_2OCH_2Ph$ | H | Cl | $NC(O)C(CH_3)_3$ | 0 | |
| 1.0753 | H | H | $CH_2OCH_2Ph$ | H | H | $NC(O)C(CH_3)_3$ | 0 | |
| 1.0754 | H | H | $CH_2OCH_2CH_2OH$ | H | F | $NC(O)C(CH_3)_3$ | 0 | |
| 1.0755 | H | H | $CH_2OCH_2CH_2OH$ | H | Cl | $NC(O)C(CH_3)_3$ | 0 | |
| 1.0756 | H | H | $CH_2OCH_2CH_2OH$ | H | H | $NC(O)C(CH_3)_3$ | 0 | |
| 1.0757 | H | H | $CH_2OCH_2CH_2Cl$ | H | F | $NO(O)O(CH_3)_3$ | 0 | |
| 1.0758 | H | H | $CH_2OCH_2CH_2Cl$ | H | Cl | $NC(O)C(CH_3)_3$ | 0 | |
| 1.0759 | H | H | $CH_2OCH_2CH_2Cl$ | H | H | $NO(O)C(CH_3)_3$ | 0 | |
| 1.0760 | H | H | $CH_2OCH_2CF_3$ | H | F | $NC(O)C(CH_3)_3$ | 0 | |
| 1.0761 | H | H | $CH_2OCH_2CF_3$ | H | Cl | $NC(O)C(CH_3)_3$ | 0 | |
| 1.0762 | H | H | $CH_2OCH_2CF_3$ | H | H | $NC(O)C(CH_3)_3$ | 0 | |
| 1.0763 | H | H | $CH_2OCH_2CH=CH_2$ | H | F | $NC(O)C(CH_3)_3$ | 0 | |
| 1.0764 | H | H | $CH_2OCH_2CH=CH_2$ | H | Cl | $NC(O)C(CH_3)_3$ | 0 | |
| 1.0765 | H | H | $CH_2OCH_2CH=CH_2$ | H | H | $NC(O)C(CH_3)_3$ | 0 | |
| 1.0766 | H | H | $CH_2O(CO)CH_3$ | H | F | $NC(O)C(CH_3)_3$ | 0 | |
| 1.0767 | H | H | $CH_2O(CO)CH_3$ | H | Cl | $NC(O)C(CH_3)_3$ | 0 | |
| 1.0768 | H | H | $CH_2O(CO)CH_3$ | H | H | $NC(O)C(CH_3)_3$ | 0 | |
| 1.0769 | H | H | $CH_2OCH_2C\equiv CH$ | H | F | $NC(O)C(CH_3)_3$ | 0 | |
| 1.0770 | H | H | $CH_2OCH_2C\equiv CH$ | H | Cl | $NC(O)C(CH_3)_3$ | 0 | |
| 1.0771 | H | H | $CH_2OCH_2C\equiv CH$ | H | H | $NC(O)C(CH_3)_3$ | 0 | |
| 1.0772 | H | H | $CH_2OCH_2C\equiv CCH_3$ | H | F | $NC(O)C(CH_3)_3$ | 0 | |
| 1.0773 | H | H | $CH_2OCH_2C\equiv CCH_3$ | H | Cl | $NC(O)C(CH_3)_3$ | 0 | |
| 1.0774 | H | H | $CH_2OCH_2C\equiv CCH_3$ | H | H | $NC(O)C(CH_3)_3$ | 0 | |
| 1.0775 | H | H | 4-methyl-2-methylene-1,2,4-triazol-3(4H)-one | H | F | $NC(O)C(CH_3)_3$ | 0 | |
| 1.0776 | H | H | 4-methyl-2-methylene-1,2,4-triazol-3(4H)-one | H | Cl | $NC(O)C(CH_3)_3$ | 0 | |
| 1.0777 | H | H | 4-methyl-2-methylene-1,2,4-triazol-3(4H)-one | H | H | $NC(O)C(CH_3)_3$ | 0 | |

TABLE 1-continued

Compounds of formula Ib:

(Ib)

| No. | $R_1$ | $R_2$ | $Z_1$ | $R_{30}$ | X | Y | p | Physical data |
|---|---|---|---|---|---|---|---|---|
| 1.0778 | H | H | (3-methyl-2-oxo-1,3,4-oxadiazol-5-yl)methyl | H | F | $NC(O)C(CH_3)_3$ | 0 | |
| 1.0779 | H | H | (3-methyl-2-oxo-1,3,4-oxadiazol-5-yl)methyl | H | Cl | $NC(O)C(CH_3)_3$ | 0 | |
| 1.0780 | H | H | (3-methyl-2-oxo-1,3,4-oxadiazol-5-yl)methyl | H | H | $NC(O)C(CH_3)_3$ | 0 | |
| 1.0781 | H | H | oxiranylmethyl | H | F | $NC(O)C(CH_3)_3$ | 0 | |
| 1.0782 | H | H | oxiranylmethyl | H | Cl | $NC(O)C(CH_3)_3$ | 0 | |
| 1.0783 | H | H | oxiranylmethyl | H | H | $NC(O)C(CH_3)_3$ | 0 | |
| 1.0784 | H | H | oxiranylmethoxymethyl | H | F | $NC(O)C(CH_3)_3$ | 0 | |
| 1.0785 | H | H | oxiranylmethoxymethyl | H | Cl | $NC(O)C(CH_3)_3$ | 0 | |
| 1.0786 | H | H | oxiranylmethoxymethyl | H | H | $NC(O)C(CH_3)_3$ | 0 | |
| 1.0787 | H | H | (oxetan-3-yloxy)methyl | H | F | $NC(O)C(CH_3)_3$ | 0 | |
| 1.0788 | H | H | (oxetan-3-yloxy)methyl | H | Cl | $NC(O)C(CH_3)_3$ | 0 | |
| 1.0789 | H | H | (oxetan-3-yloxy)methyl | H | H | $NC(O)C(CH_3)_3$ | 0 | |

TABLE 1-continued

Compounds of formula Ib:

(Ib)

| No. | R₁ | R₂ | Z₁ | R₃₀ | X | Y | p | Physical data |
|---|---|---|---|---|---|---|---|---|
| 1.0790 | H | H | (tetrahydrofuran-3-yl)OCH₂– | H | F | NC(O)C(CH₃)₃ | 0 | |
| 1.0791 | H | H | (tetrahydrofuran-3-yl)OCH₂– | H | Cl | NC(O)C(CH₃)₃ | 0 | |
| 1.0792 | H | H | (tetrahydrofuran-3-yl)OCH₂– | H | H | NC(O)C(CH₃)₃ | 0 | |
| 1.0793 | H | H | CH₂OCH₂CH₂OCH₃ | H | F | NC(O)C(CH₃)₃ | 1 | |
| 1.0794 | H | H | CH₂OCH₂CH₂OCH₃ | H | H | NC(O)C(CH₃)₃ | 1 | |
| 1.0795 | H | H | CH₂OCH₂CH₂OCH₂CH₃ | H | F | NC(O)C(CH₃)₃ | 1 | |
| 1.0796 | H | H | CH₂OCH₂CH₂OCH₂CH₃ | H | H | NC(O)C(CH₃)₃ | 1 | |
| 1.0797 | CH₃ | CH₃ | CH₂OCH₂CH₂OCH₃ | H | F | NC(O)C(CH₃)₃ | 0 | |
| 1.0798 | CH₃ | CH₃ | CH₂OCH₂CH₂OCH₃ | H | Cl | NC(O)C(CH₃)₃ | 0 | |
| 1.0799 | CH₃ | CH₃ | CH₂OCH₂CH₂OCH₃ | H | H | NC(O)C(CH₃)₃ | 0 | |
| 1.0800 | CH₃ | CH₃ | CH₂OCH₂CH₂OCH₂CH₃ | H | F | NC(O)C(CH₃)₃ | 0 | |
| 1.0801 | CH₃ | CH₃ | CH₂OCH₂CH₂OCH₂CH₃ | H | Cl | NC(O)C(CH₃)₃ | 0 | |
| 1.0802 | CH₃ | CH₃ | CH₂OCH₂CH₂OCH₂CH₃ | H | H | NC(O)C(CH₃)₃ | 0 | |
| 1.0803 | CH₃ | CH₃ | CH₂N(CH₃)SO₂CH₃ | H | F | NC(O)C(CH₃)₃ | 0 | |
| 1.0804 | CH₃ | CH₃ | CH₂N(CH₃)SO₂CH₃ | H | Cl | NC(O)C(CH₃)₃ | 0 | |
| 1.0805 | CH₃ | CH₃ | CH₂N(CH₃)SO₂CH₃ | H | H | NC(O)C(CH₃)₃ | 0 | |
| 1.0806 | CH₃ | CH₃ | CH₂OCH₂Ph | H | F | NC(O)C(CH₃)₃ | 0 | |
| 1.0807 | CH₃ | CH₃ | CH₂OCH₂Ph | H | Cl | NC(O)C(CH₃)₃ | 0 | |
| 1.0808 | CH₃ | CH₃ | CH₂OCH₂Ph | H | H | NC(O)C(CH₃)₃ | 0 | |
| 1.0809 | CH₃ | CH₃ | CH₂OCH₂CH₂OH | H | F | NC(O)C(CH₃)₃ | 0 | |
| 1.0810 | CH₃ | CH₃ | CH₂OCH₂CH₂OH | H | Cl | NC(O)C(CH₃)₃ | 0 | |
| 1.0811 | CH₃ | CH₃ | CH₂OCH₂CH₂OH | H | H | NC(O)C(CH₃)₃ | 0 | |
| 1.0812 | CH₃ | CH₃ | CH₂OCH₂CH₂Cl | H | F | NC(O)C(CH₃)₃ | 0 | |
| 1.0813 | CH₃ | CH₃ | CH₂OCH₂CH₂Cl | H | Cl | NC(O)C(CH₃)₃ | 0 | |
| 1.0814 | CH₃ | CH₃ | CH₂OCH₂CH₂Cl | H | H | NC(O)C(CH₃)₃ | 0 | |
| 1.0815 | CH₃ | CH₃ | CH₂OCH₂CF₃ | H | F | NC(O)C(CH₃)₃ | 0 | |
| 1.0816 | CH₃ | CH₃ | CH₂OCH₂CF₃ | H | Cl | NC(O)C(CH₃)₃ | 0 | |
| 1.0817 | CH₃ | CH₃ | CH₂OCH₂CF₃ | H | H | NC(O)C(CH₃)₃ | 0 | |
| 1.0818 | CH₃ | CH₃ | CH₂OCH₂CH=CH₂ | H | F | NC(O)C(CH₃)₃ | 0 | |
| 1.0819 | CH₃ | CH₃ | CH₂OCH₂CH=CH₂ | H | Cl | NC(O)C(CH₃)₃ | 0 | |
| 1.0820 | CH₃ | CH₃ | CH₂OCH₂CH=CH₂ | H | H | NC(O)C(CH₃)₃ | 0 | |
| 1.0821 | CH₃ | CH₃ | CH₂O(CO)CH₃ | H | F | NC(O)C(CH₃)₃ | 0 | |
| 1.0822 | CH₃ | CH₃ | CH₂O(CO)CH₃ | H | Cl | NC(O)C(CH₃)₃ | 0 | |
| 1.0823 | CH₃ | CH₃ | CH₂O(CO)CH₃ | H | H | NC(O)C(CH₃)₃ | 0 | |
| 1.0824 | CH₃ | CH₃ | CH₂OCH₂C≡CH | H | F | NC(O)C(CH₃)₃ | 0 | |
| 1.0825 | CH₃ | CH₃ | CH₂OCH₂C≡CH | H | Cl | NC(O)C(CH₃)₃ | 0 | |
| 1.0826 | CH₃ | CH₃ | CH₂OCH₂C≡CH | H | H | NC(O)C(CH₃)₃ | 0 | |
| 1.0827 | CH₃ | CH₃ | CH₂OCH₂C≡CCH₃ | H | F | NC(O)C(CH₃)₃ | 0 | |
| 1.0828 | CH₃ | CH₃ | CH₂OCH₂C≡CCH₃ | H | Cl | NC(O)C(CH₃)₃ | 0 | |
| 1.0829 | CH₃ | CH₃ | CH₂OCH₂C≡CCH₃ | H | H | NC(O)C(CH₃)₃ | 0 | |
| 1.0830 | CH₃ | CH₃ | (2-methyl-3-oxo-2,3-dihydro-1,2,4-triazol-4-yl)CH₂– | H | F | NC(O)C(CH₃)₃ | 0 | |

TABLE 1-continued

Compounds of formula Ib:

(Ib)

| No. | $R_1$ | $R_2$ | $Z_1$ | $R_{30}$ | X | Y | p | Physical data |
|---|---|---|---|---|---|---|---|---|
| 1.0831 | $CH_3$ | $CH_3$ | 4-(CH₂-)-2-methyl-2,4-dihydro-3H-1,2,4-triazol-3-one | H | Cl | $NC(O)C(CH_3)_3$ | 0 | |
| 1.0832 | $CH_3$ | $CH_3$ | 4-(CH₂-)-2-methyl-2,4-dihydro-3H-1,2,4-triazol-3-one | H | H | $NC(O)C(CH_3)_3$ | 0 | |
| 1.0833 | $CH_3$ | $CH_3$ | 5-(CH₂-)-3-methyl-1,3,4-oxadiazol-2(3H)-one | H | F | $NC(O)C(CH_3)_3$ | 0 | |
| 1.0834 | $CH_3$ | $CH_3$ | 5-(CH₂-)-3-methyl-1,3,4-oxadiazol-2(3H)-one | H | Cl | $NC(O)C(CH_3)_3$ | 0 | |
| 1.0835 | $CH_3$ | $CH_3$ | 5-(CH₂-)-3-methyl-1,3,4-oxadiazol-2(3H)-one | H | H | $NC(O)C(CH_3)_3$ | 0 | |
| 1.0836 | $CH_3$ | $CH_3$ | $CH_2$-oxiranyl | H | F | $NC(O)C(CH_3)_3$ | 0 | |
| 1.0837 | $CH_3$ | $CH_3$ | $CH_2$-oxiranyl | H | Cl | $NC(O)C(CH_3)_3$ | 0 | |
| 1.0838 | $CH_3$ | $CH_3$ | $CH_2$-oxiranyl | H | H | $NC(O)C(CH_3)_3$ | 0 | |
| 1.0839 | $CH_3$ | $CH_3$ | $CH_2OCH_2$-oxiranyl | H | F | $NC(O)C(CH_3)_3$ | 0 | |
| 1.0840 | $CH_3$ | $CH_3$ | $CH_2OCH_2$-oxiranyl | H | Cl | $NC(O)C(CH_3)_3$ | 0 | |
| 1.0841 | $CH_3$ | $CH_3$ | $CH_2OCH_2$-oxiranyl | H | H | $NC(O)C(CH_3)_3$ | 0 | |

TABLE 1-continued

Compounds of formula Ib:

(Ib)

| No. | $R_1$ | $R_2$ | $Z_1$ | $R_{30}$ | X | Y | p | Physical data |
|---|---|---|---|---|---|---|---|---|
| 1.0842 | $CH_3$ | $CH_3$ | $CH_2O$-oxetan-3-yl | H | F | $NC(O)C(CH_3)_3$ | 0 | |
| 1.0843 | $CH_3$ | $CH_3$ | $CH_2O$-oxetan-3-yl | H | Cl | $NC(O)C(CH_3)_3$ | 0 | |
| 1.0844 | $CH_3$ | $CH_3$ | $CH_2O$-oxetan-3-yl | H | H | $NC(O)C(CH_3)_3$ | 0 | |
| 1.0845 | $CH_3$ | $CH_3$ | $CH_2O$-tetrahydrofuran-3-yl | H | F | $NC(O)C(CH_3)_3$ | 0 | |
| 1.0846 | $CH_3$ | $CH_3$ | $CH_2O$-tetrahydrofuran-3-yl | H | Cl | $NC(O)C(CH_3)_3$ | 0 | |
| 1.0847 | $CH_3$ | $CH_3$ | $CH_2O$-tetrahydrofuran-3-yl | H | H | $NC(O)C(CH_3)_3$ | 0 | |
| 1.0848 | $CH_3$ | $CH_3$ | $CH_2OCH_2CH_2OCH_3$ | H | F | $NC(O)C(CH_3)_3$ | 1 | |
| 1.0849 | $CH_3$ | $CH_3$ | $CH_2OCH_2CH_2OCH_3$ | H | H | $NC(O)C(CH_3)_3$ | 1 | |
| 1.0850 | $CH_3$ | $CH_3$ | $CH_2OCH_2CH_2OCH_2CH_3$ | H | F | $NC(O)C(CH_3)_3$ | 1 | |
| 1.0851 | $CH_3$ | $CH_3$ | $CH_2OCH_2CH_2OCH_2CH_3$ | H | H | $NC(O)C(CH_3)_3$ | 1 | |
| 1.0852 | H | $CH_3$ | $CH_2OCH_2CH_2OCH_3$ | H | F | $NC(O)C(CH_3)_3$ | 0 | |
| 1.0853 | H | $CH_3$ | $CH_2OCH_2CH_2OCH_3$ | H | Cl | $NC(O)C(CH_3)_3$ | 0 | |
| 1.0854 | H | $CH_3$ | $CH_2OCH_2CH_2OCH_3$ | H | H | $NC(O)C(CH_3)_3$ | 0 | |
| 1.0855 | H | $CH_3$ | $CH_2OCH_2CH_2OCH_2CH_3$ | H | F | $NC(O)C(CH_3)_3$ | 0 | |
| 1.0856 | H | $CH_3$ | $CH_2OCH_2CH_2OCH_2CH_3$ | H | Cl | $NC(O)C(CH_3)_3$ | 0 | |
| 1.0857 | H | $CH_3$ | $CH_2OCH_2CH_2OCH_2CH_3$ | H | H | $NC(O)C(CH_3)_3$ | 0 | |
| 1.0858 | H | $CH_3$ | $CH_2N(CH_3)SO_2CH_3$ | H | F | $NC(O)C(CH_3)_3$ | 0 | |
| 1.0859 | H | $CH_3$ | $CH_2N(CH_3)SO_2CH_3$ | H | Cl | $NC(O)C(CH_3)_3$ | 0 | |
| 1.0860 | H | $CH_3$ | $CH_2N(CH_3)SO_2CH_3$ | H | H | $NC(O)C(CH_3)_3$ | 0 | |
| 1.0861 | H | $CH_3$ | $CH_2OCH_2Ph$ | H | F | $NC(O)C(CH_3)_3$ | 0 | |
| 1.0862 | H | $CH_3$ | $CH_2OCH_2Ph$ | H | Cl | $NC(O)C(CH_3)_3$ | 0 | |
| 1.0863 | H | $CH_3$ | $CH_2OCH_2Ph$ | H | H | $NC(O)C(CH_3)_3$ | 0 | |
| 1.0864 | H | $CH_3$ | $CH_2OCH_2CH_2OH$ | H | F | $NC(O)C(CH_3)_3$ | 0 | |
| 1.0865 | H | $CH_3$ | $CH_2OCH_2CH_2OH$ | H | Cl | $NC(O)C(CH_3)_3$ | 0 | |
| 1.0866 | H | $CH_3$ | $CH_2OCH_2CH_2OH$ | H | H | $NC(O)C(CH_3)_3$ | 0 | |
| 1.0867 | H | $CH_3$ | $CH_2OCH_2CH_2Cl$ | H | F | $NC(O)C(CH_3)_3$ | 0 | |
| 1.0868 | H | $CH_3$ | $CH_2OCH_2CH_2Cl$ | H | Cl | $NC(O)C(CH_3)_3$ | 0 | |
| 1.0869 | H | $CH_3$ | $CH_2OCH_2CH_2Cl$ | H | H | $NC(O)C(CH_3)_3$ | 0 | |
| 1.0870 | H | $CH_3$ | $CH_2OCH_2CF_3$ | H | F | $NC(O)C(CH_3)_3$ | 0 | |
| 1.0871 | H | $CH_3$ | $CH_2OCH_2CF_3$ | H | Cl | $NC(O)C(CH_3)_3$ | 0 | |
| 1.0872 | H | $CH_3$ | $CH_2OCH_2CF_3$ | H | H | $NC(O)C(CH_3)_3$ | 0 | |
| 1.0873 | H | $CH_3$ | $CH_2OCH_2CH=CH_2$ | H | F | $NC(O)C(CH_3)_3$ | 0 | |
| 1.0874 | H | $CH_3$ | $CH_2OCH_2CH=CH_2$ | H | Cl | $NC(O)C(CH_3)_3$ | 0 | |
| 1.0875 | H | $CH_3$ | $CH_2OCH_2CH=CH_2$ | H | H | $NC(O)C(CH_3)_3$ | 0 | |
| 1.0876 | H | $CH_3$ | $CH_2O(CO)CH_3$ | H | F | $NC(O)C(CH_3)_3$ | 0 | |
| 1.0877 | H | $CH_3$ | $CH_2O(CO)CH_3$ | H | Cl | $NC(O)C(CH_3)_3$ | 0 | |
| 1.0878 | H | $CH_3$ | $CH_2O(CO)CH_3$ | H | H | $NC(O)C(CH_3)_3$ | 0 | |
| 1.0879 | H | $CH_3$ | $CH_2OCH_2C\equiv CH$ | H | F | $NC(O)C(CH_3)_3$ | 0 | |
| 1.0880 | H | $CH_3$ | $CH_2OCH_2C\equiv CH$ | H | Cl | $NC(O)C(CH_3)_3$ | 0 | |

TABLE 1-continued

Compounds of formula Ib:

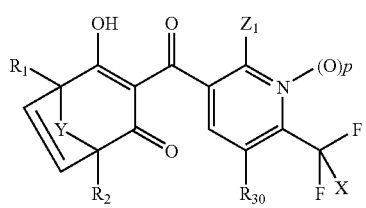

(Ib)

| No. | $R_1$ | $R_2$ | $Z_1$ | $R_{30}$ | X | Y | p | Physical data |
|---|---|---|---|---|---|---|---|---|
| 1.0881 | H | $CH_3$ | $CH_2OCH_2C\equiv CH$ | H | H | $NC(O)C(CH_3)_3$ | 0 | |
| 1.0882 | H | $CH_3$ | $CH_2OCH_2C\equiv CCH_3$ | H | F | $NC(O)C(CH_3)_3$ | 0 | |
| 1.0883 | H | $CH_3$ | $CH_2OCH_2C\equiv CCH_3$ | H | Cl | $NC(O)C(CH_3)_3$ | 0 | |
| 1.0884 | H | $CH_3$ | $CH_2OCH_2C\equiv CCH_3$ | H | H | $NC(O)C(CH_3)_3$ | 0 | |
| 1.0885 | H | $CH_3$ | triazolinone-CH2 | H | F | $NC(O)C(CH_3)_3$ | 0 | |
| 1.0886 | H | $CH_3$ | triazolinone-CH2 | H | Cl | $NC(O)C(CH_3)_3$ | 0 | |
| 1.0887 | H | $CH_3$ | triazolinone-CH2 | H | H | $NC(O)C(CH_3)_3$ | 0 | |
| 1.0888 | H | $CH_3$ | oxadiazolone-CH2 | H | F | $NC(O)C(CH_3)_3$ | 0 | |
| 1.0889 | H | $CH_3$ | oxadiazolone-CH2 | H | Cl | $NC(O)C(CH_3)_3$ | 0 | |
| 1.0890 | H | $CH_3$ | oxadiazolone-CH2 | H | H | $NC(O)C(CH_3)_3$ | 0 | |
| 1.0891 | H | $CH_3$ | $CH_2$-oxiranyl | H | F | $NC(O)C(CH_3)_3$ | 0 | |
| 1.0892 | H | $CH_3$ | $CH_2$-oxiranyl | H | Cl | $NC(O)C(CH_3)_3$ | 0 | |
| 1.0893 | H | $CH_3$ | $CH_2$-oxiranyl | H | H | $NC(O)C(CH_3)_3$ | 0 | |
| 1.0894 | H | $CH_3$ | $CH_2OCH_2$-oxiranyl | H | F | $NC(O)C(CH_3)_3$ | 0 | |

TABLE 1-continued

Compounds of formula Ib:

(Ib)

| No. | R₁ | R₂ | Z₁ | R₃₀ | X | Y | p | Physical data |
|---|---|---|---|---|---|---|---|---|
| 1.0895 | H | CH₃ |  | H | Cl | NC(O)C(CH₃)₃ | 0 | |
| 1.0896 | H | CH₃ | 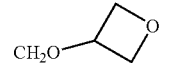 | H | H | NC(O)C(CH₃)₃ | 0 | |
| 1.0897 | H | CH₃ | 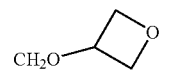 | H | F | NC(O)C(CH₃)₃ | 0 | |
| 1.0898 | H | CH₃ | 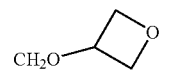 | H | Cl | NC(O)C(CH₃)₃ | 0 | |
| 1.0899 | H | CH₃ | 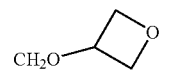 | H | H | NC(O)C(CH₃)₃ | 0 | |
| 1.0900 | H | CH₃ | 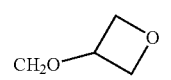 | H | F | NC(O)C(CH₃)₃ | 0 | |
| 1.0901 | H | CH₃ | 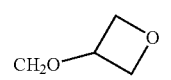 | H | Cl | NC(O)C(CH₃)₃ | 0 | |
| 1.0902 | H | CH₃ | 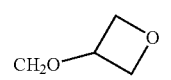 | H | H | NC(O)C(CH₃)₃ | 0 | |
| 1.0903 | H | CH₃ | CH₂OCH₂CH₂OCH₃ | H | F | NC(O)C(CH₃)₃ | 1 | |
| 1.0904 | H | CH₃ | CH₂OCH₂CH₂OCH₃ | H | H | NC(O)C(CH₃)₃ | 1 | |
| 1.0905 | H | CH₃ | CH₂OCH₂CH₂OCH₂CH₃ | H | F | NC(O)C(CH₃)₃ | 1 | |
| 1.0906 | H | CH₃ | CH₂OCH₂CH₂OCH₂CH₃ | H | H | NC(O)C(CH₃)₃ | 1 | |
| 1.0907 | H | H | CH₃ | H | F | NSO₂N(CH₃)₂ | 0 | |
| 1.0908 | H | H | CH₃ | H | Cl | NSO₂N(CH₃)₂ | 0 | |
| 1.0909 | H | H | CH₃ | H | H | NSO₂N(CH₃)₂ | 0 | |
| 1.0910 | H | H | CH₃ | CH₃ | F | NSO₂N(CH₃)₂ | 0 | |
| 1.0911 | H | H | CH₃ | CH₃ | Cl | NSO₂N(CH₃)₂ | 0 | |
| 1.0912 | H | H | CH₃ | CH₃ | H | NSO₂N(CH₃)₂ | 0 | |
| 1.0913 | H | H | CH₂CH₃ | H | F | NSO₂N(CH₃)₂ | 0 | |
| 1.0914 | H | H | CH₂CH₃ | H | Cl | NSO₂N(CH₃)₂ | 0 | |
| 1.0915 | H | H | CH₂CH₃ | H | H | NSO₂N(CH₃)₂ | 0 | |
| 1.0916 | H | H | CH₂CH₂CH₃ | H | F | NSO₂N(CH₃)₂ | 0 | |
| 1.0917 | H | H | CH₂CH₂CH₃ | H | Cl | NSO₂N(CH₃)₂ | 0 | |
| 1.0918 | H | H | CH₂CH₂CH₃ | H | H | NSO₂N(CH₃)₂ | 0 | |
| 1.0919 | H | H | CH₂OCH₃ | H | F | NSO₂N(CH₃)₂ | 0 | |
| 1.0920 | H | H | CH₂OCH₃ | H | Cl | NSO₂N(CH₃)₂ | 0 | |
| 1.0921 | H | H | CH₂OCH₃ | H | H | NSO₂N(CH₃)₂ | 0 | |
| 1.0922 | H | H | CH₂OCH₂CH₃ | H | F | NSO₂N(CH₃)₂ | 0 | |
| 1.0923 | H | H | CH₂OCH₂CH₃ | H | Cl | NSO₂N(CH₃)₂ | 0 | |
| 1.0924 | H | H | CH₂OCH₂CH₃ | H | H | NSO₂N(CH₃)₂ | 0 | |
| 1.0925 | H | H | CH₂OCH₂CH₂OCH₃ | H | F | NSO₂N(CH₃)₂ | 0 | |
| 1.0926 | H | H | CH₂OCH₂CH₂OCH₃ | H | Cl | NSO₂N(CH₃)₂ | 0 | |
| 1.0927 | H | H | CH₂OCH₂CH₂OCH₃ | H | H | NSO₂N(CH₃)₂ | 0 | |

TABLE 1-continued

Compounds of formula Ib:

(Ib)

| No. | $R_1$ | $R_2$ | $Z_1$ | $R_{30}$ | X | Y | p | Physical data |
|---|---|---|---|---|---|---|---|---|
| 1.0928 | H | H | CH$_2$OCH$_2$CH$_2$OCH$_2$CH$_3$ | H | F | NSO$_2$N(CH$_3$)$_2$ | 0 | |
| 1.0929 | H | H | CH$_2$OCH$_2$CH$_2$OCH$_2$CH$_3$ | H | Cl | NSO$_2$N(CH$_3$)$_2$ | 0 | |
| 1.0930 | H | H | CH$_2$OCH$_2$CH$_2$OCH$_2$CH$_3$ | H | H | NSO$_2$N(CH$_3$)$_2$ | 0 | |
| 1.0931 | H | H | CH$_2$CH$_2$OCH$_3$ | H | F | NSO$_2$N(CH$_3$)$_2$ | 0 | |
| 1.0932 | H | H | CH$_2$CH$_2$OCH$_3$ | H | Cl | NSO$_2$N(CH$_3$)$_2$ | 0 | |
| 1.0933 | H | H | CH$_2$CH$_2$OCH$_3$ | H | H | NSO$_2$N(CH$_3$)$_2$ | 0 | |
| 1.0934 | H | H | CH$_2$OCH$_2$C≡CH | H | F | NSO$_2$N(CH$_3$)$_2$ | 0 | |
| 1.0935 | H | H | CH$_2$OCH$_2$C≡CH | H | Cl | NSO$_2$N(CH$_3$)$_2$ | 0 | |
| 1.0936 | H | H | CH$_2$OCH$_2$C≡CH | H | H | NSO$_2$N(CH$_3$)$_2$ | 0 | |
| 1.0937 | H | H | CH$_2$OCH$_2$C≡CCH$_3$ | H | F | NSO$_2$N(CH$_3$)$_2$ | 0 | |
| 1.0938 | H | H | CH$_2$OCH$_2$C≡CCH$_3$ | H | Cl | NSO$_2$N(CH$_3$)$_2$ | 0 | |
| 1.0939 | H | H | CH$_2$OCH$_2$C≡CCH$_3$ | H | H | NSO$_2$N(CH$_3$)$_2$ | 0 | |
| 1.0940 | H | H | CH$_2$CH$_2$CH$_2$OCH$_3$ | H | F | NSO$_2$N(CH$_3$)$_2$ | 0 | |
| 1.0941 | H | H | CH$_2$CH$_2$CH$_2$OCH$_3$ | H | Cl | NSO$_2$N(CH$_3$)$_2$ | 0 | |
| 1.0942 | H | H | CH$_2$CH$_2$CH$_2$OCH$_3$ | H | H | NSO$_2$N(CH$_3$)$_2$ | 0 | |
| 1.0943 | H | H | CH$_2$OCH$_2$OCH$_3$ | H | F | NSO$_2$N(CH$_3$)$_2$ | 0 | |
| 1.0944 | H | H | CH$_2$OCH$_2$OCH$_3$ | H | Cl | NSO$_2$N(CH$_3$)$_2$ | 0 | |
| 1.0945 | H | H | CH$_2$OCH$_2$OCH$_3$ | H | H | NSO$_2$N(CH$_3$)$_2$ | 0 | |
| 1.0946 | H | H | CH$_2$N(CH$_3$)SO$_2$CH$_3$ | H | F | NSO$_2$N(CH$_3$)$_2$ | 0 | |
| 1.0947 | H | H | CH$_2$N(CH$_3$)SO$_2$CH$_3$ | H | Cl | NSO$_2$N(CH$_3$)$_2$ | 0 | |
| 1.0948 | H | H | CH$_2$N(CH$_3$)SO$_2$CH$_3$ | H | H | NSO$_2$N(CH$_3$)$_2$ | 0 | |
| 1.0949 | H | H | CF$_3$ | H | F | NSO$_2$N(CH$_3$)$_2$ | 0 | |
| 1.0950 | H | H | CF$_3$ | H | Cl | NSO$_2$N(CH$_3$)$_2$ | 0 | |
| 1.0951 | H | H | CF$_3$ | H | H | NSO$_2$N(CH$_3$)$_2$ | 0 | |
| 1.0952 | H | H | CH$_2$OCH$_2$CF$_3$ | H | F | NSO$_2$N(CH$_3$)$_2$ | 0 | |
| 1.0953 | H | H | CH$_2$OCH$_2$CF$_3$ | H | Cl | NSO$_2$N(CH$_3$)$_2$ | 0 | |
| 1.0954 | H | H | CH$_2$OCH$_2$CF$_3$ | H | H | NSO$_2$N(CH$_3$)$_2$ | 0 | |
| 1.0955 | H | H | CH$_2$OCH$_2$Ph | H | F | NSO$_2$N(CH$_3$)$_2$ | 0 | |
| 1.0956 | H | H | CH$_2$OCH$_2$Ph | H | Cl | NSO$_2$N(CH$_3$)$_2$ | 0 | |
| 1.0957 | H | H | CH$_2$OCH$_2$Ph | H | H | NSO$_2$N(CH$_3$)$_2$ | 0 | |
| 1.0958 | H | H | CH$_2$OCH$_2$CH=CH$_2$ | H | F | NSO$_2$N(CH$_3$)$_2$ | 0 | |
| 1.0959 | H | H | CH$_2$OCH$_2$CH=CH$_2$ | H | Cl | NSO$_2$N(CH$_3$)$_2$ | 0 | |
| 1.0960 | H | H | CH$_2$OCH$_2$CH=CH$_2$ | H | H | NSO$_2$N(CH$_3$)$_2$ | 0 | |
| 1.0961 | H | H | (4-methyl-3-oxo-1,2,4-triazol-1-yl)methyl | H | F | NSO$_2$N(CH$_3$)$_2$ | 0 | |
| 1.0962 | H | H | (4-methyl-3-oxo-1,2,4-triazol-1-yl)methyl | H | Cl | NSO$_2$N(CH$_3$)$_2$ | 0 | |
| 1.0963 | H | H | (4-methyl-3-oxo-1,2,4-triazol-1-yl)methyl | H | H | NSO$_2$N(CH$_3$)$_2$ | 0 | |
| 1.0964 | H | H | (3-methyl-2-oxo-1,3,4-oxadiazol-5-yl)methyl | H | F | NSO$_2$N(CH$_3$)$_2$ | 0 | |

TABLE 1-continued
Compounds of formula Ib:
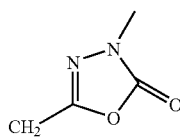
(Ib)
| No. | $R_1$ | $R_2$ | $Z_1$ | $R_{30}$ | X | Y | p | Physical data |
|---|---|---|---|---|---|---|---|---|
| 1.0965 | H | H | 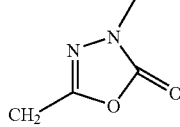 | H | Cl | $NSO_2N(CH_3)_2$ | 0 | |
| 1.0966 | H | H | 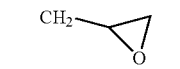 | H | H | $NSO_2N(CH_3)_2$ | 0 | |
| 1.0967 | H | H | 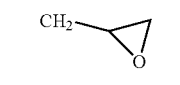 | H | F | $NSO_2N(CH_3)_2$ | 0 | |
| 1.0968 | H | H | 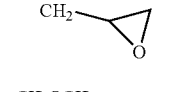 | H | Cl | $NSO_2N(CH_3)_2$ | 0 | |
| 1.0969 | H | H |  | H | H | $NSO_2N(CH_3)_2$ | 0 | |
| 1.0970 | H | H | 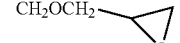 | H | F | $NSO_2N(CH_3)_2$ | 0 | |
| 1.0971 | H | H | 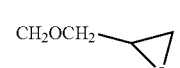 | H | Cl | $NSO_2N(CH_3)_2$ | 0 | |
| 1.0972 | H | H | 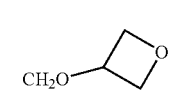 | H | H | $NSO_2N(CH_3)_2$ | 0 | |
| 1.0973 | H | H | 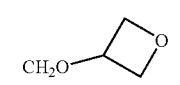 | H | F | $NSO_2N(CH_3)_2$ | 0 | |
| 1.0974 | H | H | 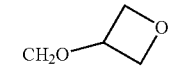 | H | Cl | $NSO_2N(CH_3)_2$ | 0 | |
| 1.0975 | H | H | 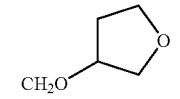 | H | H | $NSO_2N(CH_3)_2$ | 0 | |
| 1.0976 | H | H | 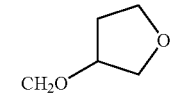 | H | F | $NSO_2N(CH_3)_2$ | 0 | |
| 1.0977 | H | H |  | H | Cl | $NSO_2N(CH_3)_2$ | 0 | |

TABLE 1-continued

Compounds of formula Ib:

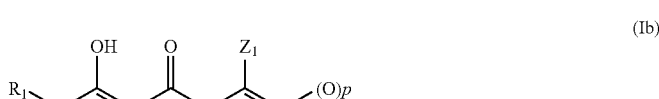

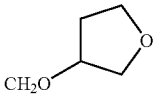

| No. | R₁ | R₂ | Z₁ | R₃₀ | X | Y | p | Physical data |
|---|---|---|---|---|---|---|---|---|
| 1.0978 | H | H | (tetrahydrofuran-3-yl-methoxy) CH₂O– | H | H | NSO₂N(CH₃)₂ | 0 | |
| 1.0979 | H | H | CH₃ | H | F | NSO₂N(CH₃)₂ | 1 | |
| 1.0980 | H | H | CH₂OCH₃ | H | F | NSO₂N(CH₃)₂ | 1 | |
| 1.0981 | H | H | CH₂OCH₂CH₂OCH₃ | H | F | NSO₂N(CH₃)₂ | 1 | |
| 1.0982 | H | H | CH₂CH₂CH₂OCH₃ | H | F | NSO₂N(CH₃)₂ | 1 | |
| 1.0983 | H | H | CH₂CH₃ | H | F | NSO₂N(CH₃)₂ | 1 | |
| 1.0984 | H | H | CH₃ | H | H | NSO₂N(CH₃)₂ | 1 | |
| 1.0985 | H | H | CH₂OCH₃ | H | H | NSO₂N(CH₃)₂ | 1 | |
| 1.0986 | H | H | CH₂OCH₂CH₂OCH₃ | H | H | NSO₂N(CH₃)₂ | 1 | |
| 1.0987 | H | H | CH₂CH₂CH₂OCH₃ | H | H | NSO₂N(CH₃)₂ | 1 | |
| 1.0988 | H | H | CH₂CH₃ | H | H | NSO₂N(CH₃)₂ | 1 | |
| 1.0989 | CH₃ | CH₃ | CH₃ | H | F | NSO₂N(CH₃)₂ | 0 | |
| 1.0990 | CH₃ | CH₃ | CH₃ | H | Cl | NSO₂N(CH₃)₂ | 0 | |
| 1.0991 | CH₃ | CH₃ | CH₃ | H | H | NSO₂N(CH₃)₂ | 0 | |
| 1.0992 | CH₃ | CH₃ | CH₃ | CH₃ | F | NSO₂N(CH₃)₂ | 0 | |
| 1.0993 | CH₃ | CH₃ | CH₃ | CH₃ | Cl | NSO₂N(CH₃)₂ | 0 | |
| 1.0994 | CH₃ | CH₃ | CH₃ | CH₃ | H | NSO₂N(CH₃)₂ | 0 | |
| 1.0995 | CH₃ | CH₃ | CH₂CH₃ | H | F | NSO₂N(CH₃)₂ | 0 | |
| 1.0996 | CH₃ | CH₃ | CH₂CH₃ | H | Cl | NSO₂N(CH₃)₂ | 0 | |
| 1.0997 | CH₃ | CH₃ | CH₂CH₃ | H | H | NSO₂N(CH₃)₂ | 0 | |
| 1.0998 | CH₃ | CH₃ | CH₂CH₂CH₃ | H | F | NSO₂N(CH₃)₂ | 0 | |
| 1.0999 | CH₃ | CH₃ | CH₂CH₂CH₃ | H | Cl | NSO₂N(CH₃)₂ | 0 | |
| 1.1000 | CH₃ | CH₃ | CH₂CH₂CH₃ | H | H | NSO₂N(CH₃)₂ | 0 | |
| 1.1001 | CH₃ | CH₃ | CH₂OCH₃ | H | F | NSO₂N(CH₃)₂ | 0 | |
| 1.1002 | CH₃ | CH₃ | CH₂OCH₃ | H | Cl | NSO₂N(CH₃)₂ | 0 | |
| 1.1003 | CH₃ | CH₃ | CH₂OCH₃ | H | H | NSO₂N(CH₃)₂ | 0 | |
| 1.1004 | CH₃ | CH₃ | CH₂OCH₂CH₃ | H | F | NSO₂N(CH₃)₂ | 0 | |
| 1.1005 | CH₃ | CH₃ | CH₂OCH₂CH₃ | H | Cl | NSO₂N(CH₃)₂ | 0 | |
| 1.1006 | CH₃ | CH₃ | CH₂OCH₂CH₃ | H | H | NSO₂N(CH₃)₂ | 0 | |
| 1.1007 | CH₃ | CH₃ | CH₂OCH₂CH₂OCH₃ | H | F | NSO₂N(CH₃)₂ | 0 | |
| 1.1008 | CH₃ | CH₃ | CH₂OCH₂CH₂OCH₃ | H | Cl | NSO₂N(CH₃)₂ | 0 | |
| 1.1009 | CH₃ | CH₃ | CH₂OCH₂CH₂OCH₃ | H | H | NSO₂N(CH₃)₂ | 0 | |
| 1.1010 | CH₃ | CH₃ | CH₂OCH₂CH₂OCH₂CH₃ | H | F | NSO₂N(CH₃)₂ | 0 | |
| 1.1011 | CH₃ | CH₃ | CH₂OCH₂CH₂OCH₂CH₃ | H | Cl | NSO₂N(CH₃)₂ | 0 | |
| 1.1012 | CH₃ | CH₃ | CH₂OCH₂CH₂OCH₂CH₃ | H | H | NSO₂N(CH₃)₂ | 0 | |
| 1.1013 | CH₃ | CH₃ | CH₂CH₂OCH₃ | H | F | NSO₂N(CH₃)₂ | 0 | |
| 1.1014 | CH₃ | CH₃ | CH₂CH₂OCH₃ | H | Cl | NSO₂N(CH₃)₂ | 0 | |
| 1.1015 | CH₃ | CH₃ | CH₂CH₂OCH₃ | H | H | NSO₂N(CH₃)₂ | 0 | |
| 1.1016 | CH₃ | CH₃ | CH₂OCH₂C≡CH | H | F | NSO₂N(CH₃)₂ | 0 | |
| 1.1017 | CH₃ | CH₃ | CH₂OCH₂C≡CH | H | Cl | NSO₂N(CH₃)₂ | 0 | |
| 1.1018 | CH₃ | CH₃ | CH₂OCH₂C≡CH | H | H | NSO₂N(CH₃)₂ | 0 | |
| 1.1019 | CH₃ | CH₃ | CH₂OCH₂C≡CCH₃ | H | F | NSO₂N(CH₃)₂ | 0 | |
| 1.1020 | CH₃ | CH₃ | CH₂OCH₂C≡CCH₃ | H | Cl | NSO₂N(CH₃)₂ | 0 | |
| 1.1021 | CH₃ | CH₃ | CH₂OCH₂C≡CCH₃ | H | H | NSO₂N(CH₃)₂ | 0 | |
| 1.1022 | CH₃ | CH₃ | CH₂CH₂CH₂OCH₃ | H | F | NSO₂N(CH₃)₂ | 0 | |
| 1.1023 | CH₃ | CH₃ | CH₂CH₂CH₂OCH₃ | H | Cl | NSO₂N(CH₃)₂ | 0 | |
| 1.1024 | CH₃ | CH₃ | CH₂CH₂CH₂OCH₃ | H | H | NSO₂N(CH₃)₂ | 0 | |
| 1.1025 | CH₃ | CH₃ | CH₂OCH₂OCH₃ | H | F | NSO₂N(CH₃)₂ | 0 | |
| 1.1026 | CH₃ | CH₃ | CH₂OCH₂OCH₃ | H | Cl | NSO₂N(CH₃)₂ | 0 | |
| 1.1027 | CH₃ | CH₃ | CH₂OCH₂OCH₃ | H | H | NSO₂N(CH₃)₂ | 0 | |
| 1.1028 | CH₃ | CH₃ | CH₂N(CH₃)SO₂CH₃ | H | F | NSO₂N(CH₃)₂ | 0 | |
| 1.1029 | CH₃ | CH₃ | CH₂N(CH₃)SO₂CH₃ | H | Cl | NSO₂N(CH₃)₂ | 0 | |
| 1.1030 | CH₃ | CH₃ | CH₂N(CH₃)SO₂CH₃ | H | H | NSO₂N(CH₃)₂ | 0 | |
| 1.1031 | CH₃ | CH₃ | CF₃ | H | F | NSO₂N(CH₃)₂ | 0 | |
| 1.1032 | CH₃ | CH₃ | CF₃ | H | Cl | NSO₂N(CH₃)₂ | 0 | |
| 1.1033 | CH₃ | CH₃ | CF₃ | H | H | NSO₂N(CH₃)₂ | 0 | |
| 1.1034 | CH₃ | CH₃ | CH₂OCH₂CF₃ | H | F | NSO₂N(CH₃)₂ | 0 | |
| 1.1035 | CH₃ | CH₃ | CH₂OCH₂CF₃ | H | Cl | NSO₂N(CH₃)₂ | 0 | |

TABLE 1-continued

Compounds of formula Ib:

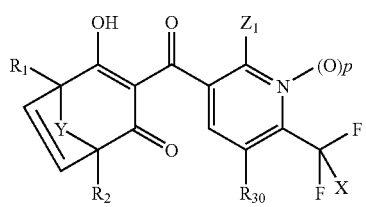

(Ib)

| No. | $R_1$ | $R_2$ | $Z_1$ | $R_{30}$ | X | Y | p | Physical data |
|---|---|---|---|---|---|---|---|---|
| 1.1036 | $CH_3$ | $CH_3$ | $CH_2OCH_2CF_3$ | H | H | $NSO_2N(CH_3)_2$ | 0 | |
| 1.1037 | $CH_3$ | $CH_3$ | $CH_2OCH_2Ph$ | H | F | $NSO_2N(CH_3)_2$ | 0 | |
| 1.1038 | $CH_3$ | $CH_3$ | $CH_2OCH_2Ph$ | H | Cl | $NSO_2N(CH_3)_2$ | 0 | |
| 1.1039 | $CH_3$ | $CH_3$ | $CH_2OCH_2Ph$ | H | H | $NSO_2N(CH_3)_2$ | 0 | |
| 1.1040 | $CH_3$ | $CH_3$ | $CH_2OCH_2CH{=}CH_2$ | H | F | $NSO_2N(CH_3)_2$ | 0 | |
| 1.1041 | $CH_3$ | $CH_3$ | $CH_2OCH_2CH{=}CH_2$ | H | Cl | $NSO_2N(CH_3)_2$ | 0 | |
| 1.1042 | $CH_3$ | $CH_3$ | $CH_2OCH_2CH{=}CH_2$ | H | H | $NSO_2N(CH_3)_2$ | 0 | |
| 1.1043 | $CH_3$ | $CH_3$ | (N-methyl-triazolinone-CH2) | H | F | $NSO_2N(CH_3)_2$ | 0 | |
| 1.1044 | $CH_3$ | $CH_3$ | (N-methyl-triazolinone-CH2) | H | Cl | $NSO_2N(CH_3)_2$ | 0 | |
| 1.1045 | $CH_3$ | $CH_3$ | (N-methyl-triazolinone-CH2) | H | H | $NSO_2N(CH_3)_2$ | 0 | |
| 1.1046 | $CH_3$ | $CH_3$ | (N-methyl-oxadiazolinone-CH2) | H | F | $NSO_2N(CH_3)_2$ | 0 | |
| 1.1047 | $CH_3$ | $CH_3$ | (N-methyl-oxadiazolinone-CH2) | H | Cl | $NSO_2N(CH_3)_2$ | 0 | |
| 1.1048 | $CH_3$ | $CH_3$ | (N-methyl-oxadiazolinone-CH2) | H | H | $NSO_2N(CH_3)_2$ | 0 | |
| 1.1049 | $CH_3$ | $CH_3$ | $CH_2$-oxiranyl | H | F | $NSO_2N(CH_3)_2$ | 0 | |
| 1.1050 | $CH_3$ | $CH_3$ | $CH_2$-oxiranyl | H | Cl | $NSO_2N(CH_3)_2$ | 0 | |
| 1.1051 | $CH_3$ | $CH_3$ | $CH_2$-oxiranyl | H | H | $NSO_2N(CH_3)_2$ | 0 | |

TABLE 1-continued

Compounds of formula Ib:

(Ib)

| No. | R₁ | R₂ | Z₁ | R₃₀ | X | Y | p | Physical data |
|---|---|---|---|---|---|---|---|---|
| 1.1052 | CH₃ | CH₃ | CH₂OCH₂— | H | F | NSO₂N(CH₃)₂ | 0 | |
| 1.1053 | CH₃ | CH₃ | CH₂OCH₂— | H | Cl | NSO₂N(CH₃)₂ | 0 | |
| 1.1054 | CH₃ | CH₃ | CH₂OCH₂—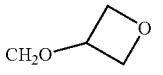 | H | H | NSO₂N(CH₃)₂ | 0 | |
| 1.1055 | CH₃ | CH₃ | 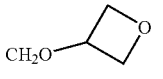 | H | F | NSO₂N(CH₃)₂ | 0 | |
| 1.1056 | CH₃ | CH₃ | 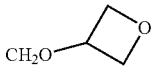 | H | Cl | NSO₂N(CH₃)₂ | 0 | |
| 1.1057 | CH₃ | CH₃ | 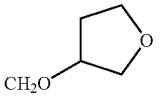 | H | H | NSO₂N(CH₃)₂ | 0 | |
| 1.1058 | CH₃ | CH₃ | 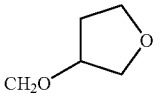 | H | F | NSO₂N(CH₃)₂ | 0 | |
| 1.1059 | CH₃ | CH₃ | 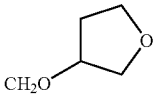 | H | Cl | NSO₂N(CH₃)₂ | 0 | |
| 1.1060 | CH₃ | CH₃ | (tetrahydrofuran-CH₂O) | H | H | NSO₂N(CH₃)₂ | 0 | |
| 1.1061 | CH₃ | CH₃ | CH₃ | H | F | NSO₂N(CH₃)₂ | 1 | |
| 1.1062 | CH₃ | CH₃ | CH₂OCH₃ | H | F | NSO₂N(CH₃)₂ | 1 | |
| 1.1063 | CH₃ | CH₃ | CH₂OCH₂CH₂OCH₃ | H | F | NSO₂N(CH₃)₂ | 1 | |
| 1.1064 | CH₃ | CH₃ | CH₂CH₂CH₂OCH₃ | H | F | NSO₂N(CH₃)₂ | 1 | |
| 1.1065 | CH₃ | CH₃ | CH₂CH₃ | H | F | NSO₂N(CH₃)₂ | 1 | |
| 1.1066 | CH₃ | CH₃ | CH₃ | H | H | NSO₂N(CH₃)₂ | 1 | |
| 1.1067 | CH₃ | CH₃ | CH₂OCH₃ | H | H | NSO₂N(CH₃)₂ | 1 | |
| 1.1068 | CH₃ | CH₃ | CH₂OCH₂CH₂OCH₃ | H | H | NSO₂N(CH₃)₂ | 1 | |
| 1.1069 | CH₃ | CH₃ | CH₂CH₂CH₂OCH₃ | H | H | NSO₂N(CH₃)₂ | 1 | |
| 1.1070 | CH₃ | CH₃ | CH₂CH₃ | H | H | NSO₂N(CH₃)₂ | 1 | |
| 1.1071 | H | CH₃ | CH₃ | H | F | NSO₂N(CH₃)₂ | 0 | |
| 1.1072 | H | CH₃ | CH₃ | H | Cl | NSO₂N(CH₃)₂ | 0 | |
| 1.1073 | H | CH₃ | CH₃ | H | H | NSO₂N(CH₃)₂ | 0 | |
| 1.1074 | H | CH₃ | CH₃ | CH₃ | F | NSO₂N(CH₃)₂ | 0 | |
| 1.1075 | H | CH₃ | CH₃ | CH₃ | Cl | NSO₂N(CH₃)₂ | 0 | |
| 1.1076 | H | CH₃ | CH₃ | CH₃ | H | NSO₂N(CH₃)₂ | 0 | |
| 1.1077 | H | CH₃ | CH₂CH₃ | H | F | NSO₂N(CH₃)₂ | 0 | |
| 1.1078 | H | CH₃ | CH₂CH₃ | H | Cl | NSO₂N(CH₃)₂ | 0 | |
| 1.1079 | H | CH₃ | CH₂CH₃ | H | H | NSO₂N(CH₃)₂ | 0 | |
| 1.1080 | H | CH₃ | CH₂CH₂CH₃ | H | F | NSO₂N(CH₃)₂ | 0 | |
| 1.1081 | H | CH₃ | CH₂CH₂CH₃ | H | Cl | NSO₂N(CH₃)₂ | 0 | |

TABLE 1-continued

Compounds of formula Ib:

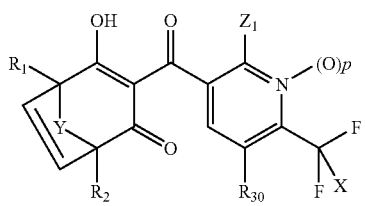

(Ib)

| No. | $R_1$ | $R_2$ | $Z_1$ | $R_{30}$ | X | Y | p | Physical data |
|---|---|---|---|---|---|---|---|---|
| 1.1082 | H | $CH_3$ | $CH_2CH_2CH_3$ | H | H | $NSO_2N(CH_3)_2$ | 0 | |
| 1.1083 | H | $CH_3$ | $CH_2OCH_3$ | H | F | $NSO_2N(CH_3)_2$ | 0 | |
| 1.1084 | H | $CH_3$ | $CH_2OCH_3$ | H | Cl | $NSO_2N(CH_3)_2$ | 0 | |
| 1.1085 | H | $CH_3$ | $CH_2OCH_3$ | H | H | $NSO_2N(CH_3)_2$ | 0 | |
| 1.1086 | H | $CH_3$ | $CH_2OCH_2CH_3$ | H | F | $NSO_2N(CH_3)_2$ | 0 | |
| 1.1087 | H | $CH_3$ | $CH_2OCH_2CH_3$ | H | Cl | $NSO_2N(CH_3)_2$ | 0 | |
| 1.1088 | H | $CH_3$ | $CH_2OCH_2CH_3$ | H | H | $NSO_2N(CH_3)_2$ | 0 | |
| 1.1089 | H | $CH_3$ | $CH_2OCH_2CH_2OCH_3$ | H | F | $NSO_2N(CH_3)_2$ | 0 | |
| 1.1090 | H | $CH_3$ | $CH_2OCH_2CH_2OCH_3$ | H | Cl | $NSO_2N(CH_3)_2$ | 0 | |
| 1.1091 | H | $CH_3$ | $CH_2OCH_2CH_2OCH_3$ | H | H | $NSO_2N(CH_3)_2$ | 0 | |
| 1.1092 | H | $CH_3$ | $CH_2OCH_2CH_2OCH_2CH_3$ | H | F | $NSO_2N(CH_3)_2$ | 0 | |
| 1.1093 | H | $CH_3$ | $CH_2OCH_2CH_2OCH_2CH_3$ | H | Cl | $NSO_2N(CH_3)_2$ | 0 | |
| 1.1094 | H | $CH_3$ | $CH_2OCH_2CH_2OCH_2CH_3$ | H | H | $NSO_2N(CH_3)_2$ | 0 | |
| 1.1095 | H | $CH_3$ | $CH_2CH_2OCH_3$ | H | F | $NSO_2N(CH_3)_2$ | 0 | |
| 1.1096 | H | $CH_3$ | $CH_2CH_2OCH_3$ | H | Cl | $NSO_2N(CH_3)_2$ | 0 | |
| 1.1097 | H | $CH_3$ | $CH_2CH_2OCH_3$ | H | H | $NSO_2N(CH_3)_2$ | 0 | |
| 1.1098 | H | $CH_3$ | $CH_2OCH_2C{\equiv}CH$ | H | F | $NSO_2N(CH_3)_2$ | 0 | |
| 1.1099 | H | $CH_3$ | $CH_2OCH_2C{\equiv}CH$ | H | Cl | $NSO_2N(CH_3)_2$ | 0 | |
| 1.1100 | H | $CH_3$ | $CH_2OCH_2C{\equiv}CH$ | H | H | $NSO_2N(CH_3)_2$ | 0 | |
| 1.1101 | H | $CH_3$ | $CH_2OCH_2C{\equiv}CCH_3$ | H | F | $NSO_2N(CH_3)_2$ | 0 | |
| 1.1102 | H | $CH_3$ | $CH_2OCH_2C{\equiv}CCH_3$ | H | Cl | $NSO_2N(CH_3)_2$ | 0 | |
| 1.1103 | H | $CH_3$ | $CH_2OCH_2C{\equiv}CCH_3$ | H | H | $NSO_2N(CH_3)_2$ | 0 | |
| 1.1104 | H | $CH_3$ | $CH_2CH_2CH_2OCH_3$ | H | F | $NSO_2N(CH_3)_2$ | 0 | |
| 1.1105 | H | $CH_3$ | $CH_2CH_2CH_2OCH_3$ | H | Cl | $NSO_2N(CH_3)_2$ | 0 | |
| 1.1106 | H | $CH_3$ | $CH_2CH_2CH_2OCH_3$ | H | H | $NSO_2N(CH_3)_2$ | 0 | |
| 1.1107 | H | $CH_3$ | $CH_2OCH_2OCH_3$ | H | F | $NSO_2N(CH_3)_2$ | 0 | |
| 1.1108 | H | $CH_3$ | $CH_2OCH_2OCH_3$ | H | Cl | $NSO_2N(CH_3)_2$ | 0 | |
| 1.1109 | H | $CH_3$ | $CH_2OCH_2OCH_3$ | H | H | $NSO_2N(CH_3)_2$ | 0 | |
| 1.1110 | H | $CH_3$ | $CH_2N(CH_3)SO_2CH_3$ | H | F | $NSO_2N(CH_3)_2$ | 0 | |
| 1.1111 | H | $CH_3$ | $CH_2N(CH_3)SO_2CH_3$ | H | Cl | $NSO_2N(CH_3)_2$ | 0 | |
| 1.1112 | H | $CH_3$ | $CH_2N(CH_3)SO_2CH_3$ | H | H | $NSO_2N(CH_3)_2$ | 0 | |
| 1.1113 | H | $CH_3$ | $CF_3$ | H | F | $NSO_2N(CH_3)_2$ | 0 | |
| 1.1114 | H | $CH_3$ | $CF_3$ | H | Cl | $NSO_2N(CH_3)_2$ | 0 | |
| 1.1115 | H | $CH_3$ | $CF_3$ | H | H | $NSO_2N(CH_3)_2$ | 0 | |
| 1.1116 | H | $CH_3$ | $CH_2OCH_2CF_3$ | H | F | $NSO_2N(CH_3)_2$ | 0 | |
| 1.1117 | H | $CH_3$ | $CH_2OCH_2CF_3$ | H | Cl | $NSO_2N(CH_3)_2$ | 0 | |
| 1.1118 | H | $CH_3$ | $CH_2OCH_2CF_3$ | H | H | $NSO_2N(CH_3)_2$ | 0 | |
| 1.1119 | H | $CH_3$ | $CH_2OCH_2Ph$ | H | F | $NSO_2N(CH_3)_2$ | 0 | |
| 1.1120 | H | $CH_3$ | $CH_2OCH_2Ph$ | H | Cl | $NSO_2N(CH_3)_2$ | 0 | |
| 1.1121 | H | $CH_3$ | $CH_2OCH_2Ph$ | H | H | $NSO_2N(CH_3)_2$ | 0 | |
| 1.1122 | H | $CH_3$ | $CH_2OCH_2CH{=}CH_2$ | H | F | $NSO_2N(CH_3)_2$ | 0 | |
| 1.1123 | H | $CH_3$ | $CH_2OCH_2CH{=}CH_2$ | H | Cl | $NSO_2N(CH_3)_2$ | 0 | |
| 1.1124 | H | $CH_3$ | $CH_2OCH_2CH{=}CH_2$ | H | H | $NSO_2N(CH_3)_2$ | 0 | |
| 1.1125 | H | $CH_3$ | (4-methyl-5-oxo-4H-1,2,4-triazol-3-yl)methyl | H | F | $NSO_2N(CH_3)_2$ | 0 | |
| 1.1126 | H | $CH_3$ | (4-methyl-5-oxo-4H-1,2,4-triazol-3-yl)methyl | H | Cl | $NSO_2N(CH_3)_2$ | 0 | |

TABLE 1-continued

Compounds of formula Ib:

(Ib)

| No. | $R_1$ | $R_2$ | $Z_1$ | $R_{30}$ | X | Y | p | Physical data |
|---|---|---|---|---|---|---|---|---|
| 1.1127 | H | $CH_3$ | ![triazolone-CH2] | H | H | $NSO_2N(CH_3)_2$ | 0 | |
| 1.1128 | H | $CH_3$ | ![oxadiazolone-CH2] | H | F | $NSO_2N(CH_3)_2$ | 0 | |
| 1.1129 | H | $CH_3$ | ![oxadiazolone-CH2] | H | Cl | $NSO_2N(CH_3)_2$ | 0 | |
| 1.1130 | H | $CH_3$ | ![oxadiazolone-CH2] | H | H | $NSO_2N(CH_3)_2$ | 0 | |
| 1.1131 | H | $CH_3$ | $CH_2$-epoxide | H | F | $NSO_2N(CH_3)_2$ | 0 | |
| 1.1132 | H | $CH_3$ | $CH_2$-epoxide | H | Cl | $NSO_2N(CH_3)_2$ | 0 | |
| 1.1133 | H | $CH_3$ | $CH_2$-epoxide | H | H | $NSO_2N(CH_3)_2$ | 0 | |
| 1.1134 | H | $CH_3$ | $CH_2OCH_2$-epoxide | H | F | $NSO_2N(CH_3)_2$ | 0 | |
| 1.1135 | H | $CH_3$ | $CH_2OCH_2$-epoxide | H | Cl | $NSO_2N(CH_3)_2$ | 0 | |
| 1.1136 | H | $CH_3$ | $CH_2OCH_2$-epoxide | H | H | $NSO_2N(CH_3)_2$ | 0 | |
| 1.1137 | H | $CH_3$ | $CH_2O$-oxetane | H | F | $NSO_2N(CH_3)_2$ | 0 | |
| 1.1138 | H | $CH_3$ | $CH_2O$-oxetane | H | Cl | $NSO_2N(CH_3)_2$ | 0 | |

TABLE 1-continued

Compounds of formula Ib:

(Ib)

[Structure: chemical structure of formula Ib showing a cyclohexenedione ring with OH, R₁, R₂, Y substituents connected via C=O to a pyridine ring bearing Z₁, N(O)p, R₃₀, and CF₂X groups]

| No. | R₁ | R₂ | Z₁ | R₃₀ | X | Y | p | Physical data |
|---|---|---|---|---|---|---|---|---|
| 1.1139 | H | CH₃ | [oxetane-CH₂O-] | H | H | NSO₂N(CH₃)₂ | 0 | |
| 1.1140 | H | CH₃ | [tetrahydrofuran-CH₂O-] | H | F | NSO₂N(CH₃)₂ | 0 | |
| 1.1141 | H | CH₃ | [tetrahydrofuran-CH₂O-] | H | Cl | NSO₂N(CH₃)₂ | 0 | |
| 1.1142 | H | CH₃ | [tetrahydrofuran-CH₂O-] | H | H | NSO₂N(CH₃)₂ | 0 | |
| 1.1143 | H | CH₃ | CH₃ | H | F | NSO₂N(CH₃)₂ | 1 | |
| 1.1144 | H | CH₃ | CH₂OCH₃ | H | F | NSO₂N(CH₃)₂ | 1 | |
| 1.1145 | H | CH₃ | CH₂OCH₂CH₂OCH₃ | H | F | NSO₂N(CH₃)₂ | 1 | |
| 1.1146 | H | CH₃ | CH₂CH₂CH₂OCH₃ | H | F | NSO₂N(CH₃)₂ | 1 | |
| 1.1147 | H | CH₃ | CH₂CH₃ | H | F | NSO₂N(CH₃)₂ | 1 | |
| 1.1148 | H | CH₃ | CH₃ | H | H | NSO₂N(CH₃)₂ | 1 | |
| 1.1149 | H | CH₃ | CH₂OCH₃ | H | H | NSO₂N(CH₃)₂ | 1 | |
| 1.1150 | H | CH₃ | CH₂OCH₂CH₂OCH₃ | H | H | NSO₂N(CH₃)₂ | 1 | |
| 1.1151 | H | CH₃ | CH₂CH₂CH₂OCH₃ | H | H | NSO₂N(CH₃)₂ | 1 | |
| 1.1152 | H | CH₃ | CH₂CH₃ | H | H | NSO₂N(CH₃)₂ | 1 | |
| 1.1153 | H | H | CH₃ | H | F | [cyclopropyl-C<] | 0 | ¹H NMR (300 MHz; CDCl₃) δ 16.58 (s, 1H); 7.55 (m, 2H); 6.48 (m, 1H); 6.40 (m, 1H); 2.94 (m, 1H): 2.72 (m, 1H); 2.50 (s, 3H); 0.90-0.65 (m, 4H). |
| 1.1154 | H | H | CH₃ | H | F | C(=C(CH₃)₂) | 0 | ¹H NMR (300 MHz; CDCl₃) δ 16.25 (s, 1H); 7.56 (m, 2H); 6.52 (m, 1H); 6.45 (m, 1H); 4.20 (m, 1H); 3.98 (m, 1H); 2.45 (s, 3H); 1.80 (s, 3H); 1.71 (s, 3H). |
| 1.1155 | H | H | CH₃ | H | H | CH₂CH(COOCH₃) | 0 | R₇ = Br; ¹H NMR (300 MHz; CDCl₃) i.a. δ 7.44 (d, 2H); 6.54 (t, 1H), 6.53 + 6.42 (2d, 1H); 3.71 + 3.68 (2s, 3H); 2.41 + 2.40 (2s, 3H); tautomeric mixture. |
| 1.1156 | H | H | CH₃ | H | H | CH₂CH(COOCH₃) | 0 | R₇ = H; NEt₃ salt (Example P14) |

TABLE 2

Compounds of formula Ic:

(Ic)

| No. | R$_1$ | R$_2$ | Z$_1$ | R$_{30}$ | X | Y | Physical data |
|---|---|---|---|---|---|---|---|
| 2.0000 | H | H | CH$_2$OCH$_2$CH$_2$OCH$_3$ | H | F | CH$_2$ | |
| 2.0001 | H | H | CH$_2$OCH$_2$CH$_2$OCH$_3$ | H | Cl | CH$_2$ | |
| 2.0002 | H | H | CH$_2$OCH$_2$CH$_2$OCH$_3$ | H | H | CH$_2$ | |
| 2.0003 | H | H | CH$_2$OCH$_2$CH$_2$OCH$_2$CH$_3$ | H | F | CH$_2$ | |
| 2.0004 | H | H | CH$_2$OCH$_2$CH$_2$OCH$_2$CH$_3$ | H | Cl | CH$_2$ | |
| 2.0005 | H | H | CH$_2$OCH$_2$CH$_2$OCH$_2$CH$_3$ | H | H | CH$_2$ | |
| 2.0006 | H | H | CH$_2$N(CH$_3$)SO$_2$CH$_3$ | H | F | CH$_2$ | |
| 2.0007 | H | H | CH$_2$N(CH$_3$)SO$_2$CH$_3$ | H | Cl | CH$_2$ | |
| 2.0008 | H | H | CH$_2$N(CH$_3$)SO$_2$CH$_3$ | H | H | CH$_2$ | |
| 2.0009 | H | H | CH$_2$OCH$_2$Ph | H | F | CH$_2$ | |
| 2.0010 | H | H | CH$_2$OCH$_2$Ph | H | Cl | CH$_2$ | |
| 2.0011 | H | H | CH$_2$OCH$_2$Ph | H | H | CH$_2$ | |
| 2.0012 | H | H | CH$_2$OCH$_2$CH$_2$OH | H | F | CH$_2$ | |
| 2.0013 | H | H | CH$_2$OCH$_2$CH$_2$OH | H | Cl | CH$_2$ | |
| 2.0014 | H | H | CH$_2$OCH$_2$CH$_2$OH | H | H | CH$_2$ | |
| 2.0015 | H | H | CH$_2$OCH$_2$CH$_2$Cl | H | F | CH$_2$ | |
| 2.0016 | H | H | CH$_2$OCH$_2$CH$_2$Cl | H | Cl | CH$_2$ | |
| 2.0017 | H | H | CH$_2$OCH$_2$CH$_2$Cl | H | H | CH$_2$ | |
| 2.0018 | H | H | CH$_2$OCH$_2$CF$_3$ | H | F | CH$_2$ | |
| 2.0019 | H | H | CH$_2$OCH$_2$CF$_3$ | H | Cl | CH$_2$ | |
| 2.0020 | H | H | CH$_2$OCH$_2$CF$_3$ | H | H | CH$_2$ | |
| 2.0021 | H | H | CH$_2$OCH$_2$CH=CH$_2$ | H | F | CH$_2$ | |
| 2.0022 | H | H | CH$_2$OCH$_2$CH=CH$_2$ | H | Cl | CH$_2$ | |
| 2.0023 | H | H | CH$_2$OCH$_2$CH=CH$_2$ | H | H | CH$_2$ | |
| 2.0024 | H | H | CH$_2$O(CO)CH$_3$ | H | F | CH$_2$ | |
| 2.0025 | H | H | CH$_2$O(CO)CH$_3$ | H | Cl | CH$_2$ | |
| 2.0026 | H | H | CH$_2$O(CO)CH$_3$ | H | H | CH$_2$ | |
| 2.0027 | H | H | CH$_2$OCH$_2$C≡CH | H | F | CH$_2$ | |
| 2.0028 | H | H | CH$_2$OCH$_2$C≡CH | H | Cl | CH$_2$ | |
| 2.0029 | H | H | CH$_2$OCH$_2$C≡CH | H | H | CH$_2$ | |
| 2.0030 | H | H | CH$_2$OCH$_2$C≡CCH$_3$ | H | F | CH$_2$ | |
| 2.0031 | H | H | CH$_2$OCH$_2$C≡CCH$_3$ | H | Cl | CH$_2$ | |
| 2.0032 | H | H | CH$_2$OCH$_2$C≡CCH$_3$ | H | H | CH$_2$ | |
| 2.0033 | H | H | (4-methyl-5-oxo-4,5-dihydro-1,2,4-triazol-1-yl)methyl | H | F | CH$_2$ | |
| 2.0034 | H | H | (4-methyl-5-oxo-4,5-dihydro-1,2,4-triazol-1-yl)methyl | H | Cl | CH$_2$ | |
| 2.0035 | H | H | (4-methyl-5-oxo-4,5-dihydro-1,2,4-triazol-1-yl)methyl | H | H | CH$_2$ | |
| 2.0036 | H | H | (3-methyl-2-oxo-2,3-dihydro-1,3,4-oxadiazol-5-yl)methyl | H | F | CH$_2$ | |

TABLE 2-continued
Compounds of formula Ic:
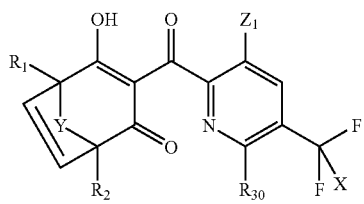
(Ic)
| No. | R₁ | R₂ | Z₁ | R₃₀ | X | Y | Physical data |
|---|---|---|---|---|---|---|---|
| 2.0037 | H | H | 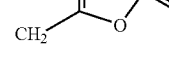 | H | Cl | CH₂ | |
| 2.0038 | H | H | 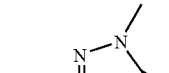 | H | H | CH₂ | |
| 2.0039 | H | H | 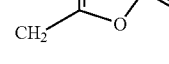 | H | F | CH₂ | |
| 2.0040 | H | H | 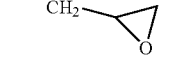 | H | Cl | CH₂ | |
| 2.0041 | H | H | 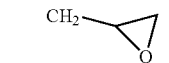 | H | H | CH₂ | |
| 2.0042 | H | H | 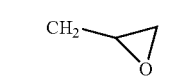 | H | F | CH₂ | |
| 2.0043 | H | H | 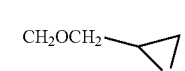 | H | Cl | CH₂ | |
| 2.0044 | H | H | 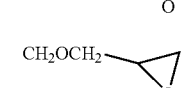 | H | H | CH₂ | |
| 2.0045 | H | H |  | H | F | CH₂ | |
| 2.0046 | H | H |  | H | Cl | CH₂ | |
| 2.0047 | H | H | 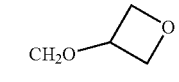 | H | H | CH₂ | |
| 2.0048 | H | H | 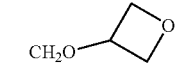 | H | F | CH₂ | |
| 2.0049 | H | H | 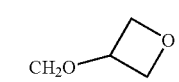 | H | Cl | CH₂ | |

TABLE 2-continued

Compounds of formula Ic:

$$\text{(Ic)}$$

Structure: A cyclohexenone ring bearing OH, R₁, R₂, Y substituents, connected via a carbonyl to a pyridine ring substituted with Z₁, R₃₀, and CF₂X group.

| No. | R₁ | R₂ | Z₁ | R₃₀ | X | Y | Physical data |
|---|---|---|---|---|---|---|---|
| 2.0050 | H | H | (tetrahydrofuran-3-yl)OCH₂— | H | H | CH₂ | |
| 2.0051 | CH₃ | CH₃ | CH₂OCH₂CH₂OCH₃ | H | F | CH₂ | |
| 2.0052 | CH₃ | CH₃ | CH₂OCH₂CH₂OCH₃ | H | Cl | CH₂ | |
| 2.0053 | CH₃ | CH₃ | CH₂OCH₂CH₂OCH₃ | H | H | CH₂ | |
| 2.0054 | CH₃ | CH₃ | CH₂OCH₂CH₂OCH₂CH₃ | H | F | CH₂ | |
| 2.0055 | CH₃ | CH₃ | CH₂OCH₂CH₂OCH₂CH₃ | H | Cl | CH₂ | |
| 2.0056 | CH₃ | CH₃ | CH₂OCH₂CH₂OCH₂CH₃ | H | H | CH₂ | |
| 2.0057 | CH₃ | CH₃ | CH₂N(CH₃)SO₂CH₃ | H | F | CH₂ | |
| 2.0058 | CH₃ | CH₃ | CH₂N(CH₃)SO₂CH₃ | H | Cl | CH₂ | |
| 2.0059 | CH₃ | CH₃ | CH₂N(CH₃)SO₂CH₃ | H | H | CH₂ | |
| 2.0060 | CH₃ | CH₃ | CH₂OCH₂Ph | H | F | CH₂ | |
| 2.0061 | CH₃ | CH₃ | CH₂OCH₂Ph | H | Cl | CH₂ | |
| 2.0062 | CH₃ | CH₃ | CH₂OCH₂Ph | H | H | CH₂ | |
| 2.0063 | CH₃ | CH₃ | CH₂OCH₂CH₂OH | H | F | CH₂ | |
| 2.0064 | CH₃ | CH₃ | CH₂OCH₂CH₂OH | H | Cl | CH₂ | |
| 2.0065 | CH₃ | CH₃ | CH₂OCH₂CH₂OH | H | H | CH₂ | |
| 2.0066 | CH₃ | CH₃ | CH₂OCH₂CH₂Cl | H | F | CH₂ | |
| 2.0067 | CH₃ | CH₃ | CH₂OCH₂CH₂Cl | H | Cl | CH₂ | |
| 2.0068 | CH₃ | CH₃ | CH₂OCH₂CH₂Cl | H | H | CH₂ | |
| 2.0069 | CH₃ | CH₃ | CH₂OCH₂CF₃ | H | F | CH₂ | |
| 2.0070 | CH₃ | CH₃ | CH₂OCH₂CF₃ | H | Cl | CH₂ | |
| 2.0071 | CH₃ | CH₃ | CH₂OCH₂CF₃ | H | H | CH₂ | |
| 2.0072 | CH₃ | CH₃ | CH₂OCH₂CH=CH₂ | H | F | CH₂ | |
| 2.0073 | CH₃ | CH₃ | CH₂OCH₂CH=CH₂ | H | Cl | CH₂ | |
| 2.0074 | CH₃ | CH₃ | CH₂OCH₂CH=CH₂ | H | H | CH₂ | |
| 2.0075 | CH₃ | CH₃ | CH₂O(CO)CH₃ | H | F | CH₂ | |
| 2.0076 | CH₃ | CH₃ | CH₂O(CO)CH₃ | H | Cl | CH₂ | |
| 2.0077 | CH₃ | CH₃ | CH₂O(CO)CH₃ | H | H | CH₂ | |
| 2.0078 | CH₃ | CH₃ | CH₂OCH₂C≡CH | H | F | CH₂ | |
| 2.0079 | CH₃ | CH₃ | CH₂OCH₂C≡CH | H | Cl | CH₂ | |
| 2.0080 | CH₃ | CH₃ | CH₂OCH₂C≡CH | H | H | CH₂ | |
| 2.0081 | CH₃ | CH₃ | CH₂OCH₂C≡CCH₃ | H | F | CH₂ | |
| 2.0082 | CH₃ | CH₃ | CH₂OCH₂C≡CCH₃ | H | Cl | CH₂ | |
| 2.0083 | CH₃ | CH₃ | CH₂OCH₂C≡CCH₃ | H | H | CH₂ | |
| 2.0084 | CH₃ | CH₃ | (4-methyl-5-oxo-4,5-dihydro-1,2,4-triazol-1-yl)CH₂— | H | F | CH₂ | |
| 2.0085 | CH₃ | CH₃ | (4-methyl-5-oxo-4,5-dihydro-1,2,4-triazol-1-yl)CH₂— | H | Cl | CH₂ | |
| 2.0086 | CH₃ | CH₃ | (4-methyl-5-oxo-4,5-dihydro-1,2,4-triazol-1-yl)CH₂— | H | H | CH₂ | |

TABLE 2-continued

Compounds of formula Ic:

(Ic)

| No. | R₁ | R₂ | Z₁ | R₃₀ | X | Y | Physical data |
|---|---|---|---|---|---|---|---|
| 2.0087 | CH₃ | CH₃ | (3-methyl-2-oxo-1,3,4-oxadiazol-5-yl)methyl | H | F | CH₂ | |
| 2.0088 | CH₃ | CH₃ | (3-methyl-2-oxo-1,3,4-oxadiazol-5-yl)methyl | H | Cl | CH₂ | |
| 2.0089 | CH₃ | CH₃ | (3-methyl-2-oxo-1,3,4-oxadiazol-5-yl)methyl | H | H | CH₂ | |
| 2.0090 | CH₃ | CH₃ | CH₂-oxiranyl | H | F | CH₂ | |
| 2.0091 | CH₃ | CH₃ | CH₂-oxiranyl | H | Cl | CH₂ | |
| 2.0092 | CH₃ | CH₃ | CH₂-oxiranyl | H | H | CH₂ | |
| 2.0093 | CH₃ | CH₃ | CH₂OCH₂-oxiranyl | H | F | CH₂ | |
| 2.0094 | CH₃ | CH₃ | CH₂OCH₂-oxiranyl | H | Cl | CH₂ | |
| 2.0095 | CH₃ | CH₃ | CH₂OCH₂-oxiranyl | H | H | CH₂ | |
| 2.0096 | CH₃ | CH₃ | CH₂O-oxetanyl | H | F | CH₂ | |
| 2.0097 | CH₃ | CH₃ | CH₂O-oxetanyl | H | Cl | CH₂ | |
| 2.0098 | CH₃ | CH₃ | CH₂O-oxetanyl | H | H | CH₂ | |

TABLE 2-continued

Compounds of formula Ic:

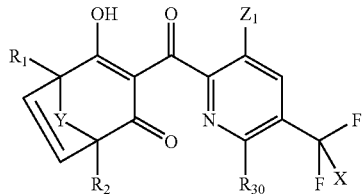

(Ic)

| No. | R₁ | R₂ | Z₁ | R₃₀ | X | Y | Physical data |
|---|---|---|---|---|---|---|---|
| 2.0099 | CH₃ | CH₃ | 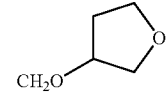 | H | F | CH₂ | |
| 2.0100 | CH₃ | CH₃ |  | H | Cl | CH₂ | |
| 2.0101 | CH₃ | CH₃ |  | H | H | CH₂ | |
| 2.0102 | H | CH₃ | CH₂OCH₂CH₂OCH₃ | H | F | CH₂ | |
| 2.0103 | H | CH₃ | CH₂OCH₂CH₂OCH₃ | H | Cl | CH₂ | |
| 2.0104 | H | CH₃ | CH₂OCH₂CH₂OCH₃ | H | H | CH₂ | |
| 2.0105 | H | CH₃ | CH₂OCH₂CH₂OCH₂CH₃ | H | F | CH₂ | |
| 2.0106 | H | CH₃ | CH₂OCH₂CH₂OCH₂CH₃ | H | Cl | CH₂ | |
| 2.0107 | H | CH₃ | CH₂OCH₂CH₂OCH₂CH₃ | H | H | CH₂ | |
| 2.0108 | H | CH₃ | CH₂N(CH₃)SO₂CH₃ | H | F | CH₂ | |
| 2.0109 | H | CH₃ | CH₂N(CH₃)SO₂CH₃ | H | Cl | CH₂ | |
| 2.0110 | H | CH₃ | CH₂N(CH₃)SO₂CH₃ | H | H | CH₂ | |
| 2.0111 | H | CH₃ | CH₂OCH₂Ph | H | F | CH₂ | |
| 2.0112 | H | CH₃ | CH₂OCH₂Ph | H | Cl | CH₂ | |
| 2.0113 | H | CH₃ | CH₂OCH₂Ph | H | H | CH₂ | |
| 2.0114 | H | CH₃ | CH₂OCH₂CH₂OH | H | F | CH₂ | |
| 2.0115 | H | CH₃ | CH₂OCH₂CH₂OH | H | Cl | CH₂ | |
| 2.0116 | H | CH₃ | CH₂OCH₂CH₂OH | H | H | CH₂ | |
| 2.0117 | H | CH₃ | CH₂OCH₂CH₂Cl | H | F | CH₂ | |
| 2.0118 | H | CH₃ | CH₂OCH₂CH₂Cl | H | Cl | CH₂ | |
| 2.0119 | H | CH₃ | CH₂OCH₂CH₂Cl | H | H | CH₂ | |
| 2.0120 | H | CH₃ | CH₂OCH₂CF₃ | H | F | CH₂ | |
| 2.0121 | H | CH₃ | CH₂OCH₂CF₃ | H | Cl | CH₂ | |
| 2.0122 | H | CH₃ | CH₂OCH₂CF₃ | H | H | CH₂ | |
| 2.0123 | H | CH₃ | CH₂OCH₂CH=CH₂ | H | F | CH₂ | |
| 2.0124 | H | CH₃ | CH₂OCH₂CH=CH₂ | H | Cl | CH₂ | |
| 2.0125 | H | CH₃ | CH₂OCH₂CH=CH₂ | H | H | CH₂ | |
| 2.0126 | H | CH₃ | CH₂O(CO)CH₃ | H | F | CH₂ | |
| 2.0127 | H | CH₃ | CH₂O(CO)CH₃ | H | Cl | CH₂ | |
| 2.0128 | H | CH₃ | CH₂O(CO)CH₃ | H | H | CH₂ | |
| 2.0129 | H | CH₃ | CH₂OCH₂C≡CH | H | F | CH₂ | |
| 2.0130 | H | CH₃ | CH₂OCH₂C≡CH | H | Cl | CH₂ | |
| 2.0131 | H | CH₃ | CH₂OCH₂C≡CH | H | H | CH₂ | |
| 2.0132 | H | CH₃ | CH₂OCH₂C≡CCH₃ | H | F | CH₂ | |
| 2.0133 | H | CH₃ | CH₂OCH₂C≡CCH₃ | H | Cl | CH₂ | |
| 2.0134 | H | CH₃ | CH₂OCH₂C≡CCH₃ | H | H | CH₂ | |
| 2.0135 | H | CH₃ | 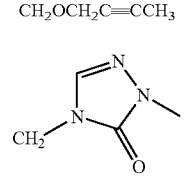 | H | F | CH₂ | |

TABLE 2-continued

Compounds of formula Ic:

$$\text{(Ic)}$$

| No. | $R_1$ | $R_2$ | $Z_1$ | $R_{30}$ | X | Y | Physical data |
|---|---|---|---|---|---|---|---|
| 2.0136 | H | $CH_3$ | 4-CH$_2$-2-methyl-1,2,4-triazol-3(2H)-one | H | Cl | $CH_2$ | |
| 2.0137 | H | $CH_3$ | 4-CH$_2$-2-methyl-1,2,4-triazol-3(2H)-one | H | H | $CH_2$ | |
| 2.0138 | H | $CH_3$ | 3-CH$_2$-4-methyl-1,3,4-oxadiazol-2(3H)-one | H | F | $CH_2$ | |
| 2.0139 | H | $CH_3$ | 3-CH$_2$-4-methyl-1,3,4-oxadiazol-2(3H)-one | H | Cl | $CH_2$ | |
| 2.0140 | H | $CH_3$ | 3-CH$_2$-4-methyl-1,3,4-oxadiazol-2(3H)-one | H | H | $CH_2$ | |
| 2.0141 | H | $CH_3$ | $CH_2$-oxiranyl | H | F | $CH_2$ | |
| 2.0142 | H | $CH_3$ | $CH_2$-oxiranyl | H | Cl | $CH_2$ | |
| 2.0143 | H | $CH_3$ | $CH_2$-oxiranyl | H | H | $CH_2$ | |
| 2.0144 | H | $CH_3$ | $CH_2OCH_2$-oxiranyl | H | F | $CH_2$ | |
| 2.0145 | H | $CH_3$ | $CH_2OCH_2$-oxiranyl | H | Cl | $CH_2$ | |
| 2.0146 | H | $CH_3$ | $CH_2OCH_2$-oxiranyl | H | H | $CH_2$ | |

TABLE 2-continued

Compounds of formula Ic:

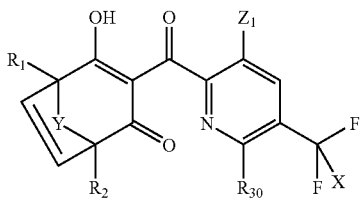

(Ic)

| No. | R₁ | R₂ | Z₁ | R₃₀ | X | Y | Physical data |
|---|---|---|---|---|---|---|---|
| 2.0147 | H | CH₃ | (oxetan-3-yl)CH₂O | H | F | CH₂ | |
| 2.0148 | H | CH₃ | (oxetan-3-yl)CH₂O | H | Cl | CH₂ | |
| 2.0149 | H | CH₃ | (oxetan-3-yl)CH₂O | H | H | CH₂ | |
| 2.0150 | H | CH₃ | (tetrahydrofuran-3-yl)CH₂O | H | F | CH₂ | |
| 2.0151 | H | CH₃ | (tetrahydrofuran-3-yl)CH₂O | H | Cl | CH₂ | |
| 2.0152 | H | CH₃ | (tetrahydrofuran-3-yl)CH₂O | H | H | CH₂ | |
| 2.0153 | H | H | CH₂OCH₂CH₂OCH₃ | CH₃ | F | CH₂ | |
| 2.0154 | H | H | CH₂OCH₂CH₂OCH₃ | CH₃ | Cl | CH₂ | |
| 2.0155 | H | H | CH₂OCH₂CH₂OCH₃ | CH₃ | H | CH₂ | |
| 2.0156 | H | H | CH₂OCH₂CH₂OCH₂CH₃ | CH₃ | F | CH₂ | |
| 2.0157 | H | H | CH₂OCH₂CH₂OCH₂CH₃ | CH₃ | Cl | CH₂ | |
| 2.0158 | H | H | CH₂OCH₂CH₂OCH₂CH₃ | CH₃ | H | CH₂ | |
| 2.0159 | H | H | CH₂N(CH₃)SO₂CH₃ | CH₃ | F | CH₂ | |
| 2.0160 | H | H | CH₂N(CH₃)SO₂CH₃ | CH₃ | Cl | CH₂ | |
| 2.0161 | H | H | CH₂N(CH₃)SO₂CH₃ | CH₃ | H | CH₂ | |
| 2.0162 | H | H | CH₂OCH₂Ph | CH₃ | F | CH₂ | |
| 2.0163 | H | H | CH₂OCH₂Ph | CH₃ | Cl | CH₂ | |
| 2.0164 | H | H | CH₂OCH₂Ph | CH₃ | H | CH₂ | |
| 2.0165 | H | H | CH₂OCH₂CH₂OH | CH₃ | F | CH₂ | |
| 2.0166 | H | H | CH₂OCH₂CH₂OH | CH₃ | Cl | CH₂ | |
| 2.0167 | H | H | CH₂OCH₂CH₂OH | CH₃ | H | CH₂ | |
| 2.0168 | H | H | CH₂OCH₂CH₂Cl | CH₃ | F | CH₂ | |
| 2.0169 | H | H | CH₂OCH₂CH₂Cl | CH₃ | Cl | CH₂ | |
| 2.0170 | H | H | CH₂OCH₂CH₂Cl | CH₃ | H | CH₂ | |
| 2.0171 | H | H | CH₂OCH₂CF₃ | CH₃ | F | CH₂ | |
| 2.0172 | H | H | CH₂OCH₂CF₃ | CH₃ | Cl | CH₂ | |
| 2.0173 | H | H | CH₂OCH₂CF₃ | CH₃ | H | CH₂ | |
| 2.0174 | H | H | CH₂OCH₂CH=CH₂ | CH₃ | F | CH₂ | |
| 2.0175 | H | H | CH₂OCH₂CH=CH₂ | CH₃ | Cl | CH₂ | |
| 2.0176 | H | H | CH₂OCH₂CH=CH₂ | CH₃ | H | CH₂ | |
| 2.0177 | H | H | CH₂O(CO)CH₃ | CH₃ | F | CH₂ | |
| 2.0178 | H | H | CH₂O(CO)CH₃ | CH₃ | Cl | CH₂ | |
| 2.0179 | H | H | CH₂O(CO)CH₃ | CH₃ | H | CH₂ | |
| 2.0180 | H | H | CH₂OCH₂C≡CH | CH₃ | F | CH₂ | |
| 2.0181 | H | H | CH₂OCH₂C≡CH | CH₃ | Cl | CH₂ | |
| 2.0182 | H | H | CH₂OCH₂C≡CH | CH₃ | H | CH₂ | |
| 2.0183 | H | H | CH₂OCH₂C≡CCH₃ | CH₃ | F | CH₂ | |
| 2.0184 | H | H | CH₂OCH₂C≡CCH₃ | CH₃ | Cl | CH₂ | |
| 2.0185 | H | H | CH₂OCH₂C≡CCH₃ | CH₃ | H | CH₂ | |

TABLE 2-continued

Compounds of formula Ic:

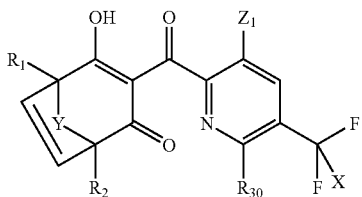

(Ic)

| No. | R₁ | R₂ | Z₁ | R₃₀ | X | Y | Physical data |
|---|---|---|---|---|---|---|---|
| 2.0186 | H | H | (4-CH₂-1,2,4-triazol-3(2H)-one, 2-methyl) | CH₃ | F | CH₂ | |
| 2.0187 | H | H | (4-CH₂-1,2,4-triazol-3(2H)-one, 2-methyl) | CH₃ | Cl | CH₂ | |
| 2.0188 | H | H | (4-CH₂-1,2,4-triazol-3(2H)-one, 2-methyl) | CH₃ | H | CH₂ | |
| 2.0189 | H | H | (3-CH₂-1,3,4-oxadiazol-2(3H)-one, 4-methyl) | CH₃ | F | CH₂ | |
| 2.0190 | H | H | (3-CH₂-1,3,4-oxadiazol-2(3H)-one, 4-methyl) | CH₃ | Cl | CH₂ | |
| 2.0191 | H | H | (3-CH₂-1,3,4-oxadiazol-2(3H)-one, 4-methyl) | CH₃ | H | CH₂ | |
| 2.0192 | H | H | CH₂-oxiranyl | CH₃ | F | CH₂ | |
| 2.0193 | H | H | CH₂-oxiranyl | CH₃ | Cl | CH₂ | |
| 2.0194 | H | H | CH₂-oxiranyl | CH₃ | H | CH₂ | |
| 2.0195 | H | H | CH₂OCH₂-oxiranyl | CH₃ | F | CH₂ | |
| 2.0196 | H | H | CH₂OCH₂-oxiranyl | CH₃ | Cl | CH₂ | |

TABLE 2-continued

Compounds of formula Ic:

(Ic)

| No. | $R_1$ | $R_2$ | $Z_1$ | $R_{30}$ | X | Y | Physical data |
|---|---|---|---|---|---|---|---|
| 2.0197 | H | H | 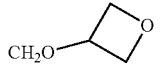 | $CH_3$ | H | $CH_2$ | |
| 2.0198 | H | H | 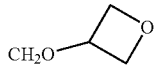 | $CH_3$ | F | $CH_2$ | |
| 2.0199 | H | H | 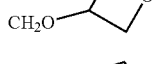 | $CH_3$ | Cl | $CH_2$ | |
| 2.0200 | H | H | 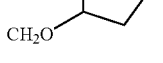 | $CH_3$ | H | $CH_2$ | |
| 2.0201 | H | H | 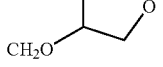 | $CH_3$ | F | $CH_2$ | |
| 2.0202 | H | H | 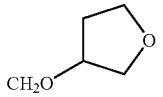 | $CH_3$ | Cl | $CH_2$ | |
| 2.0203 | H | H | 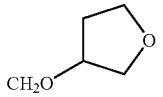 | $CH_3$ | H | $CH_2$ | |
| 2.0204 | $CH_3$ | $CH_3$ | $CH_2OCH_2CH_2OCH_3$ | $CH_3$ | F | $CH_2$ | |
| 2.0205 | $CH_3$ | $CH_3$ | $CH_2OCH_2CH_2OCH_3$ | $CH_3$ | Cl | $CH_2$ | |
| 2.0206 | $CH_3$ | $CH_3$ | $CH_2OCH_2CH_2OCH_3$ | $CH_3$ | H | $CH_2$ | |
| 2.0207 | $CH_3$ | $CH_3$ | $CH_2OCH_2CH_2OCH_2CH_3$ | $CH_3$ | F | $CH_2$ | |
| 2.0208 | $CH_3$ | $CH_3$ | $CH_2OCH_2CH_2OCH_2CH_3$ | $CH_3$ | Cl | $CH_2$ | |
| 2.0209 | $CH_3$ | $CH_3$ | $CH_2OCH_2CH_2OCH_2CH_3$ | $CH_3$ | H | $CH_2$ | |
| 2.0210 | $CH_3$ | $CH_3$ | $CH_2N(CH_3)SO_2CH_3$ | $CH_3$ | F | $CH_2$ | |
| 2.0211 | $CH_3$ | $CH_3$ | $CH_2N(CH_3)SO_2CH_3$ | $CH_3$ | Cl | $CH_2$ | |
| 2.0212 | $CH_3$ | $CH_3$ | $CH_2N(CH_3)SO_2CH_3$ | $CH_3$ | H | $CH_2$ | |
| 2.0213 | $CH_3$ | $CH_3$ | $CH_2OCH_2Ph$ | $CH_3$ | F | $CH_2$ | |
| 2.0214 | $CH_3$ | $CH_3$ | $CH_2OCH_2Ph$ | $CH_3$ | Cl | $CH_2$ | |
| 2.0215 | $CH_3$ | $CH_3$ | $CH_2OCH_2Ph$ | $CH_3$ | H | $CH_2$ | |
| 2.0216 | $CH_3$ | $CH_3$ | $CH_2OCH_2CH_2OH$ | $CH_3$ | F | $CH_2$ | |
| 2.0217 | $CH_3$ | $CH_3$ | $CH_2OCH_2CH_2OH$ | $CH_3$ | Cl | $CH_2$ | |
| 2.0218 | $CH_3$ | $CH_3$ | $CH_2OCH_2CH_2OH$ | $CH_3$ | H | $CH_2$ | |
| 2.0219 | $CH_3$ | $CH_3$ | $CH_2OCH_2CH_2Cl$ | $CH_3$ | F | $CH_2$ | |
| 2.0220 | $CH_3$ | $CH_3$ | $CH_2OCH_2CH_2Cl$ | $CH_3$ | Cl | $CH_2$ | |
| 2.0221 | $CH_3$ | $CH_3$ | $CH_2OCH_2CH_2Cl$ | $CH_3$ | H | $CH_2$ | |
| 2.0222 | $CH_3$ | $CH_3$ | $CH_2OCH_2CF_3$ | $CH_3$ | F | $CH_2$ | |
| 2.0223 | $CH_3$ | $CH_3$ | $CH_2OCH_2CF_3$ | $CH_3$ | Cl | $CH_2$ | |
| 2.0224 | $CH_3$ | $CH_3$ | $CH_2OCH_2CF_3$ | $CH_3$ | H | $CH_2$ | |
| 2.0225 | $CH_3$ | $CH_3$ | $CH_2OCH_2CH{=}CH_2$ | $CH_3$ | F | $CH_2$ | |
| 2.0226 | $CH_3$ | $CH_3$ | $CH_2OCH_2CH{=}CH_2$ | $CH_3$ | Cl | $CH_2$ | |
| 2.0227 | $CH_3$ | $CH_3$ | $CH_2OCH_2CH{=}CH_2$ | $CH_3$ | H | $CH_2$ | |
| 2.0228 | $CH_3$ | $CH_3$ | $CH_2O(CO)CH_3$ | $CH_3$ | F | $CH_2$ | |
| 2.0229 | $CH_3$ | $CH_3$ | $CH_2O(CO)CH_3$ | $CH_3$ | Cl | $CH_2$ | |
| 2.0230 | $CH_3$ | $CH_3$ | $CH_2O(CO)CH_3$ | $CH_3$ | H | $CH_2$ | |
| 2.0231 | $CH_3$ | $CH_3$ | $CH_2OCH_2C{\equiv}CH$ | $CH_3$ | F | $CH_2$ | |
| 2.0232 | $CH_3$ | $CH_3$ | $CH_2OCH_2C{\equiv}CH$ | $CH_3$ | Cl | $CH_2$ | |

TABLE 2-continued

Compounds of formula Ic:

$$\text{(Ic)}$$

[Structure of formula Ic showing a cyclohexenone with OH, R₁, R₂, Y substituents connected via a carbonyl to a pyridine ring with Z₁, R₃₀, and CF₂X substituents]

| No. | R₁ | R₂ | Z₁ | R₃₀ | X | Y | Physical data |
|---|---|---|---|---|---|---|---|
| 2.0233 | CH₃ | CH₃ | CH₂OCH₂C≡CH | CH₃ | H | CH₂ | |
| 2.0234 | CH₃ | CH₃ | CH₂OCH₂C≡CCH₃ | CH₃ | F | CH₂ | |
| 2.0235 | CH₃ | CH₃ | CH₂OCH₂C≡CCH₃ | CH₃ | Cl | CH₂ | |
| 2.0236 | CH₃ | CH₃ | CH₂OCH₂C≡CCH₃ | CH₃ | H | CH₂ | |
| 2.0237 | CH₃ | CH₃ | [N-methyl-triazolinone-CH₂-] | CH₃ | F | CH₂ | |
| 2.0238 | CH₃ | CH₃ | [N-methyl-triazolinone-CH₂-] | CH₃ | Cl | CH₂ | |
| 2.0239 | CH₃ | CH₃ | [N-methyl-triazolinone-CH₂-] | CH₃ | H | CH₂ | |
| 2.0240 | CH₃ | CH₃ | [N-methyl-oxadiazolinone-CH₂-] | CH₃ | F | CH₂ | |
| 2.0241 | CH₃ | CH₃ | [N-methyl-oxadiazolinone-CH₂-] | CH₃ | Cl | CH₂ | |
| 2.0242 | CH₃ | CH₃ | [N-methyl-oxadiazolinone-CH₂-] | CH₃ | H | CH₂ | |
| 2.0243 | CH₃ | CH₃ | CH₂-oxirane | CH₃ | F | CH₂ | |
| 2.0244 | CH₃ | CH₃ | CH₂-oxirane | CH₃ | Cl | CH₂ | |
| 2.0245 | CH₃ | CH₃ | CH₂-oxirane | CH₃ | H | CH₂ | |
| 2.0246 | CH₃ | CH₃ | CH₂OCH₂-oxirane | CH₃ | F | CH₂ | |

TABLE 2-continued

Compounds of formula Ic:

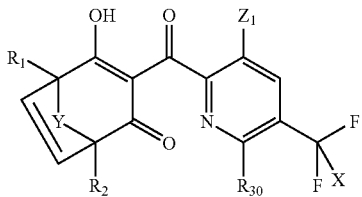

(Ic)

| No. | R$_1$ | R$_2$ | Z$_1$ | R$_{30}$ | X | Y | Physical data |
|---|---|---|---|---|---|---|---|
| 2.0247 | CH$_3$ | CH$_3$ | CH$_2$OCH$_2$-(oxiranyl) | CH$_3$ | Cl | CH$_2$ | |
| 2.0248 | CH$_3$ | CH$_3$ | CH$_2$OCH$_2$-(oxiranyl) | CH$_3$ | H | CH$_2$ | |
| 2.0249 | CH$_3$ | CH$_3$ | CH$_2$O-(oxetanyl) | CH$_3$ | F | CH$_2$ | |
| 2.0250 | CH$_3$ | CH$_3$ | CH$_2$O-(oxetanyl) | CH$_3$ | Cl | CH$_2$ | |
| 2.0251 | CH$_3$ | CH$_3$ | CH$_2$O-(oxetanyl) | CH$_3$ | H | CH$_2$ | |
| 2.0252 | CH$_3$ | CH$_3$ | CH$_2$O-(tetrahydrofuranyl) | CH$_3$ | F | CH$_2$ | |
| 2.0253 | CH$_3$ | CH$_3$ | CH$_2$O-(tetrahydrofuranyl) | CH$_3$ | Cl | CH$_2$ | |
| 2.0254 | CH$_3$ | CH$_3$ | CH$_2$O-(tetrahydrofuranyl) | CH$_3$ | H | CH$_2$ | |
| 2.0255 | H | CH$_3$ | CH$_2$OCH$_2$CH$_2$OCH$_3$ | CH$_3$ | F | CH$_2$ | |
| 2.0256 | H | CH$_3$ | CH$_2$OCH$_2$CH$_2$OCH$_3$ | CH$_3$ | Cl | CH$_2$ | |
| 2.0257 | H | CH$_3$ | CH$_2$OCH$_2$CH$_2$OCH$_3$ | CH$_3$ | H | CH$_2$ | |
| 2.0258 | H | CH$_3$ | CH$_2$OCH$_2$CH$_2$OCH$_2$CH$_3$ | CH$_3$ | F | CH$_2$ | |
| 2.0259 | H | CH$_3$ | CH$_2$OCH$_2$CH$_2$OCH$_2$CH$_3$ | CH$_3$ | Cl | CH$_2$ | |
| 2.0260 | H | CH$_3$ | CH$_2$OCH$_2$CH$_2$OCH$_2$CH$_3$ | CH$_3$ | H | CH$_2$ | |
| 2.0261 | H | CH$_3$ | CH$_2$N(CH$_3$)SO$_2$CH$_3$ | CH$_3$ | F | CH$_2$ | |
| 2.0262 | H | CH$_3$ | CH$_2$N(CH$_3$)SO$_2$CH$_3$ | CH$_3$ | Cl | CH$_2$ | |
| 2.0263 | H | CH$_3$ | CH$_2$N(CH$_3$)SO$_2$CH$_3$ | CH$_3$ | H | CH$_2$ | |
| 2.0264 | H | CH$_3$ | CH$_2$OCH$_2$Ph | CH$_3$ | F | CH$_2$ | |
| 2.0265 | H | CH$_3$ | CH$_2$OCH$_2$Ph | CH$_3$ | Cl | CH$_2$ | |
| 2.0266 | H | CH$_3$ | CH$_2$OCH$_2$Ph | CH$_3$ | H | CH$_2$ | |
| 2.0267 | H | CH$_3$ | CH$_2$OCH$_2$CH$_2$OH | CH$_3$ | F | CH$_2$ | |
| 2.0268 | H | CH$_3$ | CH$_2$OCH$_2$CH$_2$OH | CH$_3$ | Cl | CH$_2$ | |
| 2.0269 | H | CH$_3$ | CH$_2$OCH$_2$CH$_2$OH | CH$_3$ | H | CH$_2$ | |
| 2.0270 | H | CH$_3$ | CH$_2$OCH$_2$CH$_2$Cl | CH$_3$ | F | CH$_2$ | |
| 2.0271 | H | CH$_3$ | CH$_2$OCH$_2$CH$_2$Cl | CH$_3$ | Cl | CH$_2$ | |
| 2.0272 | H | CH$_3$ | CH$_2$OCH$_2$CH$_2$Cl | CH$_3$ | H | CH$_2$ | |
| 2.0273 | H | CH$_3$ | CH$_2$OCH$_2$CF$_3$ | CH$_3$ | F | CH$_2$ | |
| 2.0274 | H | CH$_3$ | CH$_2$OCH$_2$CF$_3$ | CH$_3$ | Cl | CH$_2$ | |
| 2.0275 | H | CH$_3$ | CH$_2$OCH$_2$CF$_3$ | CH$_3$ | H | CH$_2$ | |
| 2.0276 | H | CH$_3$ | CH$_2$OCH$_2$CH=CH$_2$ | CH$_3$ | F | CH$_2$ | |
| 2.0277 | H | CH$_3$ | CH$_2$OCH$_2$CH=CH$_2$ | CH$_3$ | Cl | CH$_2$ | |
| 2.0278 | H | CH$_3$ | CH$_2$OCH$_2$CH=CH$_2$ | CH$_3$ | H | CH$_2$ | |
| 2.0279 | H | CH$_3$ | CH$_2$O(CO)CH$_3$ | CH$_3$ | F | CH$_2$ | |

TABLE 2-continued

Compounds of formula Ic:

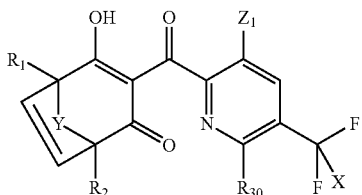

(Ic)

| No. | R$_1$ | R$_2$ | Z$_1$ | R$_{30}$ | X | Y | Physical data |
|---|---|---|---|---|---|---|---|
| 2.0280 | H | CH$_3$ | CH$_2$O(CO)CH$_3$ | CH$_3$ | Cl | CH$_2$ | |
| 2.0281 | H | CH$_3$ | CH$_2$O(CO)CH$_3$ | CH$_3$ | H | CH$_2$ | |
| 2.0282 | H | CH$_3$ | CH$_2$OCH$_2$C≡CH | CH$_3$ | F | CH$_2$ | |
| 2.0283 | H | CH$_3$ | CH$_2$OCH$_2$C≡CH | CH$_3$ | Cl | CH$_2$ | |
| 2.0284 | H | CH$_3$ | CH$_2$OCH$_2$C≡CH | CH$_3$ | H | CH$_2$ | |
| 2.0285 | H | CH$_3$ | CH$_2$OCH$_2$C≡CCH$_3$ | CH$_3$ | F | CH$_2$ | |
| 2.0286 | H | CH$_3$ | CH$_2$OCH$_2$C≡CCH$_3$ | CH$_3$ | Cl | CH$_2$ | |
| 2.0287 | H | CH$_3$ | CH$_2$OCH$_2$C≡CCH$_3$ | CH$_3$ | H | CH$_2$ | |
| 2.0288 | H | CH$_3$ | CH$_2$-(4-methyl-2-methyl-3-oxo-1,2,4-triazol-1-yl) | CH$_3$ | F | CH$_2$ | |
| 2.0289 | H | CH$_3$ | CH$_2$-(4-methyl-2-methyl-3-oxo-1,2,4-triazol-1-yl) | CH$_3$ | Cl | CH$_2$ | |
| 2.0290 | H | CH$_3$ | CH$_2$-(4-methyl-2-methyl-3-oxo-1,2,4-triazol-1-yl) | CH$_3$ | H | CH$_2$ | |
| 2.0291 | H | CH$_3$ | CH$_2$-(3-methyl-5-oxo-1,3,4-oxadiazol-2-yl) | CH$_3$ | F | CH$_2$ | |
| 2.0292 | H | CH$_3$ | CH$_2$-(3-methyl-5-oxo-1,3,4-oxadiazol-2-yl) | CH$_3$ | Cl | CH$_2$ | |
| 2.0293 | H | CH$_3$ | CH$_2$-(3-methyl-5-oxo-1,3,4-oxadiazol-2-yl) | CH$_3$ | H | CH$_2$ | |
| 2.0294 | H | CH$_3$ | CH$_2$-(oxiran-2-yl) | CH$_3$ | F | CH$_2$ | |
| 2.0295 | H | CH$_3$ | CH$_2$-(oxiran-2-yl) | CH$_3$ | Cl | CH$_2$ | |
| 2.0296 | H | CH$_3$ | CH$_2$-(oxiran-2-yl) | CH$_3$ | H | CH$_2$ | |

TABLE 2-continued

Compounds of formula Ic:

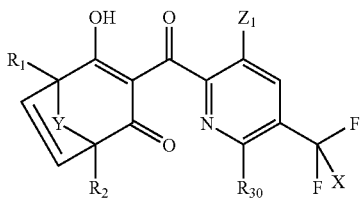

(Ic)

| No. | $R_1$ | $R_2$ | $Z_1$ | $R_{30}$ | X | Y | Physical data |
|---|---|---|---|---|---|---|---|
| 2.0297 | H | $CH_3$ | $CH_2OCH_2$-oxiranyl | $CH_3$ | F | $CH_2$ | |
| 2.0298 | H | $CH_3$ | $CH_2OCH_2$-oxiranyl | $CH_3$ | Cl | $CH_2$ | |
| 2.0299 | H | $CH_3$ | $CH_2OCH_2$-oxiranyl | $CH_3$ | H | $CH_2$ | |
| 2.0300 | H | $CH_3$ | $CH_2O$-oxetanyl | $CH_3$ | F | $CH_2$ | |
| 2.0301 | H | $CH_3$ | $CH_2O$-oxetanyl | $CH_3$ | Cl | $CH_2$ | |
| 2.0302 | H | $CH_3$ | $CH_2O$-oxetanyl | $CH_3$ | H | $CH_2$ | |
| 2.0303 | H | $CH_3$ | $CH_2O$-tetrahydrofuranyl | $CH_3$ | F | $CH_2$ | |
| 2.0304 | H | $CH_3$ | $CH_2O$-tetrahydrofuranyl | $CH_3$ | Cl | $CH_2$ | |
| 2.0305 | H | $CH_3$ | $CH_2O$-tetrahydrofuranyl | $CH_3$ | H | $CH_2$ | |

TABLE 3

Compounds of formula Id:

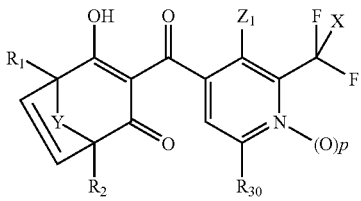

(Id)

| No. | $R_1$ | $R_2$ | $Z_1$ | $R_{30}$ | X | Y | p | Phys. data, remarks |
|---|---|---|---|---|---|---|---|---|
| 3.0000 | H | H | $CH_2OCH_2CH_2OCH_3$ | H | F | $CH_2$ | 0 | |
| 3.0001 | H | H | $CH_2OCH_2CH_2OCH_3$ | H | Cl | $CH_2$ | 0 | |

TABLE 3-continued

Compounds of formula Id:

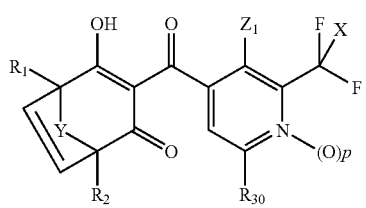

(Id)

| No. | $R_1$ | $R_2$ | $Z_1$ | $R_{30}$ | X | Y | p | Phys. data, remarks |
|---|---|---|---|---|---|---|---|---|
| 3.0002 | H | H | $CH_2OCH_2CH_2OCH_3$ | H | H | $CH_2$ | 0 | |
| 3.0003 | H | H | $CH_2OCH_2CH_2OCH_2CH_3$ | H | F | $CH_2$ | 0 | |
| 3.0004 | H | H | $CH_2OCH_2CH_2OCH_2CH_3$ | H | Cl | $CH_2$ | 0 | |
| 3.0005 | H | H | $CH_2OCH_2CH_2OCH_2CH_3$ | H | H | $CH_2$ | 0 | |
| 3.0006 | H | H | $CH_2N(CH_3)SO_2CH_3$ | H | F | $CH_2$ | 0 | |
| 3.0007 | H | H | $CH_2N(CH_3)SO_2CH_3$ | H | Cl | $CH_2$ | 0 | |
| 3.0008 | H | H | $CH_2N(CH_3)SO_2CH_3$ | H | H | $CH_2$ | 0 | |
| 3.0009 | H | H | $CH_2OCH_2Ph$ | H | F | $CH_2$ | 0 | |
| 3.0010 | H | H | $CH_2OCH_2Ph$ | H | Cl | $CH_2$ | 0 | |
| 3.0011 | H | H | $CH_2OCH_2Ph$ | H | H | $CH_2$ | 0 | |
| 3.0012 | H | H | $CH_2OCH_2CH_2OH$ | H | F | $CH_2$ | 0 | |
| 3.0013 | H | H | $CH_2OCH_2CH_2OH$ | H | Cl | $CH_2$ | 0 | |
| 3.0014 | H | H | $CH_2OCH_2CH_2OH$ | H | H | $CH_2$ | 0 | |
| 3.0015 | H | H | $CH_2OCH_2CH_2Cl$ | H | F | $CH_2$ | 0 | |
| 3.0016 | H | H | $CH_2OCH_2CH_2Cl$ | H | Cl | $CH_2$ | 0 | |
| 3.0017 | H | H | $CH_2OCH_2CH_2Cl$ | H | H | $CH_2$ | 0 | |
| 3.0018 | H | H | $CH_2OCH_2CF_3$ | H | F | $CH_2$ | 0 | |
| 3.0019 | H | H | $CH_2OCH_2CF_3$ | H | Cl | $CH_2$ | 0 | |
| 3.0020 | H | H | $CH_2OCH_2CF_3$ | H | H | $CH_2$ | 0 | |
| 3.0021 | H | H | $CH_2OCH_2CH=CH_2$ | H | F | $CH_2$ | 0 | |
| 3.0022 | H | H | $CH_2OCH_2CH=CH_2$ | H | Cl | $CH_2$ | 0 | |
| 3.0023 | H | H | $CH_2OCH_2CH=CH_2$ | H | H | $CH_2$ | 0 | |
| 3.0024 | H | H | $CH_2O(CO)CH_3$ | H | F | $CH_2$ | 0 | |
| 3.0025 | H | H | $CH_2O(CO)CH_3$ | H | Cl | $CH_2$ | 0 | |
| 3.0026 | H | H | $CH_2O(CO)CH_3$ | H | H | $CH_2$ | 0 | |
| 3.0027 | H | H | $CH_2OCH_2C\equiv CH$ | H | F | $CH_2$ | 0 | |
| 3.0028 | H | H | $CH_2OCH_2C\equiv CH$ | H | Cl | $CH_2$ | 0 | |
| 3.0029 | H | H | $CH_2OCH_2C\equiv CH$ | H | H | $CH_2$ | 0 | |
| 3.0030 | H | H | $CH_2OCH_2C\equiv CCH_3$ | H | F | $CH_2$ | 0 | |
| 3.0031 | H | H | $CH_2OCH_2C\equiv CCH_3$ | H | Cl | $CH_2$ | 0 | |
| 3.0032 | H | H | $CH_2OCH_2C\equiv CCH_3$ | H | H | $CH_2$ | 0 | |
| 3.0033 | H | H | triazolinone-CH$_2$ | H | F | $CH_2$ | 0 | |
| 3.0034 | H | H | triazolinone-CH$_2$ | H | Cl | $CH_2$ | 0 | |
| 3.0035 | H | H | triazolinone-CH$_2$ | H | H | $CH_2$ | 0 | |
| 3.0036 | H | H | oxadiazolone-CH$_2$ | H | F | $CH_2$ | 0 | |

TABLE 3-continued

Compounds of formula Id:

(Id)

| No. | $R_1$ | $R_2$ | $Z_1$ | $R_{30}$ | X | Y | p | Phys. data, remarks |
|---|---|---|---|---|---|---|---|---|
| 3.0037 | H | H | 3-methyl-2-oxo-1,3,4-oxadiazol-5-yl-methyl | H | Cl | $CH_2$ | 0 | |
| 3.0038 | H | H | 3-methyl-2-oxo-1,3,4-oxadiazol-5-yl-methyl | H | H | $CH_2$ | 0 | |
| 3.0039 | H | H | oxiranylmethyl ($CH_2$-) | H | F | $CH_2$ | 0 | |
| 3.0040 | H | H | oxiranylmethyl ($CH_2$-) | H | Cl | $CH_2$ | 0 | |
| 3.0041 | H | H | oxiranylmethyl ($CH_2$-) | H | H | $CH_2$ | 0 | |
| 3.0042 | H | H | $CH_2OCH_2$-oxiranyl | H | F | $CH_2$ | 0 | |
| 3.0043 | H | H | $CH_2OCH_2$-oxiranyl | H | Cl | $CH_2$ | 0 | |
| 3.0044 | H | H | $CH_2OCH_2$-oxiranyl | H | H | $CH_2$ | 0 | |
| 3.0045 | H | H | $CH_2O$-oxetanyl | H | F | $CH_2$ | 0 | |
| 3.0046 | H | H | $CH_2O$-oxetanyl | H | Cl | $CH_2$ | 0 | |
| 3.0047 | H | H | $CH_2O$-oxetanyl | H | H | $CH_2$ | 0 | |
| 3.0048 | H | H | $CH_2O$-tetrahydrofuranyl | H | F | $CH_2$ | 0 | |
| 3.0049 | H | H | $CH_2O$-tetrahydrofuranyl | H | Cl | $CH_2$ | 0 | |

TABLE 3-continued

Compounds of formula Id:

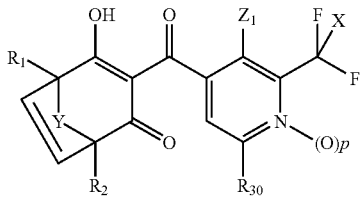

(Id)

| No. | R$_1$ | R$_2$ | Z$_1$ | R$_{30}$ | X | Y | p | Phys. data, remarks |
|---|---|---|---|---|---|---|---|---|
| 3.0050 | H | H | (tetrahydrofuran-3-yl-oxy)CH$_2$ | H | H | CH$_2$ | 0 | |
| 3.0051 | CH$_3$ | CH$_3$ | CH$_2$OCH$_2$CH$_2$OCH$_3$ | H | F | CH$_2$ | 0 | |
| 3.0052 | CH$_3$ | CH$_3$ | CH$_2$OCH$_2$CH$_2$OCH$_3$ | H | Cl | CH$_2$ | 0 | |
| 3.0053 | CH$_3$ | CH$_3$ | CH$_2$OCH$_2$CH$_2$OCH$_3$ | H | H | CH$_2$ | 0 | |
| 3.0054 | CH$_3$ | CH$_3$ | CH$_2$OCH$_2$CH$_2$OCH$_2$CH$_3$ | H | F | CH$_2$ | 0 | |
| 3.0055 | CH$_3$ | CH$_3$ | CH$_2$OCH$_2$CH$_2$OCH$_2$CH$_3$ | H | Cl | CH$_2$ | 0 | |
| 3.0056 | CH$_3$ | CH$_3$ | CH$_2$OCH$_2$CH$_2$OCH$_2$CH$_3$ | H | H | CH$_2$ | 0 | |
| 3.0057 | CH$_3$ | CH$_3$ | CH$_2$N(CH$_3$)SO$_2$CH$_3$ | H | F | CH$_2$ | 0 | |
| 3.0058 | CH$_3$ | CH$_3$ | CH$_2$N(CH$_3$)SO$_2$CH$_3$ | H | Cl | CH$_2$ | 0 | |
| 3.0059 | CH$_3$ | CH$_3$ | CH$_2$N(CH$_3$)SO$_2$CH$_3$ | H | H | CH$_2$ | 0 | |
| 3.0060 | CH$_3$ | CH$_3$ | CH$_2$OCH$_2$Ph | H | F | CH$_2$ | 0 | |
| 3.0061 | CH$_3$ | CH$_3$ | CH$_2$OCH$_2$Ph | H | Cl | CH$_2$ | 0 | |
| 3.0062 | CH$_3$ | CH$_3$ | CH$_2$OCH$_2$Ph | H | H | CH$_2$ | 0 | |
| 3.0063 | CH$_3$ | CH$_3$ | CH$_2$OCH$_2$CH$_2$OH | H | F | CH$_2$ | 0 | |
| 3.0064 | CH$_3$ | CH$_3$ | CH$_2$OCH$_2$CH$_2$OH | H | Cl | CH$_2$ | 0 | |
| 3.0065 | CH$_3$ | CH$_3$ | CH$_2$OCH$_2$CH$_2$OH | H | H | CH$_2$ | 0 | |
| 3.0066 | CH$_3$ | CH$_3$ | CH$_2$OCH$_2$CH$_2$Cl | H | F | CH$_2$ | 0 | |
| 3.0067 | CH$_3$ | CH$_3$ | CH$_2$OCH$_2$CH$_2$Cl | H | Cl | CH$_2$ | 0 | |
| 3.0068 | CH$_3$ | CH$_3$ | CH$_2$OCH$_2$CH$_2$Cl | H | H | CH$_2$ | 0 | |
| 3.0069 | CH$_3$ | CH$_3$ | CH$_2$OCH$_2$CF$_3$ | H | F | CH$_2$ | 0 | |
| 3.0070 | CH$_3$ | CH$_3$ | CH$_2$OCH$_2$CF$_3$ | H | Cl | CH$_2$ | 0 | |
| 3.0071 | CH$_3$ | CH$_3$ | CH$_2$OCH$_2$CF$_3$ | H | H | CH$_2$ | 0 | |
| 3.0072 | CH$_3$ | CH$_3$ | CH$_2$OCH$_2$CH=CH$_2$ | H | F | CH$_2$ | 0 | |
| 3.0073 | CH$_3$ | CH$_3$ | CH$_2$OCH$_2$CH=CH$_2$ | H | Cl | CH$_2$ | 0 | |
| 3.0074 | CH$_3$ | CH$_3$ | CH$_2$OCH$_2$CH=CH$_2$ | H | H | CH$_2$ | 0 | |
| 3.0075 | CH$_3$ | CH$_3$ | CH$_2$O(CO)CH$_3$ | H | F | CH$_2$ | 0 | |
| 3.0076 | CH$_3$ | CH$_3$ | CH$_2$O(CO)CH$_3$ | H | Cl | CH$_2$ | 0 | |
| 3.0077 | CH$_3$ | CH$_3$ | CH$_2$O(CO)CH$_3$ | H | H | CH$_2$ | 0 | |
| 3.0078 | CH$_3$ | CH$_3$ | CH$_2$OCH$_2$C≡CH | H | F | CH$_2$ | 0 | |
| 3.0079 | CH$_3$ | CH$_3$ | CH$_2$OCH$_2$C≡CH | H | Cl | CH$_2$ | 0 | |
| 3.0080 | CH$_3$ | CH$_3$ | CH$_2$OCH$_2$C≡CH | H | H | CH$_2$ | 0 | |
| 3.0081 | CH$_3$ | CH$_3$ | CH$_2$OCH$_2$C≡CCH$_3$ | H | F | CH$_2$ | 0 | |
| 3.0082 | CH$_3$ | CH$_3$ | CH$_2$OCH$_2$C≡CCH$_3$ | H | Cl | CH$_2$ | 0 | |
| 3.0083 | CH$_3$ | CH$_3$ | CH$_2$OCH$_2$C≡CCH$_3$ | H | H | CH$_2$ | 0 | |
| 3.0084 | CH$_3$ | CH$_3$ | (4-methyl-5-oxo-4,5-dihydro-1,2,4-triazol-1-yl)CH$_2$ | H | F | CH$_2$ | 0 | |
| 3.0085 | CH$_3$ | CH$_3$ | (4-methyl-5-oxo-4,5-dihydro-1,2,4-triazol-1-yl)CH$_2$ | H | Cl | CH$_2$ | 0 | |
| 3.0086 | CH$_3$ | CH$_3$ | (4-methyl-5-oxo-4,5-dihydro-1,2,4-triazol-1-yl)CH$_2$ | H | H | CH$_2$ | 0 | |

TABLE 3-continued

Compounds of formula Id:

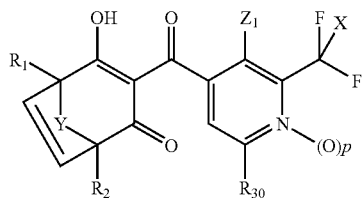

(Id)

| No. | $R_1$ | $R_2$ | $Z_1$ | $R_{30}$ | X | Y | p | Phys. data, remarks |
|---|---|---|---|---|---|---|---|---|
| 3.0087 | $CH_3$ | $CH_3$ | ![3-methyl-1,3,4-oxadiazol-2(3H)-one-CH2] | H | F | $CH_2$ | 0 | |
| 3.0088 | $CH_3$ | $CH_3$ | ![3-methyl-1,3,4-oxadiazol-2(3H)-one-CH2] | H | Cl | $CH_2$ | 0 | |
| 3.0089 | $CH_3$ | $CH_3$ | ![3-methyl-1,3,4-oxadiazol-2(3H)-one-CH2] | H | H | $CH_2$ | 0 | |
| 3.0090 | $CH_3$ | $CH_3$ | $CH_2$-oxirane | H | F | $CH_2$ | 0 | |
| 3.0091 | $CH_3$ | $CH_3$ | $CH_2$-oxirane | H | Cl | $CH_2$ | 0 | |
| 3.0092 | $CH_3$ | $CH_3$ | $CH_2$-oxirane | H | H | $CH_2$ | 0 | |
| 3.0093 | $CH_3$ | $CH_3$ | $CH_2OCH_2$-oxirane | H | F | $CH_2$ | 0 | |
| 3.0094 | $CH_3$ | $CH_3$ | $CH_2OCH_2$-oxirane | H | Cl | $CH_2$ | 0 | |
| 3.0095 | $CH_3$ | $CH_3$ | $CH_2OCH_2$-oxirane | H | H | $CH_2$ | 0 | |
| 3.0096 | $CH_3$ | $CH_3$ | $CH_2O$-oxetane | H | F | $CH_2$ | 0 | |
| 3.0097 | $CH_3$ | $CH_3$ | $CH_2O$-oxetane | H | Cl | $CH_2$ | 0 | |
| 3.0098 | $CH_3$ | $CH_3$ | $CH_2O$-oxetane | H | H | $CH_2$ | 0 | |

TABLE 3-continued

Compounds of formula Id:

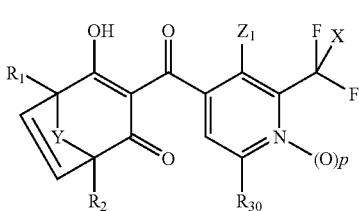

(Id)

| No. | R₁ | R₂ | Z₁ | R₃₀ | X | Y | p | Phys. data, remarks |
|---|---|---|---|---|---|---|---|---|
| 3.0099 | CH₃ | CH₃ | tetrahydrofuran-3-yl-OCH₂ | H | F | CH₂ | 0 | |
| 3.0100 | CH₃ | CH₃ | tetrahydrofuran-3-yl-OCH₂ | H | Cl | CH₂ | 0 | |
| 3.0101 | CH₃ | CH₃ | tetrahydrofuran-3-yl-OCH₂ | H | H | CH₂ | 0 | |
| 3.0102 | H | CH₃ | CH₂OCH₂CH₂OCH₃ | H | F | CH₂ | 0 | |
| 3.0103 | H | CH₃ | CH₂OCH₂CH₂OCH₃ | H | Cl | CH₂ | 0 | |
| 3.0104 | H | CH₃ | CH₂OCH₂CH₂OCH₃ | H | H | CH₂ | 0 | |
| 3.0105 | H | CH₃ | CH₂OCH₂CH₂OCH₂CH₃ | H | F | CH₂ | 0 | |
| 3.0106 | H | CH₃ | CH₂OCH₂CH₂OCH₂CH₃ | H | Cl | CH₂ | 0 | |
| 3.0107 | H | CH₃ | CH₂OCH₂CH₂OCH₂CH₃ | H | H | CH₂ | 0 | |
| 3.0108 | H | CH₃ | CH₂N(CH₃)SO₂CH₃ | H | F | CH₂ | 0 | |
| 3.0109 | H | CH₃ | CH₂N(CH₃)SO₂CH₃ | H | Cl | CH₂ | 0 | |
| 3.0110 | H | CH₃ | CH₂N(CH₃)SO₂CH₃ | H | H | CH₂ | 0 | |
| 3.0111 | H | CH₃ | CH₂OCH₂Ph | H | F | CH₂ | 0 | |
| 3.0112 | H | CH₃ | CH₂OCH₂Ph | H | Cl | CH₂ | 0 | |
| 3.0113 | H | CH₃ | CH₂OCH₂Ph | H | H | CH₂ | 0 | |
| 3.0114 | H | CH₃ | CH₂OCH₂CH₂OH | H | F | CH₂ | 0 | |
| 3.0115 | H | CH₃ | CH₂OCH₂CH₂OH | H | Cl | CH₂ | 0 | |
| 3.0116 | H | CH₃ | CH₂OCH₂CH₂OH | H | H | CH₂ | 0 | |
| 3.0117 | H | CH₃ | CH₂OCH₂CH₂Cl | H | F | CH₂ | 0 | |
| 3.0118 | H | CH₃ | CH₂OCH₂CH₂Cl | H | Cl | CH₂ | 0 | |
| 3.0119 | H | CH₃ | CH₂OCH₂CH₂Cl | H | H | CH₂ | 0 | |
| 3.0120 | H | CH₃ | CH₂OCH₂CF₃ | H | F | CH₂ | 0 | |
| 3.0121 | H | CH₃ | CH₂OCH₂CF₃ | H | Cl | CH₂ | 0 | |
| 3.0122 | H | CH₃ | CH₂OCH₂CF₃ | H | H | CH₂ | 0 | |
| 3.0123 | H | CH₃ | CH₂OCH₂CH=CH₂ | H | F | CH₂ | 0 | |
| 3.0124 | H | CH₃ | CH₂OCH₂CH=CH₂ | H | Cl | CH₂ | 0 | |
| 3.0125 | H | CH₃ | CH₂OCH₂CH=CH₂ | H | H | CH₂ | 0 | |
| 3.0126 | H | CH₃ | CH₂O(CO)CH₃ | H | F | CH₂ | 0 | |
| 3.0127 | H | CH₃ | CH₂O(CO)CH₃ | H | Cl | CH₂ | 0 | |
| 3.0128 | H | CH₃ | CH₂O(CO)CH₃ | H | H | CH₂ | 0 | |
| 3.0129 | H | CH₃ | CH₂OCH₂C≡CH | H | F | CH₂ | 0 | |
| 3.0130 | H | CH₃ | CH₂OCH₂C≡CH | H | Cl | CH₂ | 0 | |
| 3.0131 | H | CH₃ | CH₂OCH₂C≡CH | H | H | CH₂ | 0 | |
| 3.0132 | H | CH₃ | CH₂OCH₂C≡CCH₃ | H | F | CH₂ | 0 | |
| 3.0133 | H | CH₃ | CH₂OCH₂C≡CCH₃ | H | Cl | CH₂ | 0 | |
| 3.0134 | H | CH₃ | CH₂OCH₂C≡CCH₃ | H | H | CH₂ | 0 | |
| 3.0135 | H | CH₃ | (2-methyl-3-oxo-2,3-dihydro-1,2,4-triazol-4-yl)CH₂ | H | F | CH₂ | 0 | |

TABLE 3-continued

Compounds of formula Id:

$$\text{(Id)}$$

[Structure of formula Id showing a cyclohexenone ring with OH, R1, R2, Y substituents connected via a carbonyl to a pyridine ring with Z1, CF2X, R30, and N-(O)p substituents]

| No. | R₁ | R₂ | Z₁ | R₃₀ | X | Y | p | Phys. data, remarks |
|---|---|---|---|---|---|---|---|---|
| 3.0136 | H | CH₃ | 4-(2-methyl-3-oxo-2,3-dihydro-1,2,4-triazol-4-yl)methyl | H | Cl | CH₂ | 0 | |
| 3.0137 | H | CH₃ | 4-(2-methyl-3-oxo-2,3-dihydro-1,2,4-triazol-4-yl)methyl | H | H | CH₂ | 0 | |
| 3.0138 | H | CH₃ | (3-methyl-2-oxo-2,3-dihydro-1,3,4-oxadiazol-5-yl)methyl | H | F | CH₂ | 0 | |
| 3.0139 | H | CH₃ | (3-methyl-2-oxo-2,3-dihydro-1,3,4-oxadiazol-5-yl)methyl | H | Cl | CH₂ | 0 | |
| 3.0140 | H | CH₃ | (3-methyl-2-oxo-2,3-dihydro-1,3,4-oxadiazol-5-yl)methyl | H | H | CH₂ | 0 | |
| 3.0141 | H | CH₃ | CH₂-(oxiran-2-yl) | H | F | CH₂ | 0 | |
| 3.0142 | H | CH₃ | CH₂-(oxiran-2-yl) | H | Cl | CH₂ | 0 | |
| 3.0143 | H | CH₃ | CH₂-(oxiran-2-yl) | H | H | CH₂ | 0 | |
| 3.0144 | H | CH₃ | CH₂OCH₂-(oxiran-2-yl) | H | F | CH₂ | 0 | |
| 3.0145 | H | CH₃ | CH₂OCH₂-(oxiran-2-yl) | H | Cl | CH₂ | 0 | |
| 3.0146 | H | CH₃ | CH₂OCH₂-(oxiran-2-yl) | H | H | CH₂ | 0 | |

TABLE 3-continued

Compounds of formula Id:

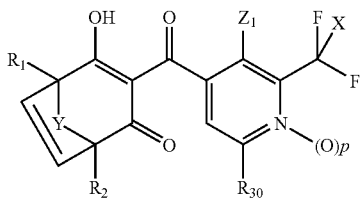

(Id)

| No. | R₁ | R₂ | Z₁ | R₃₀ | X | Y | p | Phys. data, remarks |
|---|---|---|---|---|---|---|---|---|
| 3.0147 | H | CH₃ | (oxetane-CH₂O) | H | F | CH₂ | 0 | |
| 3.0148 | H | CH₃ | (oxetane-CH₂O) | H | Cl | CH₂ | 0 | |
| 3.0149 | H | CH₃ | (oxetane-CH₂O) | H | H | CH₂ | 0 | |
| 3.0150 | H | CH₃ | (tetrahydrofuran-CH₂O) | H | F | CH₂ | 0 | |
| 3.0151 | H | CH₃ | (tetrahydrofuran-CH₂O) | H | Cl | CH₂ | 0 | |
| 3.0152 | H | CH₃ | (tetrahydrofuran-CH₂O) | H | H | CH₂ | 0 | |
| 3.0153 | H | H | CH₂OCH₂CH₂OCH₃ | CH₃ | F | CH₂ | 0 | |
| 3.0154 | H | H | CH₂OCH₂CH₂OCH₃ | CH₃ | Cl | CH₂ | 0 | |
| 3.0155 | H | H | CH₂OCH₂CH₂OCH₃ | CH₃ | H | CH₂ | 0 | |
| 3.0156 | H | H | CH₂OCH₂CH₂OCH₂CH₃ | CH₃ | F | CH₂ | 0 | |
| 3.0157 | H | H | CH₂OCH₂CH₂OCH₂CH₃ | CH₃ | Cl | CH₂ | 0 | |
| 3.0158 | H | H | CH₂OCH₂CH₂OCH₂CH₃ | CH₃ | H | CH₂ | 0 | |
| 3.0159 | H | H | CH₂N(CH₃)SO₂CH₃ | CH₃ | F | CH₂ | 0 | |
| 3.0160 | H | H | CH₂N(CH₃)SO₂CH₃ | CH₃ | Cl | CH₂ | 0 | |
| 3.0161 | H | H | CH₂N(CH₃)SO₂CH₃ | CH₃ | H | CH₂ | 0 | |
| 3.0162 | H | H | CH₂OCH₂Ph | CH₃ | F | CH₂ | 0 | |
| 3.0163 | H | H | CH₂OCH₂Ph | CH₃ | Cl | CH₂ | 0 | |
| 3.0164 | H | H | CH₂OCH₂Ph | CH₃ | H | CH₂ | 0 | |
| 3.0165 | H | H | CH₂OCH₂CH₂OH | CH₃ | F | CH₂ | 0 | |
| 3.0166 | H | H | CH₂OCH₂CH₂OH | CH₃ | Cl | CH₂ | 0 | |
| 3.0167 | H | H | CH₂OCH₂CH₂OH | CH₃ | H | CH₂ | 0 | |
| 3.0168 | H | H | CH₂OCH₂CH₂Cl | CH₃ | F | CH₂ | 0 | |
| 3.0169 | H | H | CH₂OCH₂CH₂Cl | CH₃ | Cl | CH₂ | 0 | |
| 3.0170 | H | H | CH₂OCH₂CH₂Cl | CH₃ | H | CH₂ | 0 | |
| 3.0171 | H | H | CH₂OCH₂CF₃ | CH₃ | F | CH₂ | 0 | |
| 3.0172 | H | H | CH₂OCH₂CF₃ | CH₃ | Cl | CH₂ | 0 | |
| 3.0173 | H | H | CH₂OCH₂CF₃ | CH₃ | H | CH₂ | 0 | |
| 3.0174 | H | H | CH₂OCH₂CH=CH₂ | CH₃ | F | CH₂ | 0 | |
| 3.0175 | H | H | CH₂OCH₂CH=CH₂ | CH₃ | Cl | CH₂ | 0 | |
| 3.0176 | H | H | CH₂OCH₂CH=CH₂ | CH₃ | H | CH₂ | 0 | |
| 3.0177 | H | H | CH₂O(CO)CH₃ | CH₃ | F | CH₂ | 0 | |
| 3.0178 | H | H | CH₂O(CO)CH₃ | CH₃ | Cl | CH₂ | 0 | |
| 3.0179 | H | H | CH₂O(CO)CH₃ | CH₃ | H | CH₂ | 0 | |
| 3.0180 | H | H | CH₂OCH₂C≡CH | CH₃ | F | CH₂ | 0 | |
| 3.0181 | H | H | CH₂OCH₂C≡CH | CH₃ | Cl | CH₂ | 0 | |
| 3.0182 | H | H | CH₂OCH₂C≡CH | CH₃ | H | CH₂ | 0 | |
| 3.0183 | H | H | CH₂OCH₂C≡CCH₃ | CH₃ | F | CH₂ | 0 | |
| 3.0184 | H | H | CH₂OCH₂C≡CCH₃ | CH₃ | Cl | CH₂ | 0 | |
| 3.0185 | H | H | CH₂OCH₂C≡CCH₃ | CH₃ | H | CH₂ | 0 | |

TABLE 3-continued

Compounds of formula Id:

(Id)

| No. | R$_1$ | R$_2$ | Z$_1$ | R$_{30}$ | X | Y | p | Phys. data, remarks |
|---|---|---|---|---|---|---|---|---|
| 3.0186 | H | H | CH$_2$-(4-methyl-5-oxo-4H-1,2,4-triazol-3(2H)-yl, N-methyl) | CH$_3$ | F | CH$_2$ | 0 | |
| 3.0187 | H | H | CH$_2$-(4-methyl-5-oxo-4H-1,2,4-triazol-3(2H)-yl, N-methyl) | CH$_3$ | Cl | CH$_2$ | 0 | |
| 3.0188 | H | H | CH$_2$-(4-methyl-5-oxo-4H-1,2,4-triazol-3(2H)-yl, N-methyl) | CH$_3$ | H | CH$_2$ | 0 | |
| 3.0189 | H | H | CH$_2$-(3-methyl-1,3,4-oxadiazol-2(3H)-one) | CH$_3$ | F | CH$_2$ | 0 | |
| 3.0190 | H | H | CH$_2$-(3-methyl-1,3,4-oxadiazol-2(3H)-one) | CH$_3$ | Cl | CH$_2$ | 0 | |
| 3.0191 | H | H | CH$_2$-(3-methyl-1,3,4-oxadiazol-2(3H)-one) | CH$_3$ | H | CH$_2$ | 0 | |
| 3.0192 | H | H | CH$_2$-oxiranyl | CH$_3$ | F | CH$_2$ | 0 | |
| 3.0193 | H | H | CH$_2$-oxiranyl | CH$_3$ | Cl | CH$_2$ | 0 | |
| 3.0194 | H | H | CH$_2$-oxiranyl | CH$_3$ | H | CH$_2$ | 0 | |
| 3.0195 | H | H | CH$_2$OCH$_2$-oxiranyl | CH$_3$ | F | CH$_2$ | 0 | |
| 3.0196 | H | H | CH$_2$OCH$_2$-oxiranyl | CH$_3$ | Cl | CH$_2$ | 0 | |

TABLE 3-continued

Compounds of formula Id:

(Id)

| No. | R$_1$ | R$_2$ | Z$_1$ | R$_{30}$ | X | Y | p | Phys. data, remarks |
|---|---|---|---|---|---|---|---|---|
| 3.0197 | H | H | CH$_2$OCH$_2$-(oxiranyl) | CH$_3$ | H | CH$_2$ | 0 | |
| 3.0198 | H | H | CH$_2$O-(oxetanyl) | CH$_3$ | F | CH$_2$ | 0 | |
| 3.0199 | H | H | CH$_2$O-(oxetanyl) | CH$_3$ | Cl | CH$_2$ | 0 | |
| 3.0200 | H | H | CH$_2$O-(oxetanyl) | CH$_3$ | H | CH$_2$ | 0 | |
| 3.0201 | H | H | CH$_2$O-(tetrahydrofuranyl) | CH$_3$ | F | CH$_2$ | 0 | |
| 3.0202 | H | H | CH$_2$O-(tetrahydrofuranyl) | CH$_3$ | Cl | CH$_2$ | 0 | |
| 3.0203 | H | H | CH$_2$O-(tetrahydrofuranyl) | CH$_3$ | H | CH$_2$ | 0 | |
| 3.0204 | CH$_3$ | CH$_3$ | CH$_2$OCH$_2$CH$_2$OCH$_3$ | CH$_3$ | F | CH$_2$ | 0 | |
| 3.0205 | CH$_3$ | CH$_3$ | CH$_2$OCH$_2$CH$_2$OCH$_3$ | CH$_3$ | Cl | CH$_2$ | 0 | |
| 3.0206 | CH$_3$ | CH$_3$ | CH$_2$OCH$_2$CH$_2$OCH$_3$ | CH$_3$ | H | CH$_2$ | 0 | |
| 3.0207 | CH$_3$ | CH$_3$ | CH$_2$OCH$_2$CH$_2$OCH$_2$CH$_3$ | CH$_3$ | F | CH$_2$ | 0 | |
| 3.0208 | CH$_3$ | CH$_3$ | CH$_2$OCH$_2$CH$_2$OCH$_2$CH$_3$ | CH$_3$ | Cl | CH$_2$ | 0 | |
| 3.0209 | CH$_3$ | CH$_3$ | CH$_2$OCH$_2$CH$_2$OCH$_2$CH$_3$ | CH$_3$ | H | CH$_2$ | 0 | |
| 3.0210 | CH$_3$ | CH$_3$ | CH$_2$N(CH$_3$)SO$_2$CH$_3$ | CH$_3$ | F | CH$_2$ | 0 | |
| 3.0211 | CH$_3$ | CH$_3$ | CH$_2$N(CH$_3$)SO$_2$CH$_3$ | CH$_3$ | Cl | CH$_2$ | 0 | |
| 3.0212 | CH$_3$ | CH$_3$ | CH$_2$N(CH$_3$)SO$_2$CH$_3$ | CH$_3$ | H | CH$_2$ | 0 | |
| 3.0213 | CH$_3$ | CH$_3$ | CH$_2$OCH$_2$Ph | CH$_3$ | F | CH$_2$ | 0 | |
| 3.0214 | CH$_3$ | CH$_3$ | CH$_2$OCH$_2$Ph | CH$_3$ | Cl | CH$_2$ | 0 | |
| 3.0215 | CH$_3$ | CH$_3$ | CH$_2$OCH$_2$Ph | CH$_3$ | H | CH$_2$ | 0 | |
| 3.0216 | CH$_3$ | CH$_3$ | CH$_2$OCH$_2$CH$_2$OH | CH$_3$ | F | CH$_2$ | 0 | |
| 3.0217 | CH$_3$ | CH$_3$ | CH$_2$OCH$_2$CH$_2$OH | CH$_3$ | Cl | CH$_2$ | 0 | |
| 3.0218 | CH$_3$ | CH$_3$ | CH$_2$OCH$_2$CH$_2$OH | CH$_3$ | H | CH$_2$ | 0 | |
| 3.0219 | CH$_3$ | CH$_3$ | CH$_2$OCH$_2$CH$_2$Cl | CH$_3$ | F | CH$_2$ | 0 | |
| 3.0220 | CH$_3$ | CH$_3$ | CH$_2$OCH$_2$CH$_2$Cl | CH$_3$ | Cl | CH$_2$ | 0 | |
| 3.0221 | CH$_3$ | CH$_3$ | CH$_2$OCH$_2$CH$_2$Cl | CH$_3$ | H | CH$_2$ | 0 | |
| 3.0222 | CH$_3$ | CH$_3$ | CH$_2$OCH$_2$CF$_3$ | CH$_3$ | F | CH$_2$ | 0 | |
| 3.0223 | CH$_3$ | CH$_3$ | CH$_2$OCH$_2$CF$_3$ | CH$_3$ | Cl | CH$_2$ | 0 | |
| 3.0224 | CH$_3$ | CH$_3$ | CH$_2$OCH$_2$CF$_3$ | CH$_3$ | H | CH$_2$ | 0 | |
| 3.0225 | CH$_3$ | CH$_3$ | CH$_2$OCH$_2$CH=CH$_2$ | CH$_3$ | F | CH$_2$ | 0 | |
| 3.0226 | CH$_3$ | CH$_3$ | CH$_2$OCH$_2$CH=CH$_2$ | CH$_3$ | Cl | CH$_2$ | 0 | |
| 3.0227 | CH$_3$ | CH$_3$ | CH$_2$OCH$_2$CH=CH$_2$ | CH$_3$ | H | CH$_2$ | 0 | |
| 3.0228 | CH$_3$ | CH$_3$ | CH$_2$O(CO)CH$_3$ | CH$_3$ | F | CH$_2$ | 0 | |
| 3.0229 | CH$_3$ | CH$_3$ | CH$_2$O(CO)CH$_3$ | CH$_3$ | Cl | CH$_2$ | 0 | |
| 3.0230 | CH$_3$ | CH$_3$ | CH$_2$O(CO)CH$_3$ | CH$_3$ | H | CH$_2$ | 0 | |
| 3.0231 | CH$_3$ | CH$_3$ | CH$_2$OCH$_2$C≡CH | CH$_3$ | F | CH$_2$ | 0 | |
| 3.0232 | CH$_3$ | CH$_3$ | CH$_2$OCH$_2$C≡CH | CH$_3$ | Cl | CH$_2$ | 0 | |

TABLE 3-continued

Compounds of formula Id:

(Id)

| No. | $R_1$ | $R_2$ | $Z_1$ | $R_{30}$ | X | Y | p | Phys. data, remarks |
|---|---|---|---|---|---|---|---|---|
| 3.0233 | $CH_3$ | $CH_3$ | $CH_2OCH_2C{\equiv}CH$ | $CH_3$ | H | $CH_2$ | 0 | |
| 3.0234 | $CH_3$ | $CH_3$ | $CH_2OCH_2C{\equiv}CCH_3$ | $CH_3$ | F | $CH_2$ | 0 | |
| 3.0235 | $CH_3$ | $CH_3$ | $CH_2OCH_2C{\equiv}CCH_3$ | $CH_3$ | Cl | $CH_2$ | 0 | |
| 3.0236 | $CH_3$ | $CH_3$ | $CH_2OCH_2C{\equiv}CCH_3$ | $CH_3$ | H | $CH_2$ | 0 | |
| 3.0237 | $CH_3$ | $CH_3$ | (4-methyl-3-oxo-1,2,4-triazol-1-yl)methyl | $CH_3$ | F | $CH_2$ | 0 | |
| 3.0238 | $CH_3$ | $CH_3$ | (4-methyl-3-oxo-1,2,4-triazol-1-yl)methyl | $CH_3$ | Cl | $CH_2$ | 0 | |
| 3.0239 | $CH_3$ | $CH_3$ | (4-methyl-3-oxo-1,2,4-triazol-1-yl)methyl | $CH_3$ | H | $CH_2$ | 0 | |
| 3.0240 | $CH_3$ | $CH_3$ | (3-methyl-2-oxo-1,3,4-oxadiazol-5-yl)methyl | $CH_3$ | F | $CH_2$ | 0 | |
| 3.0241 | $CH_3$ | $CH_3$ | (3-methyl-2-oxo-1,3,4-oxadiazol-5-yl)methyl | $CH_3$ | Cl | $CH_2$ | 0 | |
| 3.0242 | $CH_3$ | $CH_3$ | (3-methyl-2-oxo-1,3,4-oxadiazol-5-yl)methyl | $CH_3$ | H | $CH_2$ | 0 | |
| 3.0243 | $CH_3$ | $CH_3$ | $CH_2$-(oxiranyl) | $CH_3$ | F | $CH_2$ | 0 | |
| 3.0244 | $CH_3$ | $CH_3$ | $CH_2$-(oxiranyl) | $CH_3$ | Cl | $CH_2$ | 0 | |
| 3.0245 | $CH_3$ | $CH_3$ | $CH_2$-(oxiranyl) | $CH_3$ | H | $CH_2$ | 0 | |
| 3.0246 | $CH_3$ | $CH_3$ | $CH_2OCH_2$-(oxiranyl) | $CH_3$ | F | $CH_2$ | 0 | |

TABLE 3-continued

Compounds of formula Id:

(Id)

| No. | R₁ | R₂ | Z₁ | R₃₀ | X | Y | p | Phys. data, remarks |
|---|---|---|---|---|---|---|---|---|
| 3.0247 | CH₃ | CH₃ |  | CH₃ | Cl | CH₂ | 0 | |
| 3.0248 | CH₃ | CH₃ | 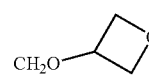 | CH₃ | H | CH₂ | 0 | |
| 3.0249 | CH₃ | CH₃ | 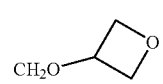 | CH₃ | F | CH₂ | 0 | |
| 3.0250 | CH₃ | CH₃ |  | CH₃ | Cl | CH₂ | 0 | |
| 3.0251 | CH₃ | CH₃ | 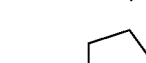 | CH₃ | H | CH₂ | 0 | |
| 3.0252 | CH₃ | CH₃ | 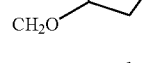 | CH₃ | F | CH₂ | 0 | |
| 3.0253 | CH₃ | CH₃ | 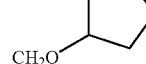 | CH₃ | Cl | CH₂ | 0 | |
| 3.0254 | CH₃ | CH₃ |  | CH₃ | H | CH₂ | 0 | |
| 3.0255 | H | CH₃ | CH₂OCH₂CH₂OCH₃ | CH₃ | F | CH₂ | 0 | |
| 3.0256 | H | CH₃ | CH₂OCH₂CH₂OCH₃ | CH₃ | Cl | CH₂ | 0 | |
| 3.0257 | H | CH₃ | CH₂OCH₂CH₂OCH₃ | CH₃ | H | CH₂ | 0 | |
| 3.0258 | H | CH₃ | CH₂OCH₂CH₂OCH₂CH₃ | CH₃ | F | CH₂ | 0 | |
| 3.0259 | H | CH₃ | CH₂OCH₂CH₂OCH₂CH₃ | CH₃ | Cl | CH₂ | 0 | |
| 3.0260 | H | CH₃ | CH₂OCH₂CH₂OCH₂CH₃ | CH₃ | H | CH₂ | 0 | |
| 3.0261 | H | CH₃ | CH₂N(CH₃)SO₂CH₃ | CH₃ | F | CH₂ | 0 | |
| 3.0262 | H | CH₃ | CH₂N(CH₃)SO₂CH₃ | CH₃ | Cl | CH₂ | 0 | |
| 3.0263 | H | CH₃ | CH₂N(CH₃)SO₂CH₃ | CH₃ | H | CH₂ | 0 | |
| 3.0264 | H | CH₃ | CH₂OCH₂Ph | CH₃ | F | CH₂ | 0 | |
| 3.0265 | H | CH₃ | CH₂OCH₂Ph | CH₃ | Cl | CH₂ | 0 | |
| 3.0266 | H | CH₃ | CH₂OCH₂Ph | CH₃ | H | CH₂ | 0 | |
| 3.0267 | H | CH₃ | CH₂OCH₂CH₂OH | CH₃ | F | CH₂ | 0 | |
| 3.0268 | H | CH₃ | CH₂OCH₂CH₂OH | CH₃ | Cl | CH₂ | 0 | |
| 3.0269 | H | CH₃ | CH₂OCH₂CH₂OH | CH₃ | H | CH₂ | 0 | |
| 3.0270 | H | CH₃ | CH₂OCH₂CH₂Cl | CH₃ | F | CH₂ | 0 | |
| 3.0271 | H | CH₃ | CH₂OCH₂CH₂Cl | CH₃ | Cl | CH₂ | 0 | |
| 3.0272 | H | CH₃ | CH₂OCH₂CH₂Cl | CH₃ | H | CH₂ | 0 | |
| 3.0273 | H | CH₃ | CH₂OCH₂CF₃ | CH₃ | F | CH₂ | 0 | |
| 3.0274 | H | CH₃ | CH₂OCH₂CF₃ | CH₃ | Cl | CH₂ | 0 | |
| 3.0275 | H | CH₃ | CH₂OCH₂CF₃ | CH₃ | H | CH₂ | 0 | |
| 3.0276 | H | CH₃ | CH₂OCH₂CH=CH₂ | CH₃ | F | CH₂ | 0 | |
| 3.0277 | H | CH₃ | CH₂OCH₂CH=CH₂ | CH₃ | Cl | CH₂ | 0 | |
| 3.0278 | H | CH₃ | CH₂OCH₂CH=CH₂ | CH₃ | H | CH₂ | 0 | |
| 3.0279 | H | CH₃ | CH₂O(CO)CH₃ | CH₃ | F | CH₂ | 0 | |

TABLE 3-continued

Compounds of formula Id:

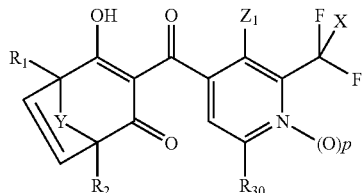

(Id)

| No. | $R_1$ | $R_2$ | $Z_1$ | $R_{30}$ | X | Y | p | Phys. data, remarks |
|---|---|---|---|---|---|---|---|---|
| 3.0280 | H | $CH_3$ | $CH_2O(CO)CH_3$ | $CH_3$ | Cl | $CH_2$ | 0 | |
| 3.0281 | H | $CH_3$ | $CH_2O(CO)CH_3$ | $CH_3$ | H | $CH_2$ | 0 | |
| 3.0282 | H | $CH_3$ | $CH_2OCH_2C\equiv CH$ | $CH_3$ | F | $CH_2$ | 0 | |
| 3.0283 | H | $CH_3$ | $CH_2OCH_2C\equiv CH$ | $CH_3$ | Cl | $CH_2$ | 0 | |
| 3.0284 | H | $CH_3$ | $CH_2OCH_2C\equiv CH$ | $CH_3$ | H | $CH_2$ | 0 | |
| 3.0285 | H | $CH_3$ | $CH_2OCH_2C\equiv CCH_3$ | $CH_3$ | F | $CH_2$ | 0 | |
| 3.0286 | H | $CH_3$ | $CH_2OCH_2C\equiv CCH_3$ | $CH_3$ | Cl | $CH_2$ | 0 | |
| 3.0287 | H | $CH_3$ | $CH_2OCH_2C\equiv CCH_3$ | $CH_3$ | H | $CH_2$ | 0 | |
| 3.0288 | H | $CH_3$ | (4-methyl-5-oxo-4,5-dihydro-1,2,4-triazol-1-yl)methyl | $CH_3$ | F | $CH_2$ | 0 | |
| 3.0289 | H | $CH_3$ | (4-methyl-5-oxo-4,5-dihydro-1,2,4-triazol-1-yl)methyl | $CH_3$ | Cl | $CH_2$ | 0 | |
| 3.0290 | H | $CH_3$ | (4-methyl-5-oxo-4,5-dihydro-1,2,4-triazol-1-yl)methyl | $CH_3$ | H | $CH_2$ | 0 | |
| 3.0291 | H | $CH_3$ | (3-methyl-2-oxo-2,3-dihydro-1,3,4-oxadiazol-5-yl)methyl | $CH_3$ | F | $CH_2$ | 0 | |
| 3.0292 | H | $CH_3$ | (3-methyl-2-oxo-2,3-dihydro-1,3,4-oxadiazol-5-yl)methyl | $CH_3$ | Cl | $CH_2$ | 0 | |
| 3.0293 | H | $CH_3$ | (3-methyl-2-oxo-2,3-dihydro-1,3,4-oxadiazol-5-yl)methyl | $CH_3$ | H | $CH_2$ | 0 | |
| 3.0294 | H | $CH_3$ | oxiranylmethyl | $CH_3$ | F | $CH_2$ | 0 | |
| 3.0295 | H | $CH_3$ | oxiranylmethyl | $CH_3$ | Cl | $CH_2$ | 0 | |
| 3.0296 | H | $CH_3$ | oxiranylmethyl | $CH_3$ | H | $CH_2$ | 0 | |

TABLE 3-continued

Compounds of formula Id:

(Id)

| No. | R₁ | R₂ | Z₁ | R₃₀ | X | Y | p | Phys. data, remarks |
|---|---|---|---|---|---|---|---|---|
| 3.0297 | H | CH₃ |  CH₂OCH₂— | CH₃ | F | CH₂ | 0 | |
| 3.0298 | H | CH₃ |  CH₂OCH₂— | CH₃ | Cl | CH₂ | 0 | |
| 3.0299 | H | CH₃ | 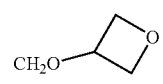 CH₂OCH₂— | CH₃ | H | CH₂ | 0 | |
| 3.0300 | H | CH₃ | 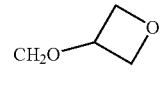 | CH₃ | F | CH₂ | 0 | |
| 3.0301 | H | CH₃ | 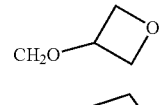 | CH₃ | Cl | CH₂ | 0 | |
| 3.0302 | H | CH₃ | 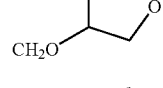 | CH₃ | H | CH₂ | 0 | |
| 3.0303 | H | CH₃ | 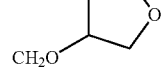 | CH₃ | F | CH₂ | 0 | |
| 3.0304 | H | CH₃ | 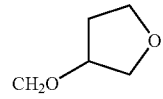 | CH₃ | Cl | CH₂ | 0 | |
| 3.0305 | H | CH₃ | 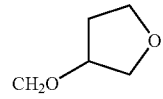 | CH₃ | H | CH₂ | 0 | |
| 3.0306 | H | H | CH₂OCH₂CH₂OCH₃ | CH₃ | F | CH₂ | 1 | |
| 3.0307 | H | H | CH₂OCH₂CH₂OCH₃ | CH₃ | Cl | CH₂ | 1 | |
| 3.0308 | H | H | CH₂OCH₂CH₂OCH₃ | CH₃ | H | CH₂ | 1 | |
| 3.0309 | H | H | CH₂OCH₂CH₂OCH₂CH₃ | CH₃ | F | CH₂ | 1 | |
| 3.0310 | H | H | CH₂OCH₂CH₂OCH₂CH₃ | CH₃ | Cl | CH₂ | 1 | |
| 3.0311 | H | H | CH₂OCH₂CH₂OCH₂CH₃ | CH₃ | H | CH₂ | 1 | |
| 3.0312 | H | H | CH₂N(CH₃)SO₂CH₃ | CH₃ | F | CH₂ | 1 | |
| 3.0313 | H | H | CH₂N(CH₃)SO₂CH₃ | CH₃ | Cl | CH₂ | 1 | |
| 3.0314 | H | H | CH₂N(CH₃)SO₂CH₃ | CH₃ | H | CH₂ | 1 | |
| 3.0315 | H | H | CH₂OCH₂Ph | CH₃ | F | CH₂ | 1 | |
| 3.0316 | H | H | CH₂OCH₂Ph | CH₃ | Cl | CH₂ | 1 | |
| 3.0317 | H | H | CH₂OCH₂Ph | CH₃ | H | CH₂ | 1 | |
| 3.0318 | H | H | CH₂OCH₂CH₂OH | CH₃ | F | CH₂ | 1 | |
| 3.0319 | H | H | CH₂OCH₂CH₂OH | CH₃ | Cl | CH₂ | 1 | |
| 3.0320 | H | H | CH₂OCH₂CH₂OH | CH₃ | H | CH₂ | 1 | |
| 3.0321 | H | H | CH₂OCH₂CH₂Cl | CH₃ | F | CH₂ | 1 | |
| 3.0322 | H | H | CH₂OCH₂CH₂Cl | CH₃ | Cl | CH₂ | 1 | |
| 3.0323 | H | H | CH₂OCH₂CH₂Cl | CH₃ | H | CH₂ | 1 | |
| 3.0324 | H | H | CH₂OCH₂CF₃ | CH₃ | F | CH₂ | 1 | |
| 3.0325 | H | H | CH₂OCH₂CF₃ | CH₃ | Cl | CH₂ | 1 | |
| 3.0326 | H | H | CH₂OCH₂CF₃ | CH₃ | H | CH₂ | 1 | |

TABLE 3-continued

Compounds of formula Id:

(Id)

| No. | $R_1$ | $R_2$ | $Z_1$ | $R_{30}$ | X | Y | p | Phys. data, remarks |
|---|---|---|---|---|---|---|---|---|
| 3.0327 | H | H | $CH_2OCH_2CH=CH_2$ | $CH_3$ | F | $CH_2$ | 1 | |
| 3.0328 | H | H | $CH_2OCH_2CH=CH_2$ | $CH_3$ | Cl | $CH_2$ | 1 | |
| 3.0329 | H | H | $CH_2OCH_2CH=CH_2$ | $CH_3$ | H | $CH_2$ | 1 | |
| 3.0330 | H | H | $CH_2O(CO)CH_3$ | $CH_3$ | F | $CH_2$ | 1 | |
| 3.0331 | H | H | $CH_2O(CO)CH_3$ | $CH_3$ | Cl | $CH_2$ | 1 | |
| 3.0332 | H | H | $CH_2O(CO)CH_3$ | $CH_3$ | H | $CH_2$ | 1 | |
| 3.0333 | H | H | $CH_2OCH_2C\equiv CH$ | $CH_3$ | F | $CH_2$ | 1 | |
| 3.0334 | H | H | $CH_2OCH_2C\equiv CH$ | $CH_3$ | Cl | $CH_2$ | 1 | |
| 3.0335 | H | H | $CH_2OCH_2C\equiv CH$ | $CH_3$ | H | $CH_2$ | 1 | |
| 3.0336 | H | H | $CH_2OCH_2C\equiv CCH_3$ | $CH_3$ | F | $CH_2$ | 1 | |
| 3.0337 | H | H | $CH_2OCH_2C\equiv CCH_3$ | $CH_3$ | Cl | $CH_2$ | 1 | |
| 3.0338 | H | H | $CH_2OCH_2C\equiv CCH_3$ | $CH_3$ | H | $CH_2$ | 1 | |
| 3.0339 | H | H | 4-CH₂-2-methyl-3-oxo-2,4-dihydro-1,2,4-triazol-4-yl | $CH_3$ | F | $CH_2$ | 1 | |
| 3.0340 | H | H | 4-CH₂-2-methyl-3-oxo-2,4-dihydro-1,2,4-triazol-4-yl | $CH_3$ | Cl | $CH_2$ | 1 | |
| 3.0341 | H | H | 4-CH₂-2-methyl-3-oxo-2,4-dihydro-1,2,4-triazol-4-yl | $CH_3$ | H | $CH_2$ | 1 | |
| 3.0342 | H | H | CH₂-(3-methyl-2-oxo-2,3-dihydro-1,3,4-oxadiazol-5-yl) | $CH_3$ | F | $CH_2$ | 1 | |
| 3.0343 | H | H | CH₂-(3-methyl-2-oxo-2,3-dihydro-1,3,4-oxadiazol-5-yl) | $CH_3$ | Cl | $CH_2$ | 1 | |
| 3.0344 | H | H | CH₂-(3-methyl-2-oxo-2,3-dihydro-1,3,4-oxadiazol-5-yl) | $CH_3$ | H | $CH_2$ | 1 | |
| 3.0345 | H | H | CH₂-oxiranyl | $CH_3$ | F | $CH_2$ | 1 | |
| 3.0346 | H | H | CH₂-oxiranyl | $CH_3$ | Cl | $CH_2$ | 1 | |

TABLE 3-continued

Compounds of formula Id:

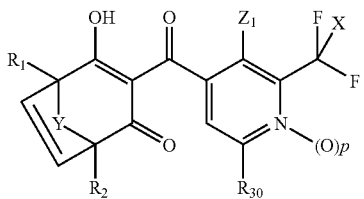

(Id)

| No. | R₁ | R₂ | Z₁ | R₃₀ | X | Y | p | Phys. data, remarks |
|---|---|---|---|---|---|---|---|---|
| 3.0347 | H | H | CH₂-(oxiranyl) | CH₃ | H | CH₂ | 1 | |
| 3.0348 | H | H | CH₂OCH₂-(oxiranyl) | CH₃ | F | CH₂ | 1 | |
| 3.0349 | H | H | CH₂OCH₂-(oxiranyl) | CH₃ | Cl | CH₂ | 1 | |
| 3.0350 | H | H | CH₂OCH₂-(oxiranyl) | CH₃ | H | CH₂ | 1 | |
| 3.0351 | H | H | CH₂O-(oxetanyl) | CH₃ | F | CH₂ | 1 | |
| 3.0352 | H | H | CH₂O-(oxetanyl) | CH₃ | Cl | CH₂ | 1 | |
| 3.0353 | H | H | CH₂O-(oxetanyl) | CH₃ | H | CH₂ | 1 | |
| 3.0354 | H | H | CH₂O-(tetrahydrofuranyl) | CH₃ | F | CH₂ | 1 | |
| 3.0355 | H | H | CH₂O-(tetrahydrofuranyl) | CH₃ | Cl | CH₂ | 1 | |
| 3.0356 | H | H | CH₂O-(tetrahydrofuranyl) | CH₃ | H | CH₂ | 1 | |
| 3.0357 | CH₃ | CH₃ | CH₂OCH₂CH₂OCH₃ | CH₃ | F | CH₂ | 1 | |
| 3.0358 | CH₃ | CH₃ | CH₂OCH₂CH₂OCH₃ | CH₃ | Cl | CH₂ | 1 | |
| 3.0359 | CH₃ | CH₃ | CH₂OCH₂CH₂OCH₃ | CH₃ | H | CH₂ | 1 | |
| 3.0360 | CH₃ | CH₃ | CH₂OCH₂CH₂OCH₂CH₃ | CH₃ | F | CH₂ | 1 | |
| 3.0361 | CH₃ | CH₃ | CH₂OCH₂CH₂OCH₂CH₃ | CH₃ | Cl | CH₂ | 1 | |
| 3.0362 | CH₃ | CH₃ | CH₂OCH₂CH₂OCH₂CH₃ | CH₃ | H | CH₂ | 1 | |
| 3.0363 | CH₃ | CH₃ | CH₂N(CH₃)SO₂CH₃ | CH₃ | F | CH₂ | 1 | |
| 3.0364 | CH₃ | CH₃ | CH₂N(CH₃)SO₂CH₃ | CH₃ | Cl | CH₂ | 1 | |
| 3.0365 | CH₃ | CH₃ | CH₂N(CH₃)SO₂CH₃ | CH₃ | H | CH₂ | 1 | |
| 3.0366 | CH₃ | CH₃ | CH₂OCH₂Ph | CH₃ | F | CH₂ | 1 | |
| 3.0367 | CH₃ | CH₃ | CH₂OCH₂Ph | CH₃ | Cl | CH₂ | 1 | |
| 3.0368 | CH₃ | CH₃ | CH₂OCH₂Ph | CH₃ | H | CH₂ | 1 | |
| 3.0369 | CH₃ | CH₃ | CH₂OCH₂CH₂OH | CH₃ | F | CH₂ | 1 | |
| 3.0370 | CH₃ | CH₃ | CH₂OCH₂CH₂OH | CH₃ | Cl | CH₂ | 1 | |
| 3.0371 | CH₃ | CH₃ | CH₂OCH₂CH₂OH | CH₃ | H | CH₂ | 1 | |
| 3.0372 | CH₃ | CH₃ | CH₂OCH₂CH₂Cl | CH₃ | F | CH₂ | 1 | |
| 3.0373 | CH₃ | CH₃ | CH₂OCH₂CH₂Cl | CH₃ | Cl | CH₂ | 1 | |

TABLE 3-continued

Compounds of formula Id:

(Id)

| No. | $R_1$ | $R_2$ | $Z_1$ | $R_{30}$ | X | Y | p | Phys. data, remarks |
|---|---|---|---|---|---|---|---|---|
| 3.0374 | $CH_3$ | $CH_3$ | $CH_2OCH_2CH_2Cl$ | $CH_3$ | H | $CH_2$ | 1 | |
| 3.0375 | $CH_3$ | $CH_3$ | $CH_2OCH_2CF_3$ | $CH_3$ | F | $CH_2$ | 1 | |
| 3.0376 | $CH_3$ | $CH_3$ | $CH_2OCH_2CF_3$ | $CH_3$ | Cl | $CH_2$ | 1 | |
| 3.0377 | $CH_3$ | $CH_3$ | $CH_2OCH_2CF_3$ | $CH_3$ | H | $CH_2$ | 1 | |
| 3.0378 | $CH_3$ | $CH_3$ | $CH_2OCH_2CH=CH_2$ | $CH_3$ | F | $CH_2$ | 1 | |
| 3.0379 | $CH_3$ | $CH_3$ | $CH_2OCH_2CH=CH_2$ | $CH_3$ | Cl | $CH_2$ | 1 | |
| 3.0380 | $CH_3$ | $CH_3$ | $CH_2OCH_2CH=CH_2$ | $CH_3$ | H | $CH_2$ | 1 | |
| 3.0381 | $CH_3$ | $CH_3$ | $CH_2O(CO)CH_3$ | $CH_3$ | F | $CH_2$ | 1 | |
| 3.0382 | $CH_3$ | $CH_3$ | $CH_2O(CO)CH_3$ | $CH_3$ | Cl | $CH_2$ | 1 | |
| 3.0383 | $CH_3$ | $CH_3$ | $CH_2O(CO)CH_3$ | $CH_3$ | H | $CH_2$ | 1 | |
| 3.0384 | $CH_3$ | $CH_3$ | $CH_2OCH_2C\equiv CH$ | $CH_3$ | F | $CH_2$ | 1 | |
| 3.0385 | $CH_3$ | $CH_3$ | $CH_2OCH_2C\equiv CH$ | $CH_3$ | Cl | $CH_2$ | 1 | |
| 3.0386 | $CH_3$ | $CH_3$ | $CH_2OCH_2C\equiv CH$ | $CH_3$ | H | $CH_2$ | 1 | |
| 3.0387 | $CH_3$ | $CH_3$ | $CH_2OCH_2C\equiv CCH_3$ | $CH_3$ | F | $CH_2$ | 1 | |
| 3.0388 | $CH_3$ | $CH_3$ | $CH_2OCH_2C\equiv CCH_3$ | $CH_3$ | Cl | $CH_2$ | 1 | |
| 3.0389 | $CH_3$ | $CH_3$ | $CH_2OCH_2C\equiv CCH_3$ | $CH_3$ | H | $CH_2$ | 1 | |
| 3.0390 | $CH_3$ | $CH_3$ | (4-methyl-3-oxo-1,2,4-triazol-1-yl)methyl | $CH_3$ | F | $CH_2$ | 1 | |
| 3.0391 | $CH_3$ | $CH_3$ | (4-methyl-3-oxo-1,2,4-triazol-1-yl)methyl | $CH_3$ | Cl | $CH_2$ | 1 | |
| 3.0392 | $CH_3$ | $CH_3$ | (4-methyl-3-oxo-1,2,4-triazol-1-yl)methyl | $CH_3$ | H | $CH_2$ | 1 | |
| 3.0393 | $CH_3$ | $CH_3$ | (3-methyl-2-oxo-1,3,4-oxadiazol-5-yl)methyl | $CH_3$ | F | $CH_2$ | 1 | |
| 3.0394 | $CH_3$ | $CH_3$ | (3-methyl-2-oxo-1,3,4-oxadiazol-5-yl)methyl | $CH_3$ | Cl | $CH_2$ | 1 | |
| 3.0395 | $CH_3$ | $CH_3$ | (3-methyl-2-oxo-1,3,4-oxadiazol-5-yl)methyl | $CH_3$ | H | $CH_2$ | 1 | |
| 3.0396 | $CH_3$ | $CH_3$ | oxiranylmethyl | $CH_3$ | F | $CH_2$ | 1 | |

TABLE 3-continued

Compounds of formula Id:

(Id)

| No. | R₁ | R₂ | Z₁ | R₃₀ | X | Y | p | Phys. data, remarks |
|---|---|---|---|---|---|---|---|---|
| 3.0397 | CH₃ | CH₃ |  | CH₃ | Cl | CH₂ | 1 | |
| 3.0398 | CH₃ | CH₃ |  | CH₃ | H | CH₂ | 1 | |
| 3.0399 | CH₃ | CH₃ |  | CH₃ | F | CH₂ | 1 | |
| 3.0400 | CH₃ | CH₃ |  | CH₃ | Cl | CH₂ | 1 | |
| 3.0401 | CH₃ | CH₃ | 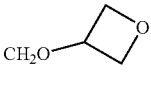 | CH₃ | H | CH₂ | 1 | |
| 3.0402 | CH₃ | CH₃ | 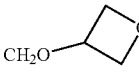 | CH₃ | F | CH₂ | 1 | |
| 3.0403 | CH₃ | CH₃ | 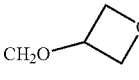 | CH₃ | Cl | CH₂ | 1 | |
| 3.0404 | CH₃ | CH₃ | 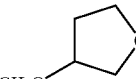 | CH₃ | H | CH₂ | 1 | |
| 3.0405 | CH₃ | CH₃ |  | CH₃ | F | CH₂ | 1 | |
| 3.0406 | CH₃ | CH₃ | 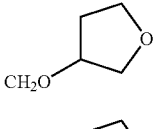 | CH₃ | Cl | CH₂ | 1 | |
| 3.0407 | CH₃ | CH₃ |  | CH₃ | H | CH₂ | 1 | |
| 3.0408 | H | CH₃ | CH₂OCH₂CH₂OCH₃ | CH₃ | F | CH₂ | 1 | |
| 3.0409 | H | CH₃ | CH₂OCH₂CH₂OCH₃ | CH₃ | Cl | CH₂ | 1 | |
| 3.0410 | H | CH₃ | CH₂OCH₂CH₂OCH₃ | CH₃ | H | CH₂ | 1 | |
| 3.0411 | H | CH₃ | CH₂OCH₂CH₂OCH₂CH₃ | CH₃ | F | CH₂ | 1 | |
| 3.0412 | H | CH₃ | CH₂OCH₂CH₂OCH₂CH₃ | CH₃ | Cl | CH₂ | 1 | |
| 3.0413 | H | CH₃ | CH₂OCH₂CH₂OCH₂CH₃ | CH₃ | H | CH₂ | 1 | |
| 3.0414 | H | CH₃ | CH₂N(CH₃)SO₂CH₃ | CH₃ | F | CH₂ | 1 | |
| 3.0415 | H | CH₃ | CH₂N(CH₃)SO₂CH₃ | CH₃ | Cl | CH₂ | 1 | |
| 3.0416 | H | CH₃ | CH₂N(CH₃)SO₂CH₃ | CH₃ | H | CH₂ | 1 | |
| 3.0417 | H | CH₃ | CH₂OCH₂Ph | CH₃ | F | CH₂ | 1 | |
| 3.0418 | H | CH₃ | CH₂OCH₂Ph | CH₃ | Cl | CH₂ | 1 | |
| 3.0419 | H | CH₃ | CH₂OCH₂Ph | CH₃ | H | CH₂ | 1 | |
| 3.0420 | H | CH₃ | CH₂OCH₂CH₂OH | CH₃ | F | CH₂ | 1 | |

TABLE 3-continued

Compounds of formula Id:

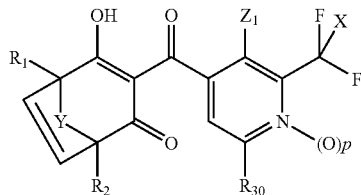

(Id)

| No. | R₁ | R₂ | Z₁ | R₃₀ | X | Y | p | Phys. data, remarks |
|---|---|---|---|---|---|---|---|---|
| 3.0421 | H | CH₃ | CH₂OCH₂CH₂OH | CH₃ | Cl | CH₂ | 1 | |
| 3.0422 | H | CH₃ | CH₂OCH₂CH₂OH | CH₃ | H | CH₂ | 1 | |
| 3.0423 | H | CH₃ | CH₂OCH₂CH₂Cl | CH₃ | F | CH₂ | 1 | |
| 3.0424 | H | CH₃ | CH₂OCH₂CH₂Cl | CH₃ | Cl | CH₂ | 1 | |
| 3.0425 | H | CH₃ | CH₂OCH₂CH₂Cl | CH₃ | H | CH₂ | 1 | |
| 3.0426 | H | CH₃ | CH₂OCH₂CF₃ | CH₃ | F | CH₂ | 1 | |
| 3.0427 | H | CH₃ | CH₂OCH₂CF₃ | CH₃ | Cl | CH₂ | 1 | |
| 3.0428 | H | CH₃ | CH₂OCH₂CF₃ | CH₃ | H | CH₂ | 1 | |
| 3.0429 | H | CH₃ | CH₂OCH₂CH=CH₂ | CH₃ | F | CH₂ | 1 | |
| 3.0430 | H | CH₃ | CH₂OCH₂CH=CH₂ | CH₃ | Cl | CH₂ | 1 | |
| 3.0431 | H | CH₃ | CH₂OCH₂CH=CH₂ | CH₃ | H | CH₂ | 1 | |
| 3.0432 | H | CH₃ | CH₂O(CO)CH₃ | CH₃ | F | CH₂ | 1 | |
| 3.0433 | H | CH₃ | CH₂O(CO)CH₃ | CH₃ | Cl | CH₂ | 1 | |
| 3.0434 | H | CH₃ | CH₂O(CO)CH₃ | CH₃ | H | CH₂ | 1 | |
| 3.0435 | H | CH₃ | CH₂OCH₂C≡CH | CH₃ | F | CH₂ | 1 | |
| 3.0436 | H | CH₃ | CH₂OCH₂C≡CH | CH₃ | Cl | CH₂ | 1 | |
| 3.0437 | H | CH₃ | CH₂OCH₂C≡CH | CH₃ | H | CH₂ | 1 | |
| 3.0438 | H | CH₃ | CH₂OCH₂C≡CCH₃ | CH₃ | F | CH₂ | 1 | |
| 3.0439 | H | CH₃ | CH₂OCH₂C≡CCH₃ | CH₃ | Cl | CH₂ | 1 | |
| 3.0440 | H | CH₃ | CH₂OCH₂C≡CCH₃ | CH₃ | H | CH₂ | 1 | |
| 3.0441 | H | CH₃ | (N-methyl-triazolone-CH₂-) | CH₃ | F | CH₂ | 1 | |
| 3.0442 | H | CH₃ | (N-methyl-triazolone-CH₂-) | CH₃ | Cl | CH₂ | 1 | |
| 3.0443 | H | CH₃ | (N-methyl-triazolone-CH₂-) | CH₃ | H | CH₂ | 1 | |
| 3.0444 | H | CH₃ | (N-methyl-oxadiazolone-CH₂-) | CH₃ | F | CH₂ | 1 | |
| 3.0445 | H | CH₃ | (N-methyl-oxadiazolone-CH₂-) | CH₃ | Cl | CH₂ | 1 | |
| 3.0446 | H | CH₃ | (N-methyl-oxadiazolone-CH₂-) | CH₃ | H | CH₂ | 1 | |

TABLE 3-continued
Compounds of formula Id:
(Id)
| No. | R₁ | R₂ | Z₁ | R₃₀ | X | Y | p | Phys. data, remarks |
|---|---|---|---|---|---|---|---|---|
| 3.0447 | H | CH₃ |  | CH₃ | F | CH₂ | 1 | |
| 3.0448 | H | CH₃ |  | CH₃ | Cl | CH₂ | 1 | |
| 3.0449 | H | CH₃ |  | CH₃ | H | CH₂ | 1 | |
| 3.0450 | H | CH₃ |  | CH₃ | F | CH₂ | 1 | |
| 3.0451 | H | CH₃ |  | CH₃ | Cl | CH₂ | 1 | |
| 3.0452 | H | CH₃ |  | CH₃ | H | CH₂ | 1 | |
| 3.0453 | H | CH₃ |  | CH₃ | F | CH₂ | 1 | |
| 3.0454 | H | CH₃ | 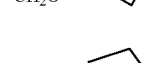 | CH₃ | Cl | CH₂ | 1 | |
| 3.0455 | H | CH₃ | 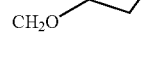 | CH₃ | H | CH₂ | 1 | |
| 3.0456 | H | CH₃ | 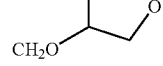 | CH₃ | F | CH₂ | 1 | |
| 3.0457 | H | CH₃ | 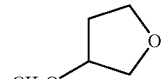 | CH₃ | Cl | CH₂ | 1 | |
| 3.0458 | H | CH₃ |  | CH₃ | H | CH₂ | 1 | |

TABLE 4

Intermediates of formulae Da and Db:

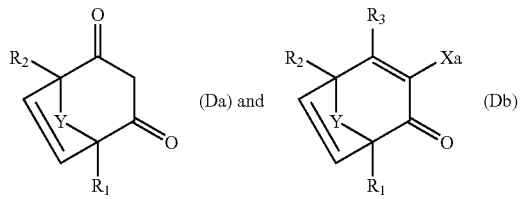

| No. | $R_1$ | $R_2$ | $R_3$ | Y | Xa | Physical data |
|---|---|---|---|---|---|---|
| 4.0001 | H | H | OH | $CH_2$ | H | see Example P9; tautomeric form Da |
| 4.0002 | H | H | $OCH_3$ | $CH_2$ | H | |
| 4.0003 | H | H | $OCH_2CH_3$ | $CH_2$ | H | |
| 4.0004 | H | H | $OC(CH_3)_2$ | $CH_2$ | H | |
| 4.0005 | H | H | OH | $CH_2CH_2$ | H | see Example P12; tautomeric form Da |
| 4.0006 | H | H | $OCH_3$ | $CH_2CH_2$ | H | |
| 4.0007 | H | H | $OCH_2CH_3$ | $CH_2CH_2$ | H | |
| 4.0008 | H | H | $OC(CH_3)_2$ | $CH_2CH_2$ | H | |
| 4.0009 | H | H | OH | O | H | $^1$H NMR (300 MHz; $CDCl_3$) δ 6.35 (s, 2H); 5.66 (s, 1H); 3.78 (d, 1H); 3.43 (d, 1H); tautomeric form Da |
| 4.0010 | H | H | $OCH_3$ | O | H | |
| 4.0011 | H | H | $OCH_2CH_3$ | O | H | |
| 4.0012 | H | H | $OC(CH_3)_2$ | O | H | |
| 4.0013 | H | H | OH | $NSO_2CH_3$ | H | |
| 4.0014 | H | H | $OCH_3$ | $NSO_2CH_3$ | H | |
| 4.0015 | H | H | $OCH_2CH_3$ | $NSO_2CH_3$ | H | |
| 4.0016 | H | H | $OC(CH_3)_2$ | $NSO_2CH_3$ | H | |
| 4.0017 | H | H | OH | $NC(O)C(CH_3)_3$ | H | |
| 4.0018 | H | H | $OCH_3$ | $NC(O)C(CH_3)_3$ | H | |
| 4.0019 | H | H | $OCH_2CH_3$ | $NC(O)C(CH_3)_3$ | H | |
| 4.0020 | H | H | $OC(CH_3)_2$ | $NC(O)C(CH_3)_3$ | H | |
| 4.0021 | H | H | OH | $CH_2$ | Cl | |
| 4.0022 | H | H | $OCH_3$ | $CH_2$ | Cl | |
| 4.0023 | H | H | $OCH_2CH_3$ | $CH_2$ | Cl | |
| 4.0024 | H | H | $OC(CH_3)_2$ | $CH_2$ | Cl | |
| 4.0025 | H | H | OH | $CH_2CH_2$ | Cl | see Preparation Example P11 |
| 4.0026 | H | H | $OCH_3$ | $CH_2CH_2$ | Cl | |
| 4.0027 | H | H | $OCH_2CH_3$ | $CH_2CH_2$ | Cl | |
| 4.0028 | H | H | $OC(CH_3)_2$ | $CH_2CH_2$ | Cl | |
| 4.0029 | H | H | OH | O | Cl | |
| 4.0030 | H | H | $OCH_3$ | O | Cl | |
| 4.0031 | H | H | $OCH_2CH_3$ | O | Cl | |
| 4.0032 | H | H | $OC(CH_3)_2$ | O | Cl | |
| 4.0033 | H | H | OH | $NSO_2CH_3$ | Cl | |
| 4.0034 | H | H | $OCH_3$ | $NSO_2CH_3$ | Cl | |
| 4.0035 | H | H | $OCH_2CH_3$ | $NSO_2CH_3$ | Cl | |
| 4.0036 | H | H | $OC(CH_3)_2$ | $NSO_2CH_3$ | Cl | |
| 4.0037 | H | H | OH | $NC(O)C(CH_3)_3$ | Cl | |
| 4.0038 | H | H | $OCH_3$ | $NC(O)C(CH_3)_3$ | Cl | |
| 4.0039 | H | H | $OCH_2CH_3$ | $NC(O)C(CH_3)_3$ | Cl | |
| 4.0040 | H | H | $OC(CH_3)_2$ | $NC(O)C(CH_3)_3$ | Cl | |
| 4.0041 | H | H | OH | $CH_2$ | Br | |
| 4.0042 | H | H | $OCH_3$ | $CH_2$ | Br | |
| 4.0043 | H | H | $OCH_2CH_3$ | $CH_2$ | Br | |
| 4.0044 | H | H | $OC(CH_3)_2$ | $CH_2$ | Br | |
| 4.0045 | H | H | OH | $CH_2CH_2$ | Br | |
| 4.0046 | H | H | $OCH_3$ | $CH_2CH_2$ | Br | |
| 4.0047 | H | H | $OCH_2CH_3$ | $CH_2CH_2$ | Br | |
| 4.0048 | H | H | $OC(CH_3)_2$ | $CH_2CH_2$ | Br | |
| 4.0049 | H | H | OH | O | Br | |
| 4.0050 | H | H | $OCH_3$ | O | Br | |
| 4.0051 | H | H | $OCH_2CH_3$ | O | Br | |
| 4.0052 | H | H | $OC(CH_3)_2$ | O | Br | |
| 4.0053 | H | H | OH | $NSO_2CH_3$ | Br | |
| 4.0054 | H | H | $OCH_3$ | $NSO_2CH_3$ | Br | |
| 4.0055 | H | H | $OCH_2CH_3$ | $NSO_2CH_3$ | Br | |
| 4.0056 | H | H | $OC(CH_3)_2$ | $NSO_2CH_3$ | Br | |
| 4.0057 | H | H | OH | $NC(O)C(CH_3)_3$ | Br | |
| 4.0058 | H | H | $OCH_3$ | $NC(O)C(CH_3)_3$ | Br | |
| 4.0059 | H | H | $OCH_2CH_3$ | $NC(O)C(CH_3)_3$ | Br | |
| 4.0060 | H | H | $OC(CH_3)_2$ | $NC(O)O(CH_3)_3$ | Br | |

TABLE 4-continued

Intermediates of formulae Da and Db:

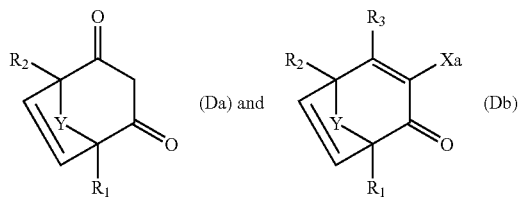

(Da) and (Db)

| No. | $R_1$ | $R_2$ | $R_3$ | Y | Xa | Physical data |
|---|---|---|---|---|---|---|
| 4.0061 | H | CH₃ | OH | CH₂ | H | ¹H NMR (300 MHz; CDCl₃) δ 6.30 (m, 1H); 6.10 (m, 1H); 3.73 (d, 1H); 3.44 (d, 1H); 1.62 (s, 3H); tautomeric form Db |
| 4.0062 | H | CH₃ | OCH₃ | CH₂ | H | |
| 4.0063 | H | CH₃ | OCH₂CH₃ | CH₂ | H | |
| 4.0064 | H | CH₃ | OC(CH₃)₃ | CH₂ | H | |
| 4.0065 | H | CH₃ | OH | CH₂CH₂ | H | |
| 4.0066 | H | CH₃ | OCH₃ | CH₂CH₂ | H | |
| 4.0067 | H | CH₃ | OCH₂CH₃ | CH₂CH₂ | H | |
| 4.0068 | H | CH₃ | OC(CH₃)₃ | CH₂CH₂ | H | |
| 4.0069 | H | CH₃ | OH | O | H | |
| 4.0070 | H | CH₃ | OCH₃ | O | H | |
| 4.0071 | H | CH₃ | OCH₂CH₃ | O | H | |
| 4.0072 | H | CH₃ | OC(CH₃)₃ | O | H | |
| 4.0073 | H | CH₃ | OH | NSO₂CH₃ | H | |
| 4.0074 | H | CH₃ | OCH₃ | NSO₂CH₃ | H | |
| 4.0075 | H | CH₃ | OCH₂CH₃ | NSO₂CH₃ | H | |
| 4.0076 | H | CH₃ | OC(CH₃)₃ | NSO₂CH₃ | H | |
| 4.0077 | H | CH₃ | OH | NC(O)O(CH₃)₃ | H | |
| 4.0078 | H | CH₃ | OCH₃ | NC(O)O(CH₃)₃ | H | |
| 4.0079 | H | CH₃ | OCH₂CH₃ | NC(O)C(CH₃)₃ | H | |
| 4.0080 | H | CH₃ | OC(CH₃)₃ | NC(O)O(CH₃)₃ | H | |
| 4.0081 | H | CH₃ | OH | CH₂ | Cl | |
| 4.0082 | H | CH₃ | OCH₃ | CH₂ | Cl | |
| 4.0083 | H | CH₃ | OCH₂CH₃ | CH₂ | Cl | |
| 4.0084 | H | CH₃ | OC(CH₃)₃ | CH₂ | Cl | |
| 4.0085 | H | CH₃ | OH | CH₂CH₂ | Cl | |
| 4.0086 | H | CH₃ | OCH₃ | CH₂CH₂ | Cl | |
| 4.0087 | H | CH₃ | OCH₂CH₃ | CH₂CH₂ | Cl | |
| 4.0088 | H | CH₃ | OC(CH₃)₃ | CH₂CH₂ | Cl | |
| 4.0089 | H | CH₃ | OH | O | Cl | |
| 4.0090 | H | CH₃ | OCH₃ | O | Cl | |
| 4.0091 | H | CH₃ | OCH₂CH₃ | O | Cl | |
| 4.0092 | H | CH₃ | OC(CH₃)₃ | O | Cl | |
| 4.0093 | H | CH₃ | OH | NSO₂CH₃ | Cl | |
| 4.0094 | H | CH₃ | OCH₃ | NSO₂CH₃ | Cl | |
| 4.0095 | H | CH₃ | OCH₂CH₃ | NSO₂CH₃ | Cl | |
| 4.0096 | H | CH₃ | OC(CH₃)₃ | NSO₂CH₃ | Cl | |
| 4.0097 | H | CH₃ | OH | NC(O)C(CH₃)₃ | Cl | |
| 4.0098 | H | CH₃ | OCH₃ | NC(O)C(CH₃)₃ | Cl | |
| 4.0099 | H | CH₃ | OCH₂CH₃ | NC(O)C(CH₃)₃ | Cl | |
| 4.0100 | H | CH₃ | OC(CH₃)₃ | NC(O)C(CH₃)₃ | Cl | |
| 4.0101 | H | CH₃ | OH | CH₂ | Br | |
| 4.0102 | H | CH₃ | OCH₃ | CH₂ | Br | |
| 4.0103 | H | CH₃ | OCH₂CH₃ | CH₂ | Br | |
| 4.0104 | H | CH₃ | OC(CH₃)₃ | CH₂ | Br | |
| 4.0105 | H | CH₃ | OH | CH₂CH₂ | Br | |
| 4.0106 | H | CH₃ | OCH₃ | CH₂CH₂ | Br | |
| 4.0107 | H | CH₃ | OCH₂CH₃ | CH₂CH₂ | Br | |
| 4.0108 | H | CH₃ | OC(CH₃)₃ | CH₂CH₂ | Br | |
| 4.0109 | H | CH₃ | OH | O | Br | |
| 4.0110 | H | CH₃ | OCH₃ | O | Br | |
| 4.0111 | H | CH₃ | OCH₂CH₃ | O | Br | |
| 4.0112 | H | CH₃ | OC(CH₃)₃ | O | Br | |
| 4.0113 | H | CH₃ | OH | NSO₂CH₃ | Br | |
| 4.0114 | H | CH₃ | OCH₃ | NSO₂CH₃ | Br | |
| 4.0115 | H | CH₃ | OCH₂CH₃ | NSO₂CH₃ | Br | |
| 4.0116 | H | CH₃ | OC(CH₃)₃ | NSO₂CH₃ | Br | |
| 4.0117 | H | CH₃ | OH | NC(O)C(CH₃)₃ | Br | |
| 4.0118 | H | CH₃ | OCH₃ | NC(O)O(CH₃)₃ | Br | |
| 4.0119 | H | CH₃ | OCH₂CH₃ | NC(O)O(CH₃)₃ | Br | |
| 4.0120 | H | CH₃ | OC(CH₃)₃ | NC(O)C(CH₃)₃ | Br | |
| 4.0121 | CH₃ | CH₃ | OH | CH₂ | H | |
| 4.0122 | CH₃ | CH₃ | OCH₃ | CH₂ | H | |

TABLE 4-continued

Intermediates of formulae Da and Db:

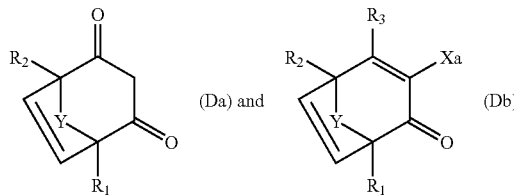

(Da) and (Db)

| No. | R₁ | R₂ | R₃ | Y | Xa | Physical data |
|---|---|---|---|---|---|---|
| 4.0123 | CH₃ | CH₃ | OCH₂CH₃ | CH₂ | H | |
| 4.0124 | CH₃ | CH₃ | OC(CH₃)₂ | CH₂ | H | |
| 4.0125 | CH₃ | CH₃ | OH | CH₂CH₂ | H | |
| 4.0126 | CH₃ | CH₃ | OCH₃ | CH₂CH₂ | H | |
| 4.0127 | CH₃ | CH₃ | OCH₂CH₃ | CH₂CH₂ | H | |
| 4.0128 | CH₃ | CH₃ | OC(CH₃)₂ | CH₂CH₂ | H | |
| 4.0129 | CH₃ | CH₃ | OH | O | H | |
| 4.0130 | CH₃ | CH₃ | OCH₃ | O | H | |
| 4.0131 | CH₃ | CH₃ | OCH₂CH₃ | O | H | |
| 4.0132 | CH₃ | CH₃ | OC(CH₃)₂ | O | H | |
| 4.0133 | CH₃ | CH₃ | OH | NSO₂CH₃ | H | |
| 4.0134 | CH₃ | CH₃ | OCH₃ | NSO₂CH₃ | H | |
| 4.0135 | CH₃ | CH₃ | OCH₂CH₃ | NSO₂CH₃ | H | |
| 4.0136 | CH₃ | CH₃ | OC(CH₃)₂ | NSO₂CH₃ | H | |
| 4.0137 | CH₃ | CH₃ | OH | NC(O)O(CH₃)₃ | H | |
| 4.0138 | CH₃ | CH₃ | OCH₃ | NC(O)C(CH₃)₃ | H | |
| 4.0139 | CH₃ | CH₃ | OCH₂CH₃ | NC(O)O(CH₃)₃ | H | |
| 4.0140 | CH₃ | CH₃ | OC(CH₃)₂ | NC(O)C(CH₃)₃ | H | |
| 4.0141 | CH₃ | CH₃ | OH | CH₂ | Cl | |
| 4.0142 | CH₃ | CH₃ | OCH₃ | CH₂ | Cl | see Preparation Example P3 |
| 4.0143 | CH₃ | CH₃ | OCH₂CH₃ | CH₂ | Cl | |
| 4.0144 | CH₃ | CH₃ | OC(CH₃)₂ | CH₂ | Cl | |
| 4.0145 | CH₃ | CH₃ | OH | CH₂CH₂ | Cl | |
| 4.0146 | CH₃ | CH₃ | OCH₃ | CH₂CH₂ | Cl | |
| 4.0147 | CH₃ | CH₃ | OCH₂CH₃ | CH₂CH₂ | Cl | |
| 4.0148 | CH₃ | CH₃ | OC(CH₃)₂ | CH₂CH₂ | Cl | |
| 4.0149 | CH₃ | CH₃ | OH | O | Cl | |
| 4.0150 | CH₃ | CH₃ | OCH₃ | O | Cl | |
| 4.0151 | CH₃ | CH₃ | OCH₂CH₃ | O | Cl | |
| 4.0152 | CH₃ | CH₃ | OC(CH₃)₂ | O | Cl | |
| 4.0153 | CH₃ | CH₃ | OH | NSO₂CH₃ | Cl | |
| 4.0154 | CH₃ | CH₃ | OCH₃ | NSO₂CH₃ | Cl | |
| 4.0155 | CH₃ | CH₃ | OCH₂CH₃ | NSO₂CH₃ | Cl | |
| 4.0156 | CH₃ | CH₃ | OC(CH₃)₂ | NSO₂CH₃ | Cl | |
| 4.0157 | CH₃ | CH₃ | OH | NO(O)O(CH₃)₃ | Cl | |
| 4.0158 | CH₃ | CH₃ | OCH₃ | NC(O)C(CH₃)₃ | Cl | |
| 4.0159 | CH₃ | CH₃ | OCH₂CH₃ | NC(O)C(CH₃)₃ | Cl | |
| 4.0160 | CH₃ | CH₃ | OC(CH₃)₂ | NC(O)C(CH₃)₃ | Cl | |
| 4.0161 | CH₃ | CH₃ | OH | CH₂ | Br | |
| 4.0162 | CH₃ | CH₃ | OCH₃ | CH₂ | Br | |
| 4.0163 | CH₃ | CH₃ | OCH₂CH₃ | CH₂ | Br | |
| 4.0164 | CH₃ | CH₃ | OC(CH₃)₂ | CH₂ | Br | |
| 4.0165 | CH₃ | CH₃ | OH | CH₂CH₂ | Br | |
| 4.0166 | CH₃ | CH₃ | OCH₃ | CH₂CH₂ | Br | |
| 4.0167 | CH₃ | CH₃ | OCH₂CH₃ | CH₂CH₂ | Br | |
| 4.0168 | CH₃ | CH₃ | OC(CH₃)₂ | CH₂CH₂ | Br | |
| 4.0169 | CH₃ | CH₃ | OH | O | Br | |
| 4.0170 | CH₃ | CH₃ | OCH₃ | O | Br | |
| 4.0171 | CH₃ | CH₃ | OCH₂CH₃ | O | Br | |
| 4.0172 | CH₃ | CH₃ | OC(CH₃)₂ | O | Br | see Preparation Example P6 |
| 4.0173 | CH₃ | CH₃ | OH | NSO₂CH₃ | Br | |
| 4.0174 | CH₃ | CH₃ | OCH₃ | NSO₂CH₃ | Br | |
| 4.0175 | CH₃ | CH₃ | OCH₂CH₃ | NSO₂CH₃ | Br | |
| 4.0176 | CH₃ | CH₃ | OC(CH₃)₂ | NSO₂CH₃ | Br | |
| 4.0177 | CH₃ | CH₃ | OH | NC(O)O(CH₃)₃ | Br | |
| 4.0178 | CH₃ | CH₃ | OCH₃ | NC(O)O(CH₃)₃ | Br | |
| 4.0179 | CH₃ | CH₃ | OCH₂CH₃ | NC(O)C(CH₃)₃ | Br | |
| 4.0180 | CH₃ | CH₃ | OC(CH₃)₂ | NC(O)C(CH₃)₃ | Br | |
| 4.0181 | H | H | OH | ⁱC▷ | H | ¹H NMR (300 MHz; CDCl₃) δ 6.30 (sxm, 2H); 3.60 (d, 1H); 3.23 (d, 1H); 2.82 (s, 1H); 0.75 (m, 4H); tautomeric form Db |

TABLE 4-continued

Intermediates of formulae Da and Db:

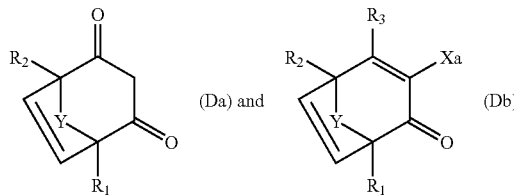

| No. | $R_1$ | $R_2$ | $R_3$ | Y | Xa | Physical data |
|---|---|---|---|---|---|---|
| 4.0182 | H | H | OH | C(=C(CH$_3$)$_2$) | H | $^1$H NMR (300 MHz; CDCl$_3$) δ 6.82 (sxm, 2H); 4.14 (sxm, 2H); 3.60 (d, 1H); 3.13 (d, 1H); 1.75 (s, 6H); tautomeric form Db |
| 4.0183 | H | H | OH | CH$_2$CH(COOCH$_3$) | H | R$_7$ = Br, see Preparation Example P13 |
| 4.0184 | H | H | OH | CH$_2$CH(COOCH$_3$) | H | R$_7$ = CH |

TABLE 5

Intermediates of formulae VII:

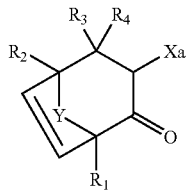

(VII)

| No. | $R_1$ | $R_2$ | $R_3$ | $R_4$ | Y | Xa | Physical data |
|---|---|---|---|---|---|---|---|
| 5.0000 | H | H | OCH$_3$ | OCH$_3$ | CH$_2$ | H | |
| 5.0001 | H | H | OCH$_2$CH$_3$ | OCH$_2$CH$_3$ | CH$_2$ | H | |
| 5.0002 | H | H | —OCH$_2$CH$_2$O— | | CH$_2$ | H | see Example P8 |
| 5.0003 | H | H | OCH$_3$ | OCH$_3$ | O | H | |
| 5.0004 | H | H | OCH$_2$CH$_3$ | OCH$_2$CH$_3$ | O | H | |
| 5.0005 | H | H | —OCH$_2$CH$_2$O— | | O | H | |
| 5.0006 | H | H | OCH$_3$ | OCH$_3$ | NSO$_2$CH$_3$ | H | |
| 5.0007 | H | H | OCH$_2$CH$_3$ | OCH$_2$CH$_3$ | NSO$_2$CH$_3$ | H | |
| 5.0008 | H | H | —OCH$_2$CH$_2$O— | | NSO$_2$CH$_3$ | H | |
| 5.0009 | H | H | OCH$_3$ | OCH$_3$ | NC(O)C(CH$_3$)$_3$ | H | |
| 5.0010 | H | H | OCH$_2$CH$_3$ | OCH$_2$CH$_3$ | NC(O)C(CH$_3$)$_3$ | H | |
| 5.0011 | H | H | —OCH$_2$CH$_2$O— | | NC(O)C(CH$_3$)$_3$ | H | |
| 5.0012 | H | H | OCH$_3$ | OCH$_3$ | CH$_2$CH$_2$ | H | |
| 5.0013 | H | H | OCH$_2$CH$_3$ | OCH$_2$CH$_3$ | CH$_2$CH$_2$ | H | |
| 5.0014 | H | H | —OCH$_2$CH$_2$O— | | CH$_2$CH$_2$ | H | |
| 5.0015 | H | H | OCH$_3$ | OCH$_3$ | CH$_2$ | Cl | |
| 5.0016 | H | H | OCH$_2$CH$_3$ | OCH$_2$CH$_3$ | CH$_2$ | Cl | |
| 5.0017 | H | H | —OCH$_2$CH$_2$O— | | CH$_2$ | Cl | |
| 5.0018 | H | H | OCH$_3$ | OCH$_3$ | O | Cl | |
| 5.0019 | H | H | OCH$_2$CH$_3$ | OCH$_2$CH$_3$ | O | Cl | |
| 5.0020 | H | H | —OCH$_2$CH$_2$O— | | O | Cl | |
| 5.0021 | H | H | OCH$_3$ | OCH$_3$ | NSO$_2$CH$_3$ | Cl | |
| 5.0022 | H | H | OCH$_2$CH$_3$ | OCH$_2$CH$_3$ | NSO$_2$CH$_3$ | Cl | |
| 5.0023 | H | H | —OCH$_2$CH$_2$O— | | NSO$_2$CH$_3$ | Cl | |
| 5.0024 | H | H | OCH$_3$ | OCH$_3$ | NC(O)C(CH$_3$)$_3$ | Cl | |
| 5.0025 | H | H | OCH$_2$CH$_3$ | OCH$_2$CH$_3$ | NC(O)C(CH$_3$)$_3$ | Cl | |
| 5.0026 | H | H | —OCH$_2$CH$_2$O— | | NC(O)C(CH$_3$)$_3$ | Cl | |
| 5.0027 | H | H | OCH$_3$ | OCH$_3$ | CH$_2$CH$_2$ | Cl | |
| 5.0028 | H | H | OCH$_2$CH$_3$ | OCH$_2$CH$_3$ | CH$_2$CH$_2$ | Cl | |
| 5.0029 | H | H | —OCH$_2$CH$_2$O— | | CH$_2$CH$_2$ | Cl | |
| 5.0030 | H | H | OCH$_3$ | OCH$_3$ | CH$_2$ | Br | |
| 5.0031 | H | H | OCH$_2$CH$_3$ | OCH$_2$CH$_3$ | CH$_2$ | Br | |
| 5.0032 | H | H | —OCH$_2$CH$_2$O— | | CH$_2$ | Br | |
| 5.0033 | H | H | OCH$_3$ | OCH$_3$ | O | Br | |
| 5.0034 | H | H | OCH$_2$CH$_3$ | OCH$_2$CH$_3$ | O | Br | |
| 5.0035 | H | H | —OCH$_2$CH$_2$O— | | O | Br | |
| 5.0036 | H | H | OCH$_3$ | OCH$_3$ | NSO$_2$CH$_3$ | Br | |
| 5.0037 | H | H | OCH$_2$CH$_3$ | OCH$_2$CH$_3$ | NSO$_2$CH$_3$ | Br | |

TABLE 5-continued

Intermediates of formulae VII:

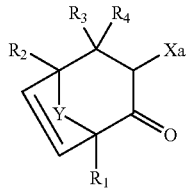

(VII)

| No. | $R_1$ | $R_2$ | $R_3$ | $R_4$ | Y | Xa | Physical data |
|---|---|---|---|---|---|---|---|
| 5.0038 | H | H | —OCH$_2$CH$_2$O— | | NSO$_2$CH$_3$ | Br | |
| 5.0039 | H | H | OCH$_3$ | OCH$_3$ | NC(O)C(CH$_3$)$_3$ | Br | |
| 5.0040 | H | H | OCH$_2$CH$_3$ | OCH$_2$CH$_3$ | NC(O)C(CH$_3$)$_3$ | Br | |
| 5.0041 | H | H | —OCH$_2$CH$_2$O— | | NC(O)C(CH$_3$)$_3$ | Br | |
| 5.0042 | H | H | OCH$_3$ | OCH$_3$ | CH$_2$CH$_2$ | Br | |
| 5.0043 | H | H | OCH$_2$CH$_3$ | OCH$_2$CH$_3$ | CH$_2$CH$_2$ | Br | |
| 5.0044 | H | H | —OCH$_2$CH$_2$O— | | CH$_2$CH$_2$ | Br | |
| 5.0045 | H | CH$_3$ | OCH$_3$ | OCH$_3$ | CH$_2$ | H | |
| 5.0046 | H | CH$_3$ | OCH$_2$CH$_3$ | OCH$_2$CH$_3$ | CH$_2$ | H | |
| 5.0047 | H | CH$_3$ | —OCH$_2$CH$_2$O— | | CH$_2$ | H | |
| 5.0048 | H | CH$_3$ | OCH$_3$ | OCH$_3$ | O | H | |
| 5.0049 | H | CH$_3$ | OCH$_2$CH$_3$ | OCH$_2$CH$_3$ | O | H | |
| 5.0050 | H | CH$_3$ | —OCH$_2$CH$_2$O— | | O | H | |
| 5.0051 | H | CH$_3$ | OCH$_3$ | OCH$_3$ | NSO$_2$CH$_3$ | H | |
| 5.0052 | H | CH$_3$ | OCH$_2$CH$_3$ | OCH$_2$CH$_3$ | NSO$_2$CH$_3$ | H | |
| 5.0053 | H | CH$_3$ | —OCH$_2$CH$_2$O— | | NSO$_2$CH$_3$ | H | |
| 5.0054 | H | CH$_3$ | OCH$_3$ | OCH$_3$ | NC(O)O(CH$_3$)$_3$ | H | |
| 5.0055 | H | CH$_3$ | OCH$_2$CH$_3$ | OCH$_2$CH$_3$ | NC(O)C(CH$_3$)$_3$ | H | |
| 5.0056 | H | CH$_3$ | —OCH$_2$CH$_2$O— | | NC(O)C(CH$_3$)$_3$ | H | |
| 5.0057 | H | CH$_3$ | OCH$_3$ | OCH$_3$ | CH$_2$CH$_2$ | H | |
| 5.0058 | H | CH$_3$ | OCH$_2$CH$_3$ | OCH$_2$CH$_3$ | CH$_2$CH$_2$ | H | |
| 5.0059 | H | CH$_3$ | —OCH$_2$CH$_2$O— | | CH$_2$CH$_2$ | H | |
| 5.0060 | H | CH$_3$ | OCH$_3$ | OCH$_3$ | CH$_2$ | Cl | |
| 5.0061 | H | CH$_3$ | OCH$_2$CH$_3$ | OCH$_2$CH$_3$ | CH$_2$ | Cl | |
| 5.0062 | H | CH$_3$ | —OCH$_2$CH$_2$O— | | CH$_2$ | Cl | |
| 5.0063 | H | CH$_3$ | OCH$_3$ | OCH$_3$ | O | Cl | |
| 5.0064 | H | CH$_3$ | OCH$_2$CH$_3$ | OCH$_2$CH$_3$ | O | Cl | |
| 5.0065 | H | CH$_3$ | —OCH$_2$CH$_2$O— | | O | Cl | |
| 5.0066 | H | CH$_3$ | OCH$_3$ | OCH$_3$ | NSO$_2$CH$_3$ | Cl | |
| 5.0067 | H | CH$_3$ | OCH$_2$CH$_3$ | OCH$_2$CH$_3$ | NSO$_2$CH$_3$ | Cl | |
| 5.0068 | H | CH$_3$ | —OCH$_2$CH$_2$O— | | NSO$_2$CH$_3$ | Cl | |
| 5.0069 | H | CH$_3$ | OCH$_3$ | OCH$_3$ | NC(O)C(CH$_3$)$_3$ | Cl | |
| 5.0070 | H | CH$_3$ | OCH$_2$CH$_3$ | OCH$_2$CH$_3$ | NC(O)C(CH$_3$)$_3$ | Cl | |
| 5.0071 | H | CH$_3$ | —OCH$_2$CH$_2$O— | | NC(O)C(CH$_3$)$_3$ | Cl | |
| 5.0072 | H | CH$_3$ | OCH$_3$ | OCH$_3$ | CH$_2$CH$_2$ | Cl | |
| 5.0073 | H | CH$_3$ | OCH$_2$CH$_3$ | OCH$_2$CH$_3$ | CH$_2$CH$_2$ | Cl | |
| 5.0074 | H | CH$_3$ | —OCH$_2$CH$_2$O— | | CH$_2$CH$_2$ | Cl | |
| 5.0075 | H | CH$_3$ | OCH$_3$ | OCH$_3$ | CH$_2$ | Br | |
| 5.0076 | H | CH$_3$ | OCH$_2$CH$_3$ | OCH$_2$CH$_3$ | CH$_2$ | Br | |
| 5.0077 | H | CH$_3$ | —OCH$_2$CH$_2$O— | | CH$_2$ | Br | |
| 5.0078 | H | CH$_3$ | OCH$_3$ | OCH$_3$ | O | Br | |
| 5.0079 | H | CH$_3$ | OCH$_2$CH$_3$ | OCH$_2$CH$_3$ | O | Br | |
| 5.0080 | H | CH$_3$ | —OCH$_2$CH$_2$O— | | O | Br | |
| 5.0081 | H | CH$_3$ | OCH$_3$ | OCH$_3$ | NSO$_2$CH$_3$ | Br | |
| 5.0082 | H | CH$_3$ | OCH$_2$CH$_3$ | OCH$_2$CH$_3$ | NSO$_2$CH$_3$ | Br | |
| 5.0083 | H | CH$_3$ | —OCH$_2$CH$_2$O— | | NSO$_2$CH$_3$ | Br | |
| 5.0084 | H | CH$_3$ | OCH$_3$ | OCH$_3$ | NC(O)O(CH$_3$)$_3$ | Br | |
| 5.0085 | H | CH$_3$ | OCH$_2$CH$_3$ | OCH$_2$CH$_3$ | NC(O)C(CH$_3$)$_3$ | Br | |
| 5.0086 | H | CH$_3$ | —OCH$_2$CH$_2$O— | | NC(O)O(CH$_3$)$_3$ | Br | |
| 5.0087 | H | CH$_3$ | OCH$_3$ | OCH$_3$ | CH$_2$CH$_2$ | Br | |
| 5.0088 | H | CH$_3$ | OCH$_2$CH$_3$ | OCH$_2$CH$_3$ | CH$_2$CH$_2$ | Br | |
| 5.0089 | H | CH$_3$ | —OCH$_2$CH$_2$O— | | CH$_2$CH$_2$ | Br | |
| 5.0090 | CH$_3$ | CH$_3$ | OCH$_3$ | OCH$_3$ | CH$_2$ | H | |
| 5.0091 | CH$_3$ | CH$_3$ | OCH$_2$CH$_3$ | OCH$_2$CH$_3$ | CH$_2$ | H | |
| 5.0092 | CH$_3$ | CH$_3$ | —OCH$_2$CH$_2$O— | | CH$_2$ | H | |
| 5.0093 | CH$_3$ | CH$_3$ | OCH$_3$ | OCH$_3$ | O | H | see Example P5 |
| 5.0094 | CH$_3$ | CH$_3$ | OCH$_2$CH$_3$ | OCH$_2$CH$_3$ | O | H | |
| 5.0095 | CH$_3$ | CH$_3$ | —OCH$_2$CH$_2$O— | | O | H | |

TABLE 5-continued

Intermediates of formulae VII:

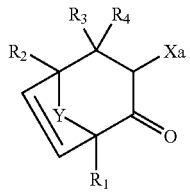

(VII)

| No. | $R_1$ | $R_2$ | $R_3$ | $R_4$ | Y | Xa | Physical data |
|---|---|---|---|---|---|---|---|
| 5.0096 | $CH_3$ | $CH_3$ | $OCH_3$ | $OCH_3$ | $NSO_2CH_3$ | H | |
| 5.0097 | $CH_3$ | $CH_3$ | $OCH_2CH_3$ | $OCH_2CH_3$ | $NSO_2CH_3$ | H | |
| 5.0098 | $CH_3$ | $CH_3$ | —$OCH_2CH_2O$— | | $NSO_2CH_3$ | H | |
| 5.0099 | $CH_3$ | $CH_3$ | $OCH_3$ | $OCH_3$ | $NC(O)O(CH_3)_3$ | H | |
| 5.0100 | $CH_3$ | $CH_3$ | $OCH_2CH_3$ | $OCH_2CH_3$ | $NC(O)O(CH_3)_3$ | H | |
| 5.0101 | $CH_3$ | $CH_3$ | —$OCH_2CH_2O$— | | $NC(O)O(CH_3)_3$ | H | |
| 5.0102 | $CH_3$ | $CH_3$ | $OCH_3$ | $OCH_3$ | $CH_2CH_2$ | H | |
| 5.0103 | $CH_3$ | $CH_3$ | $OCH_2CH_3$ | $OCH_2CH_3$ | $CH_2CH_2$ | H | |
| 5.0104 | $CH_3$ | $CH_3$ | —$OCH_2CH_2O$— | | $CH_2CH_2$ | H | |
| 5.0105 | $CH_3$ | $CH_3$ | $OCH_3$ | $OCH_3$ | $CH_2$ | Cl | |
| 5.0106 | $CH_3$ | $CH_3$ | $OCH_2CH_3$ | $OCH_2CH_3$ | $CH_2$ | Cl | |
| 5.0107 | $CH_3$ | $CH_3$ | —$OCH_2CH_2O$— | | $CH_2$ | Cl | |
| 5.0108 | $CH_3$ | $CH_3$ | $OCH_3$ | $OCH_3$ | O | Cl | see Example P3 |
| 5.0109 | $CH_3$ | $CH_3$ | $OCH_2CH_3$ | $OCH_2CH_3$ | O | Cl | |
| 5.0110 | $CH_3$ | $CH_3$ | —$OCH_2CH_2O$— | | O | Cl | |
| 5.0111 | $CH_3$ | $CH_3$ | $OCH_3$ | $OCH_3$ | $NSO_2CH_3$ | Cl | |
| 5.0112 | $CH_3$ | $CH_3$ | $OCH_2CH_3$ | $OCH_2CH_3$ | $NSO_2CH_3$ | Cl | |
| 5.0113 | $CH_3$ | $CH_3$ | —$OCH_2CH_2O$— | | $NSO_2CH_3$ | Cl | |
| 5.0114 | $CH_3$ | $CH_3$ | $OCH_3$ | $OCH_3$ | $NC(O)O(CH_3)_3$ | Cl | |
| 5.0115 | $CH_3$ | $CH_3$ | $OCH_2CH_3$ | $OCH_2CH_3$ | $NC(O)O(CH_3)_3$ | Cl | |
| 5.0116 | $CH_3$ | $CH_3$ | —$OCH_2CH_2O$— | | $NC(O)O(CH_3)_3$ | Cl | |
| 5.0117 | $CH_3$ | $CH_3$ | $OCH_3$ | $OCH_3$ | $CH_2CH_2$ | Cl | |
| 5.0118 | $CH_3$ | $CH_3$ | $OCH_2CH_3$ | $OCH_2CH_3$ | $CH_2CH_2$ | Cl | |
| 5.0119 | $CH_3$ | $CH_3$ | —$OCH_2CH_2O$— | | $CH_2CH_2$ | Cl | |
| 5.0120 | $CH_3$ | $CH_3$ | $OCH_3$ | $OCH_3$ | $CH_2$ | Br | |
| 5.0121 | $CH_3$ | $CH_3$ | $OCH_2CH_3$ | $OCH_2CH_3$ | $CH_2$ | Br | |
| 5.0122 | $CH_3$ | $CH_3$ | —$OCH_2CH_2O$— | | $CH_2$ | Br | |

TABLE 5-continued

Intermediates of formulae VII:

(VII)

| No. | R₁ | R₂ | R₃ | R₄ | Y | Xa | Physical data |
|---|---|---|---|---|---|---|---|
| 5.0123 | CH₃ | CH₃ | OCH₃ | OCH₃ | O | Br | |
| 5.0124 | CH₃ | CH₃ | OCH₂CH₃ | OCH₂CH₃ | O | Br | |
| 5.0125 | CH₃ | CH₃ | —OCH₂CH₂O— | | O | Br | |
| 5.0126 | CH₃ | CH₃ | OCH₃ | OCH₃ | NSO₂CH₃ | Br | |
| 5.0127 | CH₃ | CH₃ | OCH₂CH₃ | OCH₂CH₃ | NSO₂CH₃ | Br | |
| 5.0128 | CH₃ | CH₃ | —OCH₂CH₂O— | | NSO₂CH₃ | Br | |
| 5.0129 | CH₃ | CH₃ | OCH₃ | OCH₃ | NC(O)C(CH₃)₃ | Br | |
| 5.0130 | CH₃ | CH₃ | OCH₂CH₃ | OCH₂CH₃ | NC(O)O(CH₃)₃ | Br | |
| 5.0131 | CH₃ | CH₃ | —OCH₂CH₂O— | | NC(O)C(CH₃)₃ | Br | |
| 5.0132 | CH₃ | CH₃ | OCH₃ | OCH₃ | CH₂CH₂ | Br | |
| 5.0133 | CH₃ | CH₃ | OCH₂CH₃ | OCH₂CH₃ | CH₂CH₂ | Br | |
| 5.0134 | CH₃ | CH₃ | —OCH₂CH₂O— | | CH₂CH₂ | Br | |
| 5.0135 | H | H | —OCH₂CH₂O— | | ′C⊲ | Cl | Amorphous crystals |

TABLE 6

Intermediates of formula VI:

(VI)

| No. | A₁ | A₂ | R₁ | R₂ | Y | Xa | Physical data |
|---|---|---|---|---|---|---|---|
| 6.0000 | CH | CH | H | H | C(=CH(OAc)) | Cl | major isomer I: ¹H NMR (300 MHz: CDCl₃) δ 7.12 (s, 1H); 6.77 (dxd, 1H); 6.35 (dxd, 1H); 4.02 (d, 1H); 3.95 (d, 1H); 2.18 (s, 3H). |
| 6.0001 | CH | CH | H | H | C(=CH(OAc)) | Cl | minor isomer II: ¹H NMR (300 MHz; CDCl₃) δ 7.14 (s, 1H); 6.84 (dxd, 1H); 6.29 (dxd, 1H); 4.55 (d, 1H); 3.54 (d, 1H); 2.19 (s, 3H). |

BIOLOGICAL EXAMPLES

Example B1

Herbicidal Action Prior to Emergence of the Plants (Pre-Emergence Action)

Monocotyledonous and dicotyledonous test plants are sown in standard soil in plastic pots. Immediately after sowing, the test compounds, in the form of an aqueous suspension (prepared from a 25% wettable powder (Example F3, b) according to WO 97/34485) or in the form of an emulsion (prepared from a 25% emulsifiable concentrate (Example F1, c)), are applied by spraying in a concentration corresponding to 125 g or 250 g of active ingredient/ha (500 liters of water/ha). The test plants are then grown in a greenhouse under optimum conditions. After a test duration of 3 weeks, the test is evaluated in accordance with a scale of ten ratings (10=total damage, 0=no action). Ratings of from 10 to 6 (especially from 10 to 8) indicate good to very good herbicidal action. The compounds of formula I exhibit strong herbicidal action in this test. Examples of the good herbicidal action of the compounds are given in Table B1:

TABLE B1

| | | Pre-emergence herbicidal action: | | | | | |
|---|---|---|---|---|---|---|---|
| Ex. No. | gr/ha | Panicum | Echinochloa | Abutilon | Amaranthus | Chenopodium | Kochia |
| 1.0301 | 250 | 7 | 7 | 7 | 8 | 9 | 8 |
| 1.0411 | 250 | 10 | 9 | 10 | 10 | 10 | 10 |

Example B2

Post-Emergence Herbicidal Action

In a greenhouse, monocotyledonous and dicotyledonous test plants are grown in standard soil in plastic pots and at the 4- to 6-leaf stage are sprayed with an aqueous suspension of the test compounds of formula I prepared from a 25% wettable powder (Example F3, b) according to WO 97/34485) or with an emulsion of the test compounds of formula I prepared from a 25% emulsifiable concentrate (Example F1, c) according to WO 97/34485), in a concentration corresponding to 125 g or 250 g of active ingredient/ha (500 liters of water/ha). The test plants are then grown on in a greenhouse under optimum conditions. After a test duration of about 18 days, the test is evaluated in accordance with a scale of ten ratings (10=total damage, 0=no action). Ratings of from 10 to 6 (especially from 10 to 7) indicate good to very good herbicidal action. The compounds of formula I exhibit a strong herbicidal action in this test. Examples of the good herbicidal action of the compounds are given in Table B2:

TABLE B2

| | | Post-emergence herbicidal action: | | | | | |
|---|---|---|---|---|---|---|---|
| Ex. No. | gr/ha | Abutilon | Ipomea | Amaranthus | Chenopodium | Stellaria | Abutilon |
| 1.0301 | 250 | 9 | 8 | 8 | 8 | 8 | 8 |
| 1.0411 | 250 | 9 | 10 | 9 | 10 | 9 | 9 |
| 1.1153 | 250 | 7 | 8 | 7 | 8 | 10 | 8 |

Example B3

Comparison Test with a Compound from the Prior Art: Post-Emergence Herbicidal Action The post-emergence herbicidal action of compound No. 1.0411 according to the invention is compared with compound "A" from WO 01/94339:

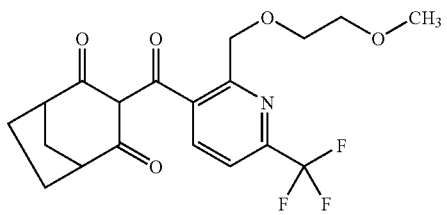

Compound "A" from WO 01/94339

-continued

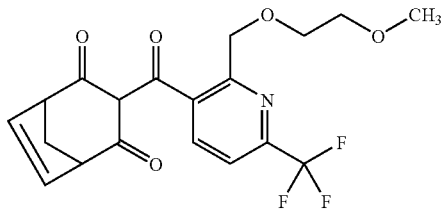

Compound 1.0411 according to the present invention

TABLE B3

| | | Post-emergence action: | | | | | |
|---|---|---|---|---|---|---|---|
| Ex. No. | gr/ha | Brachiaria | Rottboelia | Sida | Polygonum | Sinapis | Galium |
| 1.0411 | 15 | 10 | 3 | 8 | 8 | 8 | 6 |
| A | 15 | 4 | 0 | 7 | 5 | 6 | 5 |

It can be seen from Table B3 that compound No. 1.0411 according to the invention at a rate of application of 15 g/ha exhibits considerably better herbicidal action on the weeds than compound "A" from the prior art. This enhanced action was not to be expected in view of the structural similarity of the compounds.

What is claimed is:
1. A compound of formula I

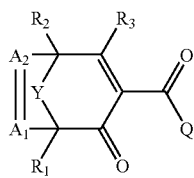

wherein

Y is oxygen, $NR_{4a}$, sulfur, sulfonyl, sulfinyl, C(O), C($=NR_{4b}$), C($=CR_{6a}R_{6b}$) or a $C_1$-$C_4$alkylene or $C_2$-$C_4$alkenylene chain, which may be interrupted by oxygen, $NR_{5a}$, sulfur, sulfonyl, sulfinyl, C(O) or C($=NR_{5b}$) and/or mono- or poly-substituted by $R_6$;

$A_1$ is nitrogen or $CR_7$;

$A_2$ is nitrogen or $CR_8$;

$R_1$, $R_2$, $R_6$, $R_7$ and $R_8$ are each independently of the others hydrogen, hydroxy, mercapto, $NO_2$, cyano, halogen, formyl, oxyiminomethylene, $C_1$-$C_6$alkoxyiminomethylene, $C_1$-$C_6$alkyl, $C_1$-$C_6$haloalkyl, $C_2$-$C_6$alkenyl, $C_2$-$C_6$haloalkenyl, $C_2$-$C_6$alkynyl, $C_2$-$C_6$haloalkynyl, $C_1$-$C_6$alkoxy, $C_1$-$C_6$haloalkoxy, $C_3$-$C_6$alkenyloxy, $C_3$-$C_6$alkynyloxy, $C_3$-$C_6$oxacycloalkyl, $C_3$-$C_6$thiacycloalkyl, $C_3$-$C_6$dioxacycloalkyl, $C_3$-$C_6$dithiacycloalkyl, $C_3$-$C_6$oxathiacycloalkyl, $C_1$-$C_6$alkoxycarbonyl, $C_1$-$C_6$alkylcarbonyl, $C_1$-$C_6$alkoxycarbonyloxy, $C_1$-$C_6$alkylcarbonyloxy, $C_1$-$C_6$alkylthio, $C_1$-$C_6$-alkylsulfonyl, $C_1$-$C_6$alkylsulfinyl, $NR_9R_{10}$, $C_3$-$C_6$cycloalkyl, tri($C_1$-$C_6$alkyl)silyl, di($C_1$-$C_6$alkyl)-phenylsilyl, tri($C_1$-$C_6$alkyl)silyloxy, di($C_1$-$C_6$alkyl)phenylsilyloxy or $Ar_1$;

or $R_1$, $R_2$, $R_6$, $R_7$, $R_8$ are each independently of the others a $C_1$-$C_6$alkyl, $C_2$-$C_6$alkenyl, $C_2$-$C_6$alkynyl or $C_3$-$C_6$cycloalkyl group, which may be interrupted by oxygen, sulfur, sulfonyl, sulfinyl, —$NR_{11}$— or —C(O)— and/or mono-, di- or tri-substituted by hydroxy, mercapto, $NO_2$, cyano, halogen, formyl, $C_1$-$C_6$alkoxy, $C_3$-$C_6$alkenyloxy, $C_3$-$C_6$alkynyloxy, $C_1$-$C_6$haloalkoxy, $C_1$-$C_2$alkoxy-$C_1$-$C_2$alkoxy, $C_1$-$C_4$alkoxycarbonyloxy, $C_1$-$C_4$alkylcarbonyloxy, $C_1$-$C_4$alkoxycarbonyl, $C_1$-$C_4$alkylcarbonyl, $C_1$-$C_6$alkylthio, $C_1$-$C_6$alkylsulfinyl, $C_1$-$C_6$alkylsulfonyl, $NR_{12}R_{13}$, $C_1$-$C_6$alkyl, $C_2$-$C_6$alkenyl, $C_2$-$C_6$alkynyl, $C_3$-$C_6$cycloalkyl, tri($C_1$-$C_6$alkyl)silyl, tri($C_1$-$C_6$alkyl)silyloxy or $Ar_2$;

or two substituents $R_6$ at the same carbon atom together form a —$CH_2O$— or a $C_2$-$C_5$alkylene chain, which may be interrupted once or twice by oxygen, sulfur, sulfinyl or sulfonyl and/or mono- or poly-substituted by $R_{6c}$, with the proviso that two hetero atoms may not be located next to one another;

or two substituents $R_6$ at different carbon atoms together form an oxygen bridge or a $C_1$-$C_4$alkylene chain, which may in turn be substituted by $R_{6c}$;

or $R_7$ and $R_8$ together form a —$CH_2CH=CH$—, —$OCH=CH$— or —$CH=CH$—$CH=CH$— bridge or a $C_3$-$C_4$alkylene chain, which may be interrupted by oxygen or —$S(O)_{n1}$— and/or mono- or poly-substituted by $R_{6d}$;

$R_3$ is hydroxy, halogen, mercapto, $C_1$-$C_8$alkylthio, $C_1$-$C_8$alkylsulfinyl, $C_1$-$C_8$alkylsulfonyl, $C_1$-$C_8$haloalkylthio, $C_1$-$C_8$haloalkylsulfinyl, $C_1$-$C_8$haloalkylsulfonyl, $C_1$-$C_4$alkoxy-$C_1$-$C_4$alkylthio, $C_1$-$C_4$alkoxy-$C_1$-$C_4$alkylsulfinyl, $C_1$-$C_4$alkoxy-$C_1$-$C_4$alkylsulfonyl, $C_3$-$C_8$alkenylthio, $C_3$-$C_8$-alkynylthio, $C_1$-$C_4$alkylthio-$C_1$-$C_4$alkylthio, $C_3$-$C_4$alkenylthio-$C_1$-$C_4$alkylthio, $C_1$-$C_4$alkoxycarbonyl-$C_1$-$C_4$alkylthio, $C_1$-$C_4$alkoxycarbonyl-$C_1$-$C_4$alkylsulfinyl, $C_1$-$C_4$alkoxycarbonyl-$C_1$-$C_4$alkylsulfonyl, $C_3$-$C_8$cycloalkylthio, $C_3$-$C_8$cycloalkylsulfinyl, $C_3$-$C_8$cycloalkylsulfonyl, phenyl-$C_1$-$C_4$alkylthio, phenyl-$C_1$-$C_4$alkylsulfinyl, phenyl-$C_1$-$C_4$alkylsulfonyl, $S(O)n_1$—$Ar_3$, phenylthio, phenylsulfinyl, phenylsulfonyl, it being possible for the phenyl-containing groups to be substituted by one or more $C_1$-$C_3$alkyl, $C_1$-$C_3$haloalkyl, $C_1$-$C_3$alkoxy, $C_1$-$C_3$haloalkoxy, $C_1$-$C_4$alkoxycarbonyl, halogen, cyano, hydroxy or nitro groups;

or $R_3$ is $O^-M^+$, wherein $M^+$ is an alkali metal cation or an ammonium cation;

Q is a radical

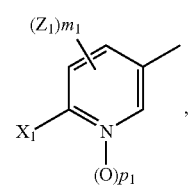

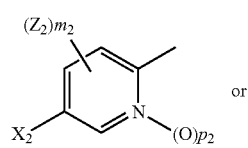

or

-continued

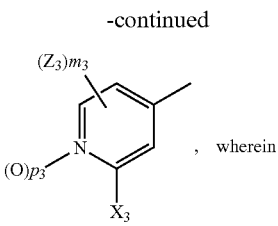

(Q₃)

, wherein $p_1$, $p_2$ and $p_3$ are 0 or 1;
$m_1$, $m_2$ and $m_3$ are 1, 2 or 3;
$X_1$, $X_2$ and $X_3$ are hydroxy, halogen, $C_1$-$C_6$alkyl, $C_1$-$C_6$haloalkyl, $C_2$-$C_6$alkenyl, $C_2$-$C_6$haloalkenyl, $C_2$-$C_6$alkynyl, $C_2$-$C_6$haloalkynyl, $C_1$-$C_6$alkoxy, $C_1$-$C_6$haloalkoxy, $C_1$-$C_6$alkylthio, $C_1$-$C_6$alkylsulfinyl, $C_1$-$C_6$alkylsulfonyl, $C_1$-$C_6$haloalkylthio, $C_1$-$C_6$haloalkylsulfinyl or $C_1$-$C_6$haloalkylsulfonyl;
$Z_1$, $Z_2$ and $Z_3$ are $C_1$-$C_6$alkyl which is substituted by the following substituents: $C_3$-$C_4$cycloalkyl or $C_3$-$C_4$cycloalkyl substituted by halogen, $C_1$-$C_6$alkyl, $C_1$-$C_3$alkoxy or $C_1$-$C_3$alkoxy-$C_1$-$C_3$alkyl; oxiranyl or oxiranyl substituted by $C_1$-$C_6$alkyl or $C_1$-$C_3$alkoxy-$C_1$-$C_3$alkyl; 3-oxetanyl or 3-oxetanyl substituted by $C_1$-$C_6$alkyl, $C_1$-$C_3$alkoxy or $C_1$-$C_3$alkoxy-$C_1$-$C_3$alkyl; 3-oxetanyloxy or 3-oxetanyloxy substituted by $C_1$-$C_6$alkyl, $C_1$-$C_3$alkoxy or $C_1$-$C_3$alkoxy-$C_1$-$C_3$-alkyl; $C_3$-$C_6$cycloalkyloxy or $C_3$-$C_4$cycloalkyloxy substituted by halogen, $C_1$-$C_6$alkyl, $C_1$-$C_3$-alkoxy or $C_1$-$C_3$alkoxy-$C_1$-$C_3$alkyl; $C_1$-$C_6$haloalkoxy; $C_1$-$C_6$alkylsulfonyloxy; $C_1$-$C_6$haloalkylsulfonyloxy; phenylsulfonyloxy; benzylsulfonyloxy, benzoyloxy; phenoxy; phenylthio; phenyl-sulfinyl; phenylsulfonyl; $Ar_{10}$; $OAr_{12}$; tri($C_1$-$C_6$alkyl)silyl or tri($C_1$-$C_6$alkyl)silyloxy, it being possible for the phenyl-containing groups to be mono- or poly-substituted by $C_1$-$C_3$alkyl, $C_1$-$C_3$haloalkyl, $C_1$-$C_3$alkoxy, $C_1$-$C_3$haloalkoxy, halogen, cyano, hydroxy or nitro;
or $Z_1$, $Z_2$ and $Z_3$ are 3-oxetanyl; 3-oxetanyl substituted by $C_1$-$C_3$alkoxy, $C_1$-$C_3$alkoxy-$C_1$-$C_3$alkyl or $C_1$-$C_6$alkyl; $C_3$-$C_6$cycloalkyl substituted by halogen, $C_1$-$C_3$alkyl or $C_1$-$C_3$alkoxy-$C_1$-$C_3$alkyl; tri($C_1$-$C_6$alkyl)silyl; tri($C_1$-$C_6$alkyl)silyloxy or CH=P(phenyl)$_3$;
or $Z_1$, $Z_2$ and $Z_3$ are a $C_1$-$C_6$alkyl, $C_2$-$C_6$alkenyl or $C_2$-$C_6$alkynyl group, which is interrupted by oxygen, —O(CO)—, —(CO)O—, —O(CO)O—, —N($R_{14}$)O—, —ON$R_{15}$—, sulfur, sulfinyl, sulfonyl,— SO$_2$NR$_{16}$—, —NR$_{17}$SO$_2$— or —NR$_{18}$— and is mono- or poly-substituted by $L_1$; it also being possible for $L_1$ to be bonded at the terminal carbon atom of the $C_1$-$C_6$alkyl, $C_2$-$C_6$alkenyl or $C_2$-$C_6$alkynyl group;
or $Z_1$, $Z_2$ and $Z_3$ are hydrogen, hydroxy, mercapto, NO$_2$, cyano, halogen, formyl, $C_1$-$C_6$alkyl, $C_1$-$C_6$haloalkyl, $C_2$-$C_6$alkenyl, $C_2$-$C_6$haloalkenyl, $C_2$-$C_6$alkynyl, $C_2$-$C_6$haloalkynyl, $C_1$-$C_6$alkoxy, $C_1$-$C_6$haloalkoxy, $C_1$-$C_6$alkoxycarbonyl, $C_1$-$C_6$alkylcarbonyl, $C_1$-$C_6$alkylthio, $C_1$-$C_6$alkylsulfonyl, $C_1$-$C_6$alkylsulfinyl, NR$_{22}$R$_{23}$, phenyl which may be mono- or poly-substituted by $C_1$-$C_3$alkyl, $C_1$-$C_3$haloalkyl, $C_1$-$C_3$alkoxy, $C_1$-$C_3$haloalkoxy, halogen, cyano, hydroxy or nitro, $C_3$-$C_6$cycloalkyl, $C_5$-$C_6$cycloalkyl substituted by $C_1$-$C_3$alkoxy, $C_1$-$C_3$alkoxy-$C_1$-$C_3$alkyl or $C_1$-$C_6$alkyl, or Ar$_5$, O—Ar$_6$, N(R$_{24}$)Ar$_7$ or S(O)n$_6$Ar$_8$;
$L_1$ is hydrogen, halogen, hydroxy, amino, formyl, nitro, cyano, mercapto, carbamoyl, P(O)(OC$_1$—C$_6$alkyl)$_2$, $C_1$-$C_6$alkoxy, $C_1$-$C_6$haloalkoxy, $C_1$-$C_6$alkoxycarbonyl, $C_2$-$C_6$alkenyl, $C_2$-$C_6$haloalkenyl, $C_2$-$C_6$alkynyl, $C_2$-$C_6$haloalkynyl, $C_3$-$C_6$cycloalkyl, halo-substituted $C_3$-$C_6$cycloalkyl, $C_3$-$C_6$alkenyloxy, $C_3$-$C_6$alkynyloxy, $C_3$-$C_6$haloalkenyloxy, cyano-$C_1$-$C_6$alkoxy, $C_1$-$C_6$alkoxy-$C_1$-$C_6$alkoxy, $C_1$-$C_6$alkylthio-$C_1$-$C_6$alkoxy, $C_1$-$C_6$alkylsulfinyl-$C_1$-$C_6$alkoxy, $C_1$-$C_6$-alkylsulfonyl-$C_1$-$C_6$alkoxy, $C_1$-$C_6$alkoxycarbonyl-$C_1$-$C_6$alkoxy, $C_1$-$C_6$alkylcarbonyloxy-$C_1$-$C_6$-alkylcarbonyl, $C_1$-$C_6$alkylthio, $C_1$-$C_6$alkylsulfinyl, $C_1$-$C_6$alkylsulfonyl, $C_1$-$C_6$haloalkylthio, $C_1$-$C_6$haloalkylsulfinyl, $C_1$-$C_6$haloalkylsulfonyl or oxiranyl, which may in turn be substituted by $C_1$-$C_6$alkyl, $C_1$-$C_3$alkoxy or $C_1$-$C_3$alkoxy-$C_1$-$C_3$alkyl, or (3-oxetanyl)-oxy, which may in turn be substituted by $C_1$-$C_6$alkyl, $C_1$-$C_3$alkoxy or $C_1$-$C_3$alkoxy-$C_1$-$C_3$alkyl, or benzoyloxy, benzyloxy, benzylthio, benzylsulfinyl, benzylsulfonyl, $C_1$-$C_6$alkylamino, di($C_1$-$C_6$alkyl)amino, R$_{19}$S(O)$_2$O—, R$_{20}$N(R$_{21}$)SO$_2$—, rhodano, phenyl, phenoxy, phenylthio, phenylsulfinyl, phenylsulfonyl, Ar$_4$ or OAr$_{11}$, it being possible for the phenyl-containing groups in turn to be substituted by one or more $C_1$-$C_3$alkyl, $C_1$-$C_3$haloalkyl, $C_1$-$C_3$alkoxy, $C_1$-$C_3$haloalkoxy, halogen, cyano, hydroxy or nitro groups;
R$_{4a}$ and R$_{5a}$ are each independently of the other hydrogen, $C_1$-$C_6$alkyl, $C_1$-$C_6$haloalkyl, cyano, formyl, $C_1$-$C_6$alkylcarbonyl, $C_1$-$C_6$alkoxycarbonyl, carbamoyl, $C_1$-$C_6$alkylaminocarbonyl, di($C_1$-$C_6$alkylamino)carbonyl, di($C_1$-$C_6$alkylamino)sulfonyl, $C_3$-$C_6$cycloalkylcarbonyl, $C_1$-$C_6$-alkylsulfonyl, phenylcarbonyl, phenylaminocarbonyl or phenylsulfonyl, it being possible for the phenyl groups to be mono- or poly-substituted by $C_1$-$C_6$alkyl, $C_1$-$C_6$haloalkyl, $C_1$-$C_6$alkoxy, $C_1$-$C_6$haloalkoxy, halogen, cyano, hydroxy or nitro;
R$_{4b}$ and R$_{5b}$ are each independently of the other hydroxy, $C_1$-$C_6$alkoxy, $C_3$-$C_6$alkenyloxy, $C_3$-$C_6$alkynyloxy or benzyloxy, it being possible for the benzyl group to be mono- or poly-substituted by $C_1$-$C_6$alkyl, $C_1$-$C_6$haloalkyl, $C_1$-$C_6$alkoxy, $C_1$-$C_6$haloalkoxy, halogen, cyano, hydroxy or nitro;
R$_9$, R$_{11}$, R$_{13}$, R$_{16}$, R$_{17}$, R$_{18}$, R$_{20}$, R$_{23}$ and R$_{24}$ are each independently of the others hydrogen, $C_1$-$C_6$alkyl, Ar$_9$, $C_1$-$C_6$haloalkyl, $C_1$-$C_6$alkylcarbonyl, $C_1$-$C_6$alkoxycarbonyl, $C_1$-$C_6$alkylsulfonyl, phenyl, it being possible for the phenyl group in turn to be mono- or poly-substituted by $C_1$-$C_6$alkyl, $C_1$-$C_6$haloalkyl, $C_1$-$C_6$alkoxy, $C_1$-$C_6$haloalkoxy, halogen, cyano, hydroxy or nitro;
R$_{6a}$ is hydrogen, $C_1$-$C_6$alkyl or $C_1$-$C_6$alkylcarbonyl; or together with R$_{6b}$ is a $C_2$-$C_5$alkylene chain;
R$_{6b}$, R$_{6d}$, R$_{10}$, R$_{12}$ and R$_{22}$ are each independently of the others hydrogen or $C_1$-$C_6$alkyl;
R$_{6c}$, R$_{14}$, R$_{15}$, R$_{19}$ and R$_{21}$ are each independently of the others $C_1$-$C_6$alkyl or $C_1$-$C_6$haloalkyl;
Ar$_1$, Ar$_2$, Ar$_3$, Ar$_4$, Ar$_5$, Ar$_6$, Ar$_7$, Ar$_8$, Ar$_9$, Ar$_{10}$, Ar$_{11}$ and Ar$_{12}$ are each independently of the others a five- to ten-membered, monocyclic or fused bicyclic ring system, which may be aromatic, partially saturated or fully saturated and may contain from 1 to 4 hetero atoms selected from nitrogen, oxygen, sulfur, C(O) and C(=NR$_{25}$), and each ring system may contain not more than two oxygen atoms, not more than two sulfur atoms, not more than two C(O) groups and not more than one C(=NR$_{25}$) group, and each ring system may itself be mono- or poly-substituted by $C_1$-$C_6$alkyl, $C_1$-$C_6$haloalkyl, $C_2$-$C_6$alkenyl, $C_2$-$C_6$haloalkenyl, $C_2$-$C_6$alkynyl, $C_2$-$C_6$haloalkynyl, $C_1$-$C_6$alkoxy, $C_1$-$C_6$haloalkoxy, $C_3$-$C_6$alkenyloxy, $C_3$-$C_6$alkynyloxy, mercapto, amino, hydroxy, $C_1$-$C_6$alkylthio, $C_1$-$C_6$haloalkylthio, $C_3$-$C_6$alkenylthio, $C_3$-$C_6$haloalkenylthio, $C_3$-$C_6$alkynylthio, $C_1$-$C_3$alkoxy-$C_1$-$C_3$alkylthio, $C_1$-$C_4$alkylcarbonyl-$C_1$-$C_3$alkylthio, $C_1$-$C_4$alkoxycarbonyl-$C_1$-$C_3$alkylthio, cyano-$C_1$-$C_3$alkylthio, $C_1$-$C_6$alkylsulfinyl, $C_1$-$C_6$haloalkysulfinyl, $C_1$-$C_6$alkylsulfonyl, $C_1$-$C_6$haloalkylsulfonyl, aminosulfonyl, $C_1$-$C_2$alkylaminosulfonyl, N,N-di($C_1$-$C_2$alkyl)aminosulfonyl, di($C_1$-$C_4$alkyl)amino, halogen, cyano, nitro or phenyl, it being possible for the phenyl group in turn to be substituted by hydroxy, $C_1$-$C_6$alkylthio, $C_1$-$C_6$haloalkylthio, $C_3$-$C_6$alkenylthio, $C_3$-$C_6$haloalkenylthio, $C_3$-$C_6$alkynylthio, $C_1$-$C_3$alkoxy-$C_1$-$C_3$alkylthio, $C_1$-$C_4$alkoxycarbonyl-$C_1$-$C_3$alkylthio, $C_1$-$C_4$alkoxycarbonyl-$C_1$-$C_3$alkylthio, cyano-$C_1$-$C_3$alkylthio, $C_1$-$C_6$alkylsulfinyl, $C_1$-$C_6$haloalkysulfinyl, $C_1$-$C_6$alkylsulfonyl, $C_1$-$C_6$haloalkylsulfonyl, aminosulfonyl, $C_1$-$C_2$alkylaminosulfonyl, N,N-di($C_1$-$C_2$alkyl)aminosulfonyl, di($C_1$-$C_4$alkyl)amino, halogen, cyano or nitro, and the substituents at the nitrogen atom in the heterocyclic ring being other than halogen, and two oxygen atoms not being located next to one another; $R_{25}$ is hydrogen, hydroxy, $C_1$-$C_6$alkyl, $C_1$-$C_6$haloalkyl, $C_1$-$C_6$alkoxy, $C_1$-$C_6$alkylcarbonyl, $C_1$-$C_6$alkoxycarbonyl or $C_1$-$C_6$alkylsulfonyl; and $n_1$ is 0, 1 or 2; and $n_6$ is 0, 1 or 2;

or an agronomically acceptable salt, enantiomer, or tautomer of such a compound.

2. A herbicidal and plant-growth-inhibiting composition, comprising a herbicidally effective amount of a compound of formula I according to claim 1 on an inert carrier.

3. A method of controlling undesired plant growth, which method comprises applying a compound of formula I according to claim 2, or a composition comprising such a compound, in a herbicidally effective amount to a plant or to the locus thereof.

4. A method of inhibiting plant growth, which method comprises applying a compound of formula I according to claim 2, or a composition comprising such a compound, in a herbicidally effective amount to a plant or to the locus thereof.

* * * * *